(12) United States Patent
Berger et al.

(10) Patent No.: US 7,880,042 B2
(45) Date of Patent: Feb. 1, 2011

(54) TETRAHYDRONAPHTHALENE DERIVATIVES, METHODS FOR THE PRODUCTION THEREOF, AND THE USE THEREOF AS ANTIPHLOGISTICS

(75) Inventors: Markus Berger, Berlin (DE); Hartmut Rehwinkel, Berlin (DE); Heike Schäcke, Berlin (DE); Stefan Bäurle, Berlin (DE); Norbert Schmees, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 0 days.

(21) Appl. No.: 11/717,782

(22) Filed: Mar. 14, 2007

(65) Prior Publication Data

US 2007/0225290 A1    Sep. 27, 2007

Related U.S. Application Data

(60) Provisional application No. 60/784,441, filed on Mar. 22, 2006.

(30) Foreign Application Priority Data

Mar. 15, 2006    (EP) .................................. 06090031

(51) Int. Cl.
C07C 13/465    (2006.01)
(52) U.S. Cl. .................. 585/26; 544/237; 544/283; 546/143; 546/171; 549/404
(58) Field of Classification Search .................. 544/237, 544/283; 546/143, 171; 549/404; 585/26
See application file for complete search history.

(56) References Cited

U.S. PATENT DOCUMENTS

| | | | |
|---|---|---|---|
| 3,907,879 A | 9/1975 | Murakami et al. | |
| 5,059,609 A | 10/1991 | Eggler et al. | |
| 5,112,834 A | 5/1992 | Senn-Bilfinger | |
| 5,446,069 A | 8/1995 | Shih et al. | |
| 5,489,584 A | 2/1996 | Vuligonda et al. | |
| 6,197,783 B1 | 3/2001 | Senn-Bilfinger et al. | |
| 6,897,224 B2 | 5/2005 | Jaroch et al. | |
| 7,348,322 B2 | 3/2008 | Gong et al. | |
| 2003/0199690 A1 | 10/2003 | Dahanukar et al. | |
| 2005/0090559 A1 | 4/2005 | Berger | |
| 2005/0171109 A1 | 8/2005 | Rehwinkel et al. | |
| 2005/0209324 A1* | 9/2005 | Rehwinkel et al. | 514/521 |
| 2005/0222154 A1 | 10/2005 | Rehwinkel et al. | |
| 2005/0272823 A1 | 12/2005 | Rehwinkel et al. | |
| 2006/0040933 A1 | 2/2006 | Jaroch et al. | |
| 2006/0084652 A1 | 4/2006 | Baeurle et al. | |
| 2006/0165915 A1 | 7/2006 | Lietzau et al. | |
| 2006/0167025 A1 | 7/2006 | Berger | |
| 2006/0202163 A1 | 9/2006 | Lietzau et al. | |
| 2006/0229305 A1 | 10/2006 | Berger et al. | |
| 2006/0247213 A1 | 11/2006 | Buckman et al. | |
| 2007/0015750 A1 | 1/2007 | Baeurle et al. | |
| 2007/0015761 A1 | 1/2007 | Mengel et al. | |
| 2007/0129359 A1 | 6/2007 | Huwe et al. | |
| 2008/0153859 A1 | 6/2008 | Rehwinkel et al. | |

FOREIGN PATENT DOCUMENTS

| | | |
|---|---|---|
| CN | 1524835 A | 9/2004 |
| EP | 0291327 A2 | 11/1988 |
| EP | 0299470 A1 | 1/1989 |
| EP | 0439265 | 7/1991 |
| EP | 05/79223 A1 | 1/1994 |
| JP | 63220242 A | 9/1988 |
| JP | 2000/256255 A2 | 9/2000 |
| WO | WO 88/08836 A2 | 11/1988 |
| WO | WO 96/20930 A | 7/1996 |
| WO | WO 99/04778 A1 | 2/1999 |
| WO | WO 99/06388 A2 | 2/1999 |
| WO | WO 99/37607 A1 | 7/1999 |
| WO | WO 99/50205 A2 | 10/1999 |
| WO | WO 00/10977 A1 | 3/2000 |
| WO | WO 01/30734 A1 | 5/2001 |
| WO | WO 02/10143 A | 2/2002 |
| WO | WO 02/16318 | 2/2002 |
| WO | WO 03/000694 A1 | 1/2003 |
| WO | WO 03/027061 A2 | 4/2003 |
| WO | WO 03/040107 A1 | 5/2003 |
| WO | WO 03/045924 A1 | 6/2003 |
| WO | WO 03/082280 A | 10/2003 |
| WO | WO 03/082827 A | 10/2003 |
| WO | WO 2004/020375 A1 | 3/2004 |
| WO | WO 2004/063163 A | 7/2004 |
| WO | WO 2004/075864 A | 9/2004 |

(Continued)

OTHER PUBLICATIONS

Jordan, V. C. Nature Reviews: Drug Discovery, 2, 2003, p. 205.*

(Continued)

*Primary Examiner*—James O Wilson
*Assistant Examiner*—Douglas M Willis
(74) *Attorney, Agent, or Firm*—Millen, White, Zelano & Branigan, P.C.

(57) ABSTRACT

The invention relates to multiply substituted tetrahydronaphthalene derivatives of the formula (Ia)

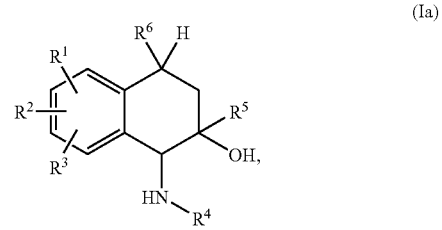

(Ia)

to processes for preparing them and to their use as antiinflammatory agents.

8 Claims, No Drawings

FOREIGN PATENT DOCUMENTS

| WO | WO 2005/003098 A1 | 1/2005 |
| --- | --- | --- |
| WO | WO 2005/021682 A1 | 3/2005 |
| WO | WO 2005/034939 A | 4/2005 |
| WO | WO 2005/090343 A | 9/2005 |
| WO | WO 2006/015870 A | 2/2006 |
| WO | WO 2006/027236 A | 3/2006 |
| WO | WO 2006/066950 A | 6/2006 |
| WO | WO 2006/100100 A | 9/2006 |
| WO | WO 2006/108699 A | 10/2006 |
| WO | WO 2006/108714 A | 10/2006 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

Jordan, V. C. Nature Reviews: Drug Discovery, 2, 2003, 205.*

Hackam, et al. JAMA, 296(14), 2006, 1731-1732.*

Evans et al., $C_2$-Symmetric Copper(II) Complexes as Chiral Lewis Acids. Catalytic Enantioselective Carbonyl-Ene Reactions With Glyoxylate and Pyruvate Esters, American Chemical Society, 2000, pp. 7936-7943.

Int'l. Search Report dated issued Jan. 18, 2006 in PCT/EP2005/009623.

Cleghorn, L.A.T. et al., "Three-component bimetallic (pd/In) mediated cascade allylation of C=X functionality—Part 1. Scope and class 1 examples with aldehydes and ketones," Journal of Organometallic Chemistry, Dec. 7, 2003, pp. 483-493, vol. 687 No. 2. Elsevier-sequoia S.A. Lausanne, CH.

Noseworthy et al., The New England Journal of Medicine, p. 949, vol. 343, No. 13, (2005).

Database CA (Online), Chemical Abstracts Service, Columbus, OH, 2004. Patonay, Tamas et al., "Synthesis of racemic and enantiomerically enriched .alpha.-Osyfunctionalized benzocyclanones and chromanones by dimethyldioxirane and dimethyldioxirane/Mn(III) salen system," XP002397131.

Database CA (Online), Chemical Abstracts Service, Columbus, OH, 2001. Ferraz, Helena et al., "The reaction of 1-tetralones with thallium trinitrate supported on clay : ring contraction vs. .alpha.-oxidation," XP002397132.

Database CA (Online), Chemical Abstracts Services, Columbus, OH, 1994. Srivastava, J.N. et al., "Syntheisis of 7-methoxy- and 6-mthoxytatralino[3,4-c]isocumarins and 7-methoxy- and 6-methoxytetralino[3,4-c]isoquinolones," XP002397133.

Database CA (Online), Chemical Abstracts Service, Columbus, OH, 1983. Thiem, Joachim et al., "2, 6-dideoxy sacchride glycosides of .alpha.-hydroxy ketones: synthesis and configurational assignment of glycosides with the tetralone substructure of olivomycin," XP002397135.

Cecil Textbook of Medicine, edited by Bennet, J.C., and Plum F., $20^{th}$ edition, vol. 1m 1004-1010, 1996.

Smoak et al., Mechanism of Ageing and Development, 125 697-706, 2004.

Saklavala et al., Arthritis Research 4(3), 146-150, 2002.

Barnes, P.J., Eur. Respir. J., 27(2), 413-426, 2006.

Bellucci et al., Tatrahedron Asymmetry, 8, 895-902, 1997.

Hachisu et al. Thiazolium ylide- catalyzed intramolecular aldehyde-ketone benzoin-forming reactionsl Advanced Synthesis & Catalysis, 2004, col. 346 (9+ 10), pp. 1097-1100: HCAPLUS abstract, Doc. No. 142:260997.

Dehmlow et al. Monodeazacinchona Alkaloid Derivatives: Synthesis and Preliminary Applications as Phase-Transfer Catalyst European Journal of Organic Chemistry, 2002 (13), pp. 2087-2093.

Nagao et al. New Ring-Expansion Reactions of Hydroxy Propenoyl Cyclic Compounds under Palladium (0)/Phosine-Catalyzed Conditions. Organic Letters, 2004, vol. 6 (13), pp. 2133-2136.

Greene. Protective Groups in Organic Synthesis, 1999, pp. 17-23.

Warner-Lambert. Expert Opinion on Therapeutic Patents, 2000, 10 (1), 121-23.

Int'l Search Report dated issued Feb. 8, 2002 in PCT/EP2007/002432.

Tchilibon et al., Biochemical Pharmacology, 70 (2005), 381-393.

Office Action dated Oct. 3, 2007 in related U.S. Appl. No. 10/962,169, filed Oct. 12, 2004.

Office Action dated Oct. 2, 2007 in related U.S. Appl. No. 10/961,406, filed Oct. 12, 2004.

Office Action dated Apr. 24, 2007 in related U.S. Appl. No. 11/222,250, filed Sep. 9, 2005.

* cited by examiner

TETRAHYDRONAPHTHALENE DERIVATIVES, METHODS FOR THE PRODUCTION THEREOF, AND THE USE THEREOF AS ANTIPHLOGISTICS

CROSS-REFERENCE TO RELATED APPLICATIONS

This application claims the benefit of the filing date of U.S. Provisional Application Ser. No. 60/784,441, filed Mar. 22, 2006.

BACKGROUND OF THE INVENTION (1) Field of the Invention

The invention relates to tetrahydronaphthalene derivatives, to processes for preparing them and to their use as antiinflammatory agents.

(2) Description of Related Art

The prior art (WO 2005/034939) discloses cyclic antiinflammatory agents of the general formula I

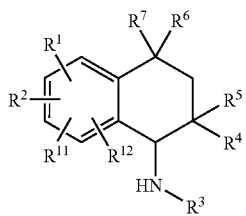

and these compounds, experimentally, show dissociations between antiinflammatory effects and unwanted metabolic effects. Moreover, the selectivity of these compounds is improved over that of other steroid receptors.

BRIEF SUMMARY OF THE INVENTION

Surprisingly it has now been found that compounds of the formulae (Ia) are particularly dissociated in respect of side-effects which can be measured in vitro in the form of TAT induction.

The present invention accordingly provides stereoisomers of the general formula (Ia),

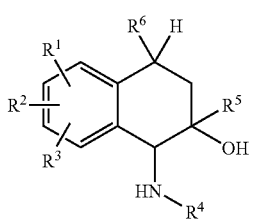

in which $R^1$ and $R^2$ independently of one another are a hydrogen atom, a hydroxyl group, a halogen atom, an optionally substituted ($C_1$-$C_{10}$) alkyl group, an optionally substituted ($C_1$-$C_{10}$) alkoxy group, a ($C_1$-$C_{10}$) alkylthio group, a ($C_1$-$C_5$) perfluoroalkyl group, a cyano group, a nitro group, or $R^1$ and $R^2$ together are a group selected from the groups
—O—($CH_2$)$_n$—O—, —O—($CH_2$)$_n$—$CH_2$—,
—O—CH=CH—, —($CH_2$)$_{n+2}$—, —NH—($CH_2$)$_{n+1}$, —N($C_1$-$C_3$ alkyl)-($CH_2$)$_{n+1}$, —NH—N=CH—, n being=1 or 2 and the terminal oxygen atoms and/or carbon atoms and/or nitrogen atoms being linked to directly adjacent ring carbon atoms, or $NR^8R^9$, $R^8$ and $R^9$ independently of one another being able to be hydrogen, $C_1$-$C_5$ alkyl or (CO)—$C_1$-$C_5$ alkyl, $R^3$ is a hydrogen atom, a hydroxyl group, a halogen atom, a cyano group, an optionally substituted ($C_1$-$C_{10}$) alkyl group, a ($C_1$-$C_{10}$) alkoxy group, a ($C_1$-$C_{10}$) alkylthio group, a ($C_1$-$C_5$) perfluoroalkyl group, $R^4$ is a $C_1$-$C_{10}$ alkyl group optionally substituted by 1-3 hydroxyl groups, halogen atoms, 1-3 ($C_1$-$C_5$) alkoxy groups, or is an optionally substituted ($C_3$-$C_7$) cycloalkyl group, an optionally substituted heterocyclyl group, an optionally substituted aryl group, a monocyclic or bicyclic heteroaryl group optionally substituted independently of one another by one or more groups selected from ($C_1$-$C_5$) alkyl groups (which may optionally be substituted by 1-3 hydroxyl or 1-3 $COOR^{13}$ groups), ($C_1$-$C_5$) alkoxy groups, halogen atoms, hydroxyl groups, $NR^8R^9$ groups, exomethylene groups and oxygen and which optionally contains 1-4 nitrogen atoms and/or 1-2 oxygen atoms and/or 1-2 sulphur atoms and/or 1-2 keto groups, it being possible for this heteroaryl group to be linked via any desired position to the amine of the tetrahydronaphthalene system, and it being possible for this heteroaryl group optionally to be hydrogenated at one or more sites, $R^5$ is a ($C_1$-$C_{10}$) alkyl group or an optionally partly or fully fluorinated ($C_1$-$C_{10}$) alkyl group, a ($C_3$-$C_7$)cycloalkyl group, a ($C_1$-$C_8$)alkyl($C_3$-$C_7$)cycloalkyl group, ($C_2$-$C_8$) alkenyl($C_3$-$C_7$)cycloalkyl group, a heterocyclyl group, a ($C_1$-$C_8$)alkylheterocyclyl group, ($C_2$-$C_8$) alkenylheterocyclyl group, an aryl group, a ($C_1$-$C_8$)alkylaryl group, a ($C_2$-$C_8$)alkenylaryl group, ($C_2$-$C_8$)alkynylaryl groups, a monocyclic or bicyclic heteroaryl group which is optionally substituted by 1-2 keto groups, 1-2 ($C_1$-$C_5$) alkyl groups, 1-2 ($C_1$-$C_5$) alkoxy groups, 1-3 halogen atoms, 1-2 exomethylene groups and which contains 1-3 nitrogen atoms and/or 1-2 oxygen atoms and/or 1-2 sulphur atoms, a ($C_1$-$C_8$)alkylheteroaryl group or a ($C_2$-$C_8$)alkenylheteroaryl group, a ($C_2$-$C_8$)alkynylheteroaryl group it being possible for these groups to be linked via any desired position to the tetrahydronaphthalene system and it being possible for these groups optionally to be hydrogenated at one or more sites, $R^6$ is a methyl, ethyl, propyl, isopropyl group or ethylene group and their salts with physiologically tolerated anions, with the exception of 6-fluoro-1-[(2-methylquinolin-5-yl)amino]-4-ethyl-2-(trifluoromethyl)-1,2,3,4-tetrahydronaphthalene-2,5-diol.

The compound known from the prior art (WO 2005/034939, Example 279) (6-fluoro-1-[(2-methylquinolin-5-yl)amino]-4-ethyl-2-(trifluoromethyl)-1,2,3,4-tetrahydronaphthalene-2,5-diol) is expressly excepted from the scope of protection of the present patent specification.

DETAILED DESCRIPTION OF THE INVENTION

The invention more particularly provides stereoisomers of the general formula Ia which on the aromatic ring of the tetrahydronaphthalene system carry substituents as $R^1$ and $R^2$ which are selected independently of one another from the group $C_1$-$C_5$ alkyl, $C_1$-$C_5$ alkoxy, COOR$^{13}$, NR$^8$R$^9$, $C_1$-$C_5$ perfluoroalkyl, halogen, hydroxyl, cyano-, nitro, and independently thereof carry as R$^3$ substituents which are selected from the group of hydrogen atom, a hydroxyl group, a halogen atom, a cyano group, an optionally substituted ($C_1$-$C_3$) alkyl group, a ($C_1$-$C_3$) alkoxy group, a ($C_1$-$C_3$) alkylthio group, a ($C_1$-$C_3$) perfluoroalkyl group.

The radical R$^4$ is attached to the tetrahydronaphthalene system via the amine. If the radical R$^4$ has two or more positions which are chemically possible for attachment to the ring system, then the present invention encompasses all of these possibilities.

The radical R$^4$ is also encompassed by the present invention if it is hydrogenated at one or more sites.

Suitable substituents of the monocyclic or bicyclic heteroaryl groups (heterocyclic groups) R$^4$, as have been defined above, and located at chemically appropriate positions, include, for example, hydroxyl, halogen atoms, especially fluorine and chlorine, ($C_1$-$C_5$) alkyl groups (which may themselves optionally be substituted by hydroxyl groups, ($C_1$-$C_5$) alkoxy groups or COOR$^{13}$ groups, R$^{13}$ being hydrogen or ($C_1$-$C_5$) alkyl), especially methyl, ($C_2$-$C_5$) alkenyl groups, fully or partly fluorinated ($C_1$-$C_5$) alkyl groups, especially CF$_3$, CFH$_2$ or C$_2$F$_5$, ($C_1$-$C_5$) alkoxy groups, especially methoxy and ethoxy, NR$^8$R$^9$ groups, especially NH$_2$, N(CH$_3$)$_2$ or NH(CH$_3$), cyano groups and also keto groups with are formed with a carbon atom of a ring of the heteroaryl group, and oxygen, which forms an N-oxide with a nitrogen atom of the ring optionally present. From this there emerges, as a preferred group of substituents on a heterocyclic group for the radical R$^4$ as defined in claim 1 and for all further claims, the group consisting of fluorine, chlorine, OH, CH$_3$, CF$_3$, CFH$_2$ or C$_2$F$_5$, OCH$_3$, OC$_2$H$_5$, NH$_2$, N(CH$_3$)$_2$ and NH(CH$_3$), cyano, keto, oxygen.

The radical R$^5$ is attached to the tetrahydronaphthalene system directly. If the radical R$^5$ has two or more positions which are chemically possible for attachment to the ring system, then the present invention encompasses all of these possibilities.

The invention therefore further provides stereoisomers of the general formula I in which R$^5$ is a ($C_1$-$C_5$) alkyl group or an optionally partly or fully fluorinated ($C_1$-$C_5$) alkyl group, a ($C_3$-$C_7$)cycloalkyl group, a ($C_1$-$C_8$)alkyl($C_3$-$C_7$)cycloalkyl group, ($C_2$-$C_8$)alkenyl($C_3$-$C_7$)cycloalkyl group, a heterocyclyl group, a ($C_1$-$C_8$)alkylheterocyclyl group, ($C_2$-$C_8$)alkenylheterocyclyl group, an aryl group, a ($C_1$-$C_8$)alkylaryl group, ($C_2$-$C_8$)alkenylaryl group.

Further provided by the invention are stereoisomers of the general formula I in which R$^5$ is an aryl group, a ($C_1$-$C_8$) alkylaryl group, ($C_2$-$C_8$)alkenylaryl group, a ($C_3$-$C_7$)cycloalkyl group, a ($C_1$-$C_8$)alkyl($C_3$-$C_7$)cycloalkyl group, ($C_2$-$C_8$)alkenyl-($C_3$-$C_7$)cycloalkyl group.

Additionally provided by the invention are stereoisomers of the general formula I in which R$^5$ is a ($C_1$-$C_{10}$) alkyl group or an optionally partly or fully fluorinated ($C_1$-$C_{10}$) alkyl group, preferably a ($C_1$-$C_5$) alkyl group or an optionally partly or fully fluorinated ($C_1$-$C_5$) alkyl group, more preferably a ($C_1$-$C_3$) alkyl group or an optionally partly or fully fluorinated ($C_1$-$C_3$) alkyl group, in particular an optionally partly or fully fluorinated ($C_1$-$C_3$) alkyl group, especially CF$_3$ or C$_2$F$_5$.

An important aspect of the invention comprises those stereoisomers of the general formula Ia wherein
I) the radicals R$^1$, R$^2$ and R$^3$ independently of one another are selected from
—OH, $C_1$-$C_4$ alkoxy, halogen, H,
II) the radical R$^4$ is selected from
a quinoline, quinazoline or phthalazine group which is substituted zero to up to two times by methyl or ethyl, and also is substituted zero to up to two times by fluorine
III) the radical R$^5$ is an optionally partly or fully fluorinated $C_1$-$C_3$ alkyl group and
IV) the radical R$^6$ is selected from —CH$_3$, —CH$_2$—CH$_3$, —(CH$_2$)$_2$—CH$_3$, —CH(CH$_3$)$_2$ or —CH═CH$_2$.

A particularly important aspect of the invention comprises those stereoisomers of the general formula Ia wherein
I) the radicals R$^1$, R$^2$ and R$^3$ independently of one another are selected from
—OH, O—CH$_3$, Cl, F, H,
II) the radical R$^4$ is selected from
2-methylquinolin-5-yl
2-methylquinazolin-5-yl
2-ethylquinazolin-5-yl
7-fluoro-2-methylquinazolin-5-yl,
8-fluoro-2-methylquinazolin-5-yl,
7,8-difluoro-2-methylquinazolin-5-yl,
quinolin-2(1H)-on-5-yl,
7-fluoroquinolin-2(1H)-on-5-yl,
8-fluoroquinolin-2(1H)-on-5-yl,
isochromen-1-on-5-yl
2-methylphthalazin-1-on-5-yl
isoquinolin-2(1H)-on-5-yl,
III) the radical R$^5$ is —CF$_3$ and
IV) the radical R$^6$ is selected from —CH$_3$, —CH$_2$—CH$_3$, —(CH$_2$)$_2$—CH$_3$, or —CH═CH$_2$—.

An extremely important aspect of the invention are those stereoisomers of the general formula Ia wherein the enantiomeric compounds are present in 1α,2α,4β configuration on the 1,2,3,4-tetrahydronaphthalen-2-ol parent structure. On the basis of the rules of IUPAC nomenclature, this corresponds, in the case of 1,6-dihyroxy substitution of the tetrahydronaphthalene, to the 5α,6α,8β configuration of the 5,6,7,8-tetrahydronaphthalene-1,6-diol parent structure (see Examples).

A particularly preferred subgroup as disclosed for the present invention is represented by those radicals, and all of their subordinate combinations, which are documented by the examples.

DEFINITIONS

The identification halogen atom or halogen denotes a fluorine, chlorine, bromine or iodine atom. A fluorine, chlorine or bromine atom is preferred.

The $C_1$-$C_{10}$ and $C_1$-$C_5$ alkyl groups R$^1$, R$^2$, R$^4$, R$^5$, R$^6$, R$^7$, R$^{11}$, R$^{12}$ and R$^{13}$ may be straight-chain or branched and are for example a methyl, ethyl, n-propyl, isopropyl, n-butyl, isobutyl, tert-butyl or n-pentyl, 2,2-dimethylpropyl, 2-methylbutyl or 3-methylbutyl group, and also the hexyl, heptyl, nonyl, decyl group and their arbitrarily branched derivatives. A methyl or ethyl group is preferred.

The abovementioned alkyl groups may optionally be substituted by 1-5 groups selected independently of one another from hydroxyl, cyano, nitro, COOR$^{13}$, $C_1$-$C_5$ alkoxy groups, halogen, NR$^8$R$^9$, a partly or fully fluorinated $C_1$-$C_3$ alkyl group;

one subgroup is represented by the substituents which are 1-3 halogen atoms and/or 1-3 hydroxyl and/or 1-3 cyano and/or 1-3 COOR$^{13}$ groups. A preferred subgroup is represented by fluorine atom, hydroxyl, methoxy and/or cyano groups.

The alkyl groups may optionally only be substituted by 1-3 hydroxyl and/or 1-3 COOR$^{13}$ groups. Preference in that case is given to hydroxyl groups.

A partly or fully fluorinated $C_1$-$C_3$ alkyl group is suitably, for example, the following partly or fully fluorinated following groups: fluoromethyl, difluoromethyl, trifluoromethyl, fluoroethyl, 1,1-difluoroethyl, 1,2-difluoroethyl, 1,1,1-trifluoroethyl, tetrafluoroethyl, pentafluoroethyl. Preferred among these are the trifluoromethyl or the pentafluoroethyl group, the fully fluorinated group also being called a perfluoroalkyl group.

The reagents which are employed optionally during the synthesis are commercialized, or the published syntheses of the corresponding reagents are part of the prior art, or published syntheses can be employed analogously.

The $C_1$-$C_{10}$ and $C_1$-$C_5$ alkoxy groups may be straight-chain or branched and are for example a methoxy, ethoxy, n-propoxy, isopropoxy, n-butoxy, isobutoxy, tert-butoxy or n-pentoxy, 2,2-dimethylpropoxy, 2-methylbutoxy or 3-methylbutoxy group. $C_1$-$C_5$ alkoxy groups are preferred. A methoxy or ethoxy group is particularly preferred.

The abovementioned alkoxy groups may optionally be substituted by 1-3 groups selected from halogen, especially fluorine, chlorine, hydroxyl and cyano.

The $C_1$-$C_5$ alkylthio groups may be straight-chain or branched and are for example a methylthio, ethylthio, n-propylthio, isopropylthio, n-butylthio, isobutylthio, tert-butylthio or n-pentylthio, 2,2-dimethylpropylthio, 2-methylbutylthio or 3-methylbutylthio group. A methylthio or ethylthio group is preferred.

The substituent $NR^8R^9$ is for example $NH_2$, $NH(CH_3)$, $N(CH_3)_2$, $NH(C_2H_5)$, $N(C_2H_5)_2$, $NH(C_3H_7)$, $N(C_3H_7)_2$, $NH(C_4H_9)$, $N(C_4H_9)_2$, $NH(C_5H_{11})$, $N(C_5H_{11})_2$, $NH(CO)CH_3$, $NH(CO)C_2H_5$, $NH(CO)C_3H_7$, $NH(CO)C_4H_9$, $NH(CO)C_5H_{11}$.

The cycloalkyl group is a saturated cyclic group having 3 to 7 ring carbon atoms which is optionally substituted by one or more groups selected from hydroxyl groups, halogen atoms, ($C_1$-$C_5$) alkyl groups, ($C_1$-$C_5$) alkoxy groups, $NR^8R^9$ groups, COOR$^{13}$ groups, CHO, cyano, such as, for example, cyclopropyl, methylcyclopropyl, cyclobutyl, methylcyclobutyl, cyclopentyl, methylcyclopentyl, cyclohexyl, methylcyclohexyl, cycloheptyl, methylcycloheptyl.

A ($C_1$-$C_8$)alkyl($C_3$-$C_7$)cycloalkyl group $R^5$ is a cycloalkyl group which is linked to the ring system via a straight-chain or branched ($C_1$-$C_8$) alkyl unit.

A ($C_2$-$C_8$)alkenyl($C_3$-$C_7$)cycloalkyl group $R^5$ is a cycloalkyl group which is attached to the ring system via a straight-chain or branched ($C_2$-$C_8$) alkenyl unit.

The heterocyclyl group is non-aromatic and may for example be pyrrolidine, imidazolidine, pyrazolidine, piperidine. Perhydroquinoline and perhydroisoquinoline are also among the heterocyclyl groups encompassed. Examples of suitable substituents for heterocyclyl and heteroaryl groups are substituents from the group of optionally substituted $C_1$-$C_5$ alkyl group, hydroxyl-, $C_1$-$C_5$ alkoxy-, $NR^5R^9$—, halogen, cyano-, COOR$^{13}$—, CHO—. The substituents may optionally also be attached to the nitrogen atom; in that case, N-oxides are also included in the definition.

Aryl groups for the purposes of the invention are aromatic or partly aromatic carbocyclic groups having 6 to 14 carbon atoms and having one ring, such as phenyl or phenylene for example, or two or more condensed rings, such as napthyl or anthranyl, for example. By way of example mention may be made of phenyl, naphthyl, tetralinyl, anthranyl, indanyl, and indenyl.

The aryl groups may be substituted at any suitable site that leads to a stable stereoisomer, by one or more radicals from the group of hydroxyl, halogen, nitro, $CF_3$, cyano, $C_1$-$C_5$ alkoxy, $C_1$-$C_5$ alkyl optionally substituted by 1-3 hydroxyl groups or COOR$^{13}$ groups.

The optionally substituted phenyl group and the naphthyl group are preferred.

A ($C_1$-$C_8$)alkylaryl group is an aryl group as already described above which is linked to the ring system via a straight-chain or branched ($C_1$-$C_8$) alkyl unit.

A ($C_2$-$C_8$)alkenylaryl group is an aryl group as already described above which is linked to the ring system via a straight-chain or branched ($C_2$-$C_8$) alkenyl unit.

A ($C_2$-$C_8$)alkynylaryl group is an aryl group as already described above which is linked to the ring system via a straight-chain or branched ($C_2$-$C_8$) alkynyl unit.

The monocyclic or bicyclic heteroaryl group may optionally be substituted by one or more substituents selected from exomethylene, halogen, $C_1$-$C_5$ alkoxy group $C_1$-$C_5$ alkyl group optionally substituted by 1-3 hydroxyl groups or 1-3 COOR$^{13}$ groups. The substituents may optionally also be attached directly to the heteroatom. N-Oxides are also included in the present invention.

The monocyclic or bicyclic heteroaryl group may optionally contain 0-9 groups from the group of nitrogen atoms, oxygen atoms, sulphur atoms or keto groups, of which a maximum of 4 nitrogen atoms, a maximum of 2 oxygen atoms, a maximum of 2 sulphur atoms and a maximum of 2 keto groups may be present.

Any subordinate combination of these groups is possible. The heteroaryl group may be hydrogenated at one or more sites.

Monocyclic heteroaryl groups may for example be pyridine, pyrazine, pyrimidine, pyridazine, triazine, azaindolizine, 2H- and 4H-pyran, 2H- and 4H-thiopyran, furan, thiophene, 1H- and 4H-pyrazole, 1H- and 2H-pyrrole, oxazole, thiazole, furazan, 1H- and 4H-imidazole, isoxazole, isothiazole, oxadiazole, triazole, tetrazole, thiadiazole.

Bicyclic heteroaryl groups may for example be phthalidyl, thiophthalidyl, indolyl, isoindolyl, dihydroindolyl, dihydroisoindolyl, indazolyl, benzothiazolyl, indolonyl, dihydroindolonyl, isoindolonyl, dihydroisoindolonyl, benzofuranyl, benzimidazolyl, dihydroisoquinolinyl, dihydroquinolinyl, benzoxazinonyl, phthalazinonyl, dihydrophthalazinonyl, quinolinyl, isoquinolinyl, quinolonyl, isoquinolonyl, quinazolinyl, quinoxalinyl, cinnolinyl, phthalazinyl, dihydrophthalazinyl, 1,7- or 1,8-naphthyridinyl, coumarinyl, isocoumarinyl, indolizinyl, isobenzofuranyl, azaindolyl, azaisoindolyl, furanopyridyl, furanopyrimidinyl, furanopyrazinyl, furanopyidazinyl, dihydrobenzofuranyl, dihydrofuranopyridyl, dihydrofuranopyrimidinyl, dihydrofuranopyrazinyl, dihydrofuranopyridazinyl, dihydrobenzofuranyl, chromenyl, isochromenyl, chromenonyl or the isochromenonyl group.

If the heteroaryl groups are partly or fully hydrogenated, then the present invention includes stereoisomers of the formula Ia in which $R^3$ is tetrahydropyranyl, 2H-pyranyl, 4H-pyranyl, piperidyl, tetrahydropyridyl, dihydropyridyl, 1H-pyridin-2-onyl, 1H-pyridin-4-onyl, 4-aminopyridyl, 1H-pyridin-4-ylideneaminyl, chromanyl, isochromanyl, thiochromanyl, decahydroquinolinyl, tetrahydroquinolinyl, dihydroquinolinyl, 5,6,7,8-tetrahydro-1H-quinolin-4-onyl, decahydroisoquinolinyl, tetrahydroisoquinolinyl, dihydroisoquinolinyl, 3,4-dihydro-2H-benz[1,4]oxazinyl, 1,2-dihydro[1,3]benzoxazin-4-onyl, 3,4-dihydro-benz[1,4]oxazin-4-onyl, 3,4-dihydro-2H-benzo[1,4]thiazinyl, 4H-benzo[1,4]thiazinyl, 1,2,3,4-tetrahydroquinoxalinyl, 1H-cinnolin-4-onyl, 3H-quinazolin-4-onyl, 1H-quinazolin-4-onyl, 3,4-dihydro-1H-quinoxalin-2-onyl, 2,3-1,2,3,4-tetrahydro[1,5]naphthyridinyl, dihydro-1H-[1,5]naphthyridyl, 1H-[1,5]naphthyrid-4-onyl, 5,6,7,8-tetrahydro-1H-naphthyridin-4-onyl, 1,2-dihydropyrido[3,2-d][1,3]oxazin-4-onyl, octahydro-1H-indolyl, 2,3-dihydro-1H-indolyl, octahydro-2H-isoindolyl, 1,3-dihydro-2H-isoindolyl, 1,2-dihydro-indazolyl, 1H-pyrrolo[2,3-b]pyridyl, 2,3-dihydro-1H-pyrrolo[2,3-b]pyridyl, 2,2-dihydro-1H-pyrrolo[2,3-b]pyridin-3-onyl.

A ($C_1$-$C_8$)alkylheteroaryl group is a heteroaryl group as already described above which is linked to the ring system via a straight-chain or branched ($C_1$-$C_8$) alkyl unit.

A ($C_2$-$C_8$)alkenylheteroaryl group is a heteroaryl group as already described above which is linked to the ring system via a straight-chain or branched ($C_2$-$C_8$) alkenyl unit.

A ($C_2$-$C_8$)alkynylheteroaryl group is a heteroaryl group as already described above which is linked to the ring system via a straight-chain or branched ($C_2$-$C_8$) alkynyl unit.

A ($C_1$-$C_8$)alkylheterocyclyl group is a heterocyclyl group as already described above which is linked to the ring system via a straight-chain or branched ($C_1$-$C_8$) alkyl unit.

A ($C_2$-$C_8$)alkenylheterocyclyl group is a heterocyclyl group as already described above which is linked to the ring system via a straight-chain or branched ($C_2$-$C_8$) alkenyl unit.

As a result of the presence of centres of asymmetry, the stereoisomers of the general formula Ia of the invention may be present as the stereoisomers. The present invention provides all of the possible stereoisomers (e.g.: RRR, RRS, RSR, SRR, RSS, SRS, SSR, SSS), both as racemates and in enantiomerically pure form. The term stereoisomers also encompasses all of the possible diastereomers and regioisomers and tautomers (e.g. keto-enol tautomers) in which the stereoisomers of the invention may be present, and which are likewise provided by the invention.

Particularly preferred stereoisomers of the compound described are those (1,2,3,4)-tetrahydronaphthalenes which carry (1S, 2R, 4R) or (1S, 2R, 4S) as the absolute configuration on the 1-amino-1,2,3,4-tetrahydronaphthalen-2-ol parent structure. Owing to the rules of IUPAC nomenclature, in the case of 1,6-dihydroxy substitution of the tetrahydronaphthalene, this corresponds to the (5S, 6R, 8R) configuration of the 5,6,7,8-tetrahydronaphtalene-1,6-diol parent structure (see Examples) or to the (5S, 6R, 8S) configuration.

The stereoisomers of the invention may also be present in the form of salts with physiologically tolerated anions, as for example in the form of the hydrochloride, sulphate, nitrate, phosphate, pivalate, maleate, fumarate, tartrate, benzoate, mesylate, citrate or succinate.

The compounds of the invention are prepared
a) by using methods known in the art to generate the open-chain precursors of the general formula (II), in which the radicals $R^1$, $R^2$, $R^3$, $R^4$ and $R^5$ have the definitions specified in claim 1,

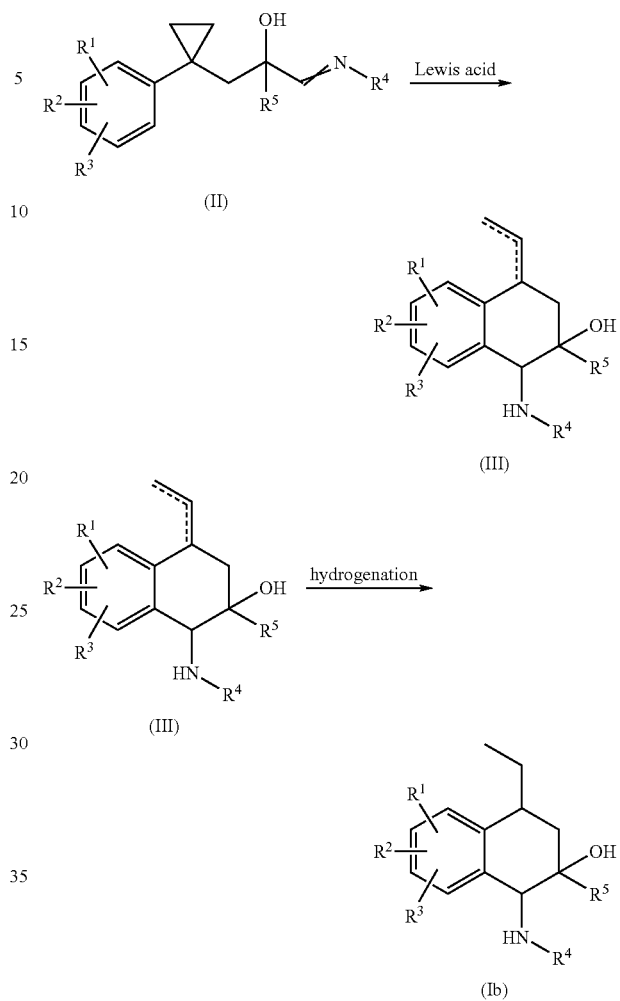

which then, either without further reagent or by addition or organic or inorganic acids or Lewis acids, under temperatures in the range from −70° C. to +80° C. (preferably in the range from −30° C. to +80° C.), are cyclized and rearranged to give the compounds of the general formula (III). A catalytic hydrogenation, which can optionally be carried out diastereoselectively, then yields compounds of the general formula (Ib) in which $R^6$ is an ethyl group.

b) by using methods known in the art to convert prepared styrenes of the general formula (IV), by means of an optionally enantioselectively conducted ene reaction with chiral Lewis acids, into the compounds of the general formula (V). Chiral Lewis acids which can be used for the enantioselective generation of the quaternary alcohol function include the following: (R)- or (S)-SEGPHOS-PdCl$_2$ (Mikami et al. *Tetrah. Asymm.* 2004, 15, 3885-89), (R)- or (S)-BINOL-Ti(OiPr)$_2$ (Ding et al. Tetrah. Lett. 2004, 45, 2009-12), (R)- or (S)-Cu $^t$BuBOX,), (R)- or (S)-Cu $^i$Pr-BOX, (R)- or (S)-Cu PhBOX, (R)- or (S)-Cu AdaBOX (Evans et al. *J. Am. Chem. Soc.* 2000, 122, 7936-43), (R)- or (S)-$^i$Pr-pybox Yb(OTf)$_3$, (R)- or (S)-$^t$Bu-pybox Yb(OTf)$_3$, (R)- or (S)-Ph-pybox Yb(OTf)$_3$ (Qian et al. *Tetrah. Asymm.* 2000, 11, 2347-57). By reduction, hydrogenation and amination, in accordance with methods known to the skilled person, the imine (VI) is generated,

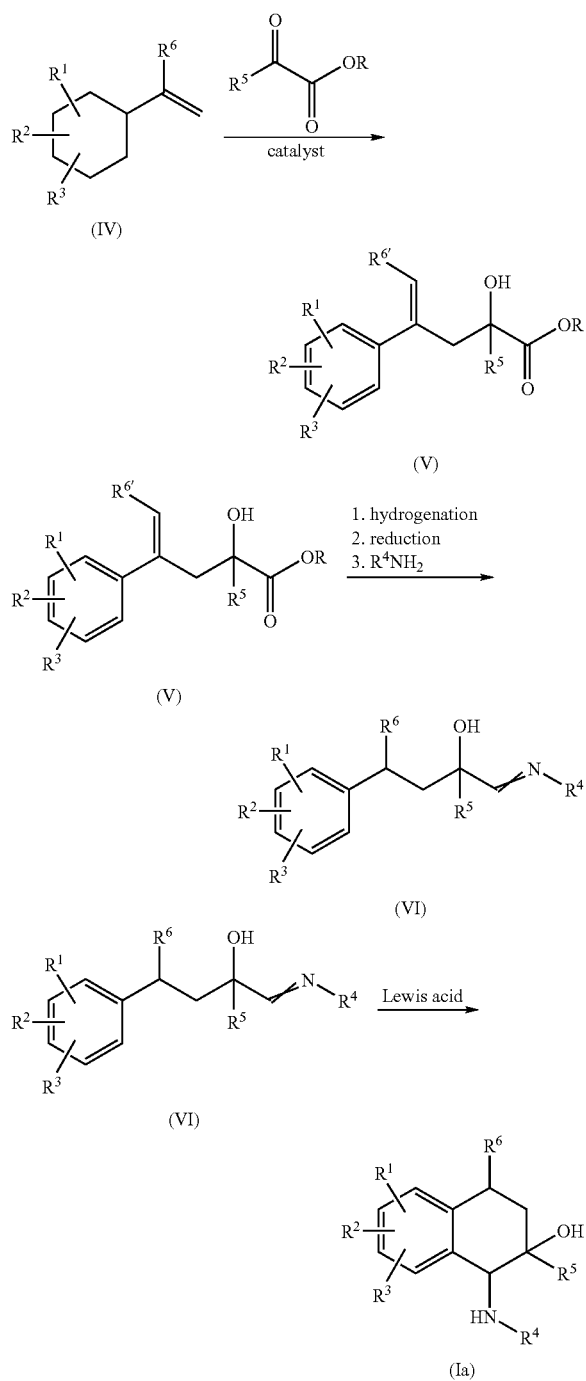

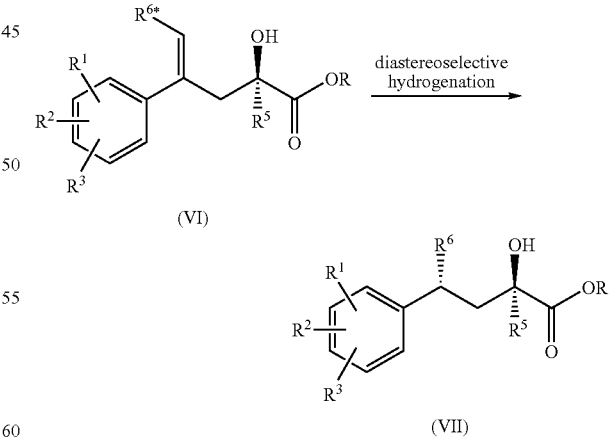

which then, either without further reagent or by addition of organic or inorganic acids or Lewis acids, under temperatures in the range from −70° C. to +80° C. (preferably in the range from −30° C. to +80° C.), is cyclized to give the compounds of the general formula (Ia). The radicals $R^1, R^2, R^3, R^4, R^5$ and $R^6$, defined in general terms in the formulae set out above, have the definitions specified in claim 1.

The present invention accordingly also provides a method of preparing the stereoisomers of the general formula (Ia) which is characterized in that imines of the general formula (VI) or (II), either without further reagent, in a solvent or concentrated organic acids, or by addition of organic or inorganic acids or Lewis acids, under temperatures in the range from −70° C. to +80° C. (preferably in the range from −30° C. to +80° C.), are cyclized to give the stereoisomers of the general formula (Ia) or (III), and also their direct precursors of the formula (V).

The new imines (IV) for the cyclization are likewise provided by the present invention, particularly those which have been disclosed by the examples.

A particularly preferred process is the method of preparing compounds of the general formula (V) in which, as catalysts of the enantioselective ene reaction, use is made of [Cu(S,S)bis(tert-butyloxazoline)](SbF$_6$)$_2$ or [Cu(R,R)bis(tert-butyloxazoline)](SbF$_6$)$_2$, and enantiomeric excesses of up to 95% are attained, which through crystallization may be increased still further.

Enantiomerically pure compounds of the formula (V) can then be converted into the enantiomerically pure compounds of the formula (VI) by chromatographic separation methods on silica gel at the stage of the hydrogenated aldehyde or of the imine.

Diastereoselective hydrogenation methods can be used alternatively to give the enantiomerically pure compound of the formula (VI).

Suitable catalysts for the abovementioned catalytic hydrogenations include the following:
1. palladium on carbon
2. Raney nickel
3. rhodium catalysts with chiral ligands, as described in the following publications:
   Weissenstein et al., *Adv. Synth. Catal.* 2003, 345, 160-164
   Imwinkelried et al., *Chimia* 1997, 51, 300
4. iridium catalysts having chiral ligands, as described in the following publications:
   Pfaltz et al., *Org. Lett.* 2004, 6, 2023-2026
   Blaser et al., *Chimia* 1999, 53, 275
5. ruthenium catalysts having chiral ligands, as described in the following publication:
   *Chirality* 2000, 12, 514-522.

The invention accordingly further provides enantiomerically pure esters of the formula (VII), which can be obtained by diastereoselective hydrogenation methods or diastereomer separations.

The binding of the substances to the glucocorticoid receptor (GR) and further steroid hormone receptors (mineral corticoid receptor (MR), progesterone receptor (PR) and androgen receptor (AR)) is examined with the aid of recombinantly prepared receptors. Cytosol preparations of Sf9 cells which had been infected with recombinant baculoviruses that code for the GR are used for the binding studies. Compared with the reference substance [$^3$H]-dexamethasone, the substances show a high affinity for the GR.

An essential molecular mechanism for the antiinflammatory effect of glucocorticoids is considered to be the GR-mediated inhibition of the transcription of cytokines, adhesion molecules, enzymes and other pro-inflammatory factors. This inhibition is brought about by interaction of the GR with other transcription factors, e.g. AP-1 and NF-kappa-B (for a review see Cato A C B and Wade E, BioEssays 18, 371-378 1996).

The stereoisomers of the general formula Ia according to the invention inhibit the lipopolysaccharide (LPS)-initiated secretion of the cytokine IL-8 in the human THP-1 monocyte cell line.

The antiinflammatory effect of the stereoisomers of the general formula Ia was tested in an animal experiment by testing in the croton oil-induced inflammation in the rat and mouse (J. Exp. Med. (1995), 182, 99-108). For this purpose, croton oil in ethanolic solution was applied topically to the animals' ears. The test substances were administered likewise topically, or systemically, at the same time as, or two hours before, the croton oil. After 16-24 hours, the ear weight was measured as a measure of the inflammatory edema, the peroxidase activity was measured as a measure of the inward migration of granulocytes, and the elastase activity was measured as a measure of the inward migration of neutrophilic granulocytes. In this test, the stereoisomers of the general formula Ia, both after topical administration and after systemic administration, inhibit the three abovementioned parameters of inflammation.

One of the commonest unwanted effects of a glucocorticoid therapy is the so-called "steroid diabetes" [cf. Hatz, H J, Glucocorticoide: Immunologische Grundlagen, Pharmakologie und Therapierichtlinien, Wissenschaftliche Verlagsgesellschaft mbH, Stuttgart, 1998]. The cause of this is stimulation of gluconeogenesis in the liver by induction of the enzymes responsible therefor and by free amino acids resulting from the breakdown of proteins (catabolic effect of the glucocorticoids). A key enzyme in catabolic metabolism in the liver is tyrosine aminotransferase (TAT). The activity of this enzyme can be determined by photometry on liver homogenates and represents a good measure of the unwanted metabolic effects of glucocorticoids. To measure the TAT induction, the animals are sacrificed 8 hours after administration of the test substances, the livers are removed, and the TAT activity in the homogenate is measured. In this test, the stereoisomers of the general formula, in doses in which they have antiinflammatory activity, induce tyrosine aminotransferase to only a small extent or not at all.

Owing to their antiinflammatory and additional antiallergic, immunosuppressive and antiproliferative effect, the stereoisomers of the invention of the general formula Ia can be used as medicaments for the treatment or prophylaxis of the following pathological states in mammalian animals and humans: in this connection, the term "DISORDER" stands for the following indications:

(i) pulmonary disorders associated with inflammatory, allergic and/or proliferative processes:
chronic obstructive lung disorders of any origin, especially bronchial asthma
bronchitis of varying origin
all types of restrictive lung disorders, especially allergic alveolitis,
all types of pulmonary oedema, especially toxic pulmonary oedema
sarcoidoses and granulomatoses, especially Boeck's disease (ii) rheumatic disorders/autoimmune diseases/joint disorders associated with inflammatory, allergic and/or proliferative processes:
all types of rheumatic disorders, especially rheumatoid arthritis, acute rheumatic fever, polymyalgia rheumatica
reactive arthritis
inflammatory soft tissue disorders of other origin
arthritic symptoms associated with degenerative joint disorders (arth roses)
traumatic arthritides
collagenoses of any origin, e.g. systemic lupus erythematosus, scleroderma, polymyositis, dermatomyositis, Sjögren's syndrome, Still's syndrome, Felty's syndrome (iii) allergies associated with inflammatory and/or proliferative processes:
all types of allergic reactions, e.g. angiooedema, hayfever, insect bite, allergic reactions to drugs, blood derivatives, contrast agents etc., anaphylactic shock, urticaria, contact dermatitis (iv) vessel inflammations (vasculitides)
polyarteritis nodosa, temporal arteritis, erythema nodosum (v) dermatological disorders associated with inflammatory, allergic and/or proliferative processes:
atopic dermatitis (especially in children)
psoriasis
pityriasis rubra pilaris
erythematous disorders induced by various noxae, e.g. radiation, chemicals, burns, etc.
bullous dermatoses
lichenoid disorders
pruritus (e.g. of allergic origin)
seborrheic eczema
rosacea
pemphigus vulgaris
Hebra's disease
balanitis
vulvitis
hair loss such as alopecia areata
cutaneous T-cell lymphomas (vi) renal disorders associated with inflammatory, allergic and/or proliferative processes:
nephrotic syndrome
all nephritides (vii) liver disorders associated with inflammatory, allergic and/or proliferative processes:
acute liver cell necrosis
acute hepatitis of varying origin, e.g. viral, toxic, drug-induced
chronic aggressive and/or chronic intermittent hepatitis (viii) gastrointestinal disorders associated with inflammatory, allergic and/or proliferative processes:
regional enteritis (Crohn's disease)
ulcerative colitis
gastritis
reflux esophagitis
gastroenteritides of other origin, e.g. indigenous sprue (ix) proctological disorders associated with inflammatory, allergic and/or proliferative processes:
anal eczema
fissures
haemorrhoids
idiopathic proctitis (x) ocular disorders associated with inflammatory, allergic and/or proliferative processes:
   allergic keratitis, uveitis, iritis,
   conjunctivitis
   blepharitis
   optic neuritis
   chorioditis
   sympathetic ophthalmia
(xi) ear-nose-throat disorders associated with inflammatory, allergic and/or proliferative processes:
   allergic rhinitis, hayfever
   otitis externa, e.g. caused by contact exema, infection etc.
   otitis media
(xii) neurological disorders associated with inflammatory, allergic and/or proliferative processes:
   cerebral oedema, especially tumour-related cerebral oedema
   multiple sclerosis
   acute encephalomyelitis
   meningitis
   various types of seizures, e.g. infantile spasms
(xiii) blood disorders associated with inflammatory, allergic and/or proliferative processes:
   acquired haemolytic anaemia
   idiopathic thrombocytopenia
(xiv) neoplastic disorders associated with inflammatory, allergic and/or proliferative processes:
   acute lymphatic leukaemia
   malignant lymphomas
   lymphogranulomatoses
   lymphosarcomas
   extensive metastases, especially associated with breast, bronchial and prostate carcinoma
(xv) endocrine disorders associated with inflammatory, allergic and/or proliferative processes:
   endocrine orbitopathy
   thyrotoxic crisis
   de Quervain's thyroiditis
   Hashimoto's thyroiditis
   Basedow's disease
(xvi) organ and tissue transplantations, graft-versus-host disease
(xvii) severe states of shock, e.g. anaphylactic shock, systemic inflammatory response syndrome (SIRS)
(xviii) emesis associated with inflammatory, allergic and/or proliferative processes:
   e.g. in combination with a 5-HT3 antagonist in cytostic-related vomiting.
(xix) pain of inflammatory origin, e.g. lumbago
(xx) replacement therapy for:
   congenital primary adrenal insufficiency, e.g. congenital adrenogenital syndrome
   acquired primary adrenal insufficiency, e.g. Addison's disease, autoimmune adrenalitis, post-infection, tumours, metastases etc.
   congenital secondary adrenal insufficiency, e.g. congenital hypopituitarism
   acquired secondary adrenal insufficiency, e.g. post-infection, tumours etc.

Medicaments comprising stereoisomers of the general formula Ia show a particular efficacy for the following disorders:
1. lung disorders
2. rheumatic disorders/autoimmune diseases
3. dermatological disorders
4. degenerative joint disorders
5. vascular inflammations
6. graft-versus-host disease
7. severe states of shock
8. emesis associated with inflammatory, allergic and/or proliferative processes
9. inflammation-related pain.

In addition, the stereoisomers of the invention of the general formula Ia can be employed for the therapy and prophylaxis of further pathological states which are not mentioned above and for which synthetic glucocorticoids are currently used (concerning this, see Hatz, H J, Glucocorticoide: Immunologische Grundlagen, Pharmakologie und Therapierichtlinien, Wissenschaftliche Verlagsgesellschaft mbH, Stuttgart, 1998).

All the aforementioned indications (i) to (xx) are described in detail in Hatz, H J, Glucocorticoide: Immunologische Grundlagen, Pharmakologie und Therapierichtlinien, Wissenschaftliche Verlagsgesellschaft mbH, Stuttgart, 1998.

The suitable dose for the therapeutic effects in the abovementioned pathological states varies and depends for example on the potency of the compound of the general formula Ia, the host, the mode of administration and the nature and severity of the conditions to be treated, and the use as prophylactic or therapeutic agent.

The invention provides for the use of the claimed compounds/stereoisomers for producing medicaments.

The invention further provides
(i) the use of one of the stereoisomers of the invention of formula Ia or mixtures thereof for producing a medicament for treating a DISORDER;
(ii) a method of treating a DISORDER that comprises administering a stereoisomer of the invention of the formula Ia, the amount being sufficient to suppress the disorder;
(iii) a pharmaceutical composition for the treatment of a DISORDER which treatment comprises one of the stereoisomers of the invention or mixtures thereof and at least one pharmaceutical excipient and/or carrier.

Satisfactory results in animals are generally to be expected when the daily doses include a range from 1 μg to 100 000 μg of the compound of the invention per kg of body weight. For larger mammals, for example humans, a recommended daily dose is in the range from 1 μg to 100 000 μg per kg of body weight. A dose of 10 to 30 000 μg per kg of body weight is preferred, and a dose of 10 to 10 000 μg per kg of body weight is more preferred.

For example, this dose is advantageously administered more than once a day. For the treatment of acute shock (e.g. anaphylactic shock) it is possible to give single doses which are well above the abovementioned doses.

The pharmaceutical products based on the novel compounds are formulated in a manner known per se by processing the active ingredient with the carrier substances, fillers, disintegration modifiers, binders, humectants, lubricants, absorbents, diluents, masking flavours, colourants etc. which are in use in pharmaceutical technology, and converting the formulation into the desired administration form. Reference should be made in this connection to Remington's Pharmaceutical Science, 15th ed. Mack Publishing Company, East Pennsylvania (1980).

Particularly suitable for oral administration are plain tablets, coated tablets, capsules, pills, powders, granules, pastilles, suspensions, emulsions or solutions.

Preparations for injection and infusion are possible for parenteral administration.

Appropriately prepared crystal suspensions can be used for intraarticular injection.

Aqueous and oily solutions or suspensions and corresponding depot preparations can be used for intramuscular injection.

The novel compounds can be used for rectal administration in the form of suppositories, capsules, solutions (e.g. in the form of enemas) and ointments both for systemic and for local therapy.

The novel compounds can be used in the form of aerosols and inhalations for their pulmonary administration.

For local use on eyes, the external auditory canal, middle ear, nasal cavity and paranasal sinuses, the novel compounds can be used as drops, ointments, and tinctures in appropriate pharmaceutical preparations.

Formulations possible for topical application are gels, ointments, greasy ointments, creams, pastes, dusting powders, lotions and tinctures. The dosage of the compounds of the general formula Ia in these preparations should be 0.01%-20% in order to achieve an adequate pharmacological effect.

The invention likewise encompasses the compounds of the invention of the general formula Ia as an active therapeutic ingredient. The invention further encompasses the compounds of the invention of the general formula Ia as an active therapeutic ingredient together with pharmaceutically tolerated and acceptable excipients and carriers.

The invention likewise encompasses a pharmaceutical composition which comprises one of the pharmaceutically active compounds of the invention or mixture thereof or a pharmaceutically tolerated salt thereof and a pharmaceutically tolerated salt or pharmaceutically tolerated excipients and carriers.

The invention further provides combination therapies or combined compositions in which a glucocorticoid receptor (GR) agonist of the formula (Ia) or a pharmaceutically acceptable salt thereof, or a pharmaceutical composition comprising a GR agonist of the formula (Ia) or a pharmaceutically acceptable salt thereof, is administered either simultaneously (where appropriate in the same composition) or successively together with one or more medicaments for the treatment of one of the pathological states mentioned above. For the treatment of rheumatoid arthritis, osteoarthritis, COPD (chronic obstructive pulmonary disease), asthma or allergic rhinitis, for example, it is possible to combine a GR agonist of the present invention with one or more medicaments for the treatment of such a condition. Where such a combination is administered by inhalation, the medicament to be combined can be selected from the following list:

a PDE4 inhibitor including an inhibitor of the PDE4D isoform;

a selective β.sub2.adrenoceptor agonist such as, for example, metaproterenol, isoproterenol, isoprenaline, albuterol, salbutamol, formoterol, salmeterol, terbutaline, orciprenaline, bitolterol mesylate, pirbuterol or indacaterol;

a muscarine receptor antagonist (for example an M1, M2 or M3 antagonist, such as, for example, a selective M3 antagonist) such as, for example, ipratropium bromide, tiotropium bromide, oxitropium bromide, pirenzepine or telenzepine;

a modulator of chemokine receptor function (such as, for example, a CCR1 receptor antagonist); or an inhibitor of p38 kinase function.

For another aspect of the present invention, a combination of this kind with a GR agonist of the formula Ia or a pharmaceutically acceptable salt thereof is employed for the treatment of COPD, asthma or allergic rhinitis and can be administered by inhalation or orally in combination with xanthine (such as, for example, aminophylline or theophylline), which can likewise be administered by inhalation or orally.

EXPERIMENTAL SECTION

Example 1

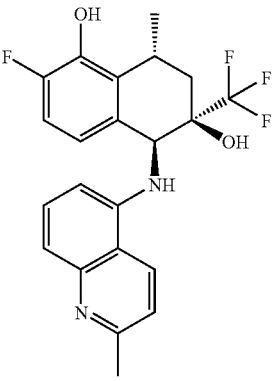

(5α,6α,8β-2-Fluoro-8-methyl-5-[(2-methylquinolin-5-yl)amino]-6-(trifluoromethyl)-5,6,7,8-tetrahydronaphthalene-1,6-diol 4-(3-Fluoro-2-methoxyphenyl)-2-hydroxy-2-(trifluoromethyl)pentanal 41.8 g (639 mmol) of zinc dust and 874 mg (3.1 mmol) of lead(II) chloride are suspended in 557 ml of THF and at room temperature 39 ml (556 mmol) of dibromomethane are added. The mixture is stirred for a further 30 minutes and at 0° C. 68.8 ml (68.8 mmol) of a 1 M titanium(IV) chloride solution in dichloromethane are added dropwise. The cooling bath is removed and after 30 minutes at room temperature 13.6 g (80.8 mmol) of 1-(3-fluoro-2-methoxyphenyl)ethan-1-one (*Chem. Commun.* 2000, 14, 1323-4) in 139 ml of THF are added dropwise. The reaction mixture is stirred for a further 1.5 hours at room temperature. It is diluted with diethyl ether and cautiously poured onto a mixture of 4 M hydrochloric acid and ice. The phases are separated and subjected to extraction with diethyl ether, the extracts are washed with water and dried over sodium sulphate and the solvent is removed. The crude product is purified by column chromatography on silica gel (hexane/isopropyl ether 0-5%) to give 9.5 g of 2-fluoro-6-(1-methyleneethyl)anisole.

1.56 g (5.7 mmol) of 1,1'-bi-2-naphthol are admixed with 5.7 ml (2.85 mmol) of a 0.5 M titanium tetraisopropoxide solution in toluene and the red solution is stirred for 2 hours at room temperature. 9.5 g (57.2 mmol) of 2-fluoro-6-(1-methyleneethyl)anisole and 12.5 ml (95 mmol) of ethyl trifluoropyruvate are added and the mixture is heated at 140° C. for 18 hours. After cooling it is immediately purified by column chromatography on silica gel (hexane/ethyl acetate 0-5%) to give 8.9 g of ethyl 4-(3-fluoro-2-methoxyphenyl)-2-hydroxy-2-(trifluoromethyl)pent-4-enoate. 8.9 g (26.5 mmol) of ethyl 4-(3-fluoro-2-methoxyphenyl)-2-hydroxy-2-(trifluoromethyl)pent-4-enoate are dissolved in 200 ml of methanol and 2 ml of acetic acid, and 890 mg of palladium on carbon (10%) are added. The suspension is shaken for 1.5 hours under a hydrogen atmosphere under atmospheric pressure until the hydrogen uptake is 560 ml. The mixture is filtered through Celite, the filter bed being rinsed thoroughly with ethyl acetate. Removal of the solvent gives 8.6 g of ethyl 4-(3-fluoro-2-methoxyphenyl)-2-hydroxy-2-(trifluoromethyl) pentanoate. 8.6 g (25.4 mmol) of ethyl 4-(3-fluoro-2-methoxyphenyl)-2-hydroxy-2-(trifluoromethyl)-pentanoate in 350 ml of diethyl ether are cooled to −30° C. and over 15 minutes 1.7 g (44.7 mmol) of lithium aluminum hydride in solid form are added in portions. The mixture is stirred for 1.5 hours, in the course of which the temperature climbs to −15° C., followed by dropwise addition in succession of ethyl acetate and water and by a further hour of stirring until a readily filterable precipitate has formed. The suspension is filtered through Celite, the filter bed being thoroughly rinsed with ethyl acetate. The phases of the filtrate are separated and extraction is carried out again with ethyl acetate. The extracts are washed with saturated sodium chloride solution and dried over sodium sulphate and the solvent is removed in vacuo. Separation by column chromatography on silica gel (hexane/diisopropyl ether 0-15%) yields 3.1 g of (2R*,4R*)-4-(3-fluoro-2-methoxyphenyl)-2-hydroxy-2-(trifluoromethyl) pentanal $^1$H-NMR (300 MHz, CDCl$_3$); δ=1.13 (d, 3H), 2.25 (dd, 1H), 2.58 (dd, 1H), 3.33 (qdd, 1H), 3.92 (s, 3H), 3.98 (s, 1H), 6.92-6.99 (m, 3H), 9.12 (s, 1H), 0.72 g of (2R*,4S*)-4-(3-fluoro-2-methoxyphenyl)-2-hydroxy-2-(trifluoromethyl)-pentanal $^1$H-NMR (300 MHz, CDCl$_3$); δ=1.21 (d, 3H), 2.33 (dd, 1H), 2.39 (dd, 1H), 3.30 (qdd, 1H), 3.74 (s, 1H), 3.94 (s, 3H), 6.90-6.99 (m, 3H), 9.71 (s, 1H), and 2.0 g of alcohol.

175 mg (0.60 mmol) of (2R*,4R*-4-(3-fluoro-2-methoxyphenyl)-2-hydroxy-2-(trifluoromethyl)pentanal, 103 mg (0.63 mmol) of 5-amino-2-methylquinoline and 0.3 ml of titanium tetraethoxide are stirred in 20 ml of toluene at 100° C. for 2 h. After the mixture is cooled, it is poured into water, with vigorous stirring to follow. The suspension is filtered through Celite, the filter bed being rinsed thoroughly with ethyl acetate. The phases of the filtrate are separated and extraction is carried out again using ethyl acetate. The extracts are dried over sodium sulphate and the solvent is removed in vacuo to give 230 mg of (2R*,4R*)-4-(3-fluoro-2-methoxyphenyl)-1-[(2-methylquinolin-5-yl)imino]-2-(trifluoromethyl)pentan-2-ol as a crude product. 230 mg of the crude imine in 12 ml of CH$_2$Cl$_2$ are admixed dropwise at −30° C. with 6 ml (6 mmol) of a 1 M boron tribromide solution. The batch is allowed to warm to room temperature and is stirred for 2 hours. It is admixed with saturated NaHCO$_3$ solution, the phases are separated, the aqueous phase is extracted with CH$_2$Cl$_2$ and the combined organic phases are dried (Na$_2$SO$_4$) and concentrated in vacuo. Column chromatography on silica gel (hexane/ethyl acetate 0-75%) yields 145 mg of product.

$^1$H-NMR (300 MHz, CDCl$_3$); δ=1.39 (d, 3H), 1.82 (dd, 1H), 2.39 (dd, 1H), 2.64 (s, 3H), 3.40 (m, 1H), 4.95 (s, 1H), 6.60 (s, 1H), 6.75 (m, 2H), 7.17 (d, 1H), 7.29 (d, 1H), 7.45 (t, 1H), 8.20 (d, 1H).

Example 2

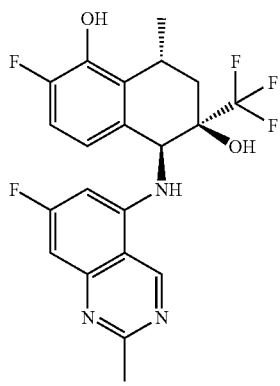

(5α,6α,8β)-2-Fluoro-5-[(7-fluoro-2-methylquinazolin-5-yl)amino]-8-methyl-6-(trifluoromethyl)-5,6,7,8-tetrahydronaphthalene-1,6-diol In the same way as in Example 1, 250 mg (0.85 mmol) of (2R*,4R*)-4-(3-fluoro-2-methoxyphenyl)-2-hydroxy-2-(trifluoromethyl)pentanal, 185 mg (1.05 mmol) of 5-amino-7-fluoro-2-methylquinazoline and 0.4 ml of titanium tetraethoxide are reacted to give (2R*,4R*)-4-(3-fluoro-2-methoxyphenyl)-1-[(7-fluoro-2-methylquinazolin-5-yl)imino]-2-(trifluoromethyl)pentan-2-ol. 430 mg of resultant crude imine are cyclized in the same way as in Example 1 at −30° C. using 8 ml (8 mmol) of 1 M boron tribromide solution to give the desired product. Column chromatography on silica gel (hexane/ethyl acetate 0-75%) yields 67 mg of product.

$^1$H-NMR (300 MHz, CD$_3$OD); δ=1.44 (d, 3H), 1.88 (dd, 1H), 2.43 (dd, 1H), 2.74 (s, 3H), 3.40 (qdd, 1H), 5.25 (s, 1H), 6.69 (d, 1H), 6.70 (dd, 1H), 6.74 (d, 1H), 6.85 (dd, 1H), 9.49 (s, 1H).

Example 2A/2B (5α,6α,8β)-2-Fluoro-5-[(7-fluoro-2-methylquinazolin-5-yl)amino]-8-methyl-6-(trifluoromethyl)-5,6,7,8-tetrahydronaphthalene-1,6-diol is cleaved by means of preparative chiral HPLC (Chiracel OD 5μ) into the enantiomerically pure compounds:

(+)-Enantiomer: analytical HPLC: R$_t$=5.5 min (Chiralcel OD 5μ, 250×4.6 mm, hexane/ethanol 5=>50% (20'), 1 ml/min flow rate)

(−)-Enantiomer: analytical HPLC: R$_t$=8.7 min (Chiralcel OD 5μ, 250×4.6 mm, hexane/ethanol 5=>50% (20'), 1 ml/min flow rate)

Example 3

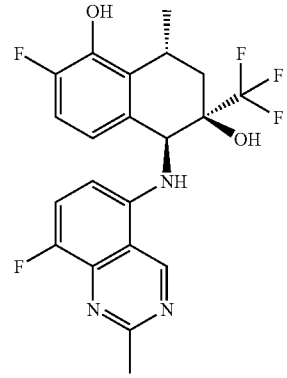

(5α,6α,8β)-2-Fluoro-5-[(8-fluoro-2-methylquinazolin-5-yl)amino]8-methyl-6-(trifluoromethyl)-5,6,7,8-tetrahydronaphthalene-1,6-diol In the same way as in Example 1, 150 mg (0.5 mmol) of (2R*,4R*)-4-(3-fluoro-2-methoxyphenyl)-2-hydroxy-2-(trifluoromethyl)pentanal, 90 mg (0.5 mmol) of 5-amino-8-fluoro-2-methylquinazoline and 0.2 ml of titanium tetraethoxide are reacted to give (2R*,4R*)-4-(3-fluoro-2-methoxyphenyl)-1-[(8-fluoro-2-methylquinazolin-5-yl)imino]-2-(trifluoromethyl)pentan-2-ol. 230 mg of resultant crude imine are cyclized in the same way as in Example 1 at −30° C. using 4 ml (4 mmol) of 1 M boron tribromide solution to give the desired product. Column chromatography on silica gel (hexane/ethyl acetate 50%) yields 42 mg of product.

$^1$H-NMR (300 MHz, CD$_3$OD); δ=1.42 (d, 3H), 1.85 (dd, 1H), 2.42 (dd, 1H), 2.80 (s, 3H), 3.41 (qdd, 1H), 5.16 (s, 1H), 6.73-6.80 (m, 1H), 6.83 (dd, 1H), 7.50 (dd, 1H), 9.58 (s, 1H).

Example 4

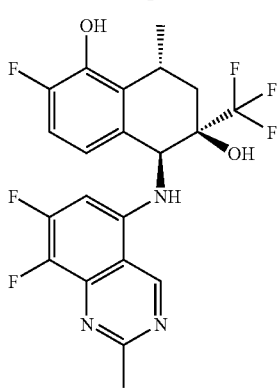

(5α,6α,8β)-5-[(7,8-Difluoro-2-methylquinazolin-5-yl)amino]-2-fluoro-8-methyl-6-(trifluoromethyl)-5,6,7,8-tetrahydronaphthalene-1,6-diol In the same way as in Example 1, 150 mg (0.5 mmol) of (2R*,4R*)-4-(3-fluoro-2-methoxyphenyl)-2-hydroxy-2-(trifluoromethyl)pentanal, 100 mg (0.51 mmol) of 5-amino-7,8-difluoro-2-methylquinazoline and 0.2 ml of titanium tetraethoxide are reacted to give (2R*,4R*)-1-[(7,8-difluoro-2-methylquinazolin-5-yl)imino]-4-(3-fluoro-2-methoxyphenyl)-2-(trifluoromethyl)pentan-2-ol. 240 mg of resultant crude imine are cyclized in the same way as in Example 1 at −30° C. using 4 ml (4 mmol) of 1 M boron tribromide solution to give the desired product. Column chromatography on silica gel (hexane/ethyl acetate 50%) yields 30 mg of product.

$^1$H-NMR (300 MHz, CD$_3$OD); δ=1.44 (d, 3H), 1.87 (dd, 1H), 2.43 (dd, 1H), 2.79 (s, 3H), 3.40 (qdd, 1H), 5.20 (s, 1H), 6.71 (dd, 1H), 6.77 (dd, 1H), 6.85 (dd, 1H), 9.52 (s, 1H).

Example 5

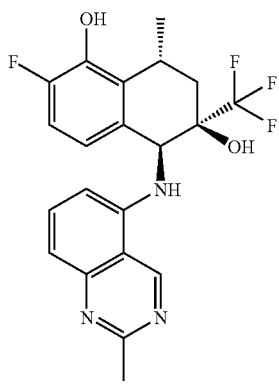

(5α,6α,8β)-2-Fluoro-8-methyl-5-[-2-methylquinazolin-5-yl)amino]-6-(trifluoromethyl)-5,6,7,8-tetrahydronaphthalene-1,6-diol In the same way as in Example 1, 135 mg (0.46 mmol) of (2R*,4R*)-4-(3-fluoro-2-methoxyphenyl)-2-hydroxy-2-(trifluoromethyl)pentanal, 100 mg (0.63 mmol) of 5-amino-2-methylquinazoline and 0.23 ml of titanium tetraethoxide are reacted to give (2R*,4R*)-4-(3-fluoro-2-methoxyphenyl)-1-[(2-methylquinazolin-5-yl)imino]-2-(trifluoromethyl)pentan-2-ol. 260 mg of resultant crude imine are cyclized, in the same way as in Example 1, at −30° C. using 5 ml (5 mmol) of 1 M boron tribromide solution to give the desired product. Column chromatography on silica gel (hexane/ethyl acetate 0-75%) yields 56 mg of product.

$^1$H-NMR (300 MHz, CD$_3$OD); δ=1.44 (d, 3H), 1.87 (dd, 1H), 2.44 (dd, 1H), 2.77 (s, 3H), 3.41 (qdd, 1H), 5.23 (s, 1H), 6.73 (dd, 1H), 6.83 (dd, 1H), 6.87 (d, 1H), 7.14 (d, 1H), 7.74 (t, 1H), 9.56 (s, 1H).

Example 6

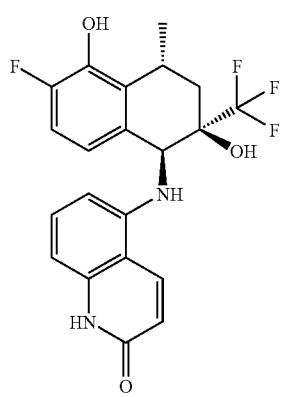

5-{[(5α,6α,8β)-1,6-Dihydroxy-2-fluoro-8-methyl-6-(trifluoromethyl)-5,6,7,8-tetrahydronaphthalen-5-yl]amino}quinolin-2(1H)-one In the same way as in Example 1, 250 mg (0.46 mmol) of (2R*,4R*)-4-(3-fluoro-2-methoxyphenyl)-2-hydroxy-2-(trifluoromethyl)pentanal, 132 mg (0.63 mmol) of 5-aminoquinolone and 0.4 ml of titanium tetraethoxide are reacted to give 5-{[(2R*,4R*)-4-(3-fluoro-2-methoxyphenyl)-2-hydroxy-2-(trifluoromethyl)pentylidene]amino}quinolin-2(1H)-one. 64 mg of imine purified by column chromatography (silica gel, hexane/ethyl acetate 0-75%) are cyclized in the same way as in Example 1 at −30° C. using 1.5 ml (1.5 mmol) of 1 M boron tribromide solution to give the desired product. Column chromatography on silica gel (hexane/ethyl acetate 0-75%) yields 52 mg of product.

$^1$H-NMR (300 MHz, CD$_3$OD); δ=1.42 (d, 3H), 1.84 (dd, 1H), 2.42 (dd, 1H), 3.40 (qdd, 1H), 5.08 (s, 1H), 6.47 (d, 1H), 6.54 (d, 1H), 6.65 (d, 1H), 6.71 (dd, 1H), 6.83 (dd, 1H), 7.32 (t, 1H), 8.17 (d, 1H).

Example 7

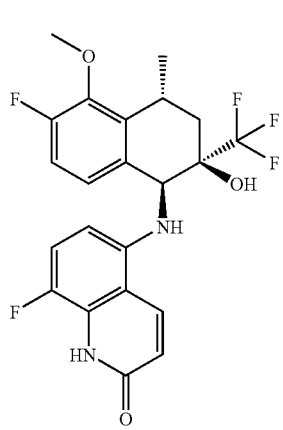

8-Fluoro-5-{[(1α,2α,4β)-6-fluoro-2-hydroxy-5-methoxy-4-methyl-2-(trifluoromethyl)-1,2,3,4-tetrahydronaphthalen-1-yl]amino}quinolin-2(1H)-one

5-Amino-8-fluoroquinolin-2(1H)-one 5,8-Difluoroquinolin-2(1H)-one and 1.18 g (8.2 mmol) of $Cu_2O$ in 620 ml of ethylene glycol are admixed under 8 bar with gaseous $NH_3$. The reaction mixture is heated at 190° C. for 19 h. After the reaction mixture has been cooled and the solvent removed, the crude product is purified by column chromatography (silica gel, hexane; $CH_2Cl_2$/MeOH 0-5%). This gives 1.03 g of 5-amino-8-fluoroquinolin-2(1H)-one as a pale yellow solid.

$^1$H-NMR (300 MHz, DMSO-d6); δ=5.58 (s, 2H), 6.23 (dd, 1H), 6.31 (d, 1H), 7.03 (dd, 1H), 8.05 (dd, 1H), 11.28 (s, 1H).

In the same way as in Example 1, 300 mg (1.01 mmol) of (2R*,4R*)-4-(3-fluoro-2-methoxyphenyl)-2-hydroxy-2-(trifluoromethyl)pentanal, 180 mg (1.01 mmol) of 5-amino-8-fluoroquinolone and 0.48 ml of titanium tetraisopropoxide in 9 ml of xylene are reacted to give 8-fluoro-5-{[(2R*,4R*)-4-(3-fluoro-2-methoxyphenyl)-2-hydroxy-2-(trifluoromethyl)pentylidene]amino}quinolin-2(1H)-one. 80 mg of imine purified by column chromatography (silica gel, hexane; $CH_2Cl_2$/i-PrOH 0-5%) are cyclized, in the same way as in Example 1, at –40° C. using 1.7 ml (1.5 mmol) of 1 M boron tribromide solution to give the desired product and the ether-cleaved Example 8.

$^1$H-NMR (300 MHz, $CD_3OD$); δ=1.38 (d, 3H), 1.85 (dd, 1H), 2.39 (dd, 1H), 3.38 (m, 1H), 3.88 (s, 3H), 5.03 (s, 1H), 6.43 (dd, 1H), 6.51 (d, 1H), 6.80-7.05 (m, 2H), 7.15 (dd, 1H), 8.14 (dd, 1H).

Example 8

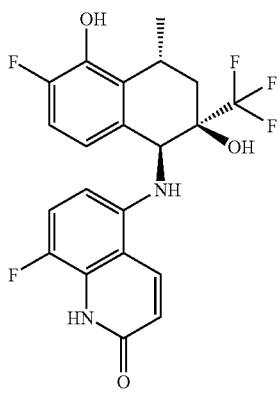

5-{[(1α,2α,4β)-6-Fluoro-2,5-dihydroxy-4-methyl-2-(trifluoromethyl)-1,2,3,4-tetrahydronaphthalen-1-yl]amino}-8-fluoroquinolin-2(1H)-one is obtained after chromatographic purification from Example 7.

$^1$H-NMR (300 MHz, $CD_3OD$); δ=1.40 (d, 3H), 1.83 (dd, 1H), 2.40 (dd, 1H), 3.38 (m, 1H), 5.03 (s, 1H), 6.45 (dd, 1H), 6.48 (d, 1H), 6.49 (dd, 1H), 6.70 (dd, 1H), 6.82 (t, 1H), 7.07 (dd, 1H), 7.17 (dd, 1H), 8.13 (dd, 1H).

Example 8A/8B

5-{[(1α,2α,4β)-6-Fluoro-2,5-dihydroxy-4-methyl-2-(trifluoromethyl)-1,2,3,4-tetrahydronaphthalen-1-yl]amino}-8-fluoroquinolin-2(1H)-one is cleaved by means of preparative chiral HPLC (Chiracel OD 20µ) into the enantiomerically pure compounds:

(–)-Enantiomer: analytical HPLC: $R_t$=7.71 min (Chirapak AD-H 5µ, 150×4.6 mm, hexane/ethanol 5%→50% (20'), 1 ml/min flow rate, 25° C.).

(+)-Enantiomer (ZK 376768): analytical HPLC: $R_t$=9.53 min (Chirapak AD-H 5µ, 150×4.6 mm, hexane/ethanol 5%→50% (20'), 1 ml/min flow rate, 25° C.).

Example 9

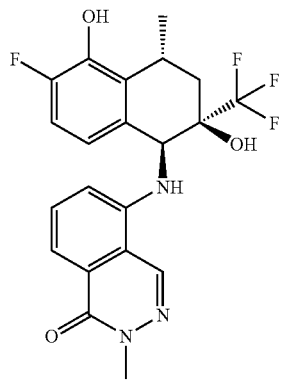

5-{[(1α,2α,4β)-6-Fluoro-2,5-dihydroxy-4-methyl-2-(trifluoromethyl)-1,2,3,4-tetrahydronaphthalen-1-yl]amino}-2-methylphthalazin-1-one In the same way as in Example 1, 295 mg (1.0 mmol) of (2R*,4R*)-4-(3-fluoro-2-methoxyphenyl)-2-hydroxy-2-(trifluoromethyl)pentanal, 217 mg (1.0 mmol) of 5-amino-2-methylphthalazin-1-one and 0.53 ml of titanium tetraethoxide are reacted to give 5-{[(2R*,4R*)-4-(3-fluoro-2-methoxyphenyl)-2-hydroxy-2-(trifluoromethyl)pentyliden]amino}-2-methylphthalazin-1-one. 590 mg of resultant crude imine are cyclized, in the same way as in Example 1, at –30° C. using 10 ml (10 mmol) of 1 M boron tribromide solution to give the desired product. Column chromatography on silica gel (hexane/ethyl acetate 0-60%) yields 204 mg of product.

$^1$H-NMR (300 MHz, $CD_3OD$); δ=1.43 (d, 3H), 1.86 (dd, 1H), 2.43 (dd, 1H), 3.40 (qdd, 1H), 3.79 (s, 3H), 5.18 (s, 1H), 6.71 (dd, 1H), 6.84 (dd, 1H), 7.16 (d, 1H), 7.59 (t, 1H), 7.60 (d, 1H), 8.50 (s, 1H).

Example 10

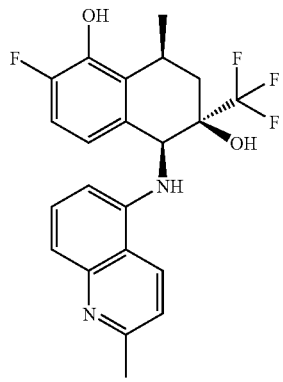

(5α,6α,8β)-2-Fluoro-8-methyl-5-[(2-methylquinolin-5-yl)amino]-6-(trifluoromethyl)-5,6,7,8-tetrahydronaphthalene-1,6-diol In the same way as in Example 1, 175 mg (0.60 mmol) of (2R*,4S*)-4-(3-fluoro-2-methoxyphenyl)-2-hydroxy-2-(trifluoromethyl)pentanal, 103 mg (0.63 mmol) of 5-amino-2-methylquinoline and 0.3 ml of titanium tetraethoxide are reacted to give (2R*,4S*)-4-(3-fluoro-2-methoxyphenyl)-1-[(2-methylquinolin-5-yl)imino]-2-(trifluoromethyl)pentan-2-ol. 230 mg of resultant crude imine are cyclized in the same way as in Example 1 at −30° C. using 5 ml (5 mmol) of 1 M boron tribromide solution to give the desired product. Column chromatography on silica gel (hexane/ethyl acetate 0-75%) yields 135 mg of product.

$^1$H-NMR (300 MHz, CD$_3$OD); δ=1.60 (d, 3H), 2.21 (d, 1H), 2.33 (dd, 1H), 2.70 (s, 3H), 3.43 (qd, 1H), 5.16 (s, 1H), 6.76-6.87 (m, 3H), 7.30 (d, 1H), 7.33 (d, 1H), 7.55 (t, 1H), 8.44 (d, 1H).

Example 11

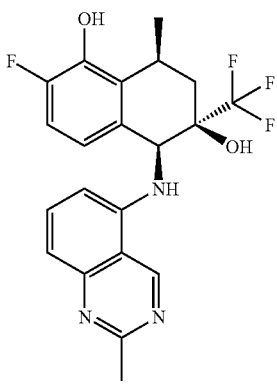

(5α,6α,8β)-2-Fluoro-5-[(2-methylquinazolin-5-yl)amino]-8-methyl-6-(trifluoromethyl)-5,6,7,8-tetrahydronaphthalene-1,6-diol In the same way as in Example 1, 135 mg (0.46 mmol) of (2R*,4S*)-4-(3-fluoro-2-methoxyphenyl)-2-hydroxy-2-(trifluoromethyl)-pentanal, 100 mg (0.63 mmol) of 5-amino-2-methylquinazoline and 0.23 ml of titanium tetraethoxide are reacted to give (2R*,4S*)-4-(3-fluoro-2-methoxyphenyl)-1-[(2-methylquinazolin-5-yl)imino]-2-(trifluoromethyl)pentan-2-ol. 260 mg of resultant crude imine are cyclized in the same way as in Example 1 at −30° C. using 5 ml (5 mmol) of 1 M boron tribromide solution to give the desired product. Column chromatography on silica gel (hexane/ethyl acetate 0-75%) yields 56 mg of product.

$^1$H-NMR (300 MHz, CD$_3$OD); δ=1.58 (d, 3H), 2.20 (dd, 1H), 2.44 (dd, 1H), 2.77 (s, 3H), 3.41 (qdd, 1H), 5.16 (s, 1H), 6.73-6.87 (m, 3H), 7.14 (d, 1H), 7.74 (t, 1H), 9.56 (s, 1H).

Example 12

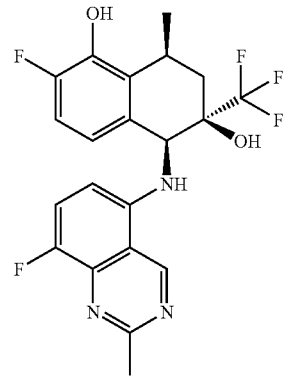

(5α,6α,8β)-2-Fluoro-5-[(8-fluoro-2-methylquinazolin-5-yl)amino]8-methyl-6-(trifluoromethyl)-5,6,7,8-tetrahydronaphthalene-1,6-diol In the same way as in Example 1, 170 mg (0.58 mmol) of (2R*,4S*)-4-(3-fluoro-2-methoxyphenyl)-2-hydroxy-2-(trifluoromethyl)pentanal, 124 mg (0.70 mmol) of 5-amino-8-fluoro-2-methylquinazoline and 0.31 ml of titanium tetraethoxide are reacted to give (2R*,4S*)-4-(3-fluoro-2-methoxyphenyl)-1-[(8-fluoro-2-methylquinazolin-5-yl)imino]-2-(trifluoromethyl)pentan-2-ol. 295 mg of resultant crude imine are cyclized in the same way as in Example 1 at −20° C. using 2.6 ml (2.6 mmol) of 1 M boron tribromide solution to give the desired product. Column chromatography on silica gel (hexane/ethyl acetate 50%) yields 25 mg of product.

$^1$H-NMR (300 MHz, CD$_3$OD); δ=1.55 (d, 3H), 2.16 (dd, 1H), 2.29 (dd, 1H), 2.79 (s, 3H), 3.38 (qdd, 1H), 5.15 (s, 1H), 6.74 (dd, 1H), 6.81-6.87 (m, 2H), 7.52 (dd, 1H), 9.62 (s, 1H).

Example 13

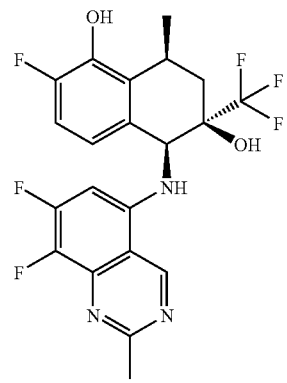

(5α,6α,8β)-5-[(7,8-Difluoro-2-methylquinazolin-5-yl)amino]-2-fluoro-8-methyl-6-(trifluoromethyl)-5,6,7,8-tetrahydronaphthalene-1,6-diol In the same way as in Example 1, 170 mg (0.58 mmol) of (2R*,4S*)-4-(3-fluoro-2-methoxyphenyl)-2-hydroxy-2-(trifluoromethyl)pentanal, 124 mg (0.60 mmol) of 5-amino-7,8-difluoro-2-methylquinazoline and 0.31 ml of titanium tetraethoxide are reacted to give (2R*,4S*)-1-[(7,8-difluoro-2-methylquinazolin-5-yl)imino]-4-(3-fluoro-2-methoxyphenyl)-2-(trifluoromethyl)pentan-2-ol. 85 mg of imine purified by column chromatography (silica gel, hexane/ethyl acetate 0-30%) are cyclized in the same way as in Example 1 at –20° C. using 0.72 ml (0.72 mmol) of 1 M boron tribromide solution to give the desired product. Preparative thin-layer chromatography on silica gel (hexane/ethyl acetate 50%) yields 15 mg of product.

¹H-NMR (300 MHz, CD₃OD); δ=1.55 (d, 3H), 2.15 (dd, 1H), 2.30 (dd, 1H), 2.78 (s, 3H), 3.37 (qdd, 1H), 5.16 (s, 1H), 6.72 (dd, 1H), 6.83 (dd, 2H), 6.86 (dd, 1H), 9.58 (s, 1H).

Example 14

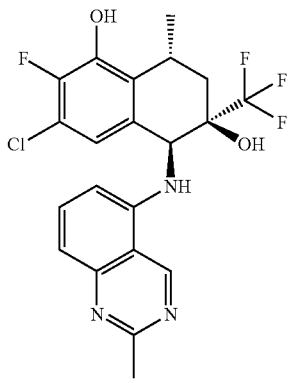

(5α,6α,8β)-3-Chloro-2-fluoro-8-methyl-5-[(2-methylquinazolin-5-yl)amino]-6-(trifluoromethyl)-5,6,7,8-tetrahydronaphthalene-1,6-diol 4-(4-Chloro-3-fluoro-2-methoxyphenyl)-2-hydroxy-2-(trifluoromethyl)pentanal 10 g (68.2 mmol) of 3-chloro-2-fluorophenol in 68 ml of dichloromethane and 7.7 ml (98.5 mmol) of pyridine are admixed dropwise at 0° C. with ml 5.1 ml (71.6 mmol) of acetyl chloride. The mixture is stirred for an hour and 100 ml of 1 M hydrochloric acid are added. The mixture is extracted with dichloromethane and the extracts are washed with water. After drying over sodium sulphate and removal of the solvent in vacuo, 13 g of 3-chloro-2-fluorophenyl acetate are obtained, quantitatively. 13 g (68.2 mmol) of 3-chloro-2-fluorophenyl acetate in 6.9 ml of 1,2-dichlorobenzene are added dropwise with ice cooling to 9.2 g (68.9 mmol) of aluminum trichloride in 6.9 ml of 1,2-dichlorobenzene and the mixture is subsequently stirred at 100° C. for 6 hours. It is cooled, diluted with dichloromethane and poured cautiously onto a mixture of 4 M hydrochloric acid and ice. The phases are separated, extraction is carried out with dichloromethane, and the extracts are washed with saturated sodium chloride solution and dried over sodium sulphate. The crude product is purified by column chromatography on silica gel (hexane/ethyl acetate 10-50%) to give 11.4 g of 1-(4-chloro-3-fluoro-2-hydroxyphenyl)ethan-1-one and 0.74 g of 1-(2-chloro-3-fluoro-4-hydroxyphenyl)ethan-1-one. 11.4 g (60.4 mmol) of 1-(4-chloro-3-fluoro-2-hydroxyphenyl)ethan-1-one are dissolved in 120 ml of acetone, and 15.5 g (112 mmol) of potassium carbonate and 6.9 ml (110 mmol) of methyl iodide are added. The mixture is stirred at 70° C. for 7 hours and the solvent is subsequently removed to a large extent. The residue is poured into water and extracted with methyl tert-butyl ether. The extracts are washed with saturated ammonium chloride solution, dried over sodium sulphate and, following the removal of the solvent in vacuo, give 11.3 g of 1-(4-chloro-3-fluoro-2-methoxyphenyl)ethan-1-one. 27.1 g (415 mmol) of zinc dust and 640 mg (2.3 mmol) of lead(II) chloride are suspended in 400 ml of THF and at room temperature 26 ml (230 mmol) of dibromomethane are added. The mixture is stirred for a further 30 minutes and with ice bath cooling 46.1 ml (46.1 mmol) of a 1 M titanium(IV) chloride solution in dichloromethane are added dropwise. After 30 minutes at 5-10° C. 9.3 g (46.1 mmol) of 1-(4-chloro-3-fluoro-2-methoxyphenyl)ethan-1-one in 92 ml of THF are added dropwise at 5° C. The reaction mixture is stirred at room temperature for a further 15 hours. It is diluted with diethyl ether and poured cautiously onto a mixture of 4 M hydrochloric acid and ice. The phases are separated, extraction is carried out with diethyl ether, the extracts are washed with water and dried over sodium sulphate and the solvent is removed. The crude product is purified by column chromatography on silica gel (hexane/ethyl acetate 10-40%) to give 2.68 g of 3-chloro-2-fluoro-6-(1-methyleneethyl)anisole.

760 mg (2.67 mmol) of 1,1'-bi-2-naphthol are admixed with 2.68 ml (1.34 mmol) of a 0.5 M titanium tetraisopropoxide solution in toluene and the red solution is stirred at room temperature for an hour. 5.07 g (28.1 mmol) of 3-chloro-2-fluoro-6-(1-methyleneethyl)anisole and 3.25 ml (26.7 mmol) of ethyl trifluoropyruvate are added and the mixture is heated at 140° C. for 17 hours. After it has cooled it is immediately purified by column chromatography on silica gel (pentane/diethyl ether 25-40%) to give 1.47 g of ethyl 4-(4-chloro-3-fluoro-2-methoxyphenyl)-2-hydroxy-2-(trifluoromethyl)pent-4-enoate. 1.47 g (3.97 mmol) of ethyl 4-(4-chloro-3-fluoro-2-methoxyphenyl)-2-hydroxy-2-(trifluoromethyl)pent-4-enoate in 40 ml of diethyl ether are cooled to –15° C. and over 10 minutes 300 mg (7.9 mmol) of lithium aluminum hydride in solid form are added in portions. The mixture is stirred for 1 hour, during which it warms to 0° C., and is poured into saturated ammonium chloride solution. Saturated tartaric acid solution is added and the mixture is stirred for 30 minutes. The phases are separated and subjected to repeated extraction with ethyl acetate. The extracts are washed with saturated sodium chloride solution and dried over sodium sulphate and the solvent is removed in vacuo. Separation by column chromatography on silica gel (hexane/ethyl acetate 0-50%) yields 0.38 g of 4-(4-chloro-3-fluoro-2-methoxyphenyl)-2-hydroxy-2-(trifluoromethyl)pent-4-enal and 0.15 g of alcohol. 0.27 g of 4-(4-chloro-3-fluoro-2-methoxyphenyl)-2-hydroxy-2-(trifluoromethyl)-pent-4-enal is dissolved in 14 ml of methanol and 0.3 ml of acetic acid, and 27 mg of palladium on carbon (10%) are added. The suspension is shaken for 2 hours under a hydrogen atmosphere under atmospheric pressure until the hydrogen uptake is 46 ml. The mixture is filtered through Celite, the filter bed being rinsed thoroughly with ethyl acetate. Removal of the solvent gives 027 g of 4-(4-chloro-3-fluoro-2-methoxyphenyl)-2-hydroxy-2-(trifluoromethyl)pentanal as a mixture of the diastereomers.

¹H-NMR (300 MHz, CDCl₃); δ=1.18 (d, 1.5H), 1.29 (d, 1.5H), 2.23 (dd, 0.5H), 2.30 (dd, 0.5H), 2.38 (dd, 0.5H), 2.55 (dd, 0.5H), 3.24 (m, 1H), 3.95 (s, 3H), 6.84 (dd, 1H), 7.05 (dd, 1H), 9.18 (s, 0.5H), 9.73 (s, 0.5H).

100 mg (0.3 mmol) of 4-(4-chloro-3-fluoro-2-methoxyphenyl)-2-hydroxy-2-(trifluoromethyl)pentanal, 48 mg (0.3 mmol) of 5-amino-2-methylquinazoline and 0.1 ml of titanium tetraethoxide are stirred in 9 ml of toluene at 100° C. for 2 h. After cooling, the mixture is poured into water and stirred vigorously. The suspension is filtered through Celite, the filter bed being rinsed thoroughly with ethyl acetate. The phases of the filtrate are separated and extraction is carried out again with ethyl acetate. The extracts are dried over sodium sulphate and the solvent is removed in vacuo to give 130 mg of 4-(3-fluoro-2-methoxyphenyl)-1-[(2-methylquinolin-5-yl)imino]-2-(trifluoromethyl)pentan-2-ol as a crude product. 130 mg of the crude imine in 6 ml of CH₂Cl₂ are admixed dropwise at −30° C. with 3 ml (3 mmol) of a 1 M of boron tribromide solution. The batch is allowed to warm to −5° C. over 3 hours. It is admixed with saturated NaHCO₃ solution, the phases are separated, the aqueous phase is extracted with ethyl acetate and the combined organic phases are dried (Na₂SO₄) and concentrated in vacuo. Column chromatography on silica gel (hexane/ethyl acetate 0-75%) yields 30 mg as a mixture of the title compound and 5α,6α,8β)-3-chloro-2-fluoro-8-methyl-5-[(2-methylquinazolin-5-yl)amino]-6-(trifluoromethyl)-5,6,7,8-tetrahydronaphthalene-1,6-diol (Ex. 23). Preparative thin-layer chromatography on amine phase (Merck) with ethyl acetate/methanol/triethylamine 25:3:1 yields 5 mg of product.

¹H-NMR (300 MHz, CDCl₃); δ=1.43 (d, 3H), 1.79 (dd, 1H), 2.42 (dd, 1H), 2.82 (s, 3H), 3.44 (qdd, 1H), 5.02 (d, 1H), 6.62 (d, 1H), 6.71 (d, 1H), 6.87 (d, 1H), 7.14 (d, 1H), 7.72 (t, 1H), 9.55 (s, 1H).

Example 15

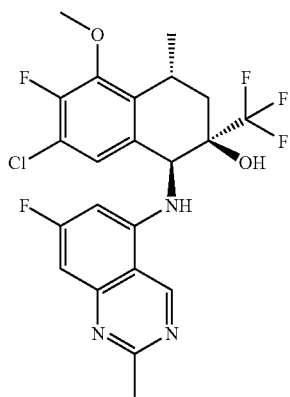

(5α,6α,8β)-3-Chloro-2-fluoro-5-[(7-fluoro-2-methylquinazolin-5-yl)amino]-1-methoxy-8-methyl-6-(trifluoromethyl)-5,6,7,8-tetrahydronaphthalen-6-ol In the same way as in Example 14, 100 mg (0.3 mmol) of 4-(4-chloro-3-fluoro-2-methoxyphenyl)-2-hydroxy-2-(trifluoromethyl)pentanal, 54 mg (0.3 mmol) of 5-amino-7-fluoro-2-methylquinazoline and 0.1 ml of titanium tetraethoxide are reacted to give 4-(4-chloro-3-fluoro-2-methoxyphenyl)-1-[(7-fluoro-2-methylquinazolin-5-yl)imino]-2-(trifluoromethyl)pentan-2-ol. 150 mg of crude imine are cyclized in the same way as in Example 14 at −30° C. with 2.5 ml (2.5 mmol) of 1 M boron tribromide solution to give the desired product. Column chromatography on silica gel (hexane/ethyl acetate 50%) and subsequent preparative thin-layer chromatography on amine phase (Merck) with ethyl acetate/methanol/triethylamine 25:3:1 yield 3.4 mg of product and 3 mg of the dihydroxy compound Ex. 16.

¹H-NMR (300 MHz, CDCl₃); δ=1.41 (d, 3H), 1.94 (dd, 1H), 2.45 (dd, 1H), 2.85 (s, 3H), 3.45 (ddq, 1H), 4.01 (s, 3H), 4.91 (d, 1H), 6.45 (d, 1H), 6.54 (br, 1H), 6.95 (d, 1H), 7.01 (d, 1H), 9.62 (s, 1H).

Example 16

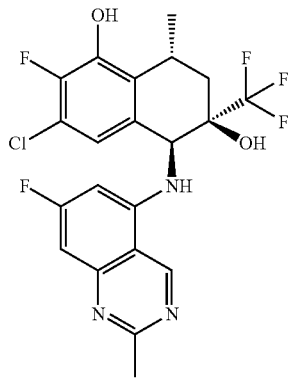

(5α,6α,8β)-3-Chloro-2-fluoro-5-[(7-fluoro-2-methylquinazolin-5-yl)amino]-8-methyl-6-(trifluoromethyl)-5,6,7,8-tetrahydronaphthalene-1.6 diol obtained as the product from Example 15 after chromatographic separation:

¹H-NMR (300 MHz, CDCl₃); δ=1.44 (d, 3H), 1.81 (dd, 1H), 2.49 (dd, 1H), 2.87 (s, 3H), 3.42 (qdd, 1H), 4.94 (d, 1H), 6.48 (d, 1H), 6.82 (d, 1H), 6.95 (d, 1H), 9.90 (s, 1H).

Example 17

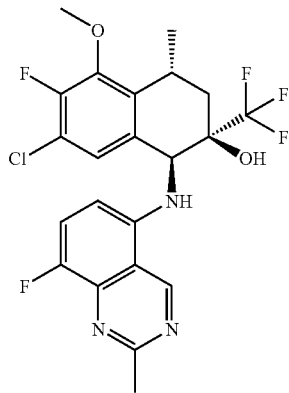

(5α,6α,8β)-3-Chloro-2-fluoro-5-[(8-fluoro-2-meth-
ylquinazolin-5-yl)amino]1-methoxy-8-methyl-6-
(trifluoromethyl)-5,6,7,8-tetrahydronaphthalen-6-ol In the same way as in Example 14, 100 mg (0.3 mmol) of 4-(4-chloro-3-fluoro-2-methoxyphenyl)-2-hydroxy-2-(trifluoromethyl)pentanal, 53 mg (0.3 mmol) of 5-amino-8-fluoro-2-methylquinazoline and 0.1 ml of titanium tetraethoxide are reacted to give 4-(4-chloro-3-fluoro-2-methoxyphenyl)-1-[(8-fluoro-2-methylquinazolin-5-yl) imino]-2-(trifluoromethyl)pentan-2-ol. 140 mg of crude imine are cyclized in the same way as in Example 14 at −30° C. with 2.5 ml (2.5 mmol) of 1 M boron tribromide solution to give the desired product. Column chromatography on silica gel (hexane/ethyl acetate 50%) and subsequent preparative thin-layer chromatography on amine phase (Merck) with ethyl acetate/methanol/triethylamine 25:3:1 yield 3 mg of product and 16 mg of the dihydroxy compound Ex. 18.

$^1$H-NMR (300 MHz, CDCl$_3$); δ=1.40 (d, 3H), 1.96 (dd, 1H), 2.42 (dd, 1H), 2.93 (s, 3H), 3.45 (ddq, 1H), 4.01 (s, 3H), 5.92 (br, 1H), 6.59 (dd, 1H), 7.10 (d, 1H), 7.50 (dd, 1H), 9.60 (s, 1H).

Example 18

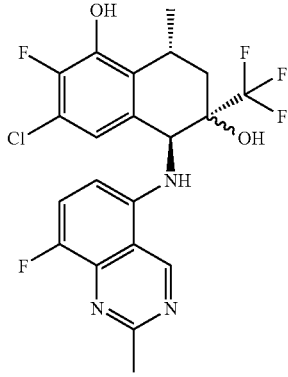

(5α,6α,8β)-3-Chloro-2-fluoro-5-[(8-fluoro-2-meth-
ylquinazolin-5-yl)amino]8-methyl-6-(trifluorom-
ethyl)-5,6,7,8-tetrahydronaphthalene-1,6-diol obtained as the product from Ex. 17 after chromatographic separation:

$^1$H-NMR (300 MHz, CD$_3$OD); δ=1.35 (d, 3H), 1.78 (dd, 1H), 2.36 (dd, 1H), 2.75 (s, 3H), 3.28 (qdd, 1H), 5.10 (s, 1H), 6.70 (dd, 1H), 6.71 (d, 1H), 7.46 (dd, 1H), 9.52 (s, 1H).

In the same way it is possible to prepare the following:

Example 19

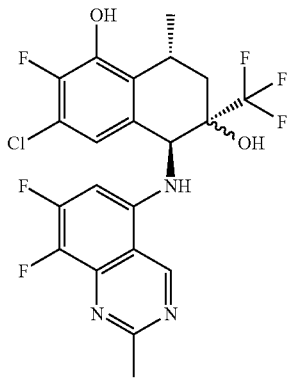

(5α,6α,8β)-3-Chloro-5-[(7,8-difluoro-2-meth-
ylquinazolin-5-yl)amino]-2-fluoro-8-methyl-6-(trif-
luoromethyl)-5,6,7,8-tetrahydronaphthalene-1,6-diol
and Example 20

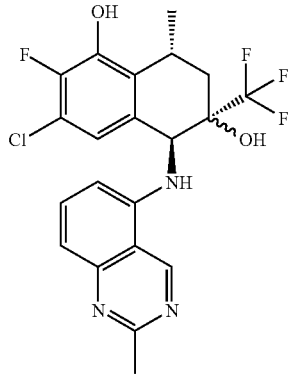

(5α,6α,8β)-3-Chloro-2-fluoro-8-methyl-5-[-2-meth-
ylquinolin-5-yl)amino]-6-(trifluoromethyl)-5,6,7,8-
tetrahydronaphthalene-1,6-diol Example 21

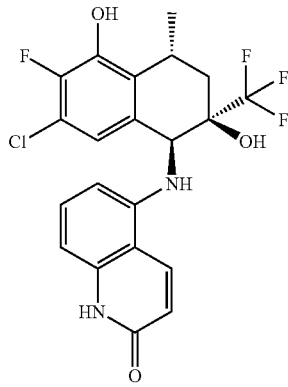

5-{[(1α,2α,4β)-7-Chloro-2,5-dihydroxy-6-fluoro-4-
methyl-2-(trifluoromethyl)-1,2,3,4-tetrahydronaph-
thalen-1-yl]-amino}quinolin-2(1H)-one In the same way as in Example 14, 100 mg (0.3 mmol) of 4-(4-chloro-3-fluoro-2-methoxyphenyl)-2-hydroxy-2-(trifluoromethyl)pentanal, 48 mg (0.3 mmol) of 5-aminoquinolone and 0.1 ml of titanium tetraethoxide are reacted to give 5-{[4-(4-chloro-3-fluoro-2-methoxyphenyl)-2-hydroxy-2-(trifluoromethyl)pentylidene]-amino}quinolin-2(1H)-one. 130 mg of crude imine are cyclized in the same way as in Example 14 at −30° C. with 2.5 ml (2.5 mmol) of 1 M boron tribromide solution to give the desired product. Column chromatography on silica gel (hexane/ethyl acetate 50%) and subsequent preparative thin-layer chromatography on amine phase (Merck) with ethyl acetate/methanol/triethylamine 25:3:1 and preparative HPLC yield 11 mg of product.

$^1$H-NMR (300 MHz, CD$_3$OD); δ=1.38 (d, 3H), 1.84 (dd, 1H), 2.42 (dd, 1H), 3.36 (qdd, 1H), 5.09 (s, 1H), 6.48 (d, 1H), 6.54 (d, 1H), 6.68 (d, 1H), 6.70 (d, 1H), 7.34 (t, 1H), 8.19 (d, 1H).

Example 21A/21B

5-{[(1α,2α,4β)-7-Chloro-2,5-dihydroxy-6-fluoro-4-methyl-2-(trifluoromethyl)-1,2,3,4-tetrahydronaphthalen-1-yl]-amino}quinolin-2(1H)-one is cleaved by means of preparative chiral HPLC (Chiracel OD 20μ) into the enantiomerically pure compounds:

Enantiomer 1: analytical HPLC: $R_t$=8.5 min (Chiralpak AD 5μ, 250×4.6 mm, hexane/ethanol 5%=>95% in 20 min, 1 ml/min flow rate)

Enantiomer 2: analytical HPLC: $R_t$=9.6 min (Chiralpak AD 5μ, 250×4.6 mm, hexane/ethanol 5%=>95% in 20 min, 1 ml/min flow rate)

In the same way it is possible to prepare the following:

Example 22

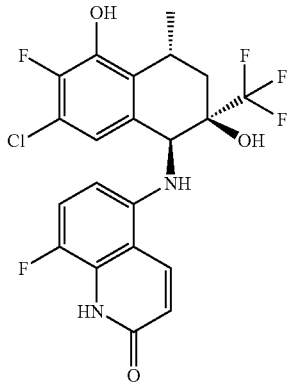

5-{[(1α,2α,4β)-7-Chloro-2,5-dihydroxy-6-fluoro-4-methyl-2-(trifluoromethyl)-1,2,3,4-tetrahydronaphthalen-1-yl]-amino}-8-fluoroquinolin-2(1H)-one

Example 23

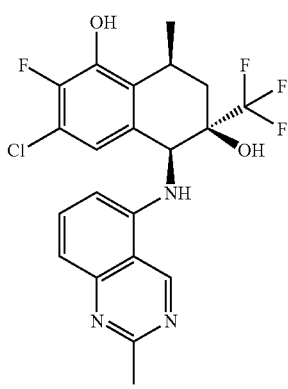

(5α,6α,8α)-3-Chloro-2-fluoro-8-methyl-5-[(2-methylquinazolin-5-yl)amino]-6-(trifluoromethyl)-5,6,7,8-tetrahydronaphthalene-1,6-diol Preparative thin-layer chromatography of the diastereomer mixture from Ex. 14 on amine phase (Merck) with ethyl acetate/methanol/triethylamine 25:3:1 yields 3 mg of product.

$^1$H-NMR (300 MHz, CD$_3$OD); δ=1.54 (d, 3H), 2.17 (dd, 1H), 2.30 (dd, 1H), 2.77 (s, 3H), 3.35 (m, 1H), 5.21 (s, 1H), 6.81 (d, 1H), 6.92 (d, 1H), 7.16 (d, 1H), 7.76 (t, 1H), 9.60 (s, 1H).

Example 24

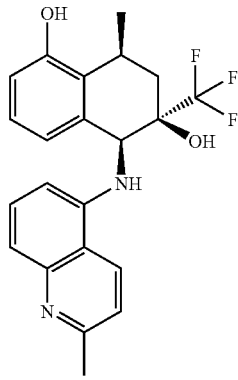

(5α,6α,8α)-8-Methyl-5-[-2-methylquinolin-5-yl)amino]-6-(trifluoromethyl)-5,6,7,8-tetrahydronaphthalene-1,6-diol 2-Hydroxy-4-(2-methoxyphenyl)-2-(trifluoromethyl)pentanal Ethyl 4-(3-chloro-2-methoxyphenyl)-2-hydroxy-2-(trifluoromethyl)pent-4-enoate can be prepared in the same way as in Example 14 from acetyl chloride and 2-chlorophenol. The reaction sequence with hydrogen over palladium on carbon and lithium aluminum hydride in the same way as in Example 14 yields in this case a mixture of 2-hydroxy-4-(2-methoxyphenyl)-2-(trifluoromethyl)pentanal and 4-(3-chloro-2-methoxyphenyl)-2-hydroxy-2-(trifluoromethyl) pentanal, which was not separated.

In the same way as in Example 1, 160 mg of the mixture of 4-(3-chloro-2-methoxyphenyl)-2-hydroxy-2-(trifluoromethyl)pentanal and 2-hydroxy-4-(2-methoxyphenyl)-2-(trifluoromethyl)pentanal, 86 mg (0.55 mmol) of 5-amino-2-methylquinoline and 0.3 ml of titanium tetraethoxide are reacted to give the corresponding imines. 230 mg of crude imine are cyclized in the same way as in Example 1 at −30° C. with 4 ml (4 mmol) of 1 M boron tribromide solution to give the desired products. Column chromatography on silica gel (hexane/ethyl acetate 50%) and subsequent preparative thin-layer chromatography on silica gel with hexane/2-propanol 17% allow separation of the individual products.

$^1$H-NMR (300 MHz, CDCl$_3$); δ=1.61 (d, 3H), 2.24 (dd, 1H), 2.33 (dd, 1H), 2.74 (s, 3H), 3.43 (qdd, 1H), 4.68 (br, 1H), 5.17 (br, 1H), 6.70 (d, 1H), 6.76 (d, 1H), 6.95 (m, 2H), 7.24 (d, 1H), 7.55 (m, 2H), 8.07 (d, 1H).

Example 25

ZK 350663

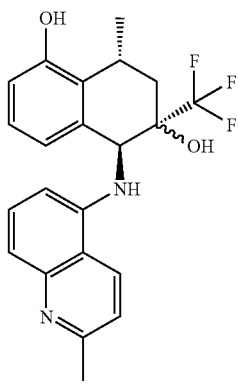

(5α,6α,8β)-8-Methyl-5-[-2-methylquinolin-5-yl)amino]-6-(trifluoromethyl)-5,6,7,8-tetrahydronaphthalene-1,6-diol obtained as product from Ex. 24 after chromatographic separation:

¹H-NMR (300 MHz, CDCl₃); δ=1.51 (d, 3H), 1.98 (dd, 1H), 2.48 (dd, 1H), 2.77 (s, 3H), 3.47 (m, 1H), 4.69 (d, 1H), 5.17 (d, 1H), 6.71 (d, 1H), 6.74 (d, 1H), 6.94 (m, 2H), 7.25 (d, 1H), 7.56 (m, 2H), 8.12 (d, 1H).

Example 26

ZK 350661

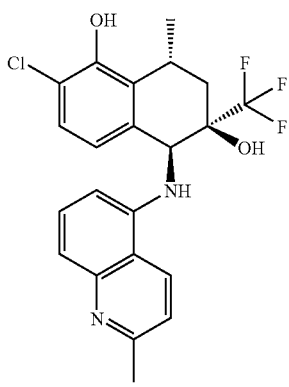

(5α,6α,8β)-8-Methyl-5-[-2-methylquinolin-5-yl)amino]-6-(trifluoromethyl)-5,6,7,8-tetrahydronaphthalene-1,6-diol obtained as product from Ex. 24 after chromatographic separation:

¹H-NMR (300 MHz, CDCl₃); δ 1.47 (d, 3H), 2.00 (dd, 1H), 2.47 (dd, 1H), 2.73 (s, 3H), 3.45 (m, 1H), 5.03 (d, 1H), 5.82 (br, 1H), 6.70 (d, 1H), 6.90 (d, 1H), 7.13 (d, 1H), 7.22 (d, 1H), 7.45 (d, 1H), 7.55 (t, 1H), 8.06 (d, 1H).

Example 27

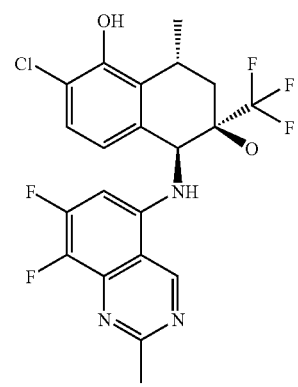

(5α,6α,8β)-8-Methyl-5-[-2-methylquinolin-5-yl)amino]-6-(trifluoromethyl)-5,6,7,8-tetrahydronaphthalene-1,6-diol In the same way as in Example 1, 100 mg of the mixture of 4-(3-chloro-2-methoxyphenyl)-2-hydroxy-2-(trifluoromethyl)pentanal and 2-hydroxy-4-(2-methoxyphenyl)-2-(trifluoromethyl)pentanal, 80 mg (0.42 mmol) of 5-amino-7,8-difluoro-2-methylquinazoline and 0.3 ml of titanium tetraethoxide are reacted to give the corresponding imines. 180 mg of crude imine are cyclized in the same way as in Example 1 at −30° C. with 4 ml (3 mmol) of 1 M boron tribromide solution to give the desired products. Column chromatography on silica gel (hexane/ethyl acetate 50%) and subsequent preparative thin-layer chromatography on silica gel with hexane/2-propanol 17% yield 7 mg of product.

¹H-NMR (300 MHz, CDCl₃); δ 1.45 (d, 3H), 1.94 (dd, 1H), 2.45 (dd, 1H), 2.91 (s, 3H), 3.46 (m, 1H), 4.85 (d, 1H), 5.70 (d, 1H), 6.48 (dd, 1H), 6.83 (d, 1H), 7.09 (d, 1H), 9.23 (s, 1H).

In the same way it is possible to prepare the following:

Example 28

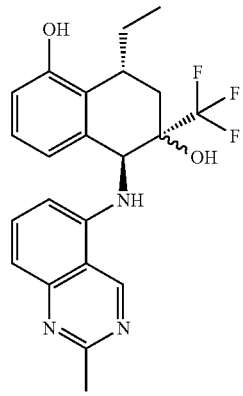

(5α,6α,8β)-8-Ethyl-5-[2-methylquinazolin-5-yl)
amino]-6-(trifluoromethyl)-5,6,7,8-tetrahydronaph-
thalene-1,6-diol Example 29

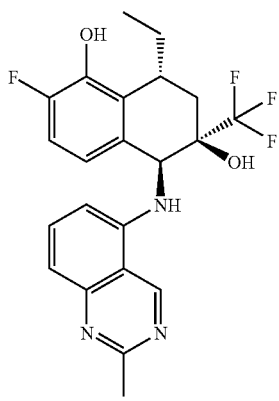

(5α,6α,8β)-8-Ethyl-2-fluoro-5-[(2-methylquinazo-
lin-5-yl)amino]-6-(trifluoromethyl)-5,6,7,8-tetrahy-
dronaphthalene-1,6-diol 4-(3-Fluoro-2-methoxyphenyl)-2-hydroxy-2-(trifluo-
romethyl)hexanal 29.04 g of (3-fluoro-2-methoxyphenyl)boronic acid, 25 g of 2-bromo-1-butene and tetrakis(triphenylphosphine)palladium are dissolved in 174 ml of toluene and 17.4 ml of 1-propanol. The mixture is heated at 120° C. in a closed vessel over 5 hours and, after cooling, is introduced into water. The aqueous phase is extracted three times with diethyl ether and the combined organic phases are washed with saturated sodium chloride solution and dried over Na$_2$SO$_4$. Following careful removal of the solvent, the residue is purified by column chromatography on silica gel (hexane/diethyl ether). This gives 16.6 g (49.7%) of 6-(but-1-en-2-yl)-2-fluoroanisole. 4.0 g (22.2 mmol) of 6-(but-1-en-2-yl)-2-fluoroanisole and 2.8 g of molecular sieve in 5.85 ml (44.4 mmol) of ethyl trifluoropyruvate are admixed dropwise over 30 minutes with 1005 mg (1.1 mmol) of [Cu(S,S)-bisphenyloxazoline)(H$_2$O)$_2$]((SbF$_6$)$_2$, in 56 ml of dichloromethane. The reaction mixture is stirred at 0° C. for 16 hours and the reaction mixture is purified by means of column chromatography on silica gel (hexane/ethyl acetate). This gives 7.2 g (92.6%) of the enantiomerically enriched ethyl (R)-4-(3-fluoro-2-methoxyphenyl)-2-hydroxy-2-(trifluoromethyl)-hex-4-enoate as an E/Z mixture (E/Z ratio 2:1, E: about 9% ee, Z: about 58% ee). 9.3 g (26.6 mmol) of ethyl (E/Z)-4-(3-fluoro-2-methoxyphenyl)-2-hydroxy-2-(trifluoromethyl)-hex-4-enoate are dissolved in 300 ml of diethyl ether under argon and the solution is cooled to −15° C. 2.02 g of lithium aluminum hydride are added in portions as a solid over 30 minutes and the mixture is stirred for a further hour, in the course of which the temperature climbs to −5° C. After a further 30 minutes at −5° C., 4 ml of ethyl acetate are added dropwise and the mixture is stirred for a further 10 minutes. It is poured onto a mixture of ice and saturated ammonium chloride solution and stirred vigorously. The phases are separated and extraction is carried out repeatedly with ethyl acetate and diethyl ether. The combined organic extracts are washed with saturated sodium chloride solution and dried over Na$_2$SO$_4$. The solvent is removed by distillation and the residue is purified by column chromatography on silica gel (hexane/ethyl acetate). This gives 5.9 g (72.6%) of (E/Z)-4-(3-fluoro-2-methoxyphenyl)-2-hydroxy-2-trifluoromethylhex-4-enal and 2.0 g of (E/Z)-4-(3-fluoro-2-methoxyphenyl)-2-trifluoromethyl-hex-4-ene-1,2-diol.

1.51 g (4.9 mmol) of (E/Z)-4-(3-fluoro-2-methoxyphenyl)-2-hydroxy-2-(trifluoromethyl)hex-4-enal are dissolved in 40 ml of methanol and 1.2 ml of acetic acid, and 80 mg of palladium on carbon (10%) are added. The suspension is shaken under a hydrogen atmosphere at atmospheric pressure until reaction is complete. The mixture is filtered through Celite, the filter bed being rinsed thoroughly with ethyl acetate. Removal of the solvent and separation by column chromatography on silica gel (hexane/diisopropyl ether 10-25%) give 530 mg of enantiomerically enriched (2R*,4R*)-4-(3-fluoro-2-methoxyphenyl)-2-hydroxy-2-(trifluoromethyl)hexanal $^1$H-NMR (300 MHz, CDCl$_3$); δ=0.77 (d, 3H), 1.65 (m, 2H), 2.32 (dd, 1H), 2.55 (dd, 1H), 3.14 (m, 1H), 3.91 (s, 3H), 3.97 (s, 1H), 6.86 (dd, 1H), 6.95-6.99 (m, 2H), 8.99 (s, 1H) and 620 mg of enantiomerically enriched (2R*,4S*)-4-(3-fluoro-2-methoxyphenyl)-2-hydroxy-2-(trifluoromethyl) hexanal $^1$H-NMR (300 MHz, CDCl$_3$); δ=0.73 (d, 3H), 1.60 (m, 2H), 2.35 (dd, 1H), 2.43 (dd, 1H), 2.96 (m, 1H), 3.63 (s, 1H), 3.92 (s, 3H), 6.84 (dd, 1H), 6.93-6.99 (m, 2H), 9.67 (s, 1H).

113 mg (0.37 mmol) of (2R*,4R*-4-(3-fluoro-2-methoxyphenyl)-2-hydroxy-2-(trifluoromethyl)hexanal, 103 mg (0.37 mmol) of 5-amino-2-methylquinazoline and 0.2 ml of titanium tetraethoxide are stirred in 15 ml of toluene for 1.5 h at 100° C. After cooling, the mixture is poured into water and stirred vigorously. The suspension is filtered through Celite, the filter bed being rinsed thoroughly with ethyl acetate. The phases of the filtrate are separated and extraction is carried out again with ethyl acetate. The extracts are dried over sodium sulphate and the solvent is removed in vacuo to give 178 mg of (2R*,4R*)-4-(3-fluoro-2-methoxyphenyl)-1-[(2-methylquinazolin-5-yl)imino]-2-(trifluoromethyl)hexan-2-ol as a crude product. 178 mg of crude imine in 20 ml of CH$_2$Cl$_2$ are admixed dropwise at −20° C. with 1.6 ml (1.6 mmol) of a 1 M boron tribromide solution. The mixture is allowed to warm to room temperature and is stirred for 1.5 hours. It is poured into saturated NaHCO$_3$ solution, the phases are separated, the aqueous phase is extracted with CH$_2$Cl$_2$ and the combined organic phases are dried (Na$_2$SO$_4$) and concentrated in vacuo. Column chromatography on silica gel (hexane/ethyl acetate 50%) yields 20 mg of product.

$^1$H-NMR (300 MHz, CD$_3$OD); δ=0.99 (t, 3H), 1.81 (ddq, 1H), 2.04 (m, 2H), 2.43 (dd, 1H), 2.82 (s, 3H), 3.43 (dddd, 1H), 5.14 (s, 1H), 6.73 (dd, 1H), 6.82 (m, 2H), 7.20 (d, 1H), 7.77 (t, 1H), 9.63 (s, 1H).

Example 29A/29B (5α,6α,8β)-8-Ethyl-2-fluoro-5-[(2-methylquinazolin-5-yl)amino]-6-(trifluoromethyl)-5,6,7,8-tetrahydronaphthalene-1,6-diol is cleaved by means of preparative chiral HPLC (Chiralpak AD 5μ) into the enantiomerically pure compounds:

(−)-Enantiomer: analytical HPLC: R$_t$=2.58 min (Chiralpak AD 5μ, 250×4.6 mm, hexane/ethanol 25%, 1 ml/min flow rate)

(+)-Enantiomer: analytical HPLC: $R_t$=5.53 min (Chiralpak AD 5μ, 250×4.6 mm, hexane/ethanol 25%, 1 ml/min flow rate)

Example 30A

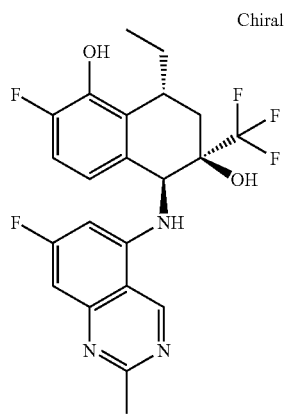

(5S,6R,8R)-8-Ethyl-2-fluoro-5-[(7-fluoro-2-methylquinazolin-5-yl)amino]-6-(trifluoromethyl)-5,6,7,8-tetrahydronaphthalene-1,6-diol (R,R)-4-(3-Fluoro-2-methoxyphenyl)-2-hydroxy-2-(trifluoromethyl)hexanal 4.0 g (22.2 mmol) of 6-(but-1-en-2-yl)-2-fluoroanisole and 2.8 g of molecular sieve in 5.85 ml (44.4 mmol) of ethyl trifluoropyruvate are admixed dropwise at 0° C. over 30 minutes with 1005 mg (1.1 mmol) of [Cu(R,R)-2,2-bis(4,5-dihydro-4-tert-butyloxazolin-2-yl)propane($H_2O$)$_2$]((SbF$_6$)$_2$, complex (*J. Org. Chem.* 1998, 63, 4541-4544) in 56 ml of dichloromethane. The reaction mixture is stirred at 0° C. for 16 hours and the reaction mixture is purified by means of column chromatography on silica gel (hexane/ethyl acetate). This gives 7.2 g (%) of ethyl (R)-4-(3-fluoro-2-methoxyphenyl)-2-hydroxy-2-(trifluoromethyl)-hex-4-enoate with an enantiomeric excess of greater than 90% in the form of an E/Z mixture. In the same way as in Example 29, the resulting unsaturated ester is converted by means of lithium aluminum hydride and hydrogen under palladium catalysis into the virtually enantiomerically pure aldehydes.

120 mg (0.4 mmol) of (R,R)-4-(3-fluoro-2-methoxyphenyl)-2-hydroxy-2-(trifluoromethyl)hexanal and 75 mg (0.42 mmol) of 5-amino-7-fluoro-2-methylquinazoline are dissolved in 10 ml of toluene and the solution is admixed with 0.1 ml (0.42 mmol) of titanium ethoxide. The reaction mixture is heated at 100° for 2 hours, cooled, poured into water and stirred vigorously.

The suspension is filtered through Celite, the filter bed being rinsed thoroughly with ethyl acetate. The phases of the filtrate are separated and extraction is carried out again with ethyl acetate. The extracts are dried over sodium sulphate and the solvent is removed in vacuo to give 205 mg of (2R,4R)-4-(3-fluoro-2-methoxyphenyl)-1-[(7-fluoro-2-methylquinolin-5-yl)imino]-2-(trifluoromethyl)-hexan-2-ol as a crude product. The crude imine is dissolved in 18 ml of $CH_2Cl_2$ and the solution is cooled to −40° C. 3.4 ml (3.4 mmol) of a 1 M BBr$_3$ solution in dichloromethane are added slowly dropwise over 5 minutes and the mixture is allowed to warm to 0° C. over 1 hour, and after 30 minutes at 0° C. is poured onto a mixture of saturated NaHCO$_3$ and ice. It is extracted repeatedly with ethyl acetate and the extracts are washed with saturated NaCl solution and dried over Na$_2$SO$_4$. Purification by column chromatography on silica gel (150 ml) with ethyl acetate affords 37 mg of product (analytical HPLC: $R_t$=9.2 min (Chiralcel OD 5μ, 250×4.6 mm, hexane/ethanol 10%, 1 ml/min flow rate) as the (−)-enantiomer.

$^1$H-NMR (300 MHz, CD$_3$OD); δ=0.96 (t, 3H), 1.76 (ddq, 1H), 2.02 (dd, 1H), 2.06 (ddq, 1H), 2.41 (dd, 1H), 2.77 (s, 3H), 3.39 (m, 1H), 5.13 (s, 1H), 6.58 (d, 1H), 6.73 (dd, 1H), 6.77 (d, 1H), 6.88 (dd, 1H), 9.51 (s, 1H).

Example 30B

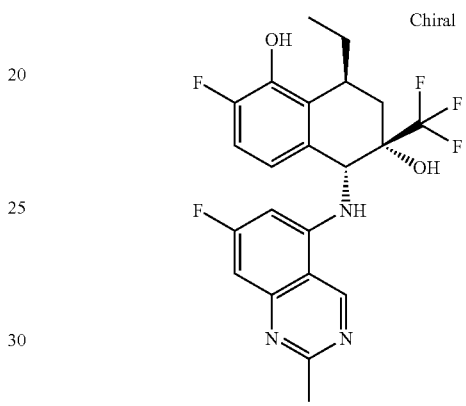

(5R,6S,8S)-8-Ethyl-2-fluoro-5-[(7-fluoro-2-methylquinazolin-5-yl)amino]-6-(trifluoromethyl)-5,6,7,8-tetrahydronaphthalene-1,6-diol Ethyl 3-[1-(3-fluoro-2-methoxyphenyl)cyclopropyl]-2-oxopropionate 26 g (180 mmol) of 2,6-difluoroanisole and 14.6 ml (198 mmol) of cyclopropyl cyanide in 500 ml of toluene are admixed dropwise at 0° C. over 40 min with 396 ml of a 0.5 molar (198 mmol) solution of bis(trimethylsilyl)potassium amide in toluene. The mixture is stirred at room temperature for 18 hours and admixed with water and 1M sulphuric acid, with ice cooling.

The organic phase is separated off and the aqueous phase is extracted repeatedly with ethyl acetate. The extracts are washed with brine, dried with sodium sulphate and concentrated in vacuo. Purification by chromatography on silica gel (hexane/ethyl acetate 10%-20%) gives 12.7 g of 1-(3-fluoro-2-methoxyphenyl)cyclopropylnitrile. 12.7 g (66.1 mmol) of the nitrile are admixed slowly in toluene at −78° C. with 82.7 ml (99.2 mmol) of diisobutylaluminium hydride solution (20% in toluene) and after 3 h at −78° C. 11.1 ml of isopropanol are added dropwise. The mixture is allowed to warm to −5° C. and 150 ml of 10% strength aqueous tartaric acid solution are added. Dilution with ether is followed by vigorous stirring; the organic phase is separated off and the aqueous phase is extracted repeatedly with ethyl acetate. The extracts are washed with brine, dried with sodium sulphate and concentrated in vacuo. This gives 11.8 g of aldehyde as a yellow oil. A solution of 16.3 g (60.7 mmol) of ethyl 2-diethylphosphono-2-ethoxyacetate in 60 ml of tetrahydrofuran is admixed under ice cooling over the course of 20 minutes with 33.4 ml (66.8 mmol) of a 2 M solution of lithium diisopropylamide in tetrahydrofuran-heptane-toluene and the mixture is stirred at 0° C. for 30 minutes. Over the course of 30 minutes a solution of 11.8 g (60.7 mmol) of I in 61 ml of tetrahydrofuran is added dropwise at 0° C. After 20 hours at RT, ice-water is added and extraction is carried out repeatedly with ether and ethyl acetate. The extracts are washed with saturated ammonium chloride solution, dried over sodium sulphate and concentrated. The crude product is hydrolysed with 170 ml of 2 M sodium hydroxide solution in 170 ml of ethanol at room temperature for 15 hours. This gives 13.9 g of acid, which are stirred with 87 ml of 2 N sulphuric acid at 90° C. for 16 hours. After the mixture has cooled, it is rendered basic with potassium carbonate, washed with ether and acidified with hydrochloric acid. Extraction with ethyl acetate, washing with saturated sodium chloride solution and removal of the solvent afford 10.2 g of the crude keto acid. 10.2 g (40.6 mmol) of 3-[1-(3-fluoro-2-methoxyphenyl)-cyclopropyl]-2-oxopropionic acid and 4.5 ml (85.3 mmol) of sulphuric acid (96% strength) are heated under reflux in 200 ml of ethanol for one hour. The batch is concentrated in vacuo and the residue is introduced into ice-water and rendered basic using saturated sodium hydrogen carbonate solution. Extraction is carried out repeatedly with ethyl acetate and the extracts are washed with saturated sodium chloride solution, dried (sodium sulphate) and concentrated in vacuo. Chromatographic purification on silica gel (hexane/ethyl acetate 20%) affords 9.6 g of ethyl 3-[1-(3-fluoro-2-methoxyphenyl)cyclopropyl]-2-oxopropionate.

$^1$H-NMR (CDCl$_3$): δ=0.90 (m, 4H), 1.29 (t, 3H), 3.09 (s, 2H), 3.99 (d, 3H), 4.20 (q, 2H), 6.87 (ddd, 1H), 6.95 (ddd, 1H), 7.07 (d, 1H).

3-[1-(3-Fluoro-2-methoxyphenyl)-cyclopropyl]-2-hydroxy-2-(trifluoromethyl)propanal 9.6 g (34.3 mmol) of ethyl 3-[1-(3-fluoro-2-methoxyphenyl)cyclopropyl]-2-oxopropionate and 34.5 ml (233 mmol) of (trifluoromethyl)trimethylsilane in 343 ml of DMF are admixed with 46.9 g of caesium carbonate at 0° C. The reaction mixture is stirred at 0° C. for 2 h and then poured into water. It is extracted repeatedly with ethyl acetate and the extracts are washed with saturated sodium chloride solution, dried with sodium sulphate and concentrated in vacuo. Purification by chromatography on silica gel (hexane/ethyl acetate 10%-40%) affords 10.4 g of ethyl 3-[1-(3-fluoro-2-methoxyphenyl)-cyclopropyl]-2-hydroxy-2-(trifluoromethyl)propanoate as a yellow oil. This oil, in 297 ml of diethyl ether, is admixed at 0° C. with 2.25 g (59.4 mmol) of lithium aluminum hydride and the mixture is stirred at RT for a further hour. 20 ml of saturated ammonium chloride solution are added cautiously to the batch at 0° C., followed by 15 minutes of vigorous stirring. The mixture is extracted repeatedly with diethyl ether and the extracts are washed with saturated sodium chloride solution, dried with sodium sulphate and concentrated in vacuo. Purification by chromatography on silica gel (hexane/ethyl acetate 10%-50%) affords 5.6 g of 3-[1-(3-fluoro-2-methoxyphenyl)cyclopropyl]-2-(trifluoromethyl)propane-1,2-diol. 5.6 g (18.1 mmol) of diol in 100 ml of dichloromethane and 61 ml of DMSO are admixed with 12.4 ml (89 mmol) of triethylamine and over 10 minutes with 11 g (70 mmol) of pyridine SO$_3$ complex in portions. The mixture is stirred for 3 hours and saturated ammonium chloride solution is added. The mixture is stirred for a further 15 minutes and the phases are separated and subjected to extraction with dichloromethane. The extracts are washed with water and dried over sodium sulphate. The solvent is removed in vacuo, and purification by chromatography on silica gel (hexane/ethyl acetate, 0-50%) affords 5.9 g of product.

$^1$H-NMR (CDCl$_3$): δ=0.68-0.76 (m, 2H), 0.90-1.02 (m, 2H), 2.03 (d, 1H), 2.91 (d, 1H), 3.85 (s, 1H), 4.03 (s, 3H), 6.80 (d, 1H), 6.87 (ddd, 1H), 6.98 (dd, 1H), 9.26 (s, 1H).

In the same way as in Example 29, from 800 mg (2.61 mmol) of 3-[1-(3-fluoro-2-methoxyphenyl)cyclopropyl]-2-hydroxy-2-(trifluoromethyl)propanal and 500 mg (2.82 mmol) of 5-amino-7-fluoro-2-methylquinazoline, 1-[(7-fluoro-2-methyl-quinazol-5-yl)imino]-3-[1-(3-fluoro-2-methoxyphenyl)cyclopropyl]-2-(trifluoromethyl)propan-2-ol is prepared quantitatively. Treatment with 24 ml (24 mmol) of BBr$_3$ solution and subsequent refluxing for 14 hours afford 55 mg of (1R,2S,Z)-4-ethylene-6-fluoro-1-[(7-fluoro-2-methylquinazolin-5-yl)amino]-2-(trifluoromethyl)-1,2,3,4-tetrahydronaphthalene-2,5-diol after chromatography on silica gel (hexane/ethyl acetate 25 to 50%) and preparative chiral HPLC on Chiracel OD-H 5μ (analytical HPLC: R$_t$=10.4 min (Chiralcel OD 10μ, 250×4.6 mm, hexane/ethanol 7%, 1 ml/min flow rate) as the (+)-enantiomer.

$^1$H-NMR (300 MHz, CD$_3$OD); δ=1.77 (d, 3H), 2.57 (d, 1H), 2,80 (s, 3H), 3.14 (d, 1H), 4.64 (s, 1H), 5.86 (q, 1H), 6.26 (dd, 1H), 6.77-6.97 (m, 2H), 7.02 (dd, 1H), 9.57 (s, 1H).

20 mg of (1R,2S,Z)-4-ethylidene-6-fluoro-1-[(7-fluoro-2-methylquinazolin-5-yl)amino]-2-(trifluoromethyl)-1,2,3,4-tetrahydronaphthalene-2,5-diol are dissolved in 1 ml of ethyl acetate and 0.07 ml of Et$_3$N under N$_2$ at RT and the solution is admixed with 2 mg of Pd—C (10%).

The mixture is shaken for 2 h under a hydrogen atmosphere (H$_2$ uptake: 17 ml) and the reaction mixture is filtered over Celite, the filter bed being rinsed thoroughly with EA. The resulting liquid is concentrated to approximately 4 ml and is stirred for 3 hours with 40 mg of activated MnO$_2$. The reaction mixture is filtered over Celite, rinsed with ethyl acetate and concentrated. Preparative thin-layer chromatography on silica gel (hexane/2-propanol 15%) yields 2 mg of the desired product as a yellow oil.

$^1$H-NMR (300 MHz, CD$_3$OD); δ=0.96 (t, 3H), 1.76 (ddq, 1H), 2.02 (dd, 1H), 2.06 (ddq, 1H), 2.41 (dd, 1H), 2.77 (s, 3H), 3.39 (m, 1H), 5.13 (s, 1H), 6.58 (d, 1H), 6.73 (dd, 1H), 6.77 (d, 1H), 6.88 (dd, 1H), 9.51 (s, 1H) and 1 mg of the other diastereomer.

Example 31

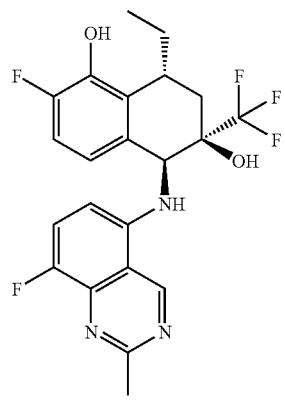

(5α,6α, 8β)-8-Ethyl-2-fluoro-5-[(8-fluoro-2-methylquinazolin-5-yl)amino]-6-(trifluoromethyl)-5,6,7,8-tetrahydronaphthalene-1,6-diol In the same way as in Example 29,123 mg (0.40 mmol) of (2R*,4R*)-4-(3-fluoro-2-methoxyphenyl)-2-hydroxy-2-(trifluoromethyl)hexanal, 72 mg (0.60 mmol) of 5-amino-8-fluoro-2-methylquinazoline and 0.22 ml of titanium tetraethoxide are reacted to give (2R*,4R*)-4-(3-fluoro-2-methoxyphenyl)-1-[(8-fluoro-2-methylquinazolin-5-yl)imino]-2-(trifluoromethyl)hexan-2-ol. 170 mg of crude imine are cyclized in the same way as in Example 29 at −30° C. with 2.8 ml (2.8 mmol) of 1 M boron tribromide solution to give the desired product. Purification by chromatography on silica gel (dichloromethane/ethyl acetate 0-40%) gives 21 mg of product.

$^1$H-NMR (300 MHz, CD$_3$OD); δ=0.97 (t, 3H), 1.77 (m, 1H), 2.03 (dd, 1H), 2.04 (m, 1H), 2.42 (dd, 1H), 2.84 (s, 3H), 3.42 (dddd, 1H), 5.10 (s, 1H), 6.71 (dd, 1H), 6.78 (dd, 1H), 6.90 (dd, 1H), 7.56 (dd, 1H), 9.63 (s, 1H).

Example 31A/31B (5α,6α,8β)-8-Ethyl-2-fluoro-5-[(8-fluoro-2-methylquinazolin-5-yl)amino]-6-(trifluoromethyl)-5,6,7,8-tetrahydronaphthalene-1,6-diol is cleaved by means of preparative chiral HPLC (Chiralcel OD-H 5μ) into the enantiomerically pure compounds:

(+)-Enantiomer: analytical HPLC: R$_t$=4.13 min (Chiralcel OD-H 5μ, 250×4.6 mm, hexane/ethanol 10%, 1 ml/min flow rate)

(−)-Enantiomer: analytical HPLC: R$_t$=10.28 min (Chiralcel OD-H 5μ, 250×4.6 mm, hexane/ethanol 10%, 1 ml/min flow rate)

Example 32

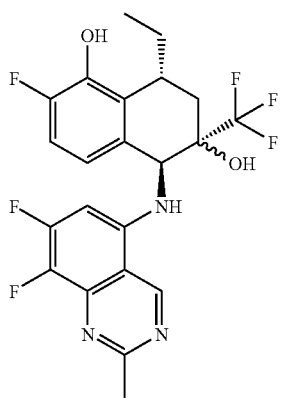

(5α,6α,8β)-5-[(7,8-Difluoro-2-methylquinazolin-5-yl)amino]-8-ethyl-2-fluoro-6-(trifluoromethyl)-5,6,7,8-tetrahydronaphthalene-1,6-diol In the same way as in Example 29, 138 mg (0.45 mmol) of (2R*,4S*)-4-(3-fluoro-2-methoxyphenyl)-2-hydroxy-2-(trifluoromethyl)hexanal, 89 mg (0.45 mmol) of 5-amino-7,8-difluoro-2-methylquinazoline and 0.24 ml of titanium tetraethoxide are reacted to give (2R*,4S*)-1-[(7,8-difluoro-2-methylquinazolin-5-yl)imino]-4-(3-fluoro-2-methoxyphenyl)-2-(trifluoromethyl)pentan-2-ol. 210 mg of crude imine are cyclized in the same way as in Example 29 at −30° C. with 3.5 ml (3.5 mmol) of 1 M boron tribromide solution to give the desired product. Purification by chromatography on silica gel (dichloromethane/ethyl acetate 0-40%) gives 21 mg of product.

$^1$H-NMR (300 MHz, CD$_3$OD); δ=0.97 (t, 3H), 1.78 (m, 1H), 2.04 (dd, 1H), 2.06 (m, 1H), 2.42 (dd, 1H), 2.84 (s, 3H), 3.39 (m, 1H), 5.13 (s, 1H), 6.72 (dd, 1H), 6.76 (dd, 1H), 6.90 (dd, 1H), 9.56 (s, 1H).

Example 33

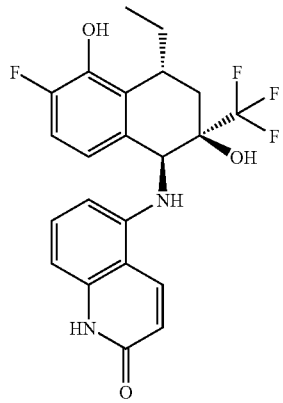

5-{[(1α,2α,4β)-4-Ethyl-6-fluoro-2,5-dihydroxy-2-(trifluoromethyl)-1,2,3,4-tetrahydronaphthalen-1-yl]amino}quinolin-2(1H)-one In the same way as in Example 29, 300 mg (0.97 mmol) of (2R*,4S*)-4-(3-fluoro-2-methoxyphenyl)-2-hydroxy-2-(trifluoromethyl)hextanal, 132 mg (0.97 mmol) of 5-aminoquinol-2(H1)-one and 0.44 ml of titanium tetraethoxide are reacted to give 5-{[(2R*,4S*-4-(3-fluoro-2-methoxyphenyl)-2-hydroxy-2-(trifluoromethyl)hexylidene]amino}quinolin-2(1H)-one. 250 mg of crude imine are cyclized in the same way as in Example 29 at −20° C. with 2 ml (2 mmol) of 1 M boron tribromide solution to give the desired product. Preparative thin-layer chromatography on silica gel (hexane/2-propanol 17%) yields 11.5 mg of desired product.

$^1$H-NMR (300 MHz, CD$_3$OD); δ=0.97 (t, 3H), 1.78 (m, 1H), 1.96-2.15 (m, 2H), 2.40 (dd, 1H), 3.42 (dddd, 1H), 5.03 (s, 1H), 6.49 (d, 1H), 6.53 (d, 1H), 6.70 (d, 1H), 6.75 (dd, 1H), 6.88 (dd, 1H), 7.36 (t, 1H), 8.23 (d, 1H).

Example 34

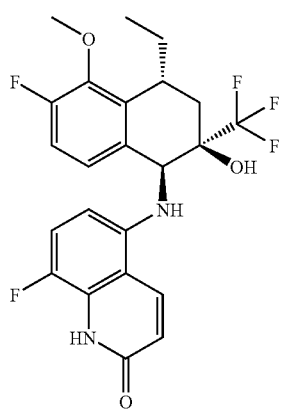

5-{[(1α,2α,4β)-4-Ethyl-6-fluoro-2-hydroxy-5-methoxy-2-(trifluoromethyl)-1,2,3,4-tetrahydronaphthalen-1-yl]amino}-8-fluoroquinolin-2(1H)-one In the same way as in Example 29, 4-(3-fluoro-2-methoxyphenyl)-2-hydroxy-2-(trifluoromethyl)hexanal and 5-amino-8-fluoroquinolin-2(1H)-one are condensed to give 8-fluoro-5-{[4-(3-fluoro-2-methoxyphenyl)-2-hydroxy-2-(trifluoromethyl)hexylidene]amino}quinolin-2(1H)-one. Reaction with 1 M boron tribromide solution after column chromatography on silica gel (hexane/ethyl acetate 33-100%) and preparative HPLC yield not only the desired product but also the methyl ether cleaved compounds Example 35 and 44.

$^1$H-NMR (400 MHz, CD$_3$OD); δ=0.92 (t, 3H), 1.70 (m, 1H), 1.86 (m, 1H), 2.02 (dd, 1H), 2.32 (dd, 1H), 3.65 (m, 1H), 3.90 (s, 3H), 4.94 (s, 1H), 6.33 (dd, 1H), 6.54 (d, 1H), 6.90-7.00 (m, 2H), 7.17 (dd, 1H), 8.17 (d, 1H).

Example 35

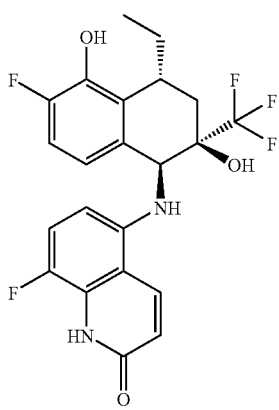

5-{[(1α,2α,4β)-4-Ethyl-6-fluoro-2,5-dihydroxy-2-(trifluoromethyl)-1,2,3,4-tetrahydronaphthalen-1-yl]amino}-8-fluoroquinolin-2(1H)-one obtained as the product from Ex. 34 after chromatographic separation:

$^1$H-NMR (400 MHz, CD$_3$OD); δ=0.93 (t, 3H), 1.73 (m, 1H), 1.90-2.02 (m, 2H), 2.85 (dd, 1H), 3.60 (m, 1H), 4.92 (s, 1H), 6.34 (dd, 1H), 6.53 (d, 1H), 6.70 (dd, 1H), 6.84 (dd, 1H), 7.17 (dd, 1H), 8.17 (dd, 1H).

Example 35A/35B

5-{[(1α,2α,4β)-4-Ethyl-6-fluoro-2,5-dihydroxy-2-(trifluoromethyl)-1,2,3,4-tetrahydronaphthalen-1-yl]amino}-8-fluoroquinolin-2(1H)-one is cleaved by means of preparative chiral HPLC (Chiralcel OD-H 5μ) into the enantiomerically pure compounds:

(−)-Enantiomer: analytical HPLC: R$_t$=7.29 min (Chiralpak AD-H 5μ, 250×4.6 mm, hexane/ethanol 5=>50% (20'), 1 ml/min flow rate)

(+)-Enantiomer: analytical HPLC: R$_t$=8.90 min (Chiralpak AD-H 5μ, 250×4.6 mm, hexane/ethanol 5=>50% (20°), 1 ml/min flow rate)

Example 36

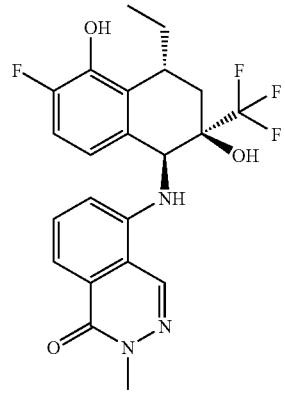

5-{[(1α,2α,4β)-4-Ethyl-6-fluoro-2,5-dihydroxy-2-(trifluoromethyl)-1,2,3,4-tetrahydronaphthalen-1-yl]amino}-2-methylphthalazin-1-one In the same way as in Example 29, 265 mg (0.86 mmol) of 4-(3-fluoro-2-methoxyphenyl)-2-hydroxy-2-(trifluoromethyl)hexanal, 150 mg (0.86 mmol) of 5-amino-2-methylphthalazin-1-one and 0.42 ml of titanium tetraethoxide are reacted to give 5-{[4-(3-fluoro-2-methoxyphenyl)-2-hydroxy-2-(trifluoromethyl)hexylidene]amino}-2-methylphthalazin-1-one. 410 mg of crude imine are cyclized in the same way as in Example 29 at −20° C. with 3.5 ml (3.5 mmol) of 1 M boron tribromide solution to give the desired product. Column chromatography on silica gel (hexane/ethyl acetate 50%) and subsequent preparative thin-layer chromatography on silica gel with dichloromethane/methanol 9:1 yield 10 mg of product and 8.6 mg of the 8α compound (Example 45).

$^1$H-NMR (300 MHz, CD$_3$OD); δ=0.85 (t, 3H), 1.66 (m, 1H), 1.90 (dd, 1H), 1.91 (m, 1H), 2.29 (dd, 1H), 3.29 (dddd, 1H), 3.72 (s, 3H), 4.89 (s, 1H), 6.63 (dd, 1H), 6.77 (dd, 1H), 6.98 (t, 1H), 7.51 (m, 2H), 8.43 (s, 1H).

In the same way it is possible to prepare the following:

Example 37

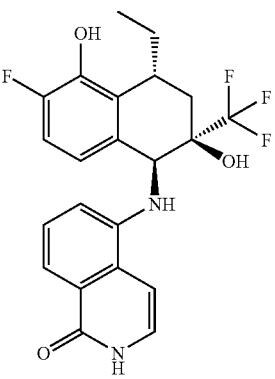

5-{[(1α,2α,4β)-4-Ethyl-6-fluoro-2,5-dihydroxy-2-(trifluoromethyl)-1,2,3,4-tetrahydronaphthalen-1-yl]amino}-isoquinolin-(2H)-one and Example 38

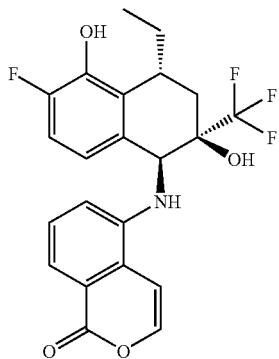

5-{[(1α,2α,4β)-4-Ethyl-6-fluoro-2,5-dihydroxy-2-(trifluoromethyl)-1,2,3,4-tetrahydronaphthalen-1-yl]amino}isochromen-1-one Example 39

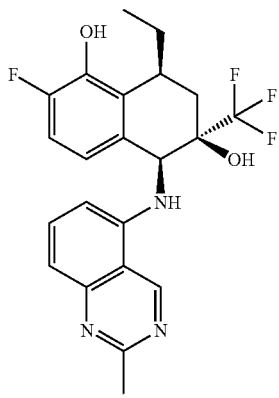

(5α,6α,8α)-8-Ethyl-2-fluoro-5-[(2-methylquinazolin-5-yl)amino]-6-(trifluoromethyl)-5,6,7,8-tetrahydronaphthalene-1,6-diol is prepared in the same way as in Example 29 from the corresponding (2R*,4S*)-4-(3-fluoro-2-methoxyphenyl)-2-hydroxy-2-(trifluoromethyl)hexanal.

$^1$H-NMR (300 MHz, CD$_3$OD); δ=1.14 (t, 3H), 2.00 (m, 1H), 2.13 (m, 1H), 2.15 (dd, 1H), 2.45 (dd, 1H), 2.80 (s, 3H), 3.11 (m, 1H), 5.28 (s, 1H), 6.78 (dd, 1H), 6.89 (dd, 1H), 6.98 (d, 1H), 7.18 (d, 1H), 7.79 (t, 1H), 9.63 (s, 1H).

Example 40

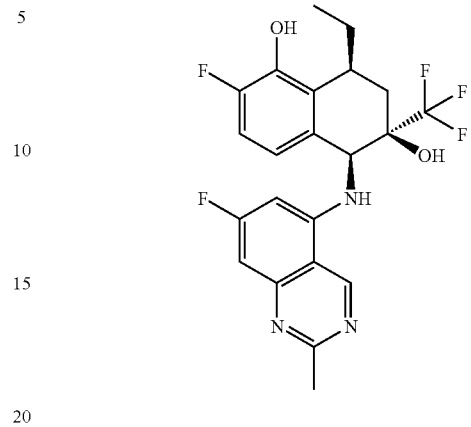

(5α,6α,8α)-8-Ethyl-2-fluoro-5-[(7-fluoro-2-methylquinazolin-5-yl)amino]-6-(trifluoromethyl)-5,6,7,8-tetrahydronaphthalene-1,6-diol is prepared in the same way as in Example 30 from the corresponding (2R*,4S*)-4-(3-fluoro-2-methoxyphenyl)-2-hydroxy-2-(trifluoromethyl)hexanal.

$^1$H-NMR (300 MHz, CD$_3$SOCD$_3$); δ=1.05 (t, 3H), 1.92-1.99 (m, 2H), 2.15 (dd, 1H), 2.25 (dd, 1H), 2.69 (s, 3H), 2.95 (m, 1H), 5.43 (d, 1H), 6.16 (s, 1H), 6.67 (dd, 1H), 6.76 (d, 1H), 6.80 (d, 1H), 6.99 (dd, 1H), 7.23 (d, 1H), 9.61 (s, 1H), 9.69 (s, 1H).

Example 41

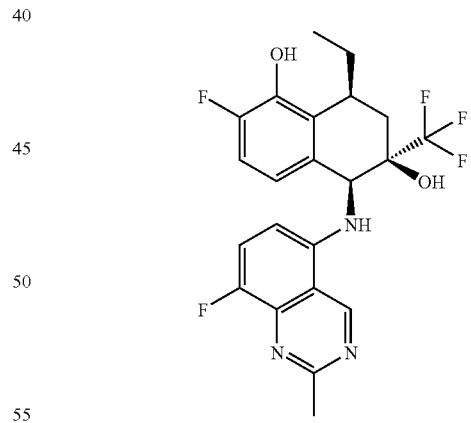

(5α,6α,8α)-8-Ethyl-2-fluoro-5-[(8-fluoro-2-methylquinazolin-5-yl)amino]-6-(trifluoromethyl)-5,6,7,8-tetrahydronaphthalene-1,6-diol In the same way as in Example 31, 123 mg (0.40 mmol) of (2R*,4R*)-4-(3-fluoro-2-methoxyphenyl)-2-hydroxy-2-(trifluoromethyl)hexanal, 72 mg (0.60 mmol) of 5-amino-8-fluoro-2-methylquinazoline and 0.22 ml of titanium tetraethoxide are reacted to give (2R*,4S*)-4-(3-fluoro-2- methoxyphenyl)-1-[(8-fluoro-2-methylquinazolin-5-yl)imino]-2-(trifluoromethyl)hexan-2-ol. 170 mg of crude imine are cyclized in the same way as in Example 31 at −30° C. with 2.8 ml (2.8 mmol) of 1 M boron tribromide solution to give the desired product. Purification by chromatography on silica gel (dichloromethane/ethyl acetate 0-40%) gives 68 mg of product.

$^1$H-NMR (300 MHz, CD$_3$OD); δ=1.14 (t, 3H), 1.98 (m, 1H), 2.09-2.15 (m, 2H), 2.43 (dd, 1H), 2.83 (s, 3H), 3.10 (m, 1H), 5.21 (s, 1H), 6.77 (dd, 1H), 6.88 (dd, 1H), 6.89 (dd, 1H), 7.57 (dd, 1H), 9.67 (s, 1H).

Example 42

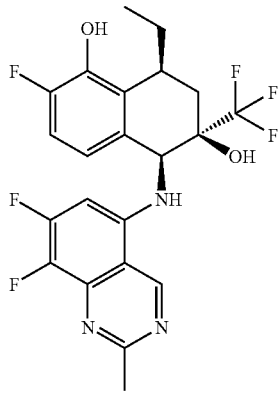

(5α, 6α, 8β)-5-[(7,8-Difluoro-2-methylquinazolin-5-yl)amino]-8-ethyl-2-fluoro-6-(trifluoromethyl)-5,6,7,8-tetrahydronaphthalene-1,6-diol In the same way as in Example 32, 138 mg (0.45 mmol) of (2R*,4S*)-4-(3-fluoro-2-methoxyphenyl)-2-hydroxy-2-(trifluoromethyl)hexanal, 89 mg (0.45 mmol) of 5-amino-7,8-difluoro-2-methylquinazoline and 0.24 ml of titanium tetraethoxide are reacted to give (2R*,4S*)-1-[(7,8-difluoro-2-methylquinazolin-5-yl)imino]-4-(3-fluoro-2-methoxyphenyl)-2-(trifluoromethyl)pentan-2-ol. 210 mg of crude imine are cyclized in the same way as in Example 32 at −30° C. with 3.5 ml (3.5 mmol) of 1 M boron tribromide solution to give the desired product. Purification by chromatography on silica gel (dichloromethane/ethyl acetate 0-40%) gives 41 mg of product.

$^1$H-NMR (300 MHz, CD$_3$OD); δ=1.14 (t, 3H), 1.96 (m, 1H), 2.09-2.20 (m, 2H), 2.42 (dd, 1H), 2.83 (s, 3H), 3.10 (m, 1H), 5.22 (s, 1H), 6.76 (dd, 1H), 6.86 (dd, 1H), 6.92 (dd, 1H), 9.62 (s, 1H).

Example 43

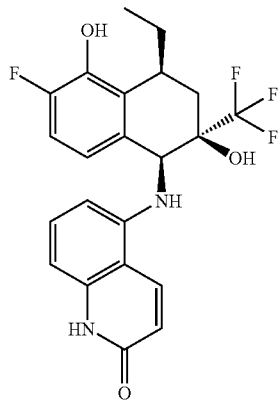

5-{[(1α,2α,4α)-4-Ethyl-6-fluoro-2,5-dihydroxy-2-(trifluoromethyl)-1,2,3,4-tetrahydronaphthalen-1-yl]amino}quinolin-2(1H)-one In the same way as in Example 29, 300 mg (0.97 mmol) of (2R*,4S*)-4-(3-fluoro-2-methoxyphenyl)-2-hydroxy-2-(trifluoromethyl)hexanal, 132 mg (0.97 mmol) of 5-aminoquinol-2(H1)-one and 0.44 ml of titanium tetraethoxide are reacted to give 5-{[(2R*,4S*)-4-(3-fluoro-2-methoxyphenyl)-2-hydroxy-2-(trifluoromethyl)hexylidene]amino}quinolin-2(1H)-one. 250 mg of crude imine are cyclized in the same way as in Example 29 at −20° C. with 2 ml (2 mmol) of 1 M boron tribromide solution to give the desired product. Preparative thin-layer chromatography on silica gel (hexane/2-propanol 17%) yields 15.4 mg of desired product.

$^1$H-NMR (300 MHz, CD$_3$OD); δ=1.13 (t, 3H), 1.97 (m, 1H), 2.08-2.15 (m, 2H), 2.43 (dd, 1H), 3.09 (m, 1H), 5.13 (s, 1H), 6.50 (d, 1H), 6.67 (d, 1H), 6.71 (d, 1H), 6.76 (dd, 1H), 6.88 (dd, 1H), 7.38 (t, 1H), 8.23 (d, 1H).

Example 44

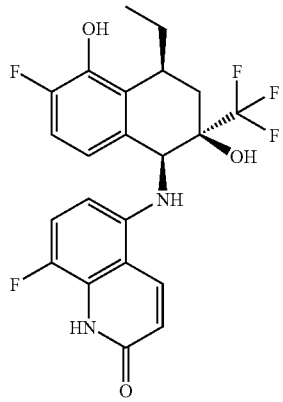

5-{[(1α,2α,4α)-4-Ethyl-6-fluoro-2,5-dihydroxy-2-(trifluoromethyl)-1,2,3,4-tetrahydronaphthalen-1-yl]amino}-8-fluoroquinolin-2(1H)-one obtained as the product from Ex. 34 after chromatographic separation:

$^1$H-NMR (300 MHz, CD$_3$OD); δ=1.07 (t, 3H), 1.90 (m, 1H), 2.00-2.13 (m, 2H), 2.17 (s, 1H), 2.37 (dd, 1H), 3.04 (m, 1H), 4.99 (s, 1H), 6.50 (d, 1H), 6.55 (dd, 1H), 6.68 (dd, 1H), 6.85 (dd, 1H), 7.18 (dd, 1H), 7.43 (d, 1H), 8.15 (dd, 1H).

Example 44A/44B

5-{[(1α,2α,4α)-4-Ethyl-6-fluoro-2,5-dihydroxy-2-(trifluoromethyl)-1,2,3,4-tetrahydronaphthalen-1-yl]amino}-8-fluoroquinolin-2(1H)-one is cleaved by means of preparative chiral HPLC (Chiralcel OD-H 5µ) into the enantiomerically pure compounds:

(−)-Enantiomer: analytical HPLC: $R_t$=7.53 min (Chiralpak AD-H 5μ, 250×4.6 mm, hexane/ethanol 5=>50% (20'), 1 ml/min flow rate)

(+)-Enantiomer: analytical HPLC: $R_t$=10.10 min (Chiralpak AD-H 5μ, 250×4.6 mm, hexane/ethanol 5=>50% (20'), 1 ml/min flow rate)

Example 45

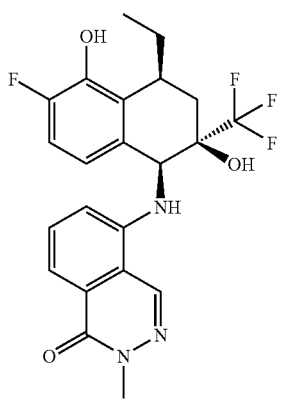

5-{[(1α,2α,4α)-4-Ethyl-6-fluoro-2,5-dihydroxy-2-(trifluoromethyl)-1,2,3,4-tetrahydronaphthalen-1-yl]amino}-2-methylphthalazin-1-one obtained as the product from Ex. 36 after chromatographic separation:

$^1$H-NMR (300 MHz, CD$_3$OD); δ=1.01 (t, 3H), 1.83 (m, 1H), 2.00 (m, 1H), 2.02 (dd, 1H), 2.30 (dd, 1H), 2.97 (m, 1H), 3.70 (s, 3H), 5.08 (s, 1H), 6.63 (dd, 1H), 6.77 (dd, 1H), 7.15 (dd, 1H), 7.51 (d, 1H), 7.52 (d, 1H), 8.44 (s, 1H).

In the same way it is possible to prepare the following:

Example 46

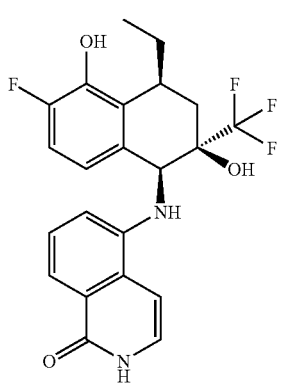

5-{[(1α,2α,4α)-4-Ethyl-6-fluoro-2,5-dihydroxy-2-(trifluoromethyl)-1,2,3,4-tetrahydronaphthalen-1-yl]amino}-isoquinolin-(2H)-one and Example 47

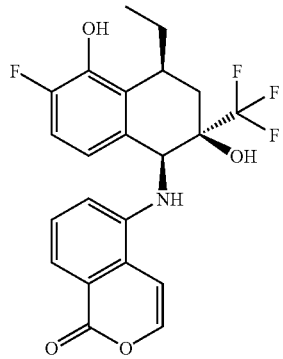

5-{[(1α,2α,4α)-4-Ethyl-6-fluoro-2,5-dihydroxy-2-(trifluoromethyl)-1,2,3,4-tetrahydronaphthalen-1-yl]amino}isochromen-1-one Example 48

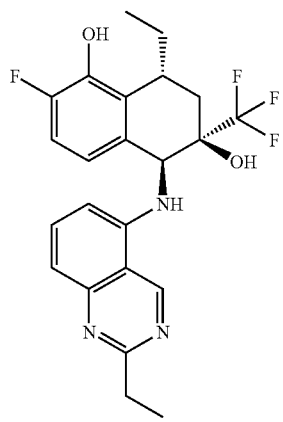

(5α,6α,8β)-5-[(2-Ethylquinazolin-5-yl)amino]-2-fluoro-8-propyl-6-(trifluoromethyl)-5,6,7,8-tetrahydronaphthalene-1,6-diol In the same way as in Example 31, 112 mg (0.37 mmol) of (4-(3-fluoro-2-methoxyphenyl)-2-hydroxy-2-(trifluoromethyl)hexanal, 60 mg (0.37 mmol) of 5-amino-2-ethylquinazoline and 0.2 ml of titanium tetraethoxide are reacted to give 1-[(2-ethylquinazolin-5-yl)imino]-4-(3-fluoro-2-methoxyphenyl)-2-(trifluoromethyl)hexan-2-ol. 280 mg of crude imine are cyclized in the same way as in Example 31 at −20° C. with 2.4 ml (2.4 mmol) of 1 M boron tribromide solution to give the desired product. Purification by chromatography on silica gel (ethyl acetate) gives 4 mg of desired product and 11 mg of the 8α compound (Example 49).

$^1$H-NMR (300 MHz, CD$_3$OD); δ=0.99 (t, 3H), 1.46 (t, 3H), 1.80 (m, 1H), 2.04 (dd, 1H), 2.05 (m, 1H), 2.43 (dd, 1H), 3.08

(q, 2H), 3.42 (dddd, 1H), 5.17 (s, 1H), 6.77 (dd, 1H), 6.81 (d, 1H), 6.89 (dd, 1H), 7.22 (d, 1H), 7.78 (t, 1H), 9.64 (s, 1H).

Example 49

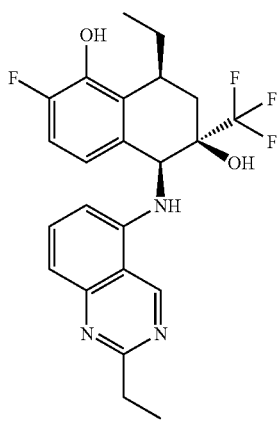

(5α,6α,8α)-5-[(2-Ethylquinazolin-5-yl)amino]-2-fluoro-8-propyl-6-(trifluoromethyl)-5,6,7,8-tetrahydronaphthalene-1,6-diol obtained as the product from Ex. 36 after chromatographic separation:
$^1$H-NMR (300 MHz, CD$_3$OD); δ=0.14 (t, 3H), 1.45 (t, 3H), 2.00 (m, 1H), 2.13 (, 1H), 2.15 (dd, 1H), 2.46 (dd, 1H), 3.07 (q, 2H), 3.10 (m, 1H), 5.28 (s, 1H), 6.78 (dd, 1H), 6.89 (dd, 1H), 6.98 (d, 1H), 7.21 (d, 1H), 7.79 (t, 1H), 9.66 (s, 1H).

Example 50

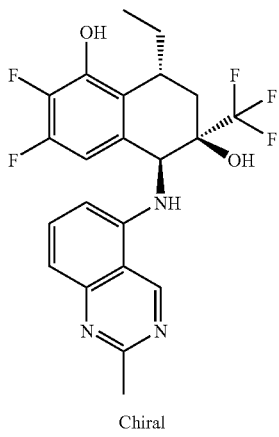

Chiral (5S,6R,8R)-8-Ethyl-2,3-difluoro-5-[(2-methylquinazolin-5-yl)amino]-6-(trifluoromethyl)-5,6,7,8-tetrahydronaphthalene-1,6-diol 4-(3,4-Difluoro-2-methoxyphenyl)-2-hydroxy-2-(trifluoromethyl)hexanal 20 g (153.7 mmol) of 2,3-difluorophenol in 150 ml of dichloromethane and 17.5 ml of pyridine are admixed dropwise at 0° C. with 14 ml (161 mmol) of propionyl chloride. The mixture is stirred for two hours and 100 ml of 2 M hydrochloric acid are added. The mixture is extracted with dichloromethane and the extracts are washed with water. Drying over sodium sulphate and the removal of the solvent in vacuo give 30.1 g of 2,3-difluorophenyl propionate.

30.1 g (161 mmol) of 2,3-difluorophenyl propionate in 16 ml of 1,2-dichlorobenzene are added dropwise to 21.5 g (161 mmol) of aluminum trichloride in 16 ml of 1,2-dichlorobenzene and the mixture is subsequently stirred at 100° C. for 6 hours. It is cooled, diluted with dichloromethane and poured cautiously onto a mixture of 2 M hydrochloric acid and ice. The phases are separated, extraction is carried out with dichloromethane and the extracts are washed with saturated sodium chloride solution and dried over sodium sulphate. The crude product is purified by column chromatography on silica gel (hexane/ethyl acetate 10-20%) to give 21.5 g of 1-(3,4-difluoro-2-hydroxyphenyl)propan-1-one. 21.4 g (115 mmol) of 1-(3,4-difluoro-2-hydroxyphenyl)propan-1-one are dissolved in 170 ml of acetone, and the solution is admixed with 29.5 g of potassium carbonate and 13 ml (209 mmol) of methyl iodide. The mixture is boiled under reflux for 4 hours and stirred at room temperature for 12 hours and then the solvent is largely removed. The residue is poured into water and subjected to extraction with diethyl ether. The extracts are washed with water, dried over sodium sulphate and, following the removal of the solvent in vacuo, give 21.2 g of 1-(3,4-difluoro-2-methoxyphenyl)propan-1-one.

31.2 g (476 mmol) of zinc dust and 740 mg (2.65 mmol) of lead(II) chloride are suspended in 320 ml of THF and at 0° C. 30 ml (265 mmol) of dibromomethane are added. The mixture is stirred at room temperature for a further 30 minutes and at 0° C. 53 ml (53 mmol) of a 1 M titanium(IV) chloride solution in dichloromethane are added dropwise. The cooling bath is removed and, after an hour, the reaction mixture is cooled to 0° C. again. 10.6 g (53 mmol) of 1-(3,4-difluoro-2-methoxyphenyl)propan-1-one in 106 ml of THF are added dropwise. The reaction mixture is stirred at room temperature for a further hour. It is diluted with diethyl ether and poured cautiously onto a mixture of 4 M hydrochloric acid and ice. The phases are separated, extracted is carried out with diethyl ether, the extracts are washed with saturated sodium chloride solution and dried over sodium sulphate and the solvent is removed. The crude product is purified by column chromatography on silica gel (hexane/diisopropyl ether 20-40%) to give 4.3 g of 2,3-difluoro-6-(1-methylenepropyl)anisole.

23.6 g (119 mmol) of 2,3-difluoro-6-(1-methylenepropyl)anisole, 31.4 ml (238 mmol) of ethyl trifluorpyruvate and 10 g of molecular sieve are added dropwise at 0° C. over 30 minutes to 2.58 g (2.98 mmol) of [Cu(R,R)bis-tert-butyl-oxazoline)(H$_2$O)$_2$]((SbF$_6$)$_2$ in 85 ml of dichloromethane. The reaction mixture is stirred at 0° C. for 16 hours and the reaction mixture is purified by means of column chromatography on silica gel (hexane/ethyl acetate 0-10%). This gives 16.7 g of ethyl (R)-4-(3,4-difluoro-2-methoxyphenyl)-2-hydroxy-2-(trifluoromethyl)hex-4-enoate as an E/Z mixture with an enantiomeric excess of greater than 80%. 16.7 g (45.3 mmol) of ethyl E/Z-4-(3,4-difluoro-2-methoxyphenyl)-2-hydroxy-2-(trifluoromethyl)-hex-4-enoate in 600 ml of diethyl ether are cooled to −5° C. and over 10 minutes 3.44 mg (90.7 mmol) of solid lithium aluminum hydride are added in portions. The mixture is stirred at room temperature for 2 hours and poured into saturated ammonium chloride solution. The suspension is filtered through Celite, the filter bed being rinsed thoroughly with ethyl acetate. The phases of the filtrate are separated and extraction is carried out again with ethyl acetate. The extracts are washed with saturated sodium chloride solution and dried over sodium sulphate and the solvent is removed in vacuo to give 13.9 of crude E/Z-4-(3,4-difluoro-2-methoxyphenyl)-2-(trifluoromethyl)-hex-4-ene-1,2-diol. 16 g (49 mmol) of (E/Z-4-(3,4-difluoro-2-methoxyphenyl)-2-(trifluoromethyl)-hex-4-ene-1,2-diol are dissolved in 680 ml of methanol and 9.4 ml of acetic acid, and 1.07 g of palladium on carbon (10%) are added. The suspension is shaken under a hydrogen atmosphere at atmospheric pressure until reaction is complete. The mixture is filtered through Celite, the filter bed being rinsed thoroughly with ethyl acetate. Removal of the solvent gives 16.1 g of crude 4-(3,4-difluoro-2-methoxyphenyl)-2-(trifluoromethyl)-hexane-1,2-diol as a mixture of the diastereomers. 16.1 g (49 mmol) of 4-(3,4-difluoro-2-methoxyphenyl)-2-(trifluoromethyl)-hexane-1,2-diol in 600 ml of dichloromethane and 220 ml of DMSO are admixed with 33.5 ml (242 mmol) of triethylamine and in portions over 10 minutes with 29.8 g (188 mmol) of pyridine SO$_3$ complex. The mixture is stirred for 3 hours and saturated ammonium chloride solution is added. The mixture is stirred for a further 5 minutes, the phases are separated and extraction is carried out with dichloromethane. The extracts are washed with water and dried over sodium sulphate. The solvent is removed in vacuo, then column chromatography on silica gel (hexane/diisopropyl ether 0-30%) gives 2.7 g of (2R,4R)-4-(3,4-difluoro-2-methoxyphenyl)-2-hydroxy-2-(trifluoromethyl)hexanal $^1$H-NMR (300 MHz, CDCl$_3$); δ=0.75 (t, 3H), 1.55-1.73 (m, 2H), 2.30 (dd, 1H), 2.54 (dd, 1H), 3.06 (m, 1H), 3.92 (s, 1H), 3.96 (s, 3H), 6.75-6.84 (m, 2H), 9.02 (s, 1H) and 3.9 g (2R,4S)-4-(3,4-difluoro-2-methoxyphenyl)-2-hydroxy-2-(trifluoromethyl)hexanal $^1$H-NMR (300 MHz, CDCl$_3$); δ 0.71 (t, 3H), 1.50-1.70 (m, 2H), 2.33 (dd, 1H), 2.41 (dd, 1H), 2.87 (m, 1H), 3.60 (s, 1H), 3.95 (s, 3H), 6.75-6.86 (m, 2H), 9.69 (s, 1H).

300 mg (0.92 mmol) of (2R,4R)-4-(3,4-difluoro-2-methoxyphenyl)-2-hydroxy-2-(trifluoromethyl)hexanal and 146 mg (0.92 mmol) of 5-amino-2-methylquinazoline are dissolved in 20 ml of toluene, and the solution is admixed with 0.29 ml (0.92 mmol) of titanium tert-butoxide and 0.1 ml of acetic acid. The reaction mixture is heated at 100° C. for 2 hours, cooled, poured into water and stirred vigorously. The suspension is filtered through Celite, the filter bed being rinsed thoroughly with ethyl acetate. The phases of the filtrate are separated and extraction is carried out again with ethyl acetate. The extracts are washed with saturated sodium chloride solution and dried over sodium sulphate and the solvent is removed in vacuo to give 349 mg of (2R,4R)-4-(3,4-difluoro-2-methoxyphenyl)-1-[(2-methylquinazolin-5-yl)imino]-2-(trifluoromethyl)hexan-2-ol as a crude product. The crude imine is dissolved in 35 ml of CH$_2$Cl$_2$ and the solution is cooled to −30° C. 6 ml (6 mmol) of a 1 M BBr$_3$ solution in dichloromethane are added slowly dropwise over 5 minutes and the reaction solution is allowed to warm to room temperature over 16 hours. It is poured onto a mixture of saturated NaHCO$_3$ solution and ice. Extraction is carried out repeatedly with ethyl acetate and the extracts are washed with saturated NaCl solution and dried over Na$_2$SO$_4$. Purification by column chromatography on silica gel (hexane/isopropanol 0-10%) and subsequent HPLC separation on a chiral stationary phase afford 70 mg of product (analytical HPLC: R$_t$=8.36 min (Chiralcel OD 5μ, 250×4.6 mm, hexane/ethanol 5%, 1 ml/min flow rate) as the (−)-enantiomer.

$^1$H-NMR (300 MHz, CD$_3$OD); δ=0.93 (t, 3H), 1.74 (ddq, 1H), 1.96 (m, 1H), 1.99 (dd, 1H), 2.38 (dd, 1H), 2.78 (s, 3H), 3.30 (m, 1H), 5.08 (s, 1H), 6.59 (dd, 1H), 6.77 (d, 1H), 7.17 (d, 1H), 7.74 (t, 1H), 9.57 (s, 1H).

Example 51

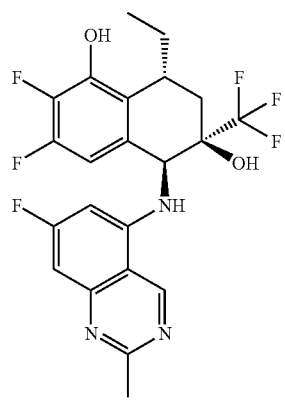

(5α,6α,8β)-8-Ethyl-2,3-difluoro-5-[(7-fluoro-2-methylquinazolin-5-yl)amino]-6-(trifluoromethyl)-5,6,7,8-tetrahydronaphthalene-1,6-diol In the same way as in Example 50, 137 mg (0.42 mmol) of (2R*,4R*)-4-(3,4-difluoro-2-methoxyphenyl)-2-hydroxy-2-(trifluoromethyl)hexanal, 78 mg (0.44 mmol) of 5-amino-7-fluoro-2-methylquinazoline and 0.2 ml of titanium tetraethoxide are reacted to give 5-{[(2R*,4R*)-4-(3,4-difluoro-2-methoxyphenyl)-1-[(7-fluoro-2-methylquinolin-5-yl)imino]-2-(trifluoromethyl)hexan-2-ol. 121 mg of chromatographically purified imine are cyclized in the same way as in Example 29 at −40° C. with 2.5 ml (2.5 mmol) of 1 M boron tribromide solution to give the desired product. Preparative thin-layer chromatography on silica gel (hexane/2-propanol 15%) yields 25 mg of desired product.

$^1$H-NMR (300 MHz, CD$_3$OD); δ=0.99 (t, 3H), 1.78 (ddq, 1H), 2.04 (dd, 1H), 2.06 (m, 1H), 2.44 (dd, 1H), 2.81 (s, 3H), 3.32 (m, 1H), 5.17 (s, 1H), 6.63 (dd, 1H), 6.66 (d, 1H), 6.83 (d, 1H), 9.56 (s, 1H).

Example 51A/51B (5α,6α,8β)-8-Ethyl-2,3-difluoro-5-[(7-fluoro-2-methylquinazolin-5-yl)amino]-6-(trifluoromethyl)-5,6,7,8-tetrahydronaphthalene-1,6-diol is cleaved by means of preparative chiral HPLC (Chiralcel OD-H 5μ) into the enantiomerically pure compounds:

(+)-Enantiomer: analytical HPLC: R$_t$=5.14 min (Chiralcel OD-H 5μ, 250×4.6 mm, hexane/ethanol 5%=>20% (20'), 1 ml/min flow rate)

(−)-Enantiomer: analytical HPLC: R$_t$=8.56 min (Chiralcel OD-H 5μ, 250×4.6 mm, hexane/ethanol 5%=>20% (20'), 1 ml/min flow rate)

In the same way it is possible to prepare the following:

Example 52

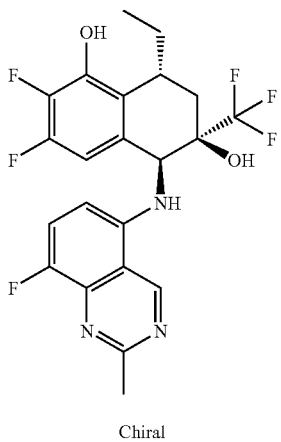

Chiral (5S,6R,8R)-8-Ethyl-2,3-difluoro-5-[(8-fluoro-2-methylquinazolin-5-yl)amino]-6-(trifluoromethyl)-5,6,7,8-tetrahydronaphthalene-1,6-diol Example 53

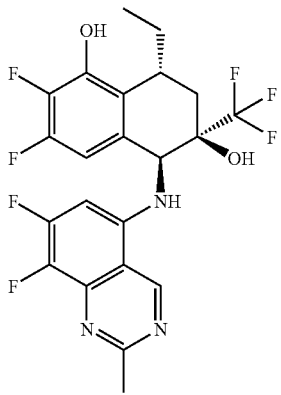

(5S,6R,8R)-8-Ethyl-2,3-difluoro-5-[(7,8-difluoro-2-methylquinazolin-5-yl)amino]-6-(trifluoromethyl)-5,6,7,8-tetrahydronaphthalene-1,6-diol Example 54

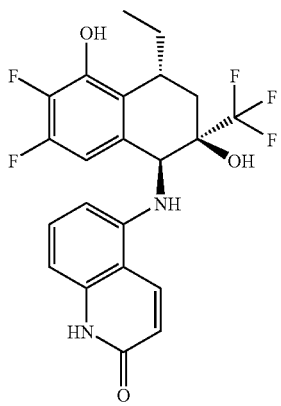

5-{[(1α,2α,4β)-4-ethyl-6,7-difluoro-2,5-dihydroxy-2-(trifluoromethyl)-1,2,3,4-tetrahydronaphthalen-1-yl]amino}quinolin-2(1H)-one In the same way as in Example 29, 210 mg (0.64 mmol) of (2R*,4R*)-4-(3,4-difluoro-2-methoxyphenyl)-2-hydroxy-2-(trifluoromethyl)hexanal, 132 mg (0.97 mmol) of 5-aminoquinolin-2(1H)-one and 0.27 ml of titanium tetraethoxide are reacted to give 5-{[(2R*,4R*)-4-(3,4-difluoro-2-methoxyphenyl)-2-hydroxy-2-(trifluoromethyl)hexylidene]amino}quinolin-2(1H)-one. 234 mg of crude imine are cyclized in the same way as in Example 29 at −40° C. with 5 ml (5 mmol) of 1 M boron tribromide solution to give the desired product. Column chromatography on silica gel (hexane/ethyl acetate 33-100%) yields 25 mg of the desired product.

$^1$H-NMR (300 MHz, CD$_3$OD); δ=0.92 (t, 3H), 1.71 (ddq, 1H), 1.94 (m, 1H), 1.96 (dd, 1H), 2.34 (dd, 1H), 3.28 (m, 1H), 4.94 (s, 1H), 6.43 (d, 1H), 6.50 (d, 1H), 6.58 (dd, 1H), 6.68 (d, 1H), 7.33 (t, 1H), 8.18 (d, 1H).

Example 54A/54B

5-{[(1α,2α,4β)-4-Ethyl-6,7-difluoro-2,5-dihydroxy-6,7-difluoro-2-(trifluoromethyl)-1,2,3,4-tetrahydronaphthalen-1-yl]amino}quinolin-2(1H)-one is cleaved by means of preparative chiral HPLC (Chiralpak OD-H 5μ) into the enantiomerically pure compounds:

(−)-Enantiomer: analytical HPLC: R$_t$=7.68 min (Chiralpak IA 5μ, 250×4.6 mm, hexane/ethanol 10%, 1 ml/min flow rate)

(+)-Enantiomer: analytical HPLC: R$_t$=9.35 min (Chiralcel IA 5μ, 250×4.6 mm, hexane/ethanol 10%, 1 ml/min flow rate)

Example 55

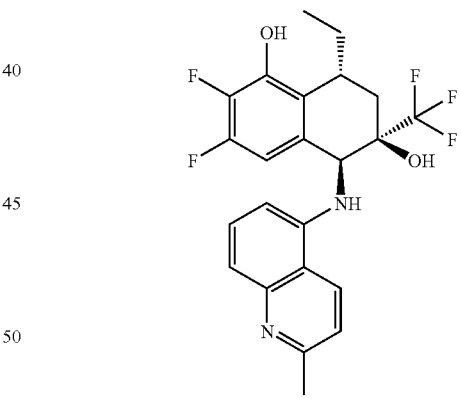

(5α,6α,8β)-8-Ethyl-2,3-difluoro-5-[(2-methylquinolin-5-yl)amino]-6-(trifluoromethyl)-5,6,7,8-tetrahydronaphthalene-1,6-diol In the same way as in Example 29, 210 mg (0.64 mmol) of (2R*,4R*)-4-(3,4-difluoro-2-methoxyphenyl)-2-hydroxy-2-(trifluoromethyl)hexanal, 132 mg (0.97 mmol) of 5-aminoquinolin-2(1H)-one and 0.27 ml of titanium tetraethoxide are reacted to give 5-{[(2R*,4R*)-4-(3,4-difluoro-2-methoxyphenyl)-2-hydroxy-2-(trifluoromethyl)hexylidene]amino}quinolin-2(1H)-one. 234 mg of crude imine are cyclized in the same way as in Example 29 at −20° C. with 2 ml (2 mmol) of 1 M boron tribromide solution to give the desired product. Preparative thin-layer chromatography on silica gel (hexane/2-propanol 17%) yields 15.4 mg of the desired product.

$^1$H-NMR (300 MHz, CD$_3$OD); δ=0.92 (t, 3H), 1.76 (ddq, 1H), 1.95 (m, 1H), 1.99 (dd, 1H), 2.38 (dd, 1H), 2.78 (s, 3H), 3.30 (m, 1H), 5.09 (s, 1H), 6.59 (dd, 1H), 6.69 (d, 1H), 7.38 (m, 2H), 7.56 (t, 1H), 8.46 (d, 1H).

Example 56

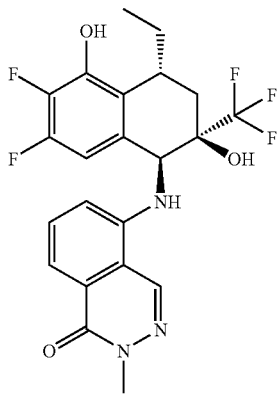

5-{[(1α,2α,4β)-4-Ethyl-6,7-difluoro-2,5-dihydroxy-2-(trifluoromethyl)-1,2,3,4-tetrahydronaphthalen-1-yl]amino}phthalazin-1-one In the same way as in Example 29, 372 mg (1.14 mmol) of (2R*,4R*)-4-(3,4-difluoro-2-methoxyphenyl)-2-hydroxy-2-(trifluoromethyl)hexanal, 200 mg (1.14 mmol) of 5-aminophthalazin-1-one and 0.36 ml of titanium tetra-tert-butoxide are reacted to give 5-{[(2R*,4R*)-4-(3,4-difluoro-2-methoxyphenyl)-2-hydroxy-2-(trifluoromethyl)hexylidene]amino}phthalazin-1-one. 560 mg of crude imine are cyclized in the same way as in Example 29 at −30° C. with 11.8 ml (11.8 mmol) of 1 M boron tribromide solution to give the desired product. Preparative thin-layer chromatography on silica gel (hexane/2-propanol 17%) yields 249 mg of the desired product $^1$H-NMR (300 MHz, CD$_3$OD); δ=0.92 (t, 3H), 1.70 (ddq, 1H), 1.95 (m, 1H), 1.96 (dd, 1H), 2.37 (dd, 1H), 3.29 (m, 1H), 3.81 (s, 3H), 5.03 (s, 1H), 6.58 (dd, 1H), 7.07 (dd, 1H), 7.61 (d, 1H), 7.62 (d, 1H), 8.51 (s, 1H).

In the same way it is possible to prepare from 3-chloro-2-fluorophenol:

Example 57

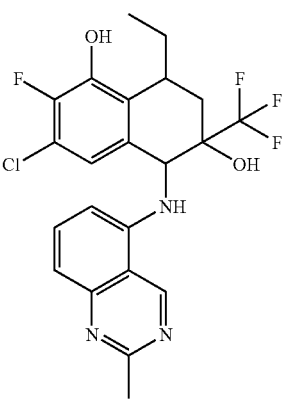

3-Chloro-8-ethyl-2-fluoro-5-[(2-methylquinazolin-5-yl)amino]-6-(trifluoromethyl)-5,6,7,8-tetrahydronaphthalene-1,6-diol and Example 58

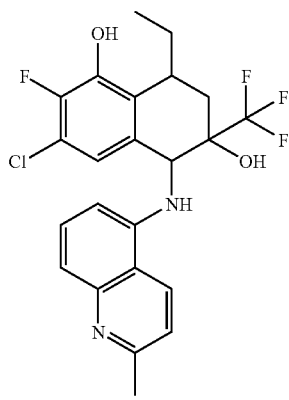

3-Chloro-8-ethyl-2-fluoro-5-[(7-fluoro-2-methylquinazolin-5-yl)amino]-6-(trifluoromethyl)-5,6,7,8-tetrahydronaphthalene-1,6-diol and Example 59

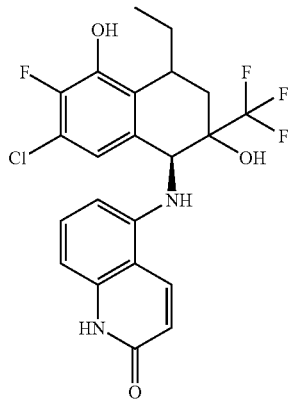

5-{[-7-Chloro-4-ethyl-6-fluoro-2,5-dihydroxy-2-(trifluoromethyl)-1,2,3,4-tetrahydronaphthalen-1-yl]amino}quinolin-2(1H)-one and Example 60

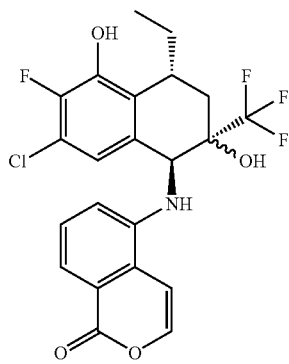

5-{[-7-Chloro-4-ethyl-6-fluoro-2,5-dihydroxy-2-(trifluoromethyl)-1,2,3,4-tetrahydronaphthalen-1-yl]amino}isochromen-1-one and Example 61

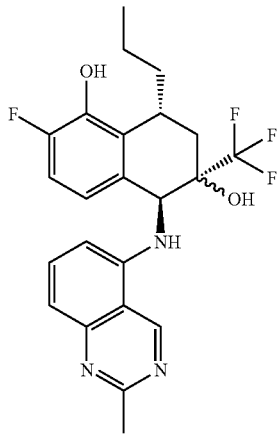

(5α,6α, 8β)-2-Fluoro-5-[(2-methylquinazolin-5-yl)amino]-8-prop-1-yl-6-(trifluoromethyl)-5,6,7,8-tetrahydronaphthalene-1,6-diol 4-(3-Fluoro-2-methoxyphenyl)-2-hydroxy-2-(trifluoromethyl)heptanal 25 g (213 mmol) of 2-fluorophenol in 150 ml of dichloromethane and 24 ml of pyridine are admixed dropwise at 0° C. with 21 ml (210 mmol) of butyryl chloride. The mixture is stirred for two hours and admixed with 100 ml of 2 M hydrochloric acid. Extraction is carried out with dichloromethane and the extracts are washed with water. Drying over sodium sulphate and the removal of the solvent in vacuo give 40 g of 2-fluorophenyl butyrate. 40 g (213 mmol) of 2-fluorophenyl butyrate in 22 ml of 1,2-dichlorobenzene are added dropwise to 28 g (213 mmol) of aluminum trichloride in 25 ml of 1,2-dichlorobenzene and the mixture is subsequently stirred at 100° C. for 20 hours. It is cooled, diluted with dichloromethane and poured cautiously onto a mixture of 2 M hydrochloric acid and ice. The phases are separated, extraction is carried out with dichloromethane and the extracts are washed with saturated sodium chloride solution and dried over sodium sulphate. The crude product is purified by column chromatography on silica gel (hexane/ethyl acetate 0-10%) to give 20.7 g of 1-(3-fluoro-2-hydroxyphenyl)butan-1-one. 20.7 g (114 mmol) of 1-(3-fluoro-2-hydroxyphenyl)butan-1-one are dissolved in 200 ml of acetone and the solution is admixed with 31.5 g of potassium carbonate and 14 ml (230 mmol) of methyl iodide. The mixture is stirred at 70° C. for 6 hours and at room temperature for 12 hours and then the solvent is largely removed. The residue is poured into water and subjected to extraction with diethyl ether. The extracts are washed with water and dried over sodium sulphate, and removal of the solvent in vacuo gives 20.7 g of 1-(3-fluoro-2-methoxyphenyl)butan-1-one. 31.7 g of zinc dust and 660 mg of lead(II) chloride are suspended in 330 ml of THF and at room temperature 29.5 ml of dibromomethane are added. The mixture is stirred for a further 30 minutes and admixed dropwise at 0° C. with ml 56 ml (56 mmol) of a 1 M titanium(IV) chloride solution in dichloromethane. The cooling bath is removed and after 30 minutes at room temperature 10.3 g (52.5 mmol) of 1-(3-fluoro-2-methoxyphenyl)butan-1-one in 50 ml of THF are added dropwise. The reaction mixture is stirred at room temperature for a further hour. It is diluted with diethyl ether and poured cautiously onto a mixture of 4 M hydrochloric acid and ice. The phases are separated, extraction is carried out with diethyl ether, the extracts are washed with water and dried over sodium sulphate and the solvent is removed. The crude product is purified by column chromatography on silica gel (hexane/diisopropyl ether 0-10%) to give 4.26 g of 2-fluoro-6-(1-methylenebutyl)anisole.

698 mg (2.56 mmol) of 1,1'-bi-2-naphthol are admixed with 2.56 ml (1.28 mmol) of a 0.5 M titanium tetraisopropoxide solution in toluene and the red solution is stirred at room temperature for 2 hours. 4.26 g (21.9 mmol) of 2-fluoro-6-(1-methylenbutyl)anisole and 5.7 ml (44 mmol) of ethyl trifluoropyruvate are added and the mixture is heated at 140° C. for 18 hours. After cooling it is immediately purified by column chromatography on silica gel (hexane/ethyl acetate 0-15%) to give 5.82 g of ethyl 4-(3-fluoro-2-methoxyphenyl)-2-hydroxy-2-(trifluoromethyl)hept-4-enoate. 2.6 g (7.1 mmol) of ethyl 4-(3-fluoro-2-methoxyphenyl)-2-hydroxy-2-(trifluoromethyl)hept-4-enoate are dissolved in 65 ml of methanol and the solution is admixed with 260 mg of palladium on carbon (10%). The suspension is shaken under a hydrogen atmosphere at atmospheric pressure for 4 hours until the hydrogen uptake is 155 ml. The mixture is filtered through Celite, the filter bed being rinsed thoroughly with ethyl acetate. Removal of the solvent gives 2.6 g of ethyl 4-(3-fluoro-2-methoxyphenyl)-2-hydroxy-2-(trifluoromethyl)heptanoate. 2.6 g (7.1 mmol) of ethyl 4-(3-fluoro-2-methoxyphenyl)-2-hydroxy-2-(trifluoromethyl)-heptanoate in 150 ml of diethyl ether are cooled to −10° C. and over 15 minutes 520 g (14.2 mmol) of solid lithium aluminum hydride are added in portions. The mixture is stirred at −15° C. for 1.5 hours, followed by dropwise addition in succession of ethyl acetate and water and by a further hour of stirring until a readily filterable precipitate is formed. The suspension is filtered through Celite, the filter bed being rinsed thoroughly with ethyl acetate. The phases of the filtrate are separated and extraction is carried out again with ethyl acetate. The extracts are washed with saturated sodium chloride solution and dried over sodium sulphate and the solvent is removed in vacuo. Separation by column chromatography on silica gel (hexane/diisopropyl ether 0-15%) yields 2.1 g of 4-(3-fluoro-2-methoxyphenyl)-2-hydroxy-2-(trifluoromethyl)heptanal as a mixture of the diastereomers.

¹H-NMR (300 MHz, CDCl₃): δ=0.70 (m, 3H), 0.95-1.60 (m, 4H), 1.95-2.20 (m, 2H), 2.32 (dd, 0.5H), 2.48 (dd, 0.5H), 2.94 (m, 0.5H), 3.26 (m, 0.5H), 3.59 (s, 0.5H), 3.84 (s, 0.5H), 3.89 (s, 3H), 6.74-6.92 (m, 3H), 8.93 (s, 0.5H), 9.62 (s, 0.5H).

300 mg (0.97 mmol) of 4-(3-fluoro-2-methoxyphenyl)-2-hydroxy-2-(trifluoromethyl)heptanal and 138 mg (0.87 mmol) of 5-amino-2-methylquinazoline are dissolved in 28 ml of toluene and the solution is admixed with 0.48 ml of titanium tetraethoxide. The reaction mixture is heated at 100° for 2 hours, cooled, poured into water and stirred vigorously. The suspension is filtered through Celite, the filter bed being rinsed thoroughly with ethyl acetate. The phases of the filtrate are separated and extraction is carried out again with ethyl acetate. The extracts are washed with saturated sodium chloride solution and dried over sodium sulphate and the solvent is removed in vacuo to give 350 mg of crude 4-(3-fluoro-2-methoxyphenyl)-1-[(2-methylquinazolin-5-yl)imino]-2-(trifluoromethyl)heptan-2-ol as a crude product. The crude imine is dissolved in 35 ml of CH₂Cl₂ and the solution is cooled to −20° C. 5.8 ml (5.8 mmol) of a 1 M BBr₃ solution in dichloromethane are added slowly dropwise over 5 minutes and the mixture is allowed to warm to room temperature over 1.5 hours. The reaction solution is poured onto a mixture of saturated NaHCO₃ solution and ice. Extraction is carried out repeatedly with ethyl acetate and the extracts are washed with saturated NaCl solution and dried over Na₂SO₄. Purification by column chromatography on silica gel (hexane/isopropanol 0-15%) and subsequent HPLC separation on chiral stationary phase afford 16 mg of product and 26 mg of the corresponding (5α,6α,8α) compound (Example 62).

¹H-NMR (300 MHz, CD₃OD); δ=1.00 (t, 3H), 1.42 (m, 2H), 1.68 (m, 1H), 2.00 (m, 1H), 2.04 (dd, 1H), 2.42 (dd, 1H), 2.81 (s, 3H), 3.48 (m, 1H), 5.16 (s, 1H), 6.75 (dd, 1H), 6.80 (d, 1H), 6.87 (dd, 1H), 7.18 (d, 1H), 7.77 (t, 1H), 9.60 (s, 1H).

Example 62

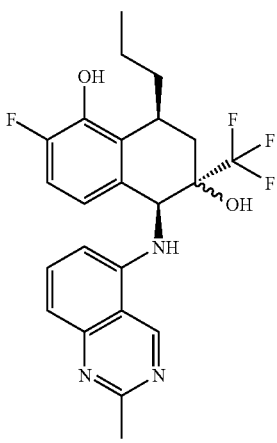

(5α,6α,8α)-2-Fluoro-5-[(2-methylquinazolin-5-yl)amino]-8-prop-1-yl-6-(trifluoromethyl)-5,6,7,8-tetrahydronaphthalene-1,6-diol Obtained as the product from Ex. 61 after chromatographic separation:

¹H-NMR (300 MHz, CD₃OD); δ=1.00 (t, 3H), 1.48 (m, 1H), 1.68 (m, 1H), 1.98 (m, 2H), 2.12 (dd, 1H), 2.37 (dd, 1H), 2.77 (s, 3H), 3.19 (m, 1H), 5.24 (s, 1H), 6.74 (dd, 1H), 6.85 (dd, 1H), 6.94 (d, 1H), 7.15 (d, 1H), 7.75 (t, 1H), 9.60 (s, 1H).

Example 63

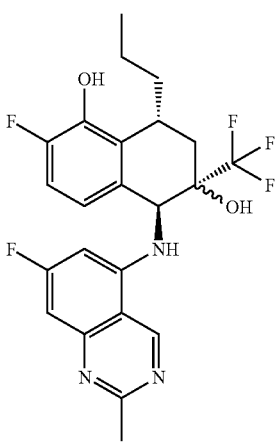

(5α,6α,8β)-2-Fluoro-5-[(7-fluoro-2-methylquinazolin-5-yl)amino]-8-prop-1-yl-6-(trifluoromethyl)-5,6,7,8-tetrahydronaphthalene-1,6-diol In the same way as in Example 61, 228 mg (0.71 mmol) of 4-(3-fluoro-2-methoxyphenyl)-2-hydroxy-2-(trifluoromethyl)heptanal, 150 mg (0.85 mmol) of 5-amino-7-fluoro-2-methylquinazoline and 0.5 ml of titanium tetraethoxide are reacted to give 4-(3-fluoro-2-methoxyphenyl)-1-[(7-fluoro-2-methylquinazolin-5-yl)imino]-2-(trifluoromethyl)heptan-2-ol. 185 mg of imine purified by column chromatography (silica gel, hexane/ethyl acetate 0-25%) are cyclized in the same way as in Example 61 at −20° C. with 3 ml (3 mmol) of 1 M boron tribromide solution to give the desired product. Column chromatography on silica gel (hexane/ethyl acetate 0-65%) yields 27 mg of product and 38 mg of the corresponding 5α,6α,8α) compound (Example 64).

¹H-NMR (300 MHz, CD₃OD); δ=0.98 (t, 3H), 1.40 (m, 2H), 1.65 (m, 1H), 2.01 (dd, 1H), 2.02 (m, 1H), 2.41 (dd, 1H), 2.76 (s, 3H), 3.43 (m, 1H), 5.14 (s, 1H), 6.59 (dd, 1H), 6.72 (dd, 1H), 6.76 (dd, 1H), 6.87 (dd, 1H), 9.50 (s, 1H).

Example 64

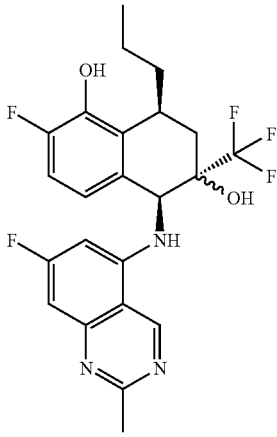

(5α,6α,8α)-Fluoro-5-[(7-fluoro-2-methylquinazolin-5-yl)amino]-8-prop-1-yl-6-(trifluoromethyl)-5,6,7,8-tetrahydronaphthalene-1,6-diol Obtained as the product from Ex. 63 after chromatographic separation:

¹H-NMR (300 MHz, CD₃OD); δ=1.00 (t, 3H), 1.48 (m, 1H), 1.67 (m, 1H), 1.97 (m, 2H), 2.15 (dd, 1H), 2.36 (dd, 1H), 2.76 (s, 3H), 3.20 (m, 1H), 5.22 (s, 1H), 6.72 (d, 1H), 6.74 (dd, 1H), 6.75 (d, 1H), 6.87 (dd, 1H), 9.60 (s, 1H).

Example 65

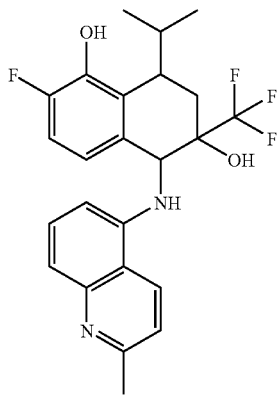

2-Fluoro-5-[(2-methylquinolin-5-yl)amino]-8-(Prop-2-yl)-6-(trifluoromethyl)-5,6,7,8-tetrahydronaphthalene-1,6-diol 4-(3-Fluoro-2-methoxyphenyl)-2-hydroxy-5-methyl-2-(trifluoromethyl)hexanal 2-Fluoro-6-(2-methyl-1-methylenepropyl)anisole can be prepared in the same way as in Example 61 from isobutyryl chloride and 2-fluorophenol. 788 mg of ytterbium(III) trifluoromethanesulphonate are admixed with 1.8 ml of ethyl trifluoropyruvate and 2.5 g (12.9 mmol) of 2-fluoro-6-(2-methyl-1-methylenepropyl)anisole in 5 ml of dichloroethane. The reaction mixture is heated at 100° C. for 16 hours and after it has cooled is immediately purified by column chromatography on silica gel (hexane/diisopropyl ether 0-8%). This gives 2.55 g of ethyl 4-(3-fluoro-2-methoxyphenyl)-2-hydroxy-5-methyl-2-(trifluoromethyl)hex-4-enoate, which in the same way as in Example 61 are reacted to give the diastereomer mixture of 4-(3-fluoro-2-methoxyphenyl)-2-hydroxy-5-methyl-2-(trifluoromethyl)hexanal.

$^1$H-NMR (300 MHz, CDCl$_3$); δ=0.69 (d, 1.5H), 0.72 (d, 1.5H), 0.96 (d, 1.5H), 0.98 (d, 1.5H), 1.55-2.24 (m, 3H), 3.10-3.30 (m, 1H), 3.89 (s, 3H), 6.78-7.08 (m, 3H), 9.05 (s, 0.5H), 9.65 (s, 0.5H).

In the same way as in Example 61, 200 mg (0.62 mmol) of 4-(3-fluoro-2-methoxyphenyl)-2-hydroxy-5-methyl-2-(trifluoromethyl)hexanal, 125 mg (0.80 mmol) of 5-amino-2-methylquinoline and 0.3 ml of titanium tetraethoxide are reacted to give 4-(3-fluoro-2-methoxyphenyl)-1-[(2-methylquinolin-5-yl)imino]-5-methyl-2-(trifluoromethyl)hexan-2-ol. 229 mg of imine purified by column chromatography (silica gel, hexane/ethyl acetate 0-35%) are cyclized in the same way as in Example 61 at −20° C. with 5 ml (5 mmol) of 1 M boron tribromide solution in dichloromethane to give the desired product. Column chromatography on silica gel (hexane/2-propanol 0-15%) and subsequent preparative HPLC (SunFire C18, water/methanol) yield 11 mg of product.

$^1$H-NMR (300 MHz, CDCl$_3$); δ=0.84 (d, 3H), 1.02 (d, 3H), 2.15 (dd, 1H), 2.37 (dd, 1H), 2.54 (m, 1H), 2.73 (s, 3H), 3.40 (m, 1H), 4.89 (d, 1H), 5.19 (br, 1H), 6.50 (d, 1H), 6.88 (m, 2H), 7.24 (d, 1H), 7.42 (d, 1H), 7.49 (t, 1H), 8.16 (d, 1H).

Example 66

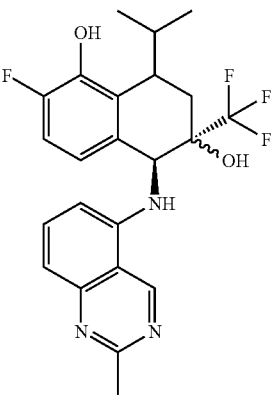

2-Fluoro-5-[(2-methylquinazolin-5-yl)amino]-8-prop-2-yl-6-(trifluoromethyl)-5,6,7,8-tetrahydronaphthalene-1,6-diol In the same way as in Example 61, 280 mg (0.87 mmol) of 4-(3-fluoro-2-methoxyphenyl)-2-hydroxy-5-methyl-2-(trifluoromethyl)hexanal, 175 mg (1.1 mmol) of 5-amino-2-methylquinazoline and 0.45 ml of titanium tetraethoxide are reacted to give 4-(3-fluoro-2-methoxyphenyl)-1-[(2-methylquinazolin-5-yl)imino]-5-methyl-2-(trifluoromethyl)hexan-2-ol. 360 mg of resulting crude imine are cyclized in the same way as in Example 61 at −30° C. with 6 ml (6 mmol) of 1 M boron tribromide solution in dichloromethane to give the desired product. Column chromatography on silica gel (hexane/ethyl acetate 0-70%) and subsequent preparative HPLC (SunFire C18, water/methanol) yield 6 mg of product.

$^1$H-NMR (300 MHz, CD$_3$OD); δ=0.82 (d, 3H), 1.06 (d, 3H), 2.12 (dd, 1H), 2.21 (dd, 1H), 2.69 (m, 1H), 2.83 (s, 3H), 3.51 (m, 1H), 5.00 (s, 1H), 6.69 (d, 1H), 6.75 (dd, 1H), 6.89 (dd, 1H), 7.20 (d, 1H), 7.77 (t, 1H), 9.63 (s, 1H).

Example 67

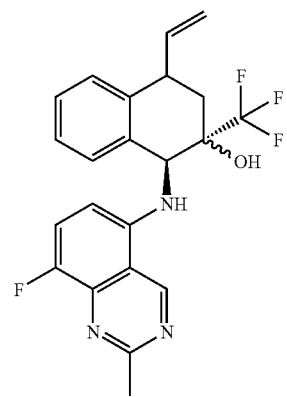

4-Ethenyl-1-[(8-fluoro-2-methylquinazolin-5-yl)amino]-2-(trifluoromethyl)-1,2,3,4-tetrahydronaphthalen-2-ol In the same way as in Example 30B, 50 mg (0.12 mmol) of cis-4'-[(8-fluoro-2-methylquinazolin-5-yl)amino]-3',4'-dihydro-3'-(trifluoromethyl)spiro[cyclopropane-1,1'(2'H)-naphthalen]-3'-ol (WO 2005/034939) in 1.2 ml of dichloromethane are admixed with 0.6 ml (0.6 mmol) of 1 M BBr$_3$ solution. Subsequent refluxing for 4 hours then preparative thin-layer chromatography on silica gel (hexane/2-propanol 10%) afford 15 mg of product.

$^1$H-NMR (300 MHz, CDCl$_3$); δ=2.08 (dd, 1H), 2.43 (dd, 1H), 2.93 (s, 3H), 3.93 (m, 1H), 5.14 (d, 1H), 5.33 (d, 1H), 5.37 (d, 1H), 5.50 (d, 1H), 5.83 (ddd, 1H), 6.77 (dd, 1H), 7.17-7.26 (m, 3H), 7.35 (d, 1H), 7.51 (dd, 1H), 9.32 (s, 1H).

Example 68

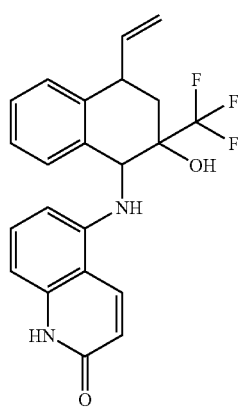

5-{[4-Ethenyl-2-hydroxy-2-fluoro-2-(trifluoromethyl)-1,2,3,4-tetrahydronaphthalen-1-yl]amino}quinolin-2(1H)-one In the same way as in Example 30B, 50 mg (0.12 mmol) of 5-{3',4'-dihydro-3'-hydroxy-3'-(trifluoromethyl)spiro[cyclohexane-1,1'(2'H)-naphthalen-4'-yl]amino}quinolin-2(1H)-one (WO 2005/034939) in 1.2 ml of dichloromethane are admixed with 0.6 ml (0.6 mmol) of 1 M BBr$_3$ solution. Subsequent refluxing for 4 hours then preparative thin-layer chromatography on silica gel (hexane/2-propanol 10%) afford 19 mg of product.

$^1$H-NMR (300 MHz, CD$_3$OD); δ=2.01 (dd, 1H), 2.43 (dd, 3H), 3.9.1 (m, 1H), 5.23 (d, 1H), 5.29 (d, 1H), 5.33 (d, 1H), 5.38 (d, 1H), 5.82 (ddd, 1H), 6.56 (m, 3H), 7.14-7.37 (m, 5H), 8.07 (d, 1H).

Example 69

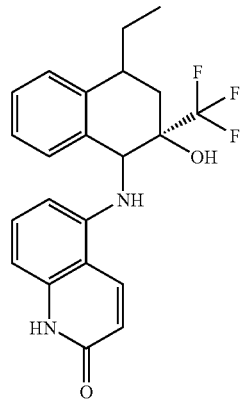

5-{[4-Ethyl-2-hydroxy-2-fluoro-2-(trifluoromethyl)-1,2,3,4-tetrahydronaphthalen-1-yl]amino}quinolin-2(1H)-one 13.6 mg (34 μmol) of 5-{[4-ethenyl-2-hydroxy-2-fluoro-2-(trifluoromethyl)-1,2,3,4-tetrahydronaphthalen-1-yl]amino}quinolin-2(1H)-one are dissolved in 2 ml of methanol under N$_2$ at RT and the solution is admixed with 3 mg of Pd—C (10%). The mixture is shaken for 1.5 hours under a hydrogen atmosphere (H$_2$ uptake: 15 ml), and the reaction mixture is filtered through Celite, the filter bed being rinsed thoroughly with methanol, to give 6 mg of product.

$^1$H-NMR (300 MHz, CD$_3$OD); δ=0.99 (t, 1.5H), 1.19 (t, 1.5H), 1.61 (dd, 0.5H), 1.75-2.20 (m, 2H), 1.92 (dd, 0.5H), 2.39 (dd, 0.5H), 2.60 (dd, 0.5H), 2.77 (m, 0.5H), 3.23 (m, 0.5H), 5.24 (s, 1H), 6.51 (d, 1H), 6.42 (d, 0.5H), 6.51 (d, 0.5H), 6.55 (d, 0.5H), 6.67 (d, 0.5H), 6.70 (d, 1H), 7.11 (t, 0.5H), 7.13 (t, 0.5H), 7.24-7.42 (m, 4H), 8.21 (d, 0.5H), 8.26 (d, 0.5H).

In the same way it is possible to prepare the following:

Example 70

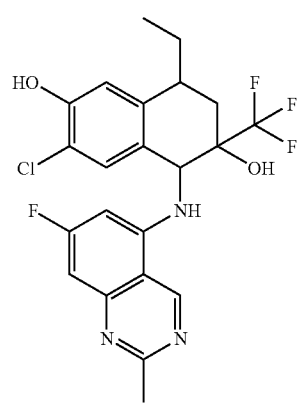

3-Chloro-8-ethyl-5-[(7-fluoro-2-methylquinazolin-5-yl)amino]-6-(trifluoromethyl)-5,6,7,8-tetrahydronaphthalene-2,6-diol and Example 71

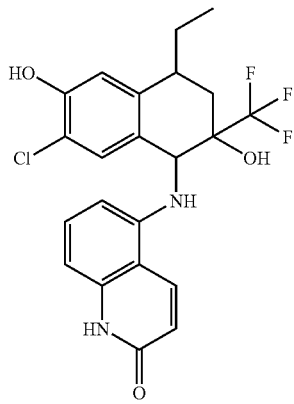

5-{[7-Chloro-2,6-dihydroxy-4-ethyl-2-(trifluoromethyl)-1,2,3,4-tetrahydronaphthalen-1-yl]-amino}quinolin-2(1H)-one and Example 72

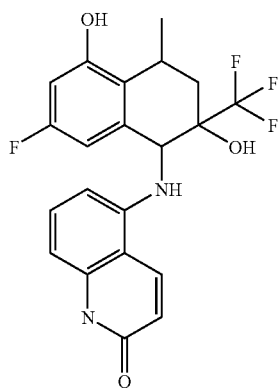

5-{[2,5-Dihydroxy-7-fluoro-4-methyl-2-(trifluoromethyl)-1,2,3,4-tetrahydronaphthalen-1-yl]amino}quinolin-2(1H)-one and Example 73

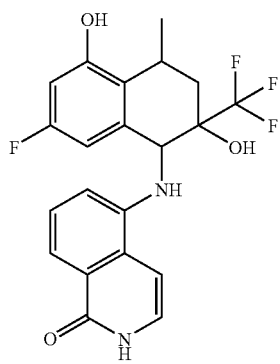

5-{[2,5-Dihydroxy-7-fluoro-4-methyl-2-(trifluoromethyl)-1,2,3,4-tetrahydronaphthalen-1-yl]amino}isoquinolin-1(2H)-one and Example 74

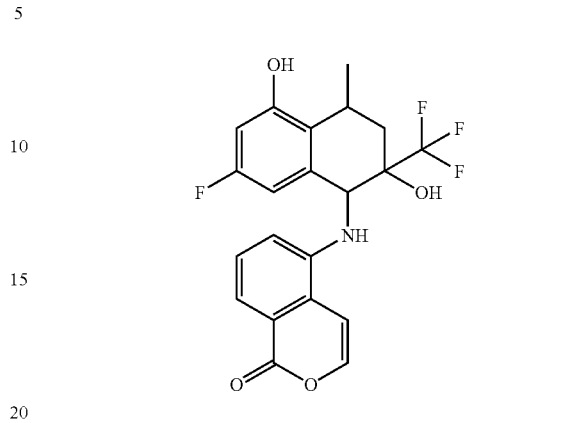

5-{[2,5-Dihydroxy-7-fluoro-4-methyl-2-(trifluoromethyl)-1,2,3,4-tetrahydronaphthalen-1-yl]amino}isochromen-1-one and Example 75

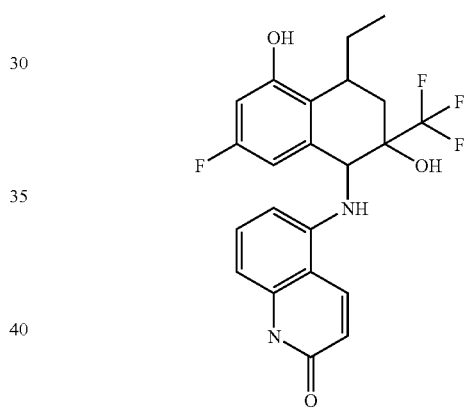

5-{[4-Ethyl-7-fluoro-2,5-dihydroxy-2-(trifluoromethyl)-1,2,3,4-tetrahydronaphthalen-1-yl]amino}quinolin-2(1H)-one and Example 76

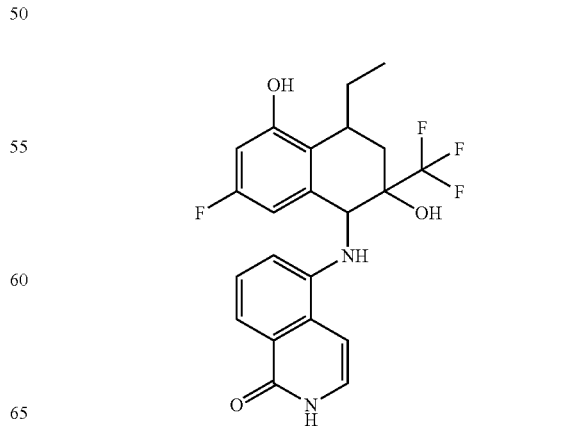

69

5-{[4-Ethyl-7-fluoro-2,5-dihydroxy-2-(trifluoromethyl)-1,2,3,4-tetrahydronaphthalen-1-yl]amino}isoquinolin-1(2H)-one and Example 77

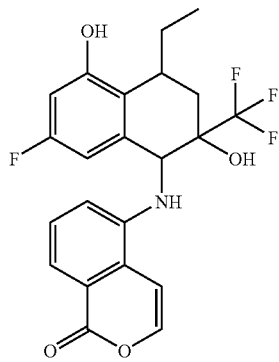

5-{[4-Ethyl-7-fluoro-2,5-dihydroxy-2-(trifluoromethyl)-1,2,3,4-tetrahydronaphthalen-1-yl]amino}isochromen-1-one and Example 78

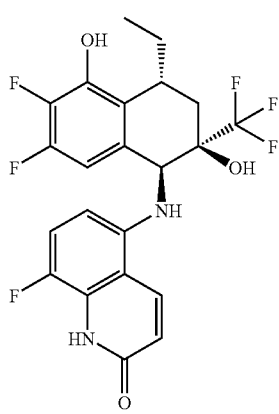

70

5-{[(1α,2α,4β)-4-Ethyl-6,7-difluoro-2,5-dihydroxy-2-(trifluoromethyl)-1,2,3,4-tetrahydronaphthalen-1-yl]amino}quinolin-2(1H)-one and Example 79

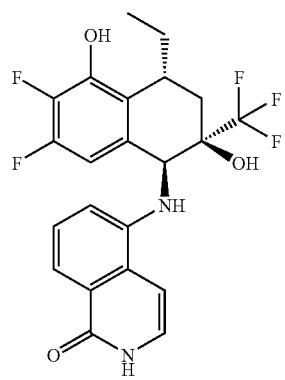

5-{[(1α,2α,4β)-4-Ethyl-6,7-difluoro-2,5-dihydroxy-2-(trifluoromethyl)-1,2,3,4-tetrahydronaphthalen-1-yl]amino}isoquinolin-1(2H)-one Example 80

Inventive Stereoisomers

| MOLSTRUCTURE | Ex. No. | IL8 IC50 | IL8 eff | TAT EC50 | TAT eff | Diss. (TAT$_{EC50}$/ IL8$_{IC50}$) |
|---|---|---|---|---|---|---|
|  | 1 | 22 nM | 79% | 1 μM | 62% | 45.5 |

-continued

| MOLSTRUCTURE | Ex. No. | IL8 IC50 | IL8 eff | TAT EC50 | TAT eff | Diss. (TAT$_{EC50}$/IL8$_{IC50}$) |
|---|---|---|---|---|---|---|
| (Chiral) | 29A | 16 nM | 77% | 120 nM | 95% | 7.5 |
| (Chiral) | 30A | 6.6 nM | 89% | 17 nM | 95% | 2.8 |
| | 43 | 12 nM | 88% | 43 nM | 100% | 3.6 |

-continued

| MOLSTRUCTURE | Ex. No. | IL8 IC50 | IL8 eff | TAT EC50 | TAT eff | Diss. (TAT$_{EC50}$/IL8$_{IC50}$) |
|---|---|---|---|---|---|---|
| (structure) | Chiral 51A | 13 nM | 72% | 150 nM | 81% | 11.5 |
| (structure) | 54 | 5.7 nM | 78% | 490 nM | 76% | 86 |
| (structure) | 65 | 38 nM | 58% | 1 μM | 73% | 26.3 |

-continued

| MOLSTRUCTURE | Ex. No. | IL8 IC50 | IL8 eff | TAT EC50 | TAT eff | Diss. (TAT$_{EC50}$/ IL8$_{IC50}$) |
|---|---|---|---|---|---|---|
| | 75 | 7.1 nM | 68% | 120 nM | 89% | 16.9 |
| | 101 | 1.8 nM | 92% | 74 nM | 97% | 41 |
| | Chiral 104B | 11 nM | 73% | 300 nM | 80% | 27 |

-continued

| MOLSTRUCTURE | Ex. No. | IL8 IC50 | IL8 eff | TAT EC50 | TAT eff | Diss. (TAT$_{EC50}$/IL8$_{IC50}$) |
|---|---|---|---|---|---|---|
| (structure) | 121B | 3.7 nM | 88% | 300 nM | 99% | 81 |

Prior-Art Compounds (WO2005/034939)

| MOLSTRUCTURE | IL8 IC50 | IL8 eff | TAT EC50 | TAT eff | Diss. (TAT$_{EC50}$/IL8$_{IC50}$) |
|---|---|---|---|---|---|
| (structure) | 20 nM | 88% | 4.3 nM | 100% | 0.22 |
| (structure) | 40 nM | 79% | 6.5 nM | 100% | 0.16 |

-continued

| MOLSTRUCTURE | IL8 IC50 | IL8 eff | TAT EC50 | TAT eff | Diss. (TAT$_{EC50}$/IL8$_{IC50}$) |
| --- | --- | --- | --- | --- | --- |
| (structure) | 22 nM | 73% | 3 nM | 98% | 0.14 |
| (structure) | 220 nM | 69% | 140 nM | 88% | 0.64 |
| (structure) | | | | | |

-continued

| MOLSTRUCTURE | IL8 IC50 | IL8 eff | TAT EC50 | TAT eff | Diss. (TAT$_{EC50}$/IL8$_{IC50}$) |
|---|---|---|---|---|---|
| | 14 nM | 68% | 3.8 nM | 92% | 0.27 |
| | 31 nM | 96% | 4.2 nM | 100% | 0.14 |

The outstanding properties of the stereoisomers of the invention are convincingly demonstrated by the exemplary selection of compounds of the present invention in comparison with a selection of compounds of the prior art (WO 2005/034939): the in vitro dissociation of IL-8 inhibition from TAT inhibition was increased in all cases by a factor of at least 5.

Examples 81A and 81B

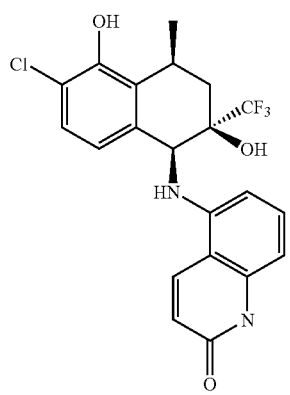

5-{[(1R,2S,4R)-6-Chloro-2,5-dihydroxy-4-methyl-2-(trifluoromethyl)-1,2,3,4-tetrahydronaphthalen-1-yl]amino}-1H-quinolin-2-one and 5-{[(1S,2R,4S)-6-chloro-2,5-dihydroxy-4-methyl-2-(trifluoromethyl)-1,2,3,4-tetrahydronaphthalen-1-yl]amino}-1H-quinolin-2-one 5-{[4-(3-Chloro-2-methoxyphenyl)-2-hydroxy-2-trifluoromethyl)pentylidene]-amino}1H-quinolin-2-one (554.1 mg, 1.16 mmol), prepared in analogy to described processes using the corresponding aldehyde, is dissolved in 5.8 ml of dichloromethane and the solution is admixed dropwise at 0° C. with 12.81 ml of a 1M solution of boron tribromide in dichloromethane. After three and a half hours of stirring at 5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, different eluent systems) produces 31.2 mg (5.6%) of the apolar diastereomer and 74.9 mg (13.3%) of the polar diastereomer (in each case as racemates). The latter is described in Examples 82A and 82B.

The apolar diastereomer (23.9 mg) is separated into its enantiomers by means of chiral HPLC (Chiralcel OD-H 5μ, eluent: hexane/ethanol). This gives 8.4 mg (35.2%) of the (−)-enantiomer ([α]$_D$=−6.4°, MeOH) and 10.5 mg (43.9%) of the (+)-enantiomer ([α]$_D$=+8.80, MeOH). No conclusion can of course be drawn concerning the absolute stereochemistry.

Examples 82A and 82B

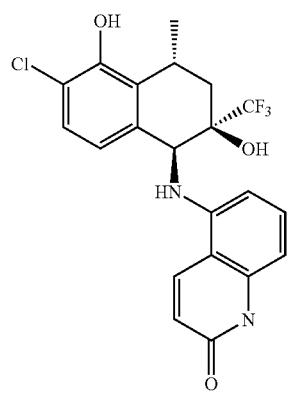

5-{[(1R,2S,4S)-6-Chloro-2,5-Dihydroxy-4-methyl-2-(trifluoromethyl)-1,2,3,4-tetrahydronaphthalen-1-yl]amino}-1H-quinolin-2-one and 5-{[(1S,2R,4R)-6-chloro-2,5-dihydroxy-4-methyl-2-(trifluoromethyl)-1,2,3,4-tetrahydronaphthalen-1-yl]amino}-1H-quinolin-2-one 65.3 mg of the polar racemic diastereomer described in Examples 81A and 81B are separated into its enantiomers by means of chiral HPLC (Chiralpak AD-H 5μ, eluent: hexane/ethanol). This gives 31.9 mg (48.9%) of the (−)-enantiomer ($[\alpha]_D$=−93.3°, MeOH) and 32.4 mg (49.6%) of the (+)-enantiomer ($[\alpha]_D$=+97.90, MeOH). No conclusion can of course be drawn concerning the absolute stereochemistry.

Examples 83A and 83B

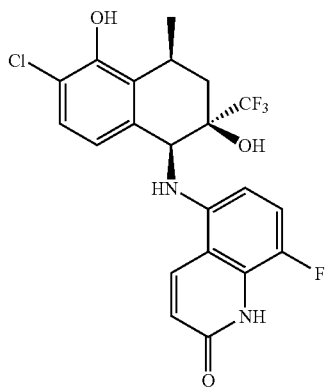

5-{[(1R,2S,4R)-6-Chloro-2,5-Dihydroxy-4-methyl-2-(trifluoromethyl)-1,2,3,4-tetrahydronaphthalen-1-yl]amino}-8-fluoro-1H-quinolin-2-one and 5-{[(1S,2R,4S)-6-chloro-2,5-dihydroxy-4-methyl-2-(trifluoromethyl)-1,2,3,4-tetrahydronaphthalen-1-yl]amino}-8-fluoro-1H-quinolin-2-one 5-{[4-(3-Chloro-2-methoxyphenyl)-2-hydroxy-2-trifluoromethyl)pentylidene]-amino}-8-fluoro-1H-quinolin-2-one (485 mg, 1.03 mmol), prepared in analogy to described processes using the corresponding aldehyde, is dissolved in 4.8 ml of dichloromethane and the solution is admixed dropwise at 0° C. with 10.3 ml of a 1M solution of boron tribromide in dichloromethane. After three hours of stirring at 5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, different eluent systems) produces 87.7 mg (18.6%) of the apolar diastereomer and 62.9 mg (13.4%) of the polar diastereomer, both as racemates. The racemate cleavage of the latter is described in Examples 84A and 84B.

The apolar diastereomer (77 mg) is separated into its enantiomers by means of chiral HPLC (Chiralcel OD-H 5μ, eluent: hexane/ethanol). This gives 38.2 mg (49.6%) of the (−)-enantiomer ($[\alpha]_D$=−8.50, MeOH) and 35.9 mg (46.6%) of the (+)-enantiomer ($[\alpha]_D$=+9.4°, MeOH). No conclusion can of course be drawn concerning the absolute stereochemistry.

Examples 84A and 84B

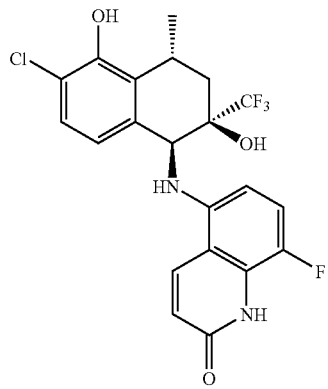

5-{[(1R,2S,4S)-6-Chloro-2,5-Dihydroxy-4-methyl-2-(trifluoromethyl)-1,2,3,4-tetrahydronaphthalen-1-yl]amino}-8-fluoro-1H-quinolin-2-one and 5-{[(1S,2R,4R)-6-chloro-2,5-dihydroxy-4-methyl-2-(trifluoromethyl)-1,2,3,4-tetrahydronaphthalen-1-yl]amino}-8-fluoro-1H-quinolin-2-one 56.9 mg of the polar racemic diastereomer described in Examples 83A and 83B are separated into its enantiomers by means of chiral HPLC (Chiralpak AD-H 5μ, eluent: hexane/ethanol). This gives 26.3 mg (46.2%) of the (−)-enantiomer ($[\alpha]_D$=−100.9°, MeOH) and 26.6 mg (46.8%) of the (+)-enantiomer ($[\alpha]_D$=98.7°, MeOH). No conclusion can of course be drawn concerning the absolute stereochemistry.

Examples 85A and 85B

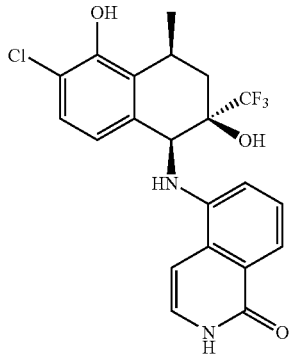

5-{[(1R,2S,4R)-6-Chloro-2,5-Dihydroxy-4-methyl-2-(trifluoromethyl)-1,2,3,4-tetrahydronaphthalen-1-yl]amino}-2H-quinolin-1-one and 5-{[(1S,2R,4S)-6-chloro-2,5-dihydroxy-4-methyl-2-(trifluoromethyl)-1,2,3,4-tetrahydronaphthalen-1-yl]amino}-2H-quinolin-1-one 5-{[4-(3-Chloro-2-methoxyphenyl)-2-hydroxy-2-trifluoromethyl)pentylidene]amino}2H-quinolin-1-one (590 mg, 1.3 mmol), prepared in analogy to described processes using the corresponding aldehyde and amine, is dissolved in 5.9 ml of dichloromethane and the solution is admixed dropwise at 0° C. with 12.8 ml of a 1M solution of boron tribromide in dichloromethane. After three hours of stirring at 5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, different eluent systems) produces 55.1 mg (9.6%) of the apolar diastereomer and 27.9 mg (4.9%) of the polar diastereomer, both as racemates. The racemate cleavage of the latter is described in Examples 86A and 86B.

The apolar diastereomer (49.6 mg) is separated into its enantiomers by means of chiral HPLC (Chiralpak AD-H 5μ, eluent: hexane/ethanol). This gives 22.4 mg (45.2%) of the (+)-enantiomer ([α]$_D$=+96.6°, MeOH) and 20.9 mg (42.1%) of the (−)-enantiomer ([α]$_D$=−95.5°, MeOH). No conclusion can of course be drawn concerning the absolute stereochemistry.

Examples 86A and 86B

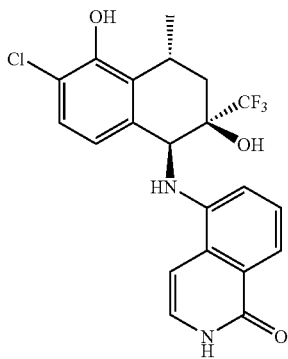

5-{[(1R,2S,4S)-6-Chloro-2,5-Dihydroxy-4-methyl-2-(trifluoromethyl)-1,2,3,4-tetrahydronaphthalen-1-yl]amino}-2H-quinolin-1-one and 5-{[(1S,2R,4R)-6-chloro-2,5-dihydroxy-4-methyl-2-(trifluoromethyl)-1,2,3,4-tetrahydronaphthalen-1-yl]amino}-2H-quinolin-1-one 21.6 mg of the polar racemic diastereomer described in Examples 85A and 85B are separated into its enantiomers by means of chiral HPLC (Chiralpak AD-H 5μ, eluent: hexane/ethanol). This gives 9.2 mg (42.6%) of the (−)-enantiomer ([α]$_D$=−0.9°, MeOH) and 9.5 mg (44%) of the (+)-enantiomer ([α]$_D$=+2.7°, MeOH). No conclusion can of course be drawn concerning the absolute stereochemistry.

Examples 87A and 87B

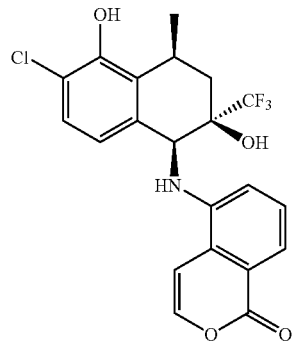

5-{[(1R,2S,4R)-6-Chloro-2,5-dihydroxy-4-methyl-2-(trifluoromethyl)-1,2,3,4-tetrahydronaphthalen-1-yl]amino}-isochromen-1-one and 5-{[(1S,2R,4S)-6-chloro-2,5-dihydroxy-4-methyl-2-(trifluoromethyl)-1,2,3,4-tetrahydronaphthalen-1-yl]amino}-isochromen-1-one 5-{[4-(3-Chloro-2-methoxyphenyl)-2-hydroxy-2-trifluoromethyl)pentylidene]-amino}isochromen-1-one (510 mg, 1.12 mmol), prepared in analogy to described processes using the corresponding aldehyde and amine, is dissolved in 5.1 ml of dichloromethane and the solution is admixed dropwise at 0° C. with 12.8 ml of a 1M solution of boron tribromide in dichloromethane. After three hours of stirring at 5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, different eluent systems) produces 108.7 mg (22%) of the apolar diastereomer and 113.9 mg (23.1%) of the polar diastereomer, both as racemates. The racemate cleavage of the latter is described in Examples 88A and 88B.

The apolar diastereomer (90 mg) is separated into its enantiomers by means of chiral HPLC (Chiralpak AD-H 5μ, eluent: hexane/ethanol). This gives 43.1 mg (47.8%) of the (+)-enantiomer ([α]$_D$=+103.3°, MeOH) and 40.4 mg (44.8%) of the (−)-enantiomer ([α]$_D$=−104.4°, MeOH). No conclusion can of course be drawn concerning the absolute stereochemistry.

Examples 88A and 88B

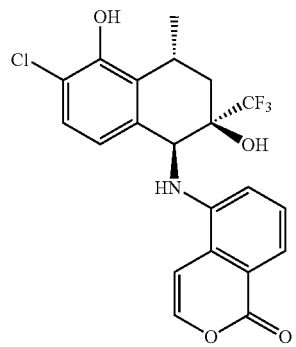

5-{[(1R,2S,4S)-6-Chloro-2,5-Dihydroxy-4-methyl-2-(trifluoromethyl)-1,2,3,4-tetrahydronaphthalen-1-yl]amino}isochromen-1-one and 5-{[(1S,2R,4R)-6-chloro-2,5-dihydroxy-4-methyl-2-(trifluoromethyl)-1,2,3,4-tetrahydronaphthalen-1-yl]amino}isochromen-1-one 82.2 mg of the polar racemic diastereomer described in Examples 87A and 87B are separated into its enantiomers by means of chiral HPLC (Chiralpak AD-H 5μ, eluent: hexane/ethanol). This gives 37.5 mg (45.6%) of the (−)-enantiomer ([α]$_D$=−104.4°, MeOH) and 40.8 mg (49.6%) of the (+)-enantiomer ([α]$_D$=+103.3°, MeOH). No conclusion can of course be drawn concerning the absolute stereochemistry.

Examples 89A and 89B

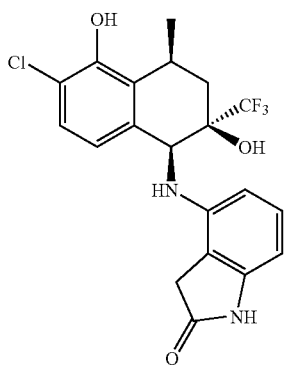

4-{[(1R,2S,4R)-6-Chloro-2,5-Dihydroxy-4-methyl-2-(trifluoromethyl)-1,2,3,4-tetrahydronaphthalen-1-yl]amino}-1,3-dihydroindol-2-one and 4-{[(1S,2R,4S)-6-chloro-2,5-dihydroxy-4-methyl-2-(trifluoromethyl)-1,2,3,4-tetrahydronaphthalen-1-yl]amino}-1,3-dihydroindol-2-one 4-{[4-(3-Chloro-2-methoxyphenyl)-2-hydroxy-2-trifluoromethyl)-pentylidene]amino}-1,3-dihydroindol-2-one (590 mg, 1.34 mmol), prepared in analogy to described processes using the corresponding aldehyde and amine, is dissolved in 5.8 ml of dichloromethane and the solution is admixed dropwise at 0° C. with 13.4 ml of a 1M solution of boron tribromide in dichloromethane. After three hours of stirring at 5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, different eluent systems) produces 36.3 mg (6.4%) of the apolar diastereomer and 60.7 mg (10.6%) of the polar diastereomer, both as racemates. The racemate cleavage of the latter is described in Examples 90A and 90B.

The apolar diastereomer (30.8 mg) is separated into its enantiomers by means of chiral HPLC (Chiralpak AD-H 5μ, eluent: methanol/ethanol). This gives 15.2 mg (49.4%) of the (−)-enantiomer ([α]$_D$=−1.7°, MeOH, more strongly coloured solution than for the (+)-enantiomer) and 14.3 mg (46.4%) of the (+)-enantiomer ([α]$_D$=+6.5°, MeOH). No conclusion can of course be drawn concerning the absolute stereochemistry.

Examples 90A and 90B

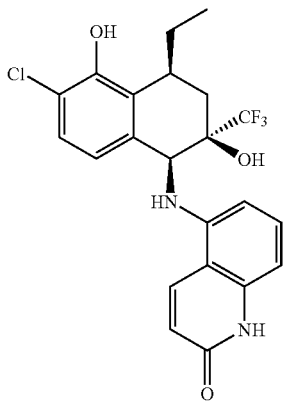

4-{[(1R,2S,4S)-6-Chloro-2,5-Dihydroxy-4-methyl-2-(trifluoromethyl)-1,2,3,4-tetrahydronaphthalen-1-yl]amino}-1,3-dihydroindol-2-one and 4-{[(1S,2R,4R)-6-chloro-2,5-dihydroxy-4-methyl-2-(trifluoromethyl)-1,2,3,4-tetrahydronaphthalen-1-yl]amino}-1,3-dihydroindol-2-one 46.2 mg of the polar racemic diastereomer described in Examples 89A and 89B are separated into its enantiomers by means of chiral HPLC (Chiralpak AD-H 5μ, eluent: hexane/ethanol). This gives 22.5 mg (48.7%) of the (−)-enantiomer ([α]$_D$=−94.1°, MeOH) and 17.4 mg (37.7%) of the (+)-enantiomer ([α]$_D$=+110.9°, MeOH). No conclusion can of course be drawn concerning the absolute stereochemistry.

Example 91

5-{[(1α,2α,4α)-6-Chloro-2,5-dihydroxy-4-ethyl-2-(trifluoromethyl)-1,2,3,4-tetrahydronaphthalen-1-yl]amino}-1H-quinolin-2-one 2-Chlorophenyl propionate A solution, cooled to 10° C., of 2-chlorophenol (100 g, 0.778 mol) in 250 ml of dichloromethane is slowly admixed with triethylamine (120.7 ml). A solution of 60.7 ml of propionyl chloride in 60 ml of dichloromethane is added slowly dropwise to this mixture over the course of an hour. Following the addition of the propionyl chloride, the mixture is allowed to come slowly to room temperature and is stirred at room temperature for a total of five hours. Following removal of the triethylammonium chloride by filtration, the filtrate is diluted with 100 ml of dichloromethane and washed with 0.1 N hydrochloric acid (500 ml), 0.1 M aqueous sodium hydroxide solution (500 ml) and water (500 ml). The organic phase is dried over sodium sulphate (100 g) for three hours. After the drying agent has been removed by filtration, the solvent is removed on a rotary evaporator. Distillation of the oily yellow residue under reduced pressure gives 129.2 g (90% yield) of 2-chlorophenyl propionate as a colourless liquid (bp 90-93° C./0.3 mm).

$^1$H-NMR (300 MHz, DMSO-d$_6$): δ=1.20 (3H), 2.67 (2H), 7.23-7.45 (3H), 7.58 (1H).

3'-Chloro-2'-hydroxypropiophenone

Anhydrous aluminum trichloride (130 g, 0.974 mol) in 150 ml of dry o-dichlorobenzene is cooled to 10° C. and 2-chlorophenyl propionate (100 g, 0.543 mol) is added slowly dropwise to this reaction mixture (15 minutes). The flask with the mixture is heated slowly in an oil bath to 110-120° C. At this temperature, HCl begins to evolve. The temperature is then raised slowly to 130-140° C. and the reaction mixture is held within this temperature range for three hours. After the oil bath has been removed and the batch has cooled, the excess aluminum chloride is broken down by addition of 350 g of crushed ice, followed by the addition of 50 ml of concentrated hydrochloric acid. After the reaction mixture has cooled, ethyl acetate (500 ml) is added. The organic phase is separated off and washed with saturated sodium hydrogen carbonate solution (500 ml) and brine (500 ml). After the organic phase has been dried and the solvent has been removed on a rotary evaporator, the residue is purified by chromatography on silica gel (eluent: toluene). This isolates 10 g (10%) of the desired compound and also 40 g (40%) of the corresponding regioisomer, 5'-chloro-3'-hydroxy propiophenone.

$^1$H-NMR (300 MHz, CDCl$_3$): δ=1.26 (3H), 3.08 (2H), 6.87 (1H), 7.58 (1H), 7.72 (1H), 12.96 (1H).

3'-Chloro-2'-methoxypropiophenone

3'-Chloro-2'-hydroxypropiophenone (10 g, 54.3 mmol) and potassium carbonate (17.5 g) in 70 ml of acetone are admixed with 7 ml of dimethyl sulphate. The reaction mixture is boiled at reflux for three hours. After it has cooled to room temperature, the batch is subjected to suction filtration through Celite and the filter cake is washed with diethyl ether. After the solvent has been removed on a rotary evaporator, the yellow oil which remains is diluted with 200 ml of diethyl ether and the organic phase is washed with 0.2 M aqueous sodium hydroxide solution (100 ml) and brine (100 ml). The organic phase is dried over sodium sulphate and the solvent is removed on a rotary evaporator. This leaves the desired title compound as a colourless oil (98% yield).

$^1$H-NMR (300 MHz, CDCl$_3$): δ=1.19 (3H), 2.96 (2H), 3.87 (3H), 7.10 (1H), 7.32-7.55 (2H).

Methyl (E,Z)-3-(3-chloro-2-methoxyphenyl)-2-pentenoate

Sodium hydride in mineral oil (4.33 g, 60% strength) is taken initially and is washed three times with hexane in order to remove the oil. After the remaining hexane has been removed in vacuo, the sodium hydride that remains (2.82 g, about 90 mmol) is admixed with 100 ml of tetrahydrofuran and the suspension is cooled to 0° C. Following the dropwise addition (20 minutes) of trimethyl phosphonoacetate (13.3 g, 63.2 mmol) the mixture is cooled again to 0° C. and subsequently a solution of 3'-chloro-2'-methoxypropiophenone (9.4 g, 47.47 mmol) in 80 ml of tetrahydrofuran is added dropwise (20 minutes). After the reaction mixture has reached room temperature, the batch is subsequently boiled at reflux for three hours. After it has cooled to room temperature, 150 ml of saturated ammonium chloride solution are added and the mixture is extracted three times with diethyl ether (500, 200, 200 ml). The combined organic extracts are washed with brine (160 ml). The aqueous phase is further extracted with diethyl ether (3×100 ml). The collected organic phases are dried (sodium sulphate) and the solvent is removed on a rotary evaporator. This leaves a pale yellow oil, which is purified by flash chromatography on silica gel (eluent: toluene). This isolates 9.4 g (78%) of the title compound as an E/Z mixture.

Methyl 3-(3-chloro-2-methoxyphenyl)-2-pentanoate

A stirred solution of methyl (E,Z)-3-(3-chloro-2-methoxyphenyl)-2-pentenoate (9 g, 35.43 mmol) in 500 ml of dry methanol is admixed with magnesium (2.10 g, 87.5 mmol) under nitrogen. The reaction mixture is stirred for two and a half hours for complete dissolution of the magnesium. During this time the temperature is held at 10° C. (ice bath). Subsequently the reaction mixture is poured into 300 ml of ice-cooled 3 N hydrochloric acid. The mixture is stirred vigorously in order to obtain a clear solution. The acidic solution is then treated with 3 N ammonium hydroxide in order to bring the pH to 8.5-9.0. Following extraction with diethyl ether (200, 200, 200 ml), the combined organic extracts are dried over sodium sulphate and filtered and the solvent is removed on a rotary evaporator. The pale yellow oil which remains is purified by flash chromatography on silica gel (eluent: toluene). This gives 7.2 g (80%) of the desired pure compound.

$^1$H-NMR (300 MHz, CDCl$_3$): δ=0.84 (3H), 1.45-1.89 (2H), 2.50-2.73 (2H), 3.43-3.69 (4H), 3.90 (3H), 6.93-7.12 (2H), 7.25 (1H).

3-(3-Chloro-2-methoxyphenyl)-2-pentanoic acid

A mixture of methyl 3-(3-chloro-2-methoxyphenyl)-2-pentanoate (7.2 g, 28.13 mmol) in 40 ml of methanol and potassium hydroxide (4.3 g) in 16 ml of water is heated at reflux under argon until ester is no longer present (~5 hours). The methanol is removed in vacuo and the mixture which remains is acidified with dilute hydrochloric acid to a pH of 1. Following extraction with diethyl ether (4×50 ml), the combined organic extracts are dried over sodium sulphate and filtered and the solvent is removed on a rotary evaporator. This leaves 6.5 g (95%) of the desired acid.

$^1$H-NMR (300 MHz, DMSO-d$_6$): δ=0.74 (3H), 1.32-1.79 (2H), 2.35-2.68 (2H, partly beneath the signal of the solvent), 3.30 (1H, beneath the water signal of the solvent), 3.78 (3H), 7.08 (1H), 7.12-7.38 (2H), 12.04 (1H).

4-(3-Chloro-2-methoxyphenyl)-1,1,1-trifluoro-2-hexanone

A solution of 3-(3-chloro-2-methoxyphenyl)-2-pentanoic acid (6.5 g, 26.86 mmol) in 50 ml of dichloromethane is admixed with oxalyl chloride (8.5 g) and the mixture is then stirred at room temperature for two hours. The solvent and the excess oxalyl chloride are stripped off under reduced pressure. The mixture obtained is cooled to −60° C. In succession, trifluoroacetic anhydride (50 g) and pyridine (10.5 g) are added. The batch is allowed to come slowly to −20° C. and is held at that temperature for four hours. Following the addition of 5 ml of water (slowly), the mixture is diluted with dichloromethane and the batch is washed with brine. After the washed batch has been dried over sodium sulphate, the solvent is removed on a rotary evaporator and the residue is chromatographed on silica gel (eluent toluene). This gives 4.9 g (62%) of the title compound.

$^1$H-NMR (300 MHz, CDCl$_3$): δ=0.88 (3H), 1.52-1.83 (2H), 3.00-3.10 (2H), 3.64 (1H), 3.95 (3H), 6.97-7.12 (2H), 7.29 (1H).

4-(3-Chloro-2-methoxyphenyl)-2-hydroxy-2-(trifluoromethyl)hexanal

A stirred solution of tosylmethyl isocyanide (3.8 g) and 4-(3-chloro-2-methoxyphenyl)-1,1,1-trifluoro-2-hexanone (4.9 g, 25 mmol) in absolute ethanol is admixed with thallium (I) ethoxide (5.2 g). After the mixture has been stirred for three hours at room temperature, the resulting solid is isolated by suction filtration. The filtrate is diluted with water and extracted with diethyl ether. After the organic phase has been dried and the solvent has been removed on a rotary evaporator, the crude 5-[2-(3-chloro-2-methoxyphenyl)butyl]-4-ethoxy-5-(trifluoromethyl)-4,5-dihydro-1,3-oxazole (yellow oil) is used without further purification in the next stage.

A solution of 5-[2-(3-chloro-2-methoxyphenyl)butyl]-4-ethoxy-5-(trifluoromethyl)-4,5-dihydro-1,3-oxazole in THF (30 ml) is admixed with 2N HCl (10 ml). The mixture is stirred at 50-60° C. overnight. Following dilution with water (150 ml) and extraction with diethyl ether, the combined organic extracts are washed with water and brine and then dried and the solvent is removed on a rotary evaporator. Flash chromatography on silica gel (eluent toluene) gives 2.7 g (50%) of the desired compound as a racemic mixture of the two diastereomers. The $^1$H-NMR spectrum below describes the signals for the mixture:

$^1$H-NMR (300 MHz, CDCl$_3$): δ=0.69-0.89 (together 3H), 1.45-1.90 (together 2H), 2.22-2.52 (2H), 3.02, 3.15 (together 1H), 3.87 (3H), 3.80, 4.10 (together 1H), 6.97-7.14 (together 2H), 7.20-7.32 (together 1H), 8.98, 9.72 (together 1H).

5-{[4-(3-Chloro-2-methoxyphenyl)-2-hydroxy-2-trifluoromethyl)hexylidene]-amino}-1H-quinolin-2-one 4-(3-Chloro-2-methoxyphenyl)-2-hydroxy-2-(trifluoromethyl)hexanal (500 mg, 1.54 mmol), 5-amino-1H-quinolin-2-one (246.6 mg, 1.54 mmol) and 2.3 ml of glacial acetic acid are stirred at room temperature for three days. The solvent is stripped off three times with toluene. The residue obtained is subsequently purified by chromatography (Flashmaster) (eluent hexane/ethyl acetate). This isolates 573.7 mg (79.8%) of the desired compound as a racemic diastereomer mixture.

5-{[4-(3-Chloro-2-methoxyphenyl)-2-hydroxy-2-trifluoromethyl)hexylidene]-amino}-1H-quinolin-2-one (410 mg, 0.88 mmol) is dissolved in 3.8 ml of dichloromethane and the solution is admixed dropwise at 0° C. with 8.78 ml of a 1M solution of boron tribromide in dichloromethane. After three hours of stirring at between 0 and 5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, different eluent systems) gives 15.1 mg (3.8%) of the apolar diastereomer and 62.9 mg (15.8%) of the polar diastereomer (characterization in Example 92) (in each case as a racemate).

Examples 91A and 91B

5-{[(1R,2S,4R)-6-Chloro-2,5-Dihydroxy-4-ethyl-2-(trifluoromethyl)-1,2,3,4-tetrahydronaphthalen-1-yl] amino}-1H-quinolin-2-one and 5-{[(1S,2R,4S)-chloro-2,5-dihydroxy-4-ethyl-2-(trifluoromethyl)-1,2,3,4-tetrahydronaphthalen-1-yl]amino}-1H-quinolin-2-one The apolar diastereomer (12 mg) described in Example 91 is separated into its enantiomers by means of chiral HPLC (Chiralpak IB 5μ, eluent: hexane/ethanol). This gives 5.8 mg (48.3%) of the (−)-enantiomer ([α]$_D$=−18.1°, MeOH) and 5.6 mg (46.7%) of the (+)-enantiomer ([α]$_D$=+16.8°, MeOH). No conclusion can of course be drawn concerning the absolute stereochemistry.

Example 92

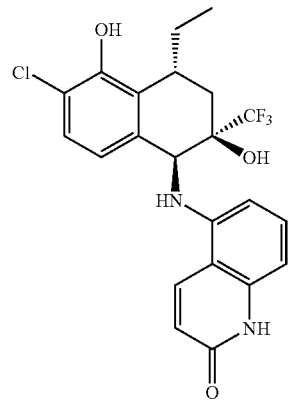

5-{[(1α,2α,4β)-6-Chloro-2,5-Dihydroxy-4-ethyl-2-(trifluoromethyl)-1,2,3,4-tetrahydronaphthalen-1-yl] amino}-1H-quinolin-2-one The synthesis of this compound was described in Example 91. 62.9 mg (15.8%) of the desired compound were isolated.

Examples 92A and 92B

5-{[(1R,2S,4S)-6-Chloro-2,5-Dihydroxy-4-ethyl-2-(trifluoromethyl)-1,2,3,4-tetrahydronaphthalen-1-yl] amino}-1H-quinolin-2-one and 5-{[(1S,2R,4R)-6-chloro-2,5-dihydroxy-4-ethyl-2-(trifluoromethyl)-1, 2,3,4-tetrahydronaphthalen-1-yl]amino}-1H-quinolin-2-one The polar diastereomer (58 mg) recited in Example 92 is separated into its enantiomers by means of chiral HPLC (Chiralpak AD-H 5μ, eluent: hexane/ethanol). This gives 28.1 mg (48.5%) of the (−)-enantiomer ([α]$_D$=−97.3°, MeOH) and 23.6 mg (40.7%) of the (+)-enantiomer ([α]$_D$=+110.2°, MeOH). No conclusion can of course be drawn concerning the absolute stereochemistry.

Example 93

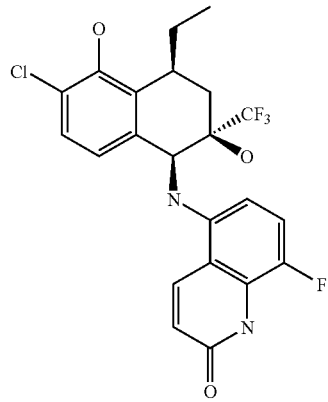

5-{[(1α,2α,4α)-6-Chloro-2,5-Dihydroxy-4-ethyl-2-(trifluoromethyl)-1,2,3,4-tetrahydronaphthalen-1-yl]amino}-8-fluoro-1H-quinolin-2-one 5-{[4-(3-Chloro-2-methoxyphenyl)-2-hydroxy-2-trifluoromethyl)hexylidene]-amino}-8-fluoro-1H-quinolin-2-one (490 mg, 1.01 mmol), prepared from the aldehyde described in Example 91 and 5-amino-8-fluoro-1H-quinolin-2-one, is dissolved in 4.4 ml of dichloromethane and the solution is admixed dropwise at 0° C. with 10.1 ml of a 1M solution of boron tribromide in dichloromethane. After three hours of stirring at between 0 and 5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, different eluent systems) gives 53.9 mg (11.3%) of the apolar diastereomer and 63 mg (13.2%) of the polar diastereomer (characterization is in Example 94) (in each case as a racemate).

Examples 93A and 93B

5-{[(1R,2S,4R)-6-Chloro-2,5-dihydroxy-4-ethyl-2-(trifluoromethyl)-1,2,3,4-tetrahydronaphthalen-1-yl]amino}-8-fluoro-1H-quinolin-2-one and 5-{[(1S,2R,4S)-6-chloro-2,5-dihydroxy-4-ethyl-2-(trifluoromethyl)-1,2,3,4-tetrahydronaphthalen-1-yl]amino}-8-fluoro-1H-quinolin-2-one The apolar diastereomer (41.2 mg) described in Example 93 is separated into its enantiomers by means of chiral HPLC (Chiralpak IB 5µ, eluent: hexane/ethanol). This gives 18 mg (43.7%) of the (−)-enantiomer ([α]$_D$=−21.2°, MeOH) and 18.7 mg (45.4%) of the (+)-enantiomer ([α]$_D$=+22.3°, MeOH). No conclusion can of course be drawn concerning the absolute stereochemistry.

Example 94

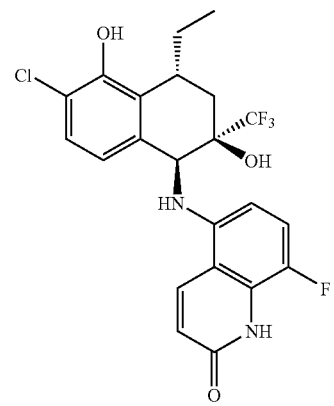

5-{[(1α,2α,4β)-6-Chloro-4-ethyl-2,5-dihydroxy-2-(trifluoromethyl)-1,2,3,4-tetrahydronaphthalen-1-yl]amino}-8-fluoro-1H-quinolin-2-one The synthesis of this compound was described in Example 93. 63 mg (13.2%) of the desired compound were isolated.

Examples 94A and 94B

5-{[(1R,2S,4S)-6-Chloro-4-ethyl-2,5-dihydroxy-2-(trifluoromethyl)-1,2,3,4-tetrahydronaphthalen-1-yl]amino}-8-fluoro-1H-quinolin-2-one and 5-{[(1S,2R,4R)-6-chloro-4-ethyl-2,5-dihydroxy-2-(trifluoromethyl)-1,2,3,4-tetrahydronaphthalen-1-yl]amino}-8-fluoro-1H-quinolin-2-one The polar diastereomer (53 mg) recited in Example 94 is separated into its enantiomers by means of chiral HPLC (Chiralpak IB 5µ, eluent: hexane/ethanol). This gives 22.7 mg (42.9%) of the (+)-enantiomer ([α]$_D$=−109.3°, MeOH) and 24.5 mg (46.3%) of the (−)-enantiomer ([α]$_D$=−111.8°, MeOH). No conclusion can of course be drawn concerning the absolute stereochemistry.

Example 95

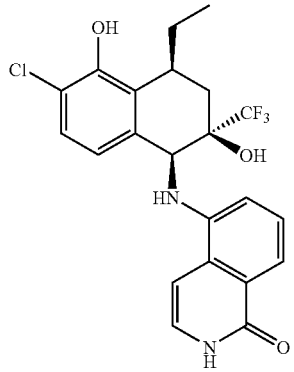

5-{[(1α,2α,4α)-6-Chloro-4-ethyl-2,5-dihydroxy-2-(trifluoromethyl)-1,2,3,4-tetrahydronaphthalen-1-yl]amino}-2H-quinolin-1-one 5-{[4-(3-Chloro-2-methoxyphenyl)-2-hydroxy-2-trifluoromethyl)hexylidene]-amino}-2H-quinolin-1-one (590 mg, 1.26 mmol), prepared from the aldehyde described in Example 91 and 5-amino-2H-quinolin-1-one, is dissolved in 5.5 ml of dichloromethane and the solution is admixed dropwise at 0° C. with 12.64 ml of a 1M solution of boron tribromide in dichloromethane. After three hours of stirring at between 0 and 5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, different eluent systems) gives 42.8 mg (7.5%) of the apolar diastereomer and 104.6 mg (18.3%) of the polar diastereomer (characterization is in Example 96) (in each case as a racemate).

Examples 95A and 95B

5-{[(1R,2S,4R)-6-Chloro-2,5-Dihydroxy-4-ethyl-2-(trifluoromethyl)-1,2,3,4-tetrahydronaphthalen-1-yl]amino}-2H-quinolin-1-one and 5-{[(1S,2R,4S)-6-chloro-2,5-Dihydroxy-4-ethyl-2-(trifluoromethyl)-1,2,3,4-tetrahydronaphthalen-1-yl]amino}-2H-quinolin-1-one The apolar diastereomer (34 mg) described in Example 95 is separated into its enantiomers by means of chiral HPLC (Chiralpak IA 5μ, eluent: hexane/ethanol). This gives 17.9 mg (52.7%) of the (+)-enantiomer ([α]$_D$=+103.0°, MeOH) and 14.2 mg (41.8%) of the (−)-enantiomer ([α]$_D$=−106.2°, MeOH). No conclusion can of course be drawn concerning the absolute stereochemistry.

Example 96

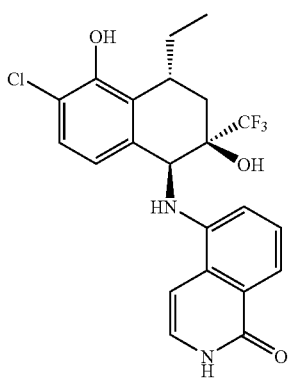

5-{[(1α,2α,4β)-6-Chloro-4-ethyl-2,5-dihydroxy-2-(trifluoromethyl)-1,2,3,4-tetrahydronaphthalen-1-yl]amino}-2H-quinolin-1-one The synthesis of this compound was described in Example 95. 104.6 mg (18.3%) of the desired compound were isolated.

Examples 96A and 96B

5-{[(1R,2S,4S)-6-Chloro-4-ethyl-2,5-dihydroxy-2-(trifluoromethyl)-1,2,3,4-tetrahydronaphthalen-1-yl]amino}-2H-quinolin-1-one and 5-{[(1S,2R,4R)-6-chloro-4-ethyl-2,5-dihydroxy-2-(trifluoromethyl)-1,2,3,4-tetrahydronaphthalen-1-yl]amino}-2H-quinolin-1-one The polar diastereomer (94.4 mg) recited in Example 96 is separated into its enantiomers by means of chiral HPLC (Chiralpak AD-H 5μ, eluent: hexane/ethanol). This gives 40.4 mg (42.8%) of the (−)-enantiomer ([α]$_D$=−14.2°, MeOH) and 48.6 mg (48.6%) of the (+)-enantiomer ([α]$_D$=+14.1°, MeOH). No conclusion can of course be drawn concerning the absolute stereochemistry.

Example 97

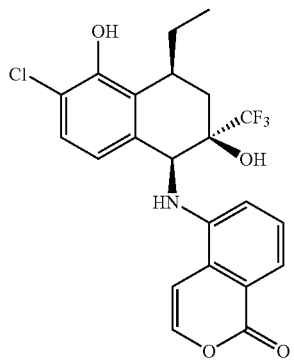

5-{[(1α,2α,4α)-6-Chloro-4-ethyl-2,5-dihydroxy-2-(trifluoromethyl)-1,2,3,4-tetrahydronaphthalen-1-yl]amino}isochromen-1-one 5-{[4-(3-Chloro-2-methoxyphenyl)-2-hydroxy-2-trifluoromethyl)hexylidene]-amino}isochromen-1-one (659 mg, 1.39 mmol), prepared from the aldehyde described in Example 91 and 5-aminoisochromen-1-one, is dissolved in 6.1 ml of dichloromethane and the solution is admixed dropwise at 0° C. with 13.89 ml of a 1M solution of boron tribromide in dichloromethane. After three hours of stirring at between 0 and 5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, different eluent systems) gives 56.6 mg (9%) of the apolar diastereomer and 214.1 mg (34%) of the polar diastereomer (characterization is in Example 98) (in each case as a racemate).

Examples 97A and 97B

5-{[(1R,2S,4R)-6-Chloro-2,5-dihydroxy-4-ethyl-2-(trifluoromethyl)-1,2,3,4-tetrahydronaphthalen-1-yl]amino}isochromen-1-one and 5-{[(1S,2R,4S)-6-chloro-2,5-dihydroxy-4-ethyl-2-(trifluoromethyl)-1,2,3,4-tetrahydronaphthalen-1-yl]amino}isochromen-1-one The apolar diastereomer (42 mg) described in Example 97 is separated into its enantiomers by means of chiral HPLC (Chiralpak IA 5µ, eluent: hexane/ethanol). This gives 18.4 mg (43.8%) of the (+)-enantiomer ([α]$_D$=+104.2°, MeOH) and 11.8 mg (28.1%) of the (−)-enantiomer ([α]$_D$=−101.3°, MeOH). No conclusion can of course be drawn concerning the absolute stereochemistry.

Example 98

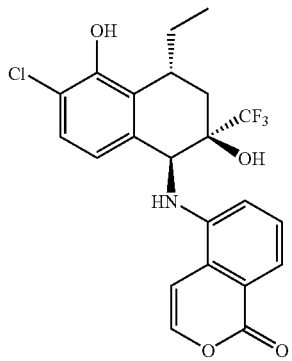

5-{[(1α,2α,4β)-6-Chloro-4-ethyl-2,5-dihydroxy-2-(trifluoromethyl)-1,2,3,4-tetrahydronaphthalen-1-yl]amino}isochromen-1-one The synthesis of this compound was described in Example 97. 214.1 mg (34%) of the desired compound were isolated.

Examples 98A and 98B

5-{[(1R,2S,4S)-6-Chloro-4-ethyl-2,5-dihydroxy-2-(trifluoromethyl)-1,2,3,4-tetrahydronaphthalen-1-yl]amino}isochromen-1-one and 5-{[(1S,2R,4R)-6-chloro-4-ethyl-2,5-dihydroxy-4-2-(trifluoromethyl)-1,2,3,4-tetrahydronaphthalen-1-yl]amino}isochromen-1-one The polar diastereomer (189 mg) recited in Example 98 is separated into its enantiomers by means of chiral HPLC (Chiralpak IA 5µ, eluent: hexane/ethanol). This gives 87.6 mg (46.4%) of the (−)-enantiomer ([α]$_D$=−25.4°, MeOH) and 86.9 mg (46.0%) of the (+)-enantiomer ([α]$_D$=+29.4°, MeOH). No conclusion can of course be drawn concerning the absolute stereochemistry.

Example 99

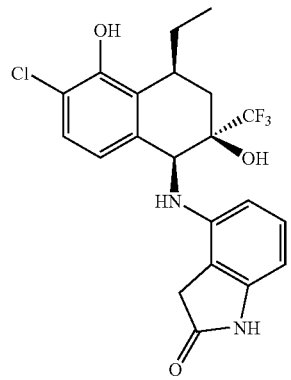

4-{[(1α,2α,4α)-6-Chloro-4-ethyl-2,5-dihydroxy-2-(trifluoromethyl)-1,2,3,4-tetrahydronaphthalen-1-yl]amino}-1,3-dihydroindol-2-one 5-{[4-(3-Chloro-2-methoxyphenyl)-2-hydroxy-2-trifluoromethyl)hexylidene]-amino}-1,3-dihydroindol-2-one (535 mg, 1.18 mmol), prepared in analogy to described processes, using the aldehyde described in Example 91 and 4-amino-1,3-dihydroindol-2-one, is dissolved in 5.1 ml of dichloromethane and the solution is admixed dropwise at 0° C. with 11.76 ml of a 1M solution of boron tribromide in dichloromethane. After three hours of stirring at 5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Chromatography on silica gel (eluent: dichloromethane/methanol) gives 32.6 mg (6.3%) of the apolar diastereomer and 125.5 mg (24.2%) of the polar diastereomer, both as racemates. The characterization of the polar diastereomer is described in Example 100.

Examples 99A and 99B

4-{[(1R,2S,4R)-6-Chloro-2,5-Dihydroxy-4-ethyl-2-(trifluoromethyl)-1,2,3,4-tetrahydronaphthalen-1-yl]amino}-1,3-dihydroindol-2-one 4-{[(1S,2R,4S)-6-chloro-2,5-dihydroxy-4-ethyl-2-(trifluoromethyl)-1,2,3,4-tetrahydronaphthalen-1-yl]amino}-1,3-dihydroindol-2-one The apolar diastereomer (25.2 mg) described in Example 99 is separated into its enantiomers by means of chiral HPLC (Chiralpak IB 5µ, eluent: hexane/ethanol). This gives 7.8 mg (31%) of the one enantiomer (retention time: 10.3-12.5 minutes) and 7.1 mg (28.2%) of the other enantiomer (retention time: 13-16.3 minutes). It was not possible to record an optical rotation, because the solutions had a green colouration. No conclusion can of course be drawn concerning the absolute stereochemistry.

Example 100

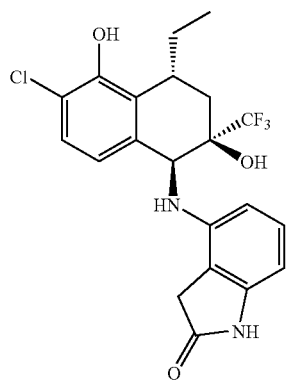

4-{[(1α,2α,4β)-6-Chloro-4-ethyl-2,5-dihydroxy-2-(trifluoromethyl)-1,2,3,4-tetrahydronaphthalen-1-yl]amino}-1,3-dihydroindol-2-one The synthesis of this compound was described in Example 99. 125.5 mg (24.2%) of the desired compound were isolated.

Examples 100A and 100B

4-{[(1R,2S,4S)-6-Chloro-2,5-dihydroxy-4-ethyl-2-(trifluoromethyl)-1,2,3,4-tetrahydronaphthalen-1-yl]amino}-1,3-dihydroindol-2-one and 4-{[(1S,2R,4R)-6-chloro-2,5-dihydroxy-4-ethyl-2-(trifluoromethyl)-1,2,3,4-tetrahydronaphthalen-1-yl]amino}-1,3-dihydroindol-2-one The polar diastereomer (115.6 mg) recited in Example 100 is separated into its enantiomers by means of chiral HPLC (Chiralpak IB 5μ, eluent: hexane/ethanol). This gives 46.8 mg (40.5%) of the (+)-enantiomer ([α]$_D$=+110.8°, MeOH) and 54.6 mg (47.2%) of the (−)-enantiomer ([α]$_D$=−84.70, MeOH). The strongly differing optical rotations can be explained by the difference in colouration between the measurement solutions. No conclusion can of course be drawn concerning the absolute stereochemistry.

Example 101

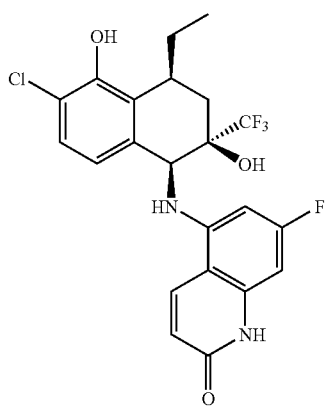

5-{[(1α,2α,4α)-6-Chloro-2,5-Dihydroxy-4-ethyl-2-(trifluoromethyl)-1,2,3,4-tetrahydronaphthalen-1-yl]amino}-7-fluoro-1H-quinolin-2-one 5-{[4-(3-Chloro-2-methoxyphenyl)-2-hydroxy-2-trifluoromethyl)hexylidene]-amino}-7-fluoro-1H-quinolin-2-one (490 mg, 1.01 mmol), prepared from the aldehyde described in Example 91 and 5-amino-7-fluoro-1H-quinolin-2-one, is dissolved in 8 ml of dichloromethane and the solution is admixed dropwise at −50° C. with 8.06 ml of a 1M solution of boron tribromide in dichloromethane (over the course of 20 minutes). After three hours of stirring at −40° C., two hours at between −40 and 0° C., one hour between 0° C. and room temperature, and 18 hours at room temperature, the batch is poured onto a mixture of saturated sodium hydrogen carbonate solution and ice, diluted with 150 ml of ethyl acetate and then stirred vigorously for 20 minutes. The ethyl acetate phase is separated off and the aqueous phase is extracted a further time with ethyl acetate (100 ml). The combined organic extracts are washed twice with water (40 ml each time) and once with brine (40 ml) and dried and the solvent is removed on a rotary evaporator. Chromatography on silica gel (eluent: dichloromethane/methanol) gives in one fraction 235.6 mg (62.1%) and in a further fraction 86.9 mg (22.9%) of the desired compounds, in each case as a diastereomer mixture differing in composition. The diastereomers (fraction with the 235.6 mg) are separated by means of HPLC (XBridge C 18 5μ, eluent: water/acetonitrile). This gives 112.4 mg (29.6%) of the desired compound and 70.1 mg (18.5%) of the compound which is epimeric in position 4 (characterization is in Example 102), in each case as a racemate.

Examples 101A and 101B

5-{[(1R,2S,4R)-6-Chloro-2,5-dihydroxy-4-ethyl-2-(trifluoromethyl)-1,2,3,4-tetrahydronaphthalen-1-yl]amino}-7-fluoro-1H-quinolin-2-one and 5-{[(1S,2R,4S)-6-chloro-2,5-Dihydroxy-4-ethyl-2-(trifluoromethyl)-1,2,3,4-tetrahydronaphthalen-1-yl]amino}-7-fluoro-1H-quinolin-2-one The diastereomer (111 mg) described in Example 101 is separated into its enantiomers by means of chiral HPLC (Chiralpak IB 5μ, eluent: hexane/ethanol). This gives 52.5 mg (31%) of the (−)-enantiomer ([α]$_D$=−33.4°, MeOH) and 50.6 mg (45.6%) of the (+)-enantiomer ([α]$_D$=+35.7°, MeOH). No conclusion can of course be drawn concerning the absolute stereochemistry.

Example 102

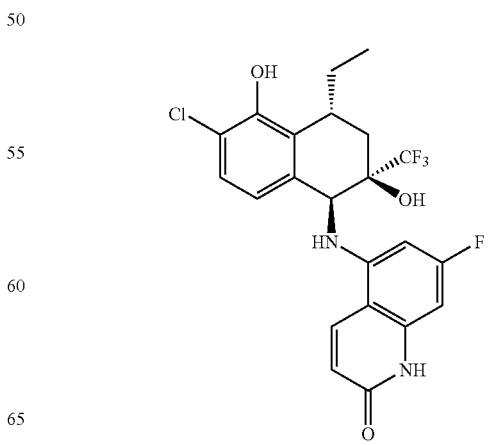

5-{[(1α,2α,4β)-6-Chloro-2,5-dihydroxy-4-ethyl-2-(trifluoromethyl)-1,2,3,4-tetrahydronaphthalen-1-yl]amino}-7-fluoro-1H-quinolin-2-one The synthesis of this compound was described in Example 101. 70.1 mg (18.5%) of the desired compound were isolated.

Examples 102A and 102B (1R,2S,4S)-5-{[6-Chloro-4-ethyl-2,5-dihydroxy-2-(trifluoromethyl)-1,2,3,4-tetrahydronaphthalen-1-yl]amino}-7-fluoro-1H-quinolin-2-one and 5-{[(1S,2R,4R)-6-chloro-4-ethyl-2,5-dihydroxy-2-(trifluoromethyl)-1,2,3,4-tetrahydronaphthalen-1-yl]amino}-7-fluoro-1H-quinolin-2-one The diastereomer (120 mg) described in Example 102 is separated into its enantiomers by means of chiral HPLC (Chiralpak IB 5μ, eluent: hexane/ethanol). This gives 53.3 mg (44.3%) of the (+)-enantiomer ([α]$_D$=+78.20, MeOH) and 52.7 mg (43.8%) of the (−)-enantiomer ([α]$_D$=−79.3°, MeOH). No conclusion can of course be drawn concerning the absolute stereochemistry.

Example 103

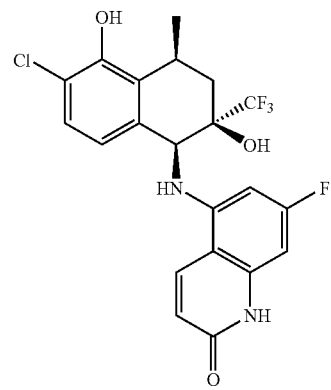

5-{[(1α,2α,4α)-6-Chloro-2,5-dihydroxy-4-methyl-2-(trifluoromethyl)-1,2,3,4-tetrahydronaphthalen-1-yl]amino}-7-fluoro-1H-quinolin-2-one 5-{[4-(3-Chloro-2-methoxyphenyl)-2-hydroxy-2-trifluoromethyl)pentylidene]-amino}-7-fluoro-1H-quinolin-2-one (382 mg, 0.81 mmol), prepared from the corresponding aldehyde and 5-amino-7-fluoro-1H-quinolin-2-one, is dissolved in 8.1 ml of dichloromethane and the solution is admixed dropwise at −50° C. with 8.1 ml of a 1M solution of boron tribromide in dichloromethane (over the course of 20 minutes). After three hours of stirring at −40° C., two hours at between −40 and 0° C., one hour between 0° C. and room temperature, and 18 hours at room temperature, the batch is poured onto a mixture of saturated sodium hydrogen carbonate solution and ice, diluted with 150 ml of ethyl acetate and then stirred vigorously for 20 minutes. The ethyl acetate phase is separated off and the aqueous phase is extracted a further time with ethyl acetate (100 ml). The combined organic extracts are washed twice with water (40 ml each time) and once with brine (40 ml) and dried and the solvent is removed on a rotary evaporator. Chromatography on the Flashmaster (eluent: dichloromethane/methanol) gives 330.7 mg of a diastereomer mixture which consists of the desired compound and of the compound which is epimeric in position 4. The diastereomers are separated by means of HPLC (Chiralpak AD-H 5μ, eluent: hexane/ethanol). This gives 191.8 mg (51.8%) of the desired compound and 95.9 mg (24.9%) of the compound which is epimeric in position 4 (characterization is in Example 104), in each case as a racemate.

Examples 103A and 103B

5-{[(1R,2S,4R)-6-Chloro-2,5-dihydroxy-4-methyl-2-(trifluoromethyl)-1,2,3,4-tetrahydronaphthalen-1-yl]amino}-7-fluoro-1H-quinolin-2-one and 5-{[(1S,2R,4S)-6-chloro-2,5-Dihydroxy-4-methyl-2-(trifluoromethyl)-1,2,3,4-tetrahydronaphthalen-1-yl]amino}-7-fluoro-1H-quinolin-2-one The diastereomer (160 mg) described in Example 103 is separated into its enantiomers by means of chiral HPLC (Chiralcel OD-H, eluent: hexane/ethanol). This gives 81 mg (50.6%) of the (+)-enantiomer ([α]$_D$=+25.80, MeOH) and 79.6 mg (49.8%) of the (−)-enantiomer ([α]$_D$=−28.4°, MeOH). No conclusion can of course be drawn concerning the absolute stereochemistry.

Example 104

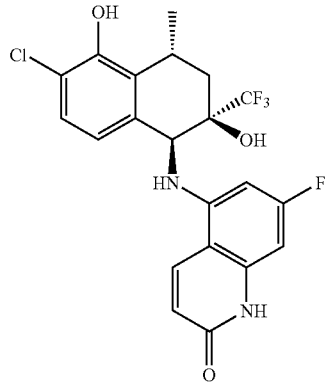

5-{[(1α,2α,4β)-6-Chloro-2,5-dihydroxy-4-methyl-2-(trifluoromethyl)-1,2,3,4-tetrahydronaphthalen-1-yl]amino}-7-fluoro-1H-quinolin-2-one The synthesis of this compound was described in Example 103. 95.9 mg (24.9%) of the desired compound were isolated.

Examples 104A and 104B

5-{[(1R,2S,4S)-6-Chloro-2,5-Dihydroxy-4-methyl-2-(trifluoromethyl)-1,2,3,4-tetrahydronaphthalen-1-yl]amino}-7-fluoro-1H-quinolin-2-one and 5-{[(1S,2R,4R)-6-chloro-2,5-dihydroxy-4-methyl-2-(trifluoromethyl)-1,2,3,4-tetrahydronaphthalen-1-yl]amino}-7-fluoro-1H-quinolin-2-one The diastereomer (80 mg) described in Example 104 is separated into its enantiomers by means of chiral HPLC (Chiralcel OD-H 5μ, eluent: hexane/ethanol). This gives 40.1 mg (50.1%) of the (+)-enantiomer ([α]$_D$=+70.20, MeOH) and 39.2 mg (49%) of the (−)-enantiomer ([α]$_D$=−67.2°, MeOH). No conclusion can of course be drawn concerning the absolute stereochemistry.

Example 106

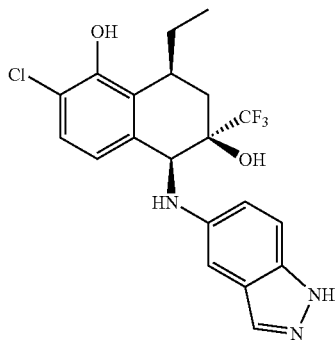

(5α,6α,8α)-2-Chloro-8-ethyl-5-[(indazol-5-yl)
amino]-6-(trifluoromethyl)-5,6,7,8-tetrahydronaph-
thalene-1,6-diol 1,1,1-Trifluoro-2-[(indazol-5-ylimino)methyl]-4-(3-chloro-2-methoxyphenyl)hexan-2-ol (760 mg, 1.73 mmol), prepared from the corresponding aldehyde and 5-aminoindazole, are dissolved in 7.6 ml of dichloromethane and the solution is admixed dropwise at −50° C. with 17.28 ml of a 1M solution of boron tribromide in dichloromethane (over the course of 20 minutes). After three hours of stirring at −40° C., two hours at between −40° C. and 0° C., one hour between 0° C. and room temperature, and 18 hours at room temperature, the batch is poured onto a mixture of saturated sodium hydrogen carbonate solution and ice, diluted with 150 ml of ethyl acetate and then stirred vigorously for 20 minutes. The ethyl acetate phase is separated off and the aqueous phase is extracted a further time with ethyl acetate (100 ml). The combined organic extracts are washed twice with water (40 ml each time) and once with brine (40 ml) and dried and the solvent is removed on a rotary evaporator. Repeated chromatography on the Flashmaster (eluent: dichloromethane/methanol) gives 74.3 mg (10.1%) of the desired compound and 236.4 mg (32.1%) of the compound which is epimeric in position 4 (in each case as a racemate). The latter compound is characterized in Example 107.

$^1$H-NMR (400 MHz, CD$_3$OD): δ=1.06 (3H), 1.86 (1H), 1.95-2.11 (2H), 2.32 (1H), 3.05 (1H), 4.80 (1H), 6.75 (1H), 6.95-7.07 (3H), 7.32 (1H), 7.80 (1H).

Example 107

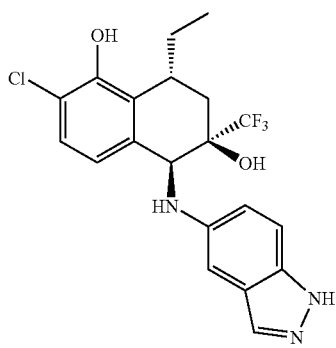

(5α,6α,8β)-2-Chloro-8-ethyl-5-[(indazol-5-yl)
amino]-6-(trifluoromethyl)-5,6,7,8-tetrahydronaph-
thalene-1,6-diol The synthesis of the compound was described in Example 106. The amount obtained was 236.4 mg (32.1%).

$^1$H-NMR (400 MHz, CD$_3$OD): δ=0.92 (3H), 1.73 (1H), 1.87-2.051 (2H), 2.32 (1H), 3.33 (1H), 4.80 (1H), 6.75 (1H), 6.91 (2H), 7.06 (1H), 7.34 (1H), 7.74 (1H).

Example 108

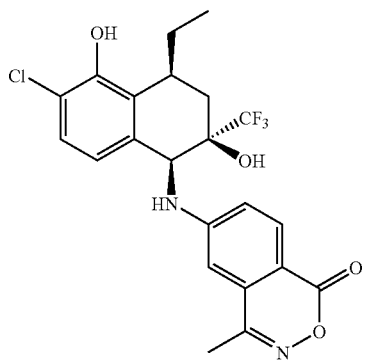

6-{[(1α,2α,4α)-6-Chloro-2,5-dihydroxy-4-ethyl-2-
(trifluoromethyl)-12,3,4-tetrahydronaphthalen-1-yl]
amino}-4-methylbenzo[d][1,2]oxazin-1-one 6-{[4-(3-Chloro-2-methoxyphenyl)-2-hydroxy-2-trifluoromethyl)hexylidene]-amino}4-methylbenzo[d][1,2]oxazin-1-one (170 mg, 0.35 mmol), prepared from the aldehyde described in Example 91 and 6-amino-4-methylbenzo[d][1,2]-oxazin-1-one, are dissolved in 3.5 ml of dichloromethane and the solution is admixed dropwise at −50° C. with 3.52 ml of a 1M solution of boron tribromide in dichloromethane (over the course of 20 minutes). After two hours of stirring at −40° C., one hour at between −40° C. and −20° C., one hour between −20° C. and −10° C., and one hour at between −10 and 0° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed twice with water (20 ml each time) and once with brine (20 ml) and dried and the solvent is removed on a rotary evaporator. Chromatography on the Flashmaster (Isolute NH$_2$, eluent: dichloromethane/methanol) gives 10.2 mg (6.2%) of the desired compound (slightly contaminated) and 26.4 mg (16%) of the compound which is epimeric in position 4 (in each case as a racemate). The latter compound is characterized in Example 109.

$^1$H-NMR (300 MHz, CD$_3$OD): δ=1.13 (3H), 1.75-2.28 (3H), 2.38 (1H), 2.49 (1H), 3.11 (1H), 5.24 (1H), 6.78 (1H), 7.06 (1H), 7.15 (1H), 7.30 (1H), 8.05 (1H).

Example 109

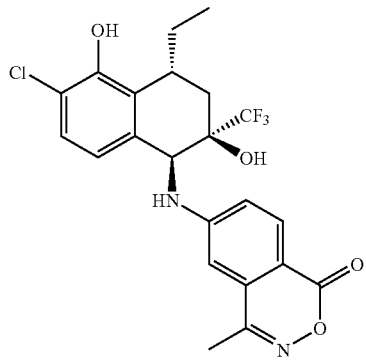

6-{[(1α,2α,4β)-6-Chloro-2,5-Dihydroxy-4-ethyl-2-(trifluoromethyl)-1,2,3,4-tetrahydronaphthalen-1-yl]amino}-4-methylbenzo[d][1,2]oxazin-1-one The synthesis of the compound was described in Example 108. The amount obtained was 26.4 mg (16%).

$^1$H-NMR (300 MHz, CD$_3$OD): δ=0.99 (3H), 1.78 (1H), 1.98-2.15 (2H), 2.36-2.51 (4H), 3.37 (1H, lying partly beneath the solvent signal), 5.22 (1H), 6.81 (1H), 7.02 (1H), 7.15 (1H), 7.25 (1H), 8.08 (1H).

Example 110

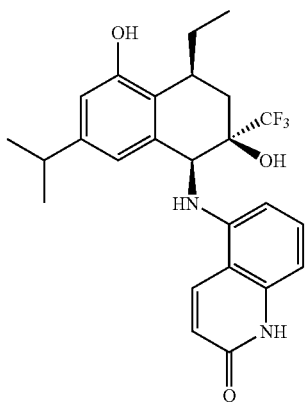

5-{[(1α,2α,4α)-7-isopropyl-2,5-Dihydroxy-4-ethyl-2-(trifluoromethyl)-1,2,3,4-tetrahydronaphthalen-1-yl]amino}-1H-quinolin-2-one (3-Isopropylphenyl)acetate 3-Isopropylphenol (40 g, 293.7 mmol) is dissolved in 287 ml of dichloromethane. At room temperature pyridine (32.17 ml, 399.43 mmol) is added. In the course of this addition, the temperature rises to 29° C. After 15-minute stirring the reaction mixture is cooled to 10-15° C. and acetyl chloride (26.2 ml, 367.13 mmol) is added dropwise over the course of 20 minutes. After overnight stirring the reaction mixture is poured onto a mixture of 190 ml of 2N HCl and ice. After 20-minute stirring the organic phase is separated off and the aqueous phase is extracted with 500 ml of dichloromethane. The combined organic extracts are washed with brine and dried over Na$_2$SO$_4$. Following the removal of the solvent on a rotary evaporator, the residue is purified by chromatography on silica gel (eluent: ethyl acetate/hexane). This isolates 48.45 g (92.6%) of the desired ester.

1H-NMR (400 MHz, CDCl$_3$): δ=1.27 (6H), 2.30 (3H), 2.91 (1H), 6.89-6.97 (2H), 7.10 (1H), 7.30 (1H).

4'-Isopropyl-2'-hydroxyacetophenone

Aluminum trichloride (35.16 g, 263.68 mmol) is introduced in 110 ml of 1,2-dichlorobenzene. Added dropwise to this mixture over the course of 15 minutes is (3-isopropylphenyl) acetate (48.45 g, 271.84 mmol) in 94 ml of 1,2-dichlorobenzene. In the course of this addition, the temperature rises to 40° C. After 17-hour stirring at 100° C. the reaction mixture is cooled and poured onto a mixture of 230 ml of 4N HCl and ice. Following extraction with diethyl ether (three times 300 ml), the combined organic extracts are washed with brine and dried over Na$_2$SO$_4$. The solvent is removed on a rotary evaporator and the residue is chromatographed on silica gel (eluent: ethyl acetate/hexane). The yield is 84.6% (41 g).

1H-NMR (300 MHz, CDCl$_3$): δ=1.27 (6H), 2.60 (3H), 2.90 (1H), 6.78 (1H), 6.85 (1H), 7.65 (1H).

4'-Isopropyl-2'-methoxyacetophenone

4'-isopropyl-2'-hydroxyacetophenone (33.4 g, 187.4 mmol) is dissolved in acetone (233 ml). Following addition of K$_2$CO$_3$ (51.8 g, 374.8 mmol) and methyl iodide (23.33 ml, 374.8 mmol) the batch is heated at reflux for three days. The reaction mixture is cooled and filtered through a glass fibre filter and the residue is washed with cold acetone. The solvent is removed and the residue is chromatographed (silica gel, eluent: ethyl acetate/hexane). This isolates 31.85 g (88.4%) of the desired compound.

1H-NMR (400 MHz, CDCl$_3$): δ=1.27 (6H), 2.60 (3H), 2.93 (1H), 3.93 (3H), 6.81 (1H), 6.88 (1H), 7.72 (1H).

4-Isopropyl-2-methoxy-1-(1-methylpropenyl)benzene

Ethyltriphenylphosphonium bromide (67.49 g, 181.79 mmol) is introduced in 675 ml of tetrahydrofuran. This white suspension is admixed over the course of 30 minutes with potassium hexamethyldisilazide (363.57 ml of a 0.5 M solution in toluene, 181.79 mmol), at a temperature between −5° C. and 0° C. The resulting red suspension is then stirred at room temperature for two and a half hours. Following dropwise addition (35 minutes) of 4'-isopropyl-2'-methoxyacetophenone (23.3 g, 121.19 mmol), in solution in 280 ml of tetrahydrofuran, the temperature rises to 29° C. The orange-brown reaction mixture is stirred at room temperature for four days. The batch is poured into 100 ml of water and admixed with ethyl acetate (250 ml). After 10-minute stirring, the organic phase is separated off and washed with water (40 ml) and brine (40 ml). After drying (Na$_2$SO$_4$) and removal of the solvent on a rotary evaporator, the residue is chromatographed on silica gel (eluent: ethyl acetate/hexane). This isolates more than 100% (26.44 g) of the product as an E/Z mixture, although one of the stereoisomers is predominant.

1H-NMR (300 MHz, CDCl$_3$): δ=1.29 (6H), 1.50 (3H), 2.00 (3H), 2.92 (1H), 3.82 (3H), 5.60 (1H), 6.73-6.85 (2H), 6.97 (1H).

Ethyl 4-(4-isopropyl-2-methoxyphenyl)-2-hydroxy-2-(trifluoromethyl)-hex-4-enoate Ytterbium(III) trifluoromethanesulphonate (3.25 g, 5.23 mmol) in 116 ml of dichloromethane is admixed dropwise at room temperature with ethyl trifluoropyruvate (9.55 ml, 78.5 mmol). Following the addition of 4-isopropyl-2-methoxy-1-(1-methylpropenyl)benzene (10.7 g, 52.37 mmol), in solution in 29.5 ml of dichloromethane, the reaction mixture is stirred at room temperature for two days. In parallel a second batch is carried out with the same quantities and under the same conditions. Water (100 ml) is added to each of the two reactions. For further working up, the two batches are combined. The dichloromethane phase is separated off and the aqueous phase is extracted a further time with dichloromethane (300 ml). The combined organic extracts are washed with water (100 ml) and brine (100 ml) and then dried ($Na_2SO_4$). After removal of the solvent on a rotary evaporator, the residue is purified by repeated chromatography on silica gel (eluent: ethyl acetate/hexane). The yield of ene product, which is used in the next stage, is 9.08 g, only 40% being the described compound and 60% being the corresponding ethyl 4-(4-isopropyl-2-methoxyphenyl)-2-hydroxy-3-methyl-2-(trifluoromethyl)pent-4-enoate.

4-(4-isopropyl-2-methoxyphenyl)-2-hydroxy-2-(trifluoromethyl)hex-4-en-1-ol

The above-described mixture of ethyl 4-(4-isopropyl-2-methoxyphenyl)-2-hydroxy-2-(trifluoromethyl)hexen-4-enoat and ethyl 4-(4-isopropyl-2-methoxyphenyl)-2-hydroxy-3-methyl-2-(trifluoromethyl)pent-4-enoate (9.05 g, 24.18 mmol) is dissolved in diethyl ether (235 ml). Lithium aluminum hydride (1.83 g, 48.34 mmol) is added in portions over the course of 30 minutes at 5° C. The reaction mixture is stirred at room temperature for two and a half hours. Saturated sodium hydrogen carbonate solution (12 ml) is added dropwise with ice cooling. Following removal of the ice bath, the reaction mixture is stirred vigorously at room temperature for two hours. The precipitate is filtered off with suction on a glass fibre filter and the residue is washed with diethyl ether (200 ml). The organic phase is washed twice with brine (50 ml each time) and then dried ($Na_2SO_4$). Chromatography on silica gel (eluent: ethyl acetate/hexane) gives 5.62 g (69.9%) of a mixture of 4-(4-isopropyl-2-methoxyphenyl)-2-hydroxy-2-(trifluoromethyl)hex-4-en-1-ol and 4-(4-isopropyl-2-methoxyphenyl)-2-hydroxy-3-methyl-2-(trifluoromethyl)pent-4-en-1-ol (ratio 25:75) and 2.22 g (27.6%) of a further mixture (ratio 65:35).

4-(4-Isopropyl-2-methoxyphenyl)-2-hydroxy-2-(trifluoromethyl)hexan-1-ol

The mixture of 4-(4-isopropyl-2-methoxyphenyl)-2-hydroxy-2-(trifluoromethyl)-hex-4-en-1-ol and 4-(4-isopropyl-2-methoxyphenyl)-2-hydroxy-3-methyl-2-(trifluoromethyl)pent-4-en-1-ol (4.6 g, 13.84 mmol) is dissolved in ethanol (100 ml). Following addition of 10% Pd/carbon (0.7 g) hydrogen is introduced into the reaction mixture for four hours via a balloon. The catalyst is filtered off with suction (glass fibre filter) and the precipitate is washed with ethanol. Following removal of the solvent on a rotary evaporator, the residue (4.59 g, 99.2%) is used in crude form in the next step. It consists of a mixture of 4-(4-isopropyl-2-methoxyphenyl)-2-hydroxy-2-(trifluoromethyl)hexan-1-ol and 4-(4-isopropyl-2-methoxyphenyl)-2-hydroxy-3-methyl-2-(trifluoromethyl)pentan-1-ol (ratio 30:70).

4-(4-Isopropyl-2-methoxyphenyl)-2-hydroxy-2-(trifluoromethyl)hexanal

The above-described mixture of 4-(4-isopropyl-2-methoxyphenyl)-2-hydroxy-2-(trifluoromethyl)hexan-1-ol and 4-(4-isopropyl-2-methoxyphenyl)-2-hydroxy-3-methyl-2-(trifluoromethyl)pentan-1-ol (5.35 g, 16 mmol) is dissolved in dichloromethane (164 ml). Following addition of dimethyl sulphoxide (54.8 ml) and triethylamine (11.1 ml) the $SO_3$/pyridine complex (6.37 g, 40 mmol) is added in portions over the course of 40 minutes. After four-hour stirring at room temperature, the batch is poured onto a mixture of saturated $NH_4Cl$ solution and ice. The mixture is extracted twice with diethyl ether (250 ml each time) and the combined extracts are washed twice with brine (50 ml each time). Following removal of the solvent by evaporation, the residue is chromatographed on silica gel (eluent: hexane/diethyl ether). This isolates 3.05 g (57%) of a mixture of the two aldehydes, 4-(4-isopropyl-2-methoxyphenyl)-2-hydroxy-2-(trifluoromethyl)-hexanal and 4-(4-isopropyl-2-methoxyphenyl)-2-hydroxy-3-methyl-2-(trifluoromethyl)pentanal.

5-{([4-(4-Isopropyl-2-methoxyphenyl)-2-hydroxy-2-trifluoromethyl)hexylidene]-amino}-1H-quinolin-2-one The mixture of 4-(4-isopropyl-2-methoxyphenyl)-2-hydroxy-2-(trifluoromethyl)-hexanal and 4-(4-isopropyl-2-methoxyphenyl)-2-hydroxy-3-methyl-2-(trifluoromethyl) pentanal (600 mg, 1.8 mmol), 5-amino-1H-quinolin-2-one (287.4 mg, 1.79 mmol) and 2.67 ml of acetic acid are stirred at room temperature for 3 days. The reaction mixture is stripped three times with toluene and the residue is chromatographed on (Flashmaster, eluent: ethyl acetate/hexane). This isolates 732.8 mg (86.1%) of the desired imine, in the form of a mixture of 5-{[4-(4-isopropyl-2-methoxyphenyl)-2-hydroxy-2-(trifluoromethyl)hexylidene]amino}-1H-quinolin-2-one and 5-{[4-(4-isopropyl-2-methoxyphenyl)-2-hydroxy-3-methyl-2-(trifluoromethyl)pentylidene]amino}-1H-quinolin-2-one.

The mixture of 5-{[4-(4-isopropyl-2-methoxyphenyl)-2-hydroxy-2-trifluoromethyl)hexylidene]amino}-1H-quinolin-2-one and 5-{[4-(4-isopropyl-2-methoxyphenyl)-2-hydroxy-3-methyl-2-trifluoromethyl)pentylidene]amino}-1H-quinolin-2-one (580 mg, 1.22 mmol) is dissolved in 5.6 ml of dichloromethane and is admixed dropwise at −10° C. with 12.22 ml of a 1M solution of boron tribromide in dichloromethane. After stirring for three and a half hours in the temperature range between −10 and +5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, dichloromethane/methanol) gives 17.2 mg (6.11%) of the desired compound.

1H-NMR (300 MHz, CD$_3$OD): δ=0.98-1.12 (9H), 1.87 (1H), 1.95-2.15 (2H), 2.36 (1H), 2.59 (1H), 2.94 (1H), 5.04 (1H), 6.45 (1H), 6.51-6.74 (4H), 7.34 (1H), 8.18 (1H).

Example 111

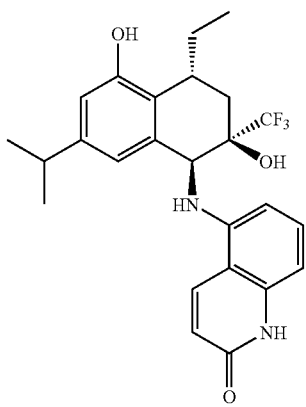

5-{[(1α,2α,4β)-7-isopropyl-2,5-dihydroxy-4-ethyl-2-(trifluoromethyl)-1,2,3,4-tetrahydronaphthalen-1-yl]amino}-1H-quinolin-2-one 5-{[4-(4-Isopropyl-2-methoxyphenyl)-2-hydroxy-2-trifluoromethyl)hexylidene]-amino}-1H-quinolin-2-one The mixture of 4-(4-isopropyl-2-methoxyphenyl)-2-hydroxy-2-(trifluoromethyl)-hexanal and 4-(4-isopropyl-2-methoxyphenyl)-2-hydroxy-3-methyl-2-(trifluoromethyl)-pentanal (600 mg, 1.8 mmol), 5-amino-1H-quinolin-2-one (287.4 mg, 1.79 mmol) and 2.67 ml of acetic acid are stirred at room temperature for 11 days. The reaction mixture is stripped three times with toluene and the residue is chromatographed (Flashmaster, eluent: ethyl acetate/hexane). This isolates 554.1 mg (65.1%) of the desired imine, as a mixture of 5-{[4-(4-isopropyl-2-methoxyphenyl)-2-hydroxy-2-trifluoromethyl)hexylidene]amino}-1H-quinolin-2-one and 5-{[4-(4-isopropyl-2-methoxyphenyl)-2-hydroxy-3-methyl-2-trifluoromethyl)pentylidene]amino}-1H-quinolin-2-one.

The mixture of 5-{[4-(4-isopropyl-2-methoxyphenyl)-2-hydroxy-2-trifluoromethyl)hexylidene]amino}-1H-quinolin-2-one and 5-{[4-(4-isopropyl-2-methoxyphenyl)-2-hydroxy-3-methyl-2-trifluoromethyl)pentylidene]amino}-1H-quinolin-2-one (554.1 mg, 1.16 mmol) is dissolved in 5.1 ml of dichloromethane and admixed dropwise at –20° C. with 11.68 ml of a 1M solution of boron tribromide in dichloromethane. After stirring for three and a half hours in the temperature range between –20 and 0° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, different eluent systems) gives 30.1 mg (11.25%) of the desired compound.

1H-NMR (300 MHz, CD$_3$OD): δ=0.91 (3H), 1.00-1.09 (6H), 1.69 (1H), 1.88-2.04 (2H), 2.33 (1H), 2.62 (1H), 3.24 (1H, lying partly beneath the solvent signal), 4.99 (1H), 6.44-6.51 (2H), 6.58 (1H), 6.60-6.70 (2H), 7.32 (1H), 8.20 (1H).

Example 112

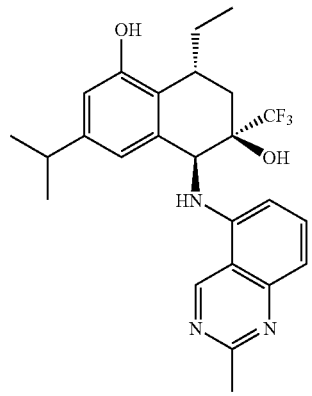

(5α,6α,8β)-8-Ethyl-3-isopropyl-5-[2-methylquinazolin-5-ylamino]-6-(trifluoromethyl)-5,6,7,8-tetrahydronaphthalene-1,6-diol The mixture of 1,1,1-trifluoro-2-[(2-methylquinazolin-5-ylimino)-methyl-]-4-(4-isopropyl-2-methoxyphenyl)hexan-2-ol and 1,1,1-trifluoro-3-methyl-2-[(2-methylquinazolin-5-ylimino)methyl-]-4-(4-isopropyl-2-methoxyphenyl)pentan-2-ol (558.2 mg, 1.18 mmol), prepared from the mixture of aldehydes described in Example 110 and 5-amino-2-methylquinazoline is dissolved in 5.1 ml of dichloromethane and admixed dropwise at –20° C. with 11.79 ml of a 1M solution of boron tribromide in dichloromethane. After stirring for three and a half hours in the temperature range between –20 and +5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography (Flashmaster, different phases, eluent: dichloromethane/methanol) gives 30.5 mg (11.3%) of the desired compound.

1H-NMR (400 MHz, CD$_3$OD): δ=0.92 (3H), 1.00-1.08 (6H), 1.70 (1H), 1.91-2.08 (2H), 2.38 (1H), 2.60 (1H), 3.29 (1H, lying partly beneath the solvent signal), 5.12 (1H), 6.55-6.65 (2H), 6.78 (1H), 7.13 (1H), 7.74 (1H), 9.59 (1H).

Example 113

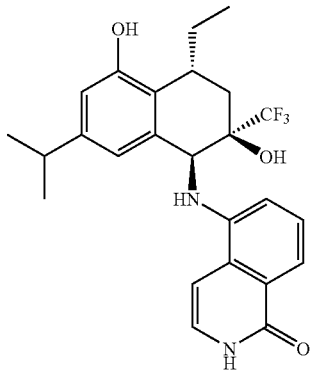

5-{[(1α,2α,4β)-7-isopropyl-2,5-Dihydroxy-4-ethyl-2-(trifluoromethyl)-1,2,3,4-tetrahydronaphthalen-1-yl]amino}-2H-quinolin-1-one The mixture of 5-{[4-(4-isopropyl-2-methoxyphenyl)-2-hydroxy-2-trifluoromethyl)hexylidene]amino}-2H-quinolin-1-one and 5-{[4-(4-isopropyl-2-methoxyphenyl)-2-hydroxy-3-methyl-2-trifluoromethyl)pentylidene]amino}-2H-quinolin-1-one (500.8 mg, 1.06 mmol), prepared from the mixture of aldehydes described in Example 110 and 5-amino-2H-quinolin-1-one is dissolved in 4.6 ml of dichloromethane and admixed dropwise at −20° C. with 10.6 ml of a 1M solution of boron tribromide in dichloromethane. After stirring for three and a half hours in the temperature range between −20 and +50° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Chromatography on the Flashmaster (NH$_2$ phase, eluent: dichloromethane/methanol) gives 29.1 mg (12%) of the desired compound.

1H-NMR (300 MHz, CD$_3$OD): δ=0.91 (3H), 0.96-1.08 (6H), 1.69 (1H), 1.91-2.04 (2H), 2.33 (1H), 2.60 (1H), 3.25 (1H, lying partly beneath the solvent signal), 4.98 (1H), 6.58 (1H), 6.62 (1H), 6.81-6.93 (2H), 7.13 (1H), 7.32 (1H), 7.62 (1H).

Example 114

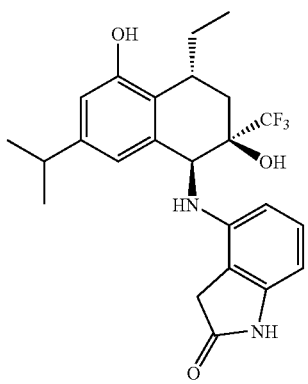

4-{[(1α,2α,4β)-7-isopropyl-2,5-Dihydroxy-4-ethyl-2-(trifluoromethyl)-1,2,3,4-tetrahydronaphthalen-1-yl]amino}-1,3-dihydroindol-2-one The mixture of 5-{[4-(4-isopropyl-2-methoxyphenyl)-2-hydroxy-2-trifluoromethyl)hexylidene]amino}-1,3-dihydroindol-2-one and 5-{[4-(4-isopropyl-2-methoxyphenyl)-2-hydroxy-3-methyl-2-trifluoromethyl)pentylidene]amino}-1,3-dihydroindol-2-one (578.6 mg, 1.26 mmol), prepared from the mixture of aldehydes described in Example 110 and 4-amino-1,3-dihydroindol-2-one is dissolved in 5.5 ml of dichloromethane and admixed dropwise at −20° C. with 12.5 ml of a 1M solution of boron tribromide in dichloromethane. After stirring for three and a half hours in the temperature range between −20 and +5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Chromatography on the Flashmaster (NH$_2$ phase, eluent: dichloromethane/methanol) gives 38.6 mg (13.8%) of the desired compound.

1H-NMR (400 MHz, CD$_3$OD): δ=0.90 (3H), 1.03-1.11 (6H), 1.68 (1H), 1.83-2.00 (2H), 2.30 (1H), 2.65 (1H), 3.19-3.40 (3H, lying partly beneath the water signal), 4.89 (1H), 6.29 (1H), 6.35 (1H), 6.55 (1H), 6.69 (1H), 7.03 (1H).

Example 115

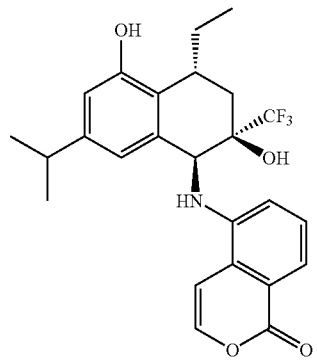

5-{[(1α,2α,4β)-7-isopropyl-2,5-Dihydroxy-4-ethyl-2-(trifluoromethyl)-1,2,3,4-tetrahydronaphthalen-1-yl]amino}-isochromen-1-one The mixture of 5-{[4-(4-isopropyl-2-methoxyphenyl)-2-hydroxy-2-trifluoromethyl)hexylidene]amino}-isochromen-1-one and 5-{[4-(4-isopropyl-2-methoxyphenyl)-2-hydroxy-3-methyl-2-trifluoromethyl)pentylidene]amino}-isochromen-1-one (678.4 mg, 1.42 mmol), prepared from the mixture of aldehydes described in Example 110 and 5-aminoisochromen-1-one is dissolved in 6.22 ml of dichloromethane and admixed dropwise at −20° C. with 14.3 ml of a 1M solution of boron tribromide in dichloromethane. After stirring for three and a half hours in the temperature range between −20 and +5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography on the Flashmaster (NH$_2$ phase, eluent: dichloromethane/methanol) gives 9.2 mg (2.8%) of the desired compound.

1H-NMR (400 MHz, CD$_3$OD): δ=0.91 (3H), 0.98-1.11 (6H), 1.67 (1H), 1.99-2.05 (2H), 2.32 (1H), 2.62 (1H), 3.25 (1H, lying partly beneath the solvent signal), 4.97 (1H), 6.56-6.62 (2H), 6.87 (1H), 7.02 (1H), 7.31-7.45 (2H), 7.58 (1H).

Example 116

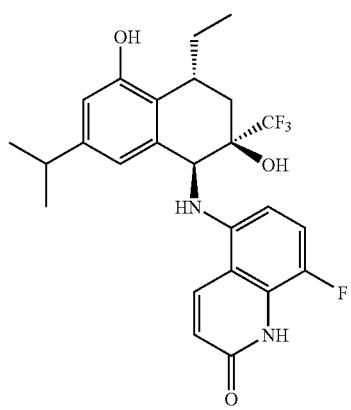

5-{[(1α,2α,4β)-7-isopropyl-2,5-dihydroxy-4-ethyl-2-(trifluoromethyl)-1,2,3,4-tetrahydronaphthalen-1-yl]amino}-8-fluoro-1H-quinolin-2-one The mixture of 5-{[4-(4-isopropyl-2-methoxyphenyl)-2-hydroxy-2-trifluoromethyl)hexylidene]amino}-8-fluoro-1H-quinolin-2-one and 5-{[4-(4-isopropyl-2-methoxyphenyl)-2-hydroxy-3-methyl-2-trifluoromethyl)pentylidene]amino}-8-fluoro-1H-quinolin-2-one (680 mg, 1.38 mmol), prepared from the mixture of aldehydes described in Example 110 and 5-amino-8-fluoro-1H-quinolin-2-one is dissolved in 6.8 ml of dichloromethane and admixed dropwise at −10° C. with 13.81 ml of a 1M solution of boron tribromide in dichloromethane. After stirring for three and a half hours in the temperature range between −10 and +5° C., the batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed with water (20 ml) and brine (20 ml) and dried and the solvent is removed on a rotary evaporator. Repeated chromatography including HPLC (different phases, different eluents) gives 31 mg (9.4%) of the desired compound and 9.9 mg (3%) of the compound which is epimeric in position 4 (characterization is in Example 117).

1H-NMR (300 MHz, CD$_3$OD): δ=0.91 (3H), 1.00-1.10 (6H), 1.68 (1H), 1.88-2.03 (2H), 2.32 (1H), 2.62 (1H), 3.25 (1H, lying partly beneath the solvent signal), 4.92 (1H), 6.39 (1H), 6.49-6.63 (3H), 7.19 (1H), 8.19 (1H).

Example 117

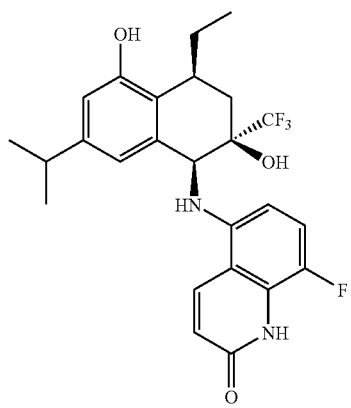

5-{[(1α,2α,4β)-7-isopropyl-2,5-Dihydroxy-4-ethyl-2-(trifluoromethyl)-1,2,3,4-tetrahydronaphthalen-1-yl]amino}-8-fluoro-1H-quinolin-2-one The synthesis of the compound was described in Example 116. 9.9 mg (3%) of the desired compound are obtained.

1H-NMR (300 MHz, CD$_3$OD): δ=1.05-1.18 (9H), 1.91 (1H), 2.04-2.20 (2H), 2.40 (1H), 2.67 (1H), 2.99 (1H), 4.99 (1H), 6.50-6.69 (4H), 7.28 (1H), 8.20 (1H).

Example 118

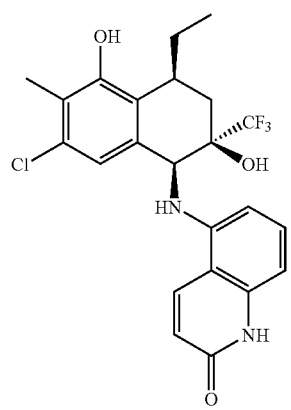

5-{[(1α,2α,4α)-7-chloro-2,5-Dihydroxy-4-ethyl-6-methyl-2-(trifluoromethyl)-1,2,3,4-tetrahydronaphthalen-1-yl]amino}-1H-quinolin-2-one 4-(4-Chloro-3-methyl-2-methoxyphenyl)-2-hydroxy-2-(trifluoromethyl)hexanal 1 g (2.93 mmol) of 4-(4-chloro-3-methyl-2-methoxyphenyl)-2-(trifluoromethyl)-hexane-1,2-diol (prepared in analogy to the sequence described in Example 110: acetylation of the corresponding phenol, Fries displacement of the acetyl group, etherification of the phenol, Wittig reaction, ene reaction, reduction of the ester to the alcohol) is reacted conventionally with SO$_3$/pyridine complex. After three-hour stirring at room temperature the reaction mixture is poured onto a mixture of saturated NH$_4$Cl solution and ice. It is extracted three times with methyl tert-butyl ether. The combined organic extracts are washed twice with brine and dried (Na$_2$SO$_4$). Following removal of the solvent on a rotary evaporator, the residue is purified by means of flash chromatography (silica gel, eluent: hexane/ethyl acetate). This gives 290 mg (29.2%) of the desired aldehyde as a mixture of the two diastereomers (in each case as a racemate).

5-{[4-(4-Chloro-3-methyl-2-methoxyphenyl)-2-hydroxy-2-(trifluoromethyl)hexylidene]amino}-1H-quinolin-2-one 4-(4-Chloro-3-methyl-2-methoxyphenyl)-2-hydroxy-2-(trifluoromethyl)hexanal (290 mg, 0.86 mmol), 5-amino-1H-quinolin-2-one (137.4 mg, 0.86 mmol) and 3 ml of acetic acid are stirred at room temperature for two days. The reaction mixture is stripped twice with toluene and dichloromethane and the residue is chromatographed (Flashmaster, eluent: dichloromethane/methanol). This isolates 327.8 mg (79.5%) of the desired imine, 5-{[4-(4-chloro-3-methyl-2-methoxyphenyl)-2-hydroxy-2-trifluoromethyl)hexylidene]amino}-1H-quinolin-2-one, as a mixture of the two diastereomers (in each case as a racemate).

The imine described in the preceding section, 5-{[4-(4-chloro-3-methyl-2-methoxyphenyl)-2-hydroxy-2-trifluoromethyl)hexylidene]amino}-1H-quinolin-2-one (327.8 mg, (0.68 mmol)), is introduced in 3.2 ml of dichloromethane and this initial charge is admixed dropwise at −40° C. with 6.82 ml of a 1 M solution of $BBr_3$ in dichloromethane. After three hours of stirring in the temperature range between −40 and +10° C. there is no longer any starting material present. The reaction mixture is poured cautiously onto a mixture of saturated $NaHCO_3$ solution and ice and is extracted three times with ethyl acetate. The combined organic extracts are washed with brine and dried over $Na_2SO_4$ and the residue, following removal of the solvent on a rotary evaporator, is chromatographed. Repeated chromatography (various systems, eluent: dichloromethane/methanol) isolates 9.3 mg (2.9%) of the desired compound (contaminated) and 39.2 mg (12.3%) of the compound which is epimeric in position 4 (see Example 119).

1H-NMR (300 MHz, $CD_3OD$): δ =1.08 (3H), 1.85-2.10 (3H), 2.22 (3H), 2.40 (1H), 3.01 (1H), 5.08 (1H), 6.48 (1H), 6.59 (1H), 6.68 (1H), 6.82 (1H), 7.38 (1H), 8.19 (1H).

Example 119

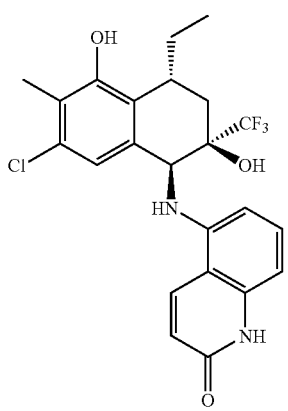

5-{[(1α,2α,4β)-7-Chloro-2,5-Dihydroxy-4-ethyl-6-methyl-2-(trifluoromethyl)-1,2,3,4-tetrahydronaphthalen-1-yl]amino}-1H-quinolin-2-one 39.2 mg (12.3%) of the compound identified in the title were obtained (see Example 118) in the form of a racemate. Racemate cleavage is described in the following example.

Examples 119A and 119B

5-{[(1R,2S,4S)-7-Chloro-2,5-Dihydroxy-6-methyl-4-ethyl-2-(trifluoromethyl)-1,2,3,4-tetrahydronaphthalen-1-yl]amino}-1H-quinolin-2-one and 5-{[(1S,2R,4R)-7-chloro-2,5-dihydroxy-6-methyl-4-ethyl-2-(trifluoromethyl)-1,2,3,4-tetrahydronaphthalen-1-yl]amino}-1H-quinolin-2-one The compound recited in Example 119 (104 mg) is separated into its enantiomers by means of chiral HPLC (Chiralpak IA 5μ, eluent: hexane/ethanol). This gives 43.2 mg (41.5%) of one enantiomer (retention time: 10.5-12.7 minutes) and 40.7 mg (45.2%) of the other enantiomer (retention time: 15.1-18 minutes). No conclusion can of course be drawn concerning the absolute stereochemistry.

Example 120

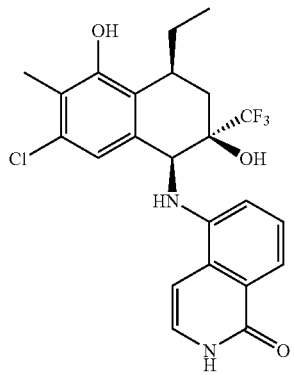

5-{[(1α,2α,4α)-7-Chloro-2,5-Dihydroxy-6-methyl-4-ethyl-2-(trifluoromethyl)-1,2,3,4-tetrahydronaphthalen-1-yl]amino}-2H-quinolin-1-one 5-{[4-(4-Chloro-3-methyl-2-methoxyphenyl)-2-hydroxy-2-trifluoromethyl)hexylidene]amino}-2H-quinolin-1-one (366 mg, 0.76 mmol), prepared from the aldehyde described in Example 118 and 5-amino-2H-quinolin-1-one, is dissolved in 3.7 ml of dichloromethane and this initial charge is admixed dropwise at −40° C. with 7.62 ml of a 1M solution of boron tribromide in dichloromethane. After three hours of stirring in the temperature range between −40 and +10° C. there is no longer any starting material present. The reaction mixture is poured cautiously onto a mixture of saturated $NaHCO_3$ solution and ice and is extracted three times with ethyl acetate. The combined organic extracts are washed with brine and dried over $Na_2SO_4$ and the residue, following removal of the solvent on a rotary evaporator, is chromatographed repeatedly. This isolates 10.5 mg (3%) of the desired compound (slightly contaminated) and 12.7 mg (3.6%) of the compound which is epimeric in position 4 (see Example 121).

1H-NMR (300 MHz, $CD_3OD$): δ =1.09 (3H), 1.82-2.11 (3H), 2.22 (3H), 2.39 (1H), 3.02 (1H), 5.03 (1H), 6.79-6.83 (2H), 7.07 (1H), 7.13 (1H), 7.38 (1H), 7.69 (1H).

Example 121

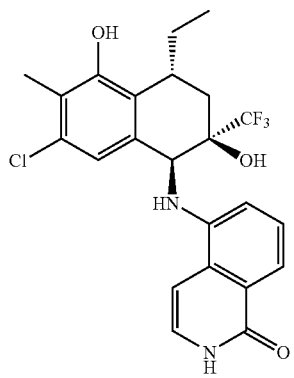

5-{[(1α,2α,4β)-7-Chloro-2,5-Dihydroxy-6-methyl-4-ethyl-2-(trifluoromethyl)-1,2,3,4-tetrahydronaphthalen-1-yl]amino}-2H-quinolin-1-one 12.7 mg (3.6%) of the compound identified in the title were obtained (see Example 120) in the form of a racemate. Racemate cleavage is described in the following example.

Examples 121A and 121B

5-{[(1R,2S,4S)-7-Chloro-2,5-Dihydroxy-6-methyl-4-ethyl-2-(trifluoromethyl)-1,2,3,4-tetrahydronaphthalen-1-yl]amino}-2H-quinolin-1-one and 5-{[(1S,2R,4R)-7-chloro-2,5-Dihydroxy-6-methyl-4-ethyl-2-(trifluoromethyl)-1,2,3,4-tetrahydronaphthalen-1-yl]amino}-2H-quinolin-1-one The compound recited in Example 121 (64 mg) is separated into its enantiomers by means of chiral HPLC (Chiralpak IA 5µ, eluent: hexane/ethanol). This gives 28.1 mg (43.9%) of one enantiomer (retention time: 13.8-16 minutes) and 33.3 mg (52%) of the other enantiomer (retention time: 16-20 minutes; still contains 13.6% of a contaminating impurity and 1.6% of the enantiomer having the shorter retention time). No conclusion can of course be drawn concerning the absolute stereochemistry.

Example 122

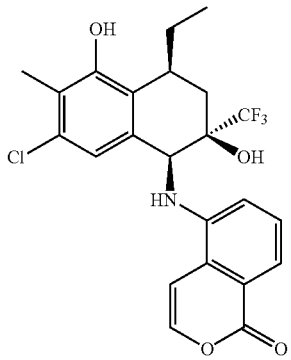

5-{[(1α,2α,4α)-7-Chloro-2,5-Dihydroxy-6-methyl-4-ethyl-2-(trifluoromethyl)-1,2,3,4-tetrahydronaphthalen-1-yl]amino}isochromen-1-one 5-{[4-(4-Chloro-3-methyl-2-methoxyphenyl)-2-hydroxy-2-trifluoromethyl)hexylidene]amino}isochromen-1-one (408.6 mg, 0.85 mmol), prepared from the aldehyde described in Example 118 and 5-aminoisochromen-1-one, is dissolved in 4 ml of dichloromethane and the solution is admixed dropwise at –40° C. with 8.5 ml of a 1M solution of boron tribromide in dichloromethane. After stirring for three hours in the temperature range between –40 and +10° C. there is no longer any starting material present. The reaction mixture is poured cautiously onto a mixture of saturated NaHCO₃ solution and ice and is extracted three times with ethyl acetate. The combined organic extracts are washed with brine and dried over Na₂SO₄ and the residue, following removal of the solvent on a rotary evaporator, is chromatographed repeatedly. This isolates 20.7 mg (5.2%) of the title compound (contaminated).

1H-NMR (300 MHz, CD₃OD): δ=1.08 (3H), 1.80-2.12 (3H), 2.22 (3H), 2.49 (1H), 3.03 (1H), 5.03 (1H), 6.65 (1H), 6.83 (1H), 7.18 (1H), 7.30-7.45 (2H), 7.58 (1H).

Example 123

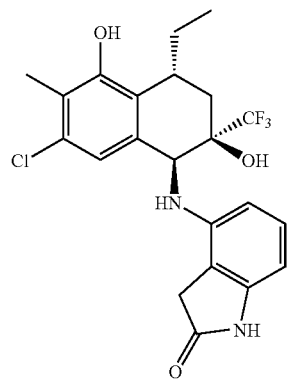

4-{[(1α,2α,4β)-7-Chloro-2,5-dihydroxy-6-methyl-4-ethyl-2-(trifluoromethyl)-1,2,3,4-tetrahydronaphthalen-1-yl]amino}-1,3-dihydroindol-2-one 5-{[4-(4-Chloro-3-methyl-2-methoxyphenyl)-2-hydroxy-2-trifluoromethyl)hexylidene]amino}1,3-dihydroindol-2-one (295.8 mg, 0.63 mmol), prepared from the aldehyde described in Example 118 and 5-amino-1,3-dihydroindol-2-one, is dissolved in 3 ml of dichloromethane and the solution is admixed dropwise at –40° C. with 6.3 ml of a 1M solution of boron tribromide in dichloromethane. After stirring for three hours in the temperature range between –40 and +10° C. there is no longer any starting material present. The reaction mixture is poured cautiously onto a mixture of saturated NaHCO₃ solution and ice and is extracted three times with ethyl acetate. The combined organic extracts are washed with brine and dried over Na₂SO₄ and the residue, following removal of the solvent on a rotary evaporator, is chromatographed repeatedly. This isolates 19.1 mg (6.6%) of the title compound.

1H-NMR (300 MHz, CD₃OD): δ=0.90 (3H), 1.69 (1H), 1.80-2.00 (2H), 2.22 (3H), 2.30 (1H), 3.25-3.43 (3H, the signals lying partly beneath the solvent signal), 4.89 (1H), 6.28-6.32 (2H), 6.89 (1H), 7.05 (1H).

Example 124

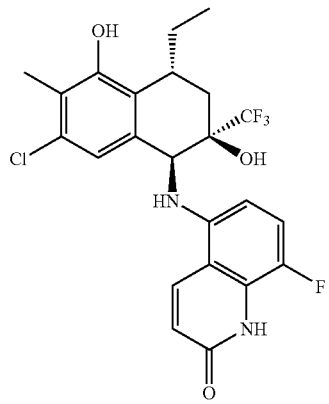

5-{[(1α,2α,4β)-7-Chloro-2,5-Dihydroxy-4-ethyl-6-methyl-2-(trifluoromethyl)-1,2,3,4-tetrahydronaphthalen-1-yl]amino}-8-fluoro-1H-quinolin-2-one 5-{[4-(4-Chloro-3-methyl-2-methoxyphenyl)-2-hydroxy-2-trifluoromethyl)hexylidene]amino}-8-fluoro-1H-quinolin-2-one (628.8 mg, 1.26 mmol), prepared from the aldehyde described in Example 118 and 5-amino-8-fluoro-1H-quinolin-2-one, is dissolved in 7.3 ml of dichloromethane and the solution is admixed dropwise at −40° C. with 12.6 ml of a 1M solution of boron tribromide in dichloromethane. After stirring for three hours in the temperature range between −40 and +10° C. there is no longer any starting material present. The reaction mixture is poured cautiously onto a mixture of saturated NaHCO₃ solution and ice and is extracted three times with ethyl acetate. The combined organic extracts are washed with brine and dried over Na₂SO₄ and the residue, following removal of the solvent on a rotary evaporator, is chromatographed twice (Flashmaster, eluent: dichloromethane/methanol. This isolates 52.8 mg (8.6%) of the desired compound.

Examples 124A and 124B

5-{[(1R,2S,4S)-7-Chloro-2,5-Dihydroxy-4-ethyl-6-methyl-2-(trifluoromethyl)-1,2,3,4-tetrahydronaphthalen-1-yl]amino}-8-fluoro-1H-quinolin-2-one and 5-{[(1S,2R,4R)-7-chloro-2,5-Dihydroxy-4-ethyl-6-methyl-2-(trifluoromethyl)-1,2,3,4-tetrahydronaphthalen-1-yl]amino}-8-fluoro-1H-quinolin-2-one The compound recited in Example 124 (35.4 mg) is separated into its enantiomers by means of chiral HPLC (Chiralpak IA 5μ, eluent: hexane/ethanol). This gives 14.5 mg (41%) of one enantiomer (retention time: 9.1-10.4 minutes) and 17.5 mg (49.4%) of the other enantiomer (retention time: 10.9-13.2 minutes). No conclusion can of course be drawn concerning the absolute stereochemistry.

Example 125

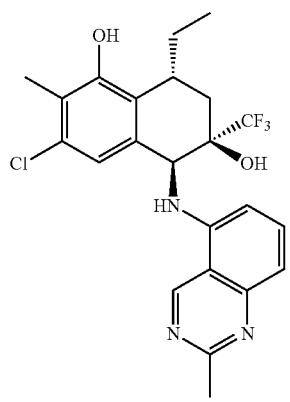

(5α,6α,8β)-3-Chloro-8-ethyl-2-methyl-5-[2-methylquinazolin-5-ylamino]-6-(trifluoromethyl)-5,6,7,8-tetrahydronaphthalene-1,6-diol 1,1,1-Trifluoro-2-[(2-methylquinazolin-5-ylimino)methyl-]-4-(4-chloro-3-methyl-2-methoxyphenyl)hexan-2-ol (353.1 mg, 0.74 mmol), prepared from the aldehyde described in Example 118 and 5-amino-2-methylquinazoline is dissolved in 3.6 ml of dichloromethane and admixed dropwise at −20° C. with 7.36 ml of a 1M solution of boron tribromide in dichloromethane. After stirring for three and a half hours in the temperature range between −20 and +5° C., the batch is poured onto a mixture of saturated sodium hydrogen carbonate solution and ice and is extracted three times with ethyl acetate. The combined organic extracts are washed with brine and dried (Na₂SO₄) and the solvent is removed on a rotary evaporator. Repeated chromatography (Flashmaster, different phases, eluent: dichloromethane/methanol) gives 34.6 mg (10.1%) of the desired compound.

1H-NMR (300 MHz, CD₃OD): δ = 0.95 (3H), 1.70 (1H), 1.85-2.07 (2H), 2.23 (3H), 2.38 (1H), 3.35 (1H, the signal lying partly beneath the solvent signal), 5.09 (1H), 6.76 (1H), 6.82 (1H), 7.18 (1H), 7.78 (1H), 9.59 (1H).

Example 126

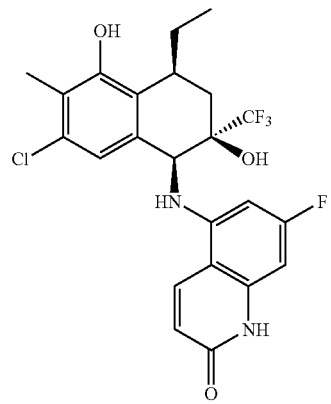

5-{[(1α,2α,4α)-7-Chloro-2,5-Dihydroxy-4-ethyl-6-methyl-2-(trifluoromethyl)-1,2,3,4-tetrahydronaphthalen-1-yl]amino}-7-fluoro-1H-quinolin-2-one 5-{[4-(4-Chloro-3-methyl-2-methoxyphenyl)-2-hydroxy-2-trifluoromethyl)hexylidene]amino}-7-fluoro-1H-quinolin-2-one (367.3 mg (0.74 mmol), prepared from the aldehyde described in Example 118 and 5-amino-7-fluoro-1H-quinolin-2-one, is introduced in 8 ml of dichloromethane and admixed dropwise at −40° C. with 7.36 ml of a 1M solution of BBr₃ in dichloromethane. After three hours of stirring at −40° C. the reaction is allowed to come slowly up to room temperature. After overnight stirring at room temperature the reaction mixture is poured cautiously onto a mixture of saturated NaHCO₃ solution and ice and is extracted three times with ethyl acetate. The combined organic extracts are washed with brine and dried over Na₂SO₄ and the residue, following removal of the solvent on a rotary evaporator, is chromatographed (Flashmaster, eluent: dichloromethane/methanol). This isolates 304.9 mg (85.4%), in the form of a mixture of the desired compound with the compound which is epimeric in position 4. 100 mg of this mixture are separated by HPLC (Kromasil NH₂ 5μ, eluent: hexane/ethanol). This gives 28.7 mg (27.3%) of the title compound and 38.7 mg (36.9%) of the compound which is epimeric in position 4 (Example 127).

Examples 126A and 126B

5-{[(1R,2S,4R)-7-Chloro-2,5-Dihydroxy-4-ethyl-6-methyl-2-(trifluoromethyl)-1,2,3,4-tetrahydronaphthalen-1-yl]amino}-7-fluoro-1H-quinolin-2-one and 5-{[(1S,2R,4S)-7-chloro-2,5-Dihydroxy-4-ethyl-6-methyl-2-(trifluoromethyl)-1,2,3,4-tetrahydronaphthalen-1-yl]amino}-7-fluoro-1H-quinolin-2-one The racemic compound recited in Example 126 (17.2 mg) is separated into its enantiomers by means of chiral HPLC (Chiralpak AD-H 5μ, eluent: hexane/ethanol). This gives 5.3 mg (31.2%) of one enantiomer (retention time: 8.8-11.5 minutes) and 5.0 mg (29.4%) of the other enantiomer (retention time: 13.7-15.8 minutes). No conclusion can of course be drawn concerning the absolute stereochemistry.

Example 127

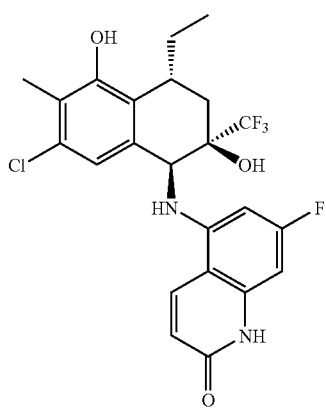

5-{[(1α,2α,4β)-7-Chloro-2,5-dihydroxy-4-ethyl-6-methyl-2-(trifluoromethyl)-1,2,3,4-tetrahydronaphthalen-1-yl]amino}-7-fluoro-1H-quinolin-2-one 38.7 mg (36.9%) of the compound identified in the title were obtained (see Example 126) in the form of a racemate. Racemate cleavage is described in the following example.

Examples 127A and 127B

5-{[(1R,2S,4S)-7-Chloro-2,5-dihydroxy-4-ethyl-6-methyl-2-(trifluoromethyl)-1,2,3,4-tetrahydronaphthalen-1-yl]amino}-7-fluoro-1H-quinolin-2-one and 5-{[(1S,2R,4R)-7-chloro-2,5-dihydroxy-4-ethyl-6-methyl-2-(trifluoromethyl)-1,2,3,4-tetrahydronaphthalen-1-yl]amino}-7-fluoro-1H-quinolin-2-one 27.2 mg of the compound recited in Example 127 are separated into its enantiomers by means of chiral HPLC (Chiralpak IA 5μ, eluent: hexane/ethanol). This gives 7.7 mg (28.3%) of one enantiomer (retention time: 11.2-14.5 minutes) and 10.4 mg (38.2%) of the other enantiomer (retention time: 14.5-17.9 minutes). No conclusion can of course be drawn concerning the absolute stereochemistry.

Example 128

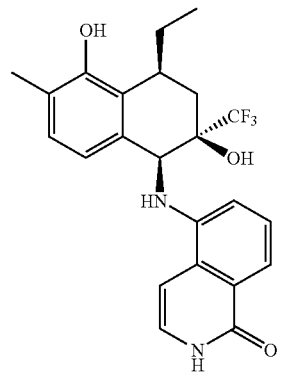

5-{[(1α,2α,4α)-4-Ethyl-2,5-dihydroxy-6-methyl-2-(trifluoromethyl)-1,2,3,4-tetrahydronaphthalen-1-yl]amino}-2H-quinolin-1-one 5-{[4-(4-Chloro-3-methyl-2-methoxyphenyl)-2-hydroxy-2-trifluoromethyl)-hexylidene]amino}-2H-quinolin-1-one (366.5 mg, 0.76 mmol), prepared from the aldehyde described in Example 118 and 5-amino-2H-quinolin-1-one, is introduced in 3.7 ml of dichloromethane and this initial charge is admixed dropwise at –40° C. with 7.62 ml of a 1M solution of BBr₃ in dichloromethane. After three hours of stirring in the temperature range between –40 and +10° C. the batch is poured onto a mixture of saturated sodium hydrogen carbonate solution and ice and is extracted three times with ethyl acetate. The combined organic extracts are washed with brine and then dried (Na₂SO₄) and the solvent is removed on a rotary evaporator. Repeated chromatography (Flashmaster, different phases, eluent: dichloromethane/methanol) gives 5.2 mg (1.6%) of the title compound. The dechloro compound has formed during the synthesis of the aldehyde, probably in one of the reduction steps.

1H-NMR (300 MHz, CD₃OD): δ=1.09 (3H), 1.83-2.13 (3H), 2.18 (3H), 2.40 (1H), 3.08 (1H), 5.03 (1H), 6.68 (1H), 6.79 (1H), 6.85 (1H), 7.02-7.13 (2H), 7.33 (1H), 7.65 (1H).

Example 129

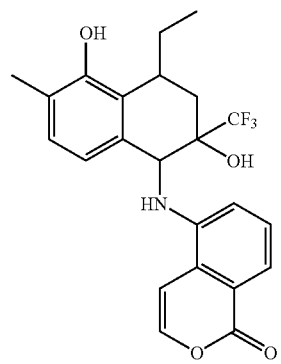

5-{[4-Ethyl-2,5-dihydroxy-6-methyl-2-(trifluoromethyl)-1,2,3,4-tetrahydronaphthalen-1-yl]amino}isochromen-1-one 5-{[4-(4-Chloro-3-methyl-2-methoxyphenyl)-2-hydroxy-2-trifluoromethyl)hexylidene]amino}isochromen-1-one (408.6 mg, 0.85 mmol), prepared from the aldehyde described in Example 118 and 5-aminoisochromen-1-one, is dissolved in 4 ml of dichloromethane and this initial charge is admixed dropwise at −40° C. with 8.48 ml of a 1M solution of BBr$_3$ in dichloromethane. After three hours of stirring in the temperature range between −40 and +10° C. the batch is poured onto a mixture of saturated sodium hydrogen carbonate solution and ice and is extracted three times with ethyl acetate. The combined organic extracts are washed with brine and then dried (Na$_2$SO$_4$) and the solvent is removed on a rotary evaporator. Repeated chromatography (Flashmaster, different phases, eluent: dichloromethane/methanol) gives 13.3 mg (3.6%) of the title compound as a stereoisomer mixture. This dechloro compound has formed during the preparation of the aldehyde, probably in one of the reduction steps.

Example 130

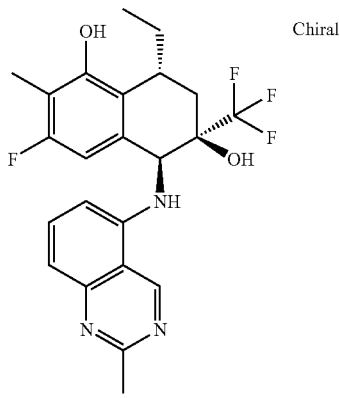

(5S,6R,8R)-8-Ethyl-2,3-difluoro-5-[(2-methylquinazolin-5-yl)amino]-6-(trifluoromethyl)-5,6,7,8-tetrahydronaphthalene-1,6-diol 4-(4-Fluoro-2-methoxy-3-methylphenyl)-2-hydroxy-2-(trifluoromethyl)hexanal 18.6 g (147 mmol) of 3-fluoro-2-methylphenol (Lock et al. Chem. Ber. 1936, 69, 2253-55) in 150 ml of dichloromethane and 16.6 ml of pyridine are admixed dropwise at 0° C. with 13.5 ml (155 mmol) of propionyl chloride. The mixture is stirred for two hours and 100 ml of 2 M hydrochloric acid are added. The mixture is extracted with dichloromethane and washed with water. Drying over sodium sulphate and removal of the solvent in vacuo give 20.6 g of 3-fluoro-2-methylphenyl propionate. 20.6 g (113 mmol) of 3-fluoro-2-methylphenylpropionate in 12 ml of 1,2-dichlorobenzene are added dropwise to 15.1 g (113 mmol) of aluminum trichloride in 12 ml of 1,2-dichlorobenzene and the mixture is subsequently stirred at 100° C. for 6 hours. It is cooled, diluted with dichloromethane and poured cautiously onto a mixture of 2 M hydrochloric acid and ice. The phases are separated, extraction is carried out with dichloromethane and the extracts are washed with saturated sodium chloride solution and dried over sodium sulphate. The crude product is purified by column chromatography on silica gel (hexane/ethyl acetate 10-20%) to give 19 g of 1-(4-fluoro-2-hydroxy-3-methylphenyl)propan-1-one. 7.96 g (43.8 mmol) of 1-(4-fluoro-2-hydroxy-3-methylphenyl)propan-1-one are dissolved in 65 ml of acetone and the solution is admixed with 11.3 g of potassium carbonate and 4.96 ml (79 mmol) of methyl iodide. The mixture is boiled under reflux for 20 hours, with the addition after 16 hours of a further 3 g of potassium carbonate and 1.5 ml (22 mmol) of methyl iodide. The solvent is largely removed and the residue is poured into water and extracted with diethyl ether. The extracts are washed with water and dried over sodium sulphate and, after the solvent has been removed in vacuo, 7.9 g of 1-(4-fluoro-2-methoxy-3-methylphenyl)propan-1-one are obtained. 27.3 g (416 mmol) of zinc dust and 570 mg (2.05 mmol) of lead(II) chloride are suspended in 211 ml of THF and the suspension is admixed at room temperature with 25.4 ml (364 mmol) of dibromomethane. Stirring is carried out at room temperature for a further 30 minutes, followed by dropwise addition at 0° C. of 49 ml (49 mmol) of a 1 M titanium(IV) chloride solution in dichloromethane. The cooling bath is removed and, after an hour, the reaction mixture is cooled again to 0° C. 9.5 g (48 mmol) of 1-(4-fluoro-2-methoxy-3-methylphenyl)propan-1-one in 28 ml of THF are added dropwise. The mixture is stirred at room temperature for a further two hours. The reaction mixture is diluted with diethyl ether and poured cautiously onto a mixture of 4 M hydrochloric acid and ice. The phases are separated, extraction is carried out with diethyl ether, the extracts are washed with saturated sodium chloride solution and dried over sodium sulphate, and the solvent is removed. The crude product is purified by column chromatography on silica gel (hexane/diisopropyl ether 0-20%) to give 5.7 g of 3-fluoro-2-methyl-6-(1-methylenepropyl)anisole.

$^1$H-NMR (300 MHz, CDCl$_3$); δ=1.01 (t, 3H), 2.20 (d, 1H), 2.47 (qdd, 2H), 3.68 (s, 1H), 5.02 (ddd, 1H), 5.14 (ddd, 1H), 6.76 (dd, 1H), 6.94 (dd, 1H).

5.7 g (29.3 mmol) of 3-fluoro-2-methyl-6-(1-methylenepropyl)anisole, 7.7 ml (170 mmol) of ethyl trifluoropyruvate and 15 g of molecular sieve are admixed dropwise at 0° C. over 30 minutes with 0.76 g (0.88 mmol) of [Cu(R,R)-2,2-bis(4,5-dihydro-4-tert-butyloxazolin-2-yl)propane)(H$_2$O)$_2$]((SbF$_6$)$_2$, in 38 ml of dichloromethane. The reaction mixture is stirred at 0° C. for 16 hours and the reaction mixture is purified by means of column chromatography on silica gel (hexane/ethyl acetate 0-20%). This gives 8.7 g of ethyl (R)-4-(4-fluoro-2-methoxy-3-methylphenyl)-2-hydroxy-2-(trifluoromethyl)hex-4-enoate as an E/Z mixture with an enantiomeric excess of greater than 80%, and in this way 13.9 of crude E/Z-4-(4-fluoro-2-methoxy-3-methylphenyl)-2-(trifluoromethyl)hex-4-ene-1,2-diol. 4.0 g (11 mmol) of ethyl (2R,4E/Z)-4-(4-fluoro-2-methoxy-3-methylphenyl)-2-hydroxy-2-(trifluoromethyl)hex-4-enoate are dissolved in 180 ml of 2,2,2-trifluoroethanol and the solution is admixed with 400 mg of palladium on carbon (10%). The suspension is shaken under a hydrogen atmosphere at 100 bar until reaction is complete. The mixture is filtered through Celite, the filter bed being rinsed thoroughly with ethyl acetate. The concentrated crude product is purified by column chromatography on silica gel (hexane/ethyl acetate 15%)to give 3.7 g (10 mmol) of ethyl (2R,4R/S)-4-(4-fluoro-2-methoxy-3-methylphenyl)-2-hydroxy-2-(trifluoromethyl)hexanoate as a diastereomer mixture. 3.7 g (10 mmol) of ethyl (2R,4R/S)-4-(4-fluoro-2-methoxy-3-methylphenyl)-2-hydroxy-2-(trifluoromethyl)hexanoate are cooled to −15° C. in 132 ml of diethyl ether and admixed over 10 minutes with solid lithium aluminum hydride, 1.03 g (27.3 mmol), in portions. The mixture is stirred at −10° C. for 3 hours, and ethyl acetate and water are added cautiously. The suspension is filtered through Celite, the filter bed being rinsed thoroughly with ethyl acetate.

The phases of the filtrate are separated and extraction is carried out again with ethyl acetate. The extracts are washed with saturated sodium chloride solution and dried over sodium sulphate. Removal of the solvent gives 3.4 g of crude 4-(4-fluoro-2-methoxy-3-methylphenyl)-2-hydroxy-2-(trifluoromethyl)hexanal as a mixture of the diastereomers. Column chromatography on silica gel (hexane/diisopropyl ether 0-30%) yields 1.04 g of (2R,4R)-4-(4-fluoro-2-methoxy-3-methylphenyl)-2-hydroxy-2-(trifluoromethyl)hexanal $^1$H-NMR (300 MHz, CDCl$_3$); δ=0.82 (t, 3H), 1.55-1.73 (m, 2H), 2.33 (dd, 1H), 2.36 (dd, 1H), 3.07 (m, 1H), 3.72 (s, 3H), 4.20 (s, 1H), 6.81 (dd, 1H), 6.94 (dd, 1H), 8.89 (s, 1H).

and 1.13 g of (2R,4S)-4-(4-fluoro-2-methoxy-3-methylphenyl)-2-hydroxy-2-(trifluoromethyl)hexanal.

$^1$H-NMR (300 MHz, CDCl$_3$); δ 0.71 (t, 3H), 1.50-1.70 (m, 2H), 2.34 (dd, 1H), 2.39 (dd, 1H), 2.93 (m, 1H), 3.73 (s, 3H), 3.89 (s, 1H), 6.81 (dd, 1H), 6.93 (dd, 2H), 9.69 (s, 1H).

300 mg (0.93 mmol) of (2R,4R)-4-(4-fluoro-2-methoxy-3-methylphenyl)-2-hydroxy-2-(trifluoromethyl)hexanal and 165 mg (1.04 mmol) of 5-amino-2-methylquinazoline are dissolved in 20 ml of toluene and the solution is admixed with 0.56 ml (1.86 mmol) of titanium tert-butoxide and 0.11 ml of acetic acid. The reaction mixture is heated at 100° for 2 hours, cooled, poured into water and stirred vigorously. The suspension is filtered through Celite, the filter bed being rinsed thoroughly with ethyl acetate. The phases of the filtrate are separated and extraction is carried out again with ethyl acetate. The extracts are washed with saturated sodium chloride solution and dried over sodium sulphate and the solvent is removed in vacuo to give 530 mg of (2R,4R)-4-(3,4-difluoro-2-methoxyphenyl)-1-[(2-methylquinazolin-5-yl)imino]-2-(trifluoromethyl)hexan-2-ol as a crude product. Purification by column chromatography on silica gel (hexane/ethyl acetate 0-50%) yields 250 mg of the pure imine, which are dissolved in 22 ml of CH$_2$Cl$_2$ and cooled to −30° C. 4.3 ml (4.3 mmol) of a 1M BBr$_3$ solution in dichloromethane are added slowly dropwise over 5 minutes and the mixture is allowed to come to room temperature over 22 hours. The reaction solution is poured onto a mixture of saturated NaHCO$_3$ solution and ice. It is extracted repeatedly with ethyl acetate and the extracts are washed with saturated NaCl solution and dried over Na$_2$SO$_4$. Column chromatography purification on silica gel (hexane/ethyl acetate 0-100%) 147 mg of product.

$^1$H-NMR (300 MHz, CD$_3$OD); δ=0.92 (t, 3H), 1.68 (ddq, 1H), 1.92 (m, 1H), 2.01 (dd, 1H), 2.08 (d, 3H), 2.35 (dd, 1H), 2.78 (s, 3H), 3.33 (m, 1H), 5.08 (s, 1H), 6.50 (d, 1H), 6.74 (d, 1H), 7.17 (d, 1H), 7.74 (t, 1H), 9.57 (s, 1H).

Example 131

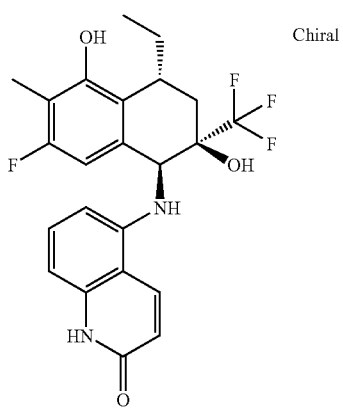

5-{[(1S,2R,4R)-4-Ethyl-7-fluoro-2,5-dihydroxy-6-methyl-2-(trifluoromethyl)-1,2,3,4-tetrahydronaphthalen-1-yl]amino}quinolin-2(1H)-one In the same way as in Example 130, 300 mg (0.93 mmol) of (2R,4R)-4-(4-fluoro-2-methoxy-3-methylphenyl)-2-hydroxy-2-(trifluoromethyl)hexanal, 149 mg (0.93 mmol) of 5-aminoquinolin-2(1H)-one and 0.27 ml of titanium tert-butoxide are reacted to give 5-{[(2R,4R)-4-(4-fluoro-2-methoxy-3-methylphenyl)-2-hydroxy-2-(trifluoromethyl)hexylidene]amino}quinolin-2(1H)-one. 210 mg of chromatographically purified imine (silica gel, hexane/ethyl acetate 0-80%) are cyclized in the same way as in Example 130 at −30° C. with 3.6 ml (3.6 mmol) of 1 M boron tribromide solution to give the desired product. Column chromatography on silica gel (hexane/ethyl acetate 0-100%) yields 203 mg of desired product.

$^1$H-NMR (300 MHz, CD$_3$OD); δ=0.90 (t, 3H), 1.66 (ddq, 1H), 1.89 (m, 1H), 1.99 (dd, 1H), 2.08 (d, 3H), 2.32 (dd, 1H), 3.33 (m, 1H), 4.95 (s, 1H), 6.42 (d, 1H), 6.47 (d, 1H), 6.49 (d, 1H), 6.67 (d, 1H), 7.32 (t, 1H), 8.19 (d, 1H).

Example 132

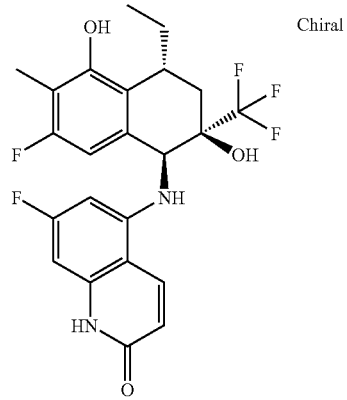

5-{[(1S,2R,4R)-4-Ethyl-7-fluoro-2,5-dihydroxy-6-methyl-2-(trifluoromethyl)-1,2,3,4-tetrahydronaphthalen-1-yl]amino}-7-fluoroquinolin-2(1H)-one In the same way as in Example 130, 271 mg (0.51 mmol) of (2R,4R)-4-(4-fluoro-2-methoxy-3-methylphenyl)-2-hydroxy-2-(trifluoromethyl)hexanal, 90 mg (0.51 mmol) of 5-amino-7-fluoroquinolin-2(1H)-one and 0.32 ml (1.02 mmol) of titanium tert-butoxide are reacted to give 7-fluoro-5-{[(2R,4R)-4-(4-fluoro-2-methoxy-3-methylphenyl)-2-hydroxy-2-(trifluoromethyl)hexylidene]-amino}quinolin-2(1H)-one. 320 mg of crude imine are cyclized in the same way as in Example 130 at −30° C. with 4.1 ml (4.1 mmol) of 1 M boron tribromide solution to give the desired product. Column chromatography on silica gel (hexane/ethyl acetate 50%) yields 165 mg of desired product.

$^1$H-NMR (300 MHz, CD$_3$OD); δ=0.91 (t, 3H), 1.68 (ddq, 1H), 1.90 (m, 1H), 1.99 (dd, 1H), 2.09 (s, 3H), 2.33 (dd, 1H), 3.32 (m, 1H), 4.93 (s, 1H), 6.21 (d, 1H), 6.38 (d, 1H), 6.42 (d, 1H), 6.45 (d, 1H), 8.13 (d, 1H).

Example 133

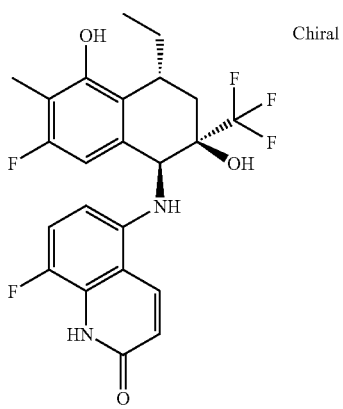

5-{[(1S,2R,4R)-4-Ethyl-7-fluoro-2,5-dihydroxy-6-methyl-2-(trifluoromethyl)-1,2,3,4-tetrahydronaphthalen-1-yl]amino}-8-fluoroquinolin-2(1H)-one In the same way as in Example 130, 300 mg (0.93 mmol) of (2R,4R)-4-(4-fluoro-2-methoxy-3-methylphenyl)-2-hydroxy-2-(trifluoromethyl)hexanal, 165 mg (0.93 mmol) of 5-amino-8-fluoroquinolin-2(1H)-one and 0.58 ml of titanium tert-butoxide are reacted to give 8-fluoro-5-{[(2R,4R)-4-(4-fluoro-2-methoxy-3-methylphenyl)-2-hydroxy-2-(trifluoromethyl)hexylidene]amino}quinolin-2(1H)-one. 280 mg of chromatographically purified imine (silica gel, hexane/ethyl acetate 0-75%) are cyclized in the same way as in Example 130 at −30° C. with 4.6 ml (4.6 mmol) of 1 M boron tribromide solution to give the desired product. Column chromatography on silica gel (hexane/ethyl acetate 0-100%) yields 230 mg of desired product.

$^1$H-NMR (300 MHz, CD$_3$OD); δ=0.90 (t, 3H), 1.67 (ddq, 1H), 1.90 (m, 1H), 1.97 (dd, 1H), 2.08 (s, 3H), 2.31 (dd, 1H), 3.32 (m, 1H), 4.89 (s, 1H), 6.32 (dd, 1H), 6.49 (d, 1H), 6.54 (d, 1H), 7.17 (t, 1H), 8.18 (d, 1H).

Example 134

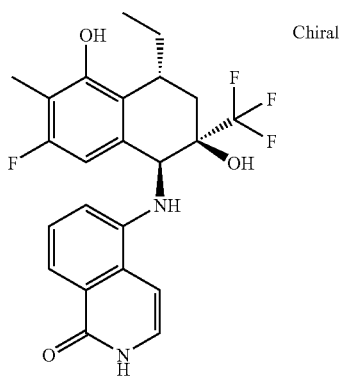

5-{[(1S,2R,4R)-4-Ethyl-7-fluoro-2,5-dihydroxy-6-methyl-2-(trifluoromethyl)-1,2,3,4-tetrahydronaphthalen-1-yl]amino}isoquinolin-1 (2H)-one In the same way as in Example 130, 200 mg (0.62 mmol) of (2R,4R)-4-(4-fluoro-2-methoxy-3-methylphenyl)-2-hydroxy-2-(trifluoromethyl)hexanal, 100 mg (0.62 mmol) of 5-aminoisoquinolin-1(2H)-one and 0.39 ml (1.25 mmol) of titanium tert-butoxide are reacted to give 5-{[(2R,4R)-4-(4-fluoro-2-methoxy-3-methylphenyl)-2-hydroxy-2-(trifluoromethyl)hexylidene]amino}isoquinolin-1 (2H)-one. 460 mg of crude imine are cyclized in the same way as in Example 130 at −30° C. with 7.9 ml (7.9 mmol) of 1 M boron tribromide solution to give the desired product. Column chromatography on silica gel (hexane/ethyl acetate 50-100%) yields 223 mg of desired product.

$^1$H-NMR (300 MHz, CD$_3$OD); δ=0.91 (t, 3H), 1.69 (ddq, 1H), 1.90 (m, 1H), 2.02 (dd, 1H), 2.08 (s, 3H), 2.32 (dd, 1H), 3.31 (m, 1H), 4.95 (s, 1H), 6.48 (d, 1H), 6.82 (d, 1H), 6.85 (d, 1H), 7.15 (d, 1H), 7.33 (t, 1H), 7.65 (d, 1H).

Example 135

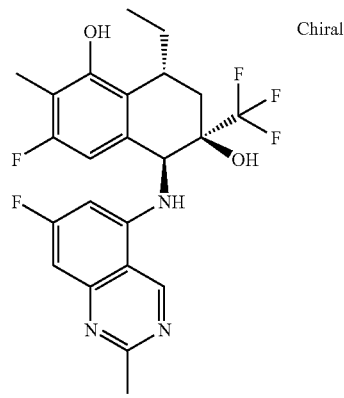

(5S,6R,8R)-8-Ethyl-3-fluoro-5-[(7-fluoro-2-methylquinazolin-5-yl)amino]-2-methyl-6-(trifluoromethyl)-5,6,7,8-tetrahydronaphthalene-1,6-diol In the same way as in Example 130, 300 mg (0.93 mmol) of (2R,4R)-4-(4-fluoro-2-methoxy-3-methylphenyl)-2-hydroxy-2-(trifluoromethyl)hexanal, 183 mg (1.03 mmol) of 5-amino-7-fluoro-2-methylquinazoline and 0.58 ml (1.86 mmol) of titanium tert-butoxide is reacted to give 5-{[(2R, 4R)-4-(4-fluoro-2-methoxy-3-methylphenyl)-1-[(7-fluoro-2-methylquinazolin-5-yl)imino]-2-(trifluoromethyl)hexan-2-ol. 460 mg of crude imine are cyclized in the same way as in Example 130 at −30° C. with 7.6 ml (7.6 mmol) of 1 M boron tribromide solution to give the desired product. Column chromatography on silica gel (hexane/ethyl acetate 0-65%) yields 135 mg of desired product.

$^1$H-NMR (300 MHz, CDCl$_3$); δ=0.90 (t, 3H), 1.64 (ddq, 1H), 1.87 (ddq, 1H), 1.96 (s, 3H), 2.03 (dd, 1H), 2.39 (dd, 1H), 2.84 (s, 3H), 3.29 (m, 1H), 4.80 (d, 1H), 6.19 (d, 1H), 6.34 (d, 1H), 6.62 (d, 1H), 6.87 (d, 1H), 9.31 (s, 1H).

Example 136

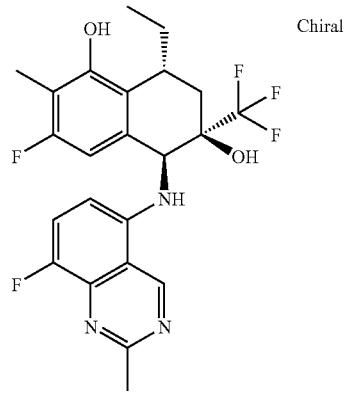

(5S,6R,8R)-8-Ethyl-3-fluoro-5-[(8-fluoro-2-meth-ylquinazolin-5-yl)amino]-2-methyl-6-(trifluoromethyl)-5,6,7,8-tetrahydronaphthalene-1,6-diol In the same way as in Example 130, 300 mg (0.93 mmol) of (2R,4R)-4-(4-fluoro-2-methoxy-3-methylphenyl)-2-hydroxy-2-(trifluoromethyl)hexanal, 183 mg (1.03 mmol) of 5-amino-8-fluoro-2-methylquinazoline and 0.58 ml (1.86 mmol) of titanium tert-butoxide is reacted to give 5-{[(2R,4R)-4-(4-fluoro-2-methoxy-3-methylphenyl)-1-[(8-fluoro-2-methylquinazolin-5-yl)imino]-2-(trifluoromethyl)hexan-2-ol. 450 mg of crude imine are cyclized in the same way as in Example 130 at −30° C. with 7.6 ml (7.6 mmol) of 1 M boron tribromide solution to give the desired product. Column chromatography on silica gel (hexane/ethyl acetate 0-65%) yields 77 mg of desired product.

$^1$H-NMR (300 MHz, CDCl$_3$); δ=0.88 (t, 3H), 1.62 (ddq, 1H), 1.86 (ddq, 1H), 1.94 (s, 3H), 2.02 (dd, 1H), 2.37 (dd, 1H), 2.83 (s, 3H), 3.26 (m, 1H), 4.79 (d, 1H), 5.83 (d, 1H), 6.49 (dd, 1H), 6.65 (d, 1H), 7.46 (dd, 1H), 9.44 (s, 1H).

Example 137

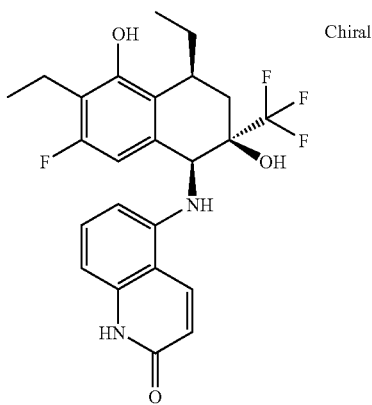

5-{[(1S,2R,4S)-4,6-Diethyl-7-fluoro-2,5-dihydroxy-2-(trifluoromethyl)-1,2,3,4-tetrahydronaphthalen-1-yl]amino}quinolin-2(1H)-one 4-(3-Ethyl-4-fluoro-2-methoxyphenyl)-2-hydroxy-2-(trifluoromethyl)hexanal 615 mg (4 mmol) of 2'-fluoro-6-hydroxyacetophenone in diethylene glycol are admixed with 224 mg (4 mmol) of potassium hydroxide and 240 mg (4.8 mmol) of hydrazine hydrate and the mixture is heated at 160° C. for 3 hours. The bath temperature is subsequently raised to 210° C. for 3 hours, the reaction vessel at this point being closed with a distillation bridge. After the reaction mixture has been cooled, it is poured into saturated ammonium chloride solution and extracted with diethyl ether, and the extracts are washed with water and saturated sodium chloride solution and dried over sodium sulphate. Removal of the solvent gives 600 mg of crude 2-ethyl-3-fluorophenol. 600 mg (4 mmol) of 2-ethyl-3-fluorophenol in 10 ml of dichloromethane and 0.64 ml of pyridine are admixed dropwise at 0° C. with 0.48 ml (5.5 mmol) of propionyl chloride. The mixture is stirred for 4 hours and 20 ml of 2 M hydrochloric acid are added. It is extracted with dichloromethane and the extracts are washed with water. Drying over sodium sulphate, removal of the solvent in vacuo and chromatography on silica gel (hexane/ethyl acetate 25%) give 580 mg of 2-ethyl-3-fluorophenyl propionate. 580 mg (3 mmol) of 2-ethyl-3-fluorophenylpropionate in 2 ml of 1,2-dichlorobenzene are added dropwise to 0.4 g (3 mmol) of aluminum trichloride in 3 ml of 1,2-dichlorobenzene and the mixture is subsequently stirred at 100° C. for 3 hours and at room temperature for 16 hours. It is cooled, diluted with dichloromethane and poured cautiously onto a mixture of 2 M hydrochloric acid and ice. The phases are separated and extracted with dichloromethane and the extracts are washed with water and saturated sodium chloride solution and dried over sodium sulphate. The crude product is purified by column chromatography on silica gel (hexane/ethyl acetate 10%) to give 580 mg of 1-(3-ethyl-4-fluoro-2-hydroxyphenyl)propan-1-one. 580 mg (3 mmol) of 1-(3-ethyl-4-fluoro-2-hydroxyphenyl)propan-1-one are dissolved in 4.6 ml of acetone and the solution is admixed with 0.77 g (5.4 mmol) of potassium carbonate and 0.33 ml (5.4 mmol) of methyl iodide. The mixture is heated at 70° C. for 4 hours and stirred at room temperature for 12 hours and subsequently the solvent is largely removed. The residue is poured into water and extracted with diethyl ether. The extracts are washed with water and dried over sodium sulphate and the solvent is removed in vacuo to give 700 mg of 1-(3-ethyl-4-fluoro-2-methoxyphenyl)propan-1-one as a crude product. 2.66 g (40 mmol) of zinc dust and 56 mg (0.2 mmol) of lead(II) chloride are suspended in 20 ml of THF and the suspension is admixed at 0° C. with 2.5 ml (35 mmol) of dibromomethane. The mixture is stirred for a further 30 minutes at room temperature and is admixed dropwise at 0° C. with 4.7 ml (4.7 mmol) of a 1 M titanium(IV) chloride solution in dichloromethane. The cooling bath is removed and after an hour the reaction mixture is cooled again to 0° C. 700 mg (3.3 mmol) of 1-(3-ethyl-4-fluoro-2-methoxyphenyl)propan-1-one in 3 ml of THF are added dropwise. The reaction mixture is stirred at room temperature for one hour further. It is diluted with diethyl ether and poured cautiously onto a mixture of 4 M hydrochloric acid and ice, the temperature not exceeding 5° C. The phases are separated and extracted with diethyl ether, the extracts are washed with water and saturated sodium chloride solution and dried over sodium sulphate, and the solvent is removed. The crude product is purified by column chromatography on silica gel (hexane/diisopropyl ether 0-20%) to give 650 mg of 2-ethyl-3-fluoro-6-(1-methylenepropyl)anisole. 650 mg (3.2 mmol) of 2-ethyl-3-fluoro-6-(1-methylenepropyl)anisole, 1.3 ml (9.6 mmol) of ethyl trifluoropyruvate and 2 g of molecular sieve are admixed dropwise at 0° C. over 30 minutes with 23 mg (0.026 mmol) of [Cu(R,R)-2,2-bis(4,5-dihydro-4-tert-butyloxazolin-2-yl)propane)(H$_2$O)$_2$](SbF$_6$)$_2$ in 85 ml of dichloromethane. The reaction mixture is stirred at 0° C. for 16 hours and is purified by means of column chromatography on silica gel (hexane/ethyl acetate 0-10%). This gives 600 mg of ethyl (R)-4-(3-ethyl-4-fluoro-2-methoxyphenyl)-2-hydroxy-2-(trifluoromethyl)hex-4-enoate as an E/Z mixture with an enantiomeric excess of greater than 80%. 200 mg (0.53 mmol) of ethyl E/Z-4-(3,4-difluoro-2-methoxyphenyl)-2-hydroxy-2-(trifluoromethyl)-hex-4-enoate in 8 ml of diethyl ether are cooled to −5° C. and admixed in portions with 40 mg (1.06 mmol) of solid lithium aluminum hydride. The mixture is stirred at room temperature for an hour and poured into saturated ammonium chloride solution. The phases are separated and extraction is carried out repeatedly with ethyl acetate. The extracts are washed with saturated sodium chloride solution and dried over sodium sulphate and the solvent is removed in vacuo to give, after chromatography on silica gel (hexane/diisopropyl ether, 25%), (2R,4E/Z)-4-(3-ethyl-4-fluoro-2-methoxyphenyl)-2-hydroxy-2-(trifluoromethyl)hex-4-enal. 102 mg of (2R,4E/Z)-4-(3-ethyl-4-fluoro-2-methoxyphenyl)-2-hydroxy-2-(trifluoromethyl)hex-4-enal are dissolved in 5 ml of trifluoroethanol and the solution is admixed with 50 mg of palladium on carbon (10%). The suspension is shaken under a hydrogen atmosphere at atmospheric pressure until reaction is complete. The mixture is filtered through Celite, the filter bed being rinsed thoroughly with ethyl acetate. Removal of the solvent gives 16.1 88 mg of crude (2R,4R/S)-4-(3-ethyl-4-fluoro-2-methoxyphenyl)-2-hydroxy-2-(trifluoromethyl) hexanal as a mixture of the diastereomers.

45 mg (0.13 mmol) of (2R,4R/S)-4-(3-ethyl-4-fluoro-2-methoxyphenyl)-2-hydroxy-2-(trifluoromethyl)hexanal and 21.4 mg (0.13 mmol) of 5-aminoquinolin-2(1h)-one are dissolved in 20 ml of toluene and the solution is admixed with 0.56 ml (1.86 mmol) of titanium tert-butoxide and 0.11 ml of acetic acid. The reaction mixture is heated at 1000 for 2 hours, cooled, poured into water and stirred vigorously. The suspension is filtered through Celite, the filter bed being rinsed thoroughly with ethyl acetate. The phases of the filtrate are separated and extraction is carried out again with ethyl acetate. The extracts are washed with saturated sodium chloride solution and dried over sodium sulphate and the solvent is removed in vacuo to give 80 mg of (5-{[(2R,4R/S)-4-(3-ethyl-4-fluoro-2-methoxyphenyl)-2-hydroxy-2-(trifluoromethyl)hexylidene]amino}quinolin-2(1H)-one as a crude product. The imine is dissolved in 4.4 ml of $CH_2Cl_2$ and the solution is cooled to −30° C. 1.5 ml (1.5 mmol) of a 1M $BBr_3$ solution in dichloromethane are added slowly dropwise over 15 minutes and the reaction solution is allowed to warm to room temperature over 22 hours. It is poured onto a mixture of saturated $NaHCO_3$ solution and ice. It is extracted repeatedly with ethyl acetate and the extracts are washed with saturated NaCl solution and dried over $Na_2SO_4$. Purification by column chromatography on silica gel (hexane/isopropanol 16%) and subsequent preparative thin-layer chromatography on an amine phase (Merck $NH_2F_{254}$, ethyl acetate/triethylamine, 2%) yield 8 mg of the title compound and 6 mg of the corresponding 8R-diastereomer.

$^1$H-NMR (300 MHz, $CD_3OD$); δ=1.07 (t, 3H), 1.08 (t, 3H), 1.92 (m, 2H), 2.03 (dd, 1H), 2.41 (dd, 1H), 2.62 (q, 2H), 2.99 (m, 1H), 5.06 (s, 1H), 6.47 (d, 2H), 6.59 (d, 1H), 6.67 (d, 1H), 7.34 (t, 1H), 8.20 (d, 1H).

Example 138

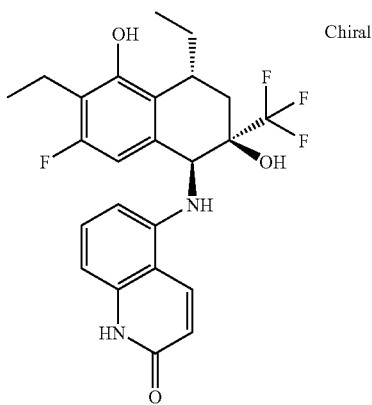

5-{[(1S,2R,4R)-4,6-Diethyl-7-fluoro-2,5-dihydroxy-2-(trifluoromethyl)-1,2,3,4-tetrahydronaphthalen-1-yl]amino}quinolin-2(1H)-one 6 mg of the desired product are obtained as described in Example 137 after preparative thin-layer chromatography on silica gel and amine phase.

$^1$H-NMR (300 MHz, $CD_3OD$); δ=0.91 (t, 3H), 1.08 (t, 3H), 1.67 (ddq, 1H), 1.89 (m, 1H), 2.00 (dd, 1H), 2.32 (dd, 1H), 2.63 (q, 2H), 3.32 (m, 1H), 4.95 (s, 1H), 6.42 (d, 1H), 6.47 (d, 1H), 6.50 (d, 1H), 6.67 (d, 1H), 7.32 (t, 1H), 8.19 (d, 1H).

Example 139

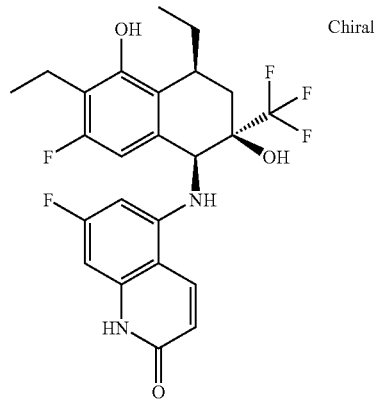

5-{[(1S,2R,4S)-4,6-Diethyl-7-fluoro-2,5-dihydroxy-2-(trifluoromethyl)-1,2,3,4-tetrahydronaphthalen-1-yl]amino}-7-fluoroquinolin-2(1H)-one In the same way as in Example 137, 45 mg (0.13 mmol) of (2R,4R/S)-4-(3-ethyl-4-fluoro-2-methoxyphenyl)-2-hydroxy-2-(trifluoromethyl)hexanal, 23 mg (0.13 mmol) of 5-amino-7-fluoroquinolin-2(1H)-one and 0.09 ml (0.27 mmol) of titanium tert-butoxide are reacted to give 5-{[(2R,4R/S)-4-(3-ethyl-4-fluoro-2-methoxyphenyl)-2-hydroxy-2-(trifluoromethyl)hexylidene]amino}-7-fluoroquinolin-2 (1H)-one. 80 mg of crude imine are cyclized in the same way as in Example 137 at −30° C. with 1.3 ml (1.3 mmol) of 1 M boron tribromide solution. Purification by column chromatography on silica gel (hexane/isopropanol 16%) and subsequent preparative thin-layer chromatography on an amine phase (Merck $NH_2F_{254}$, ethyl acetate/triethylamine, 2%) yield 7 mg of the title compound and 5 mg of the corresponding (8R)-diastereomer.

$^1$H-NMR (300 MHz, $CD_3OD$); δ=1.07 (t, 3H), 1.08 (t, 3H), 1.92 (m, 2H), 2.06 (dd, 1H), 2.39 (dd, 1H), 2.63 (q, 2H), 2.99 (m, 1H), 5.04 (s, 1H), 6.38 (d, 2H), 6.40 (d, 1H), 6.45 (d, 1H), 8.15 (d, 1H).

Example 140

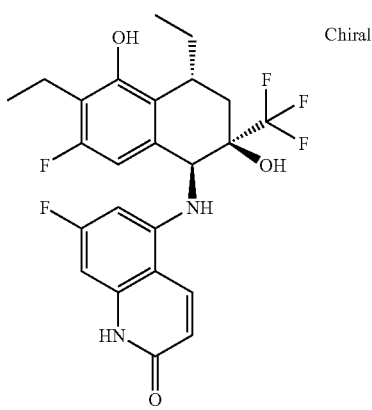

5-{[(1S,2R,4R)-4,6-Diethyl-7-fluoro-2,5-dihydroxy-2-(trifluoromethyl)-1,2,3,4-tetrahydronaphthalen-1-yl]amino}-7-fluoroquinolin-2(1H)-one 5 mg of the desired product are obtained as described in Example 139 after preparative thin-layer chromatography on silica gel and amine phase.

$^1$H-NMR (300 MHz, CD$_3$OD); δ=0.91 (t, 3H), 1.09 (t, 3H), 1.67 (ddq, 1H), 1.91 (m, 1H), 1.99 (dd, 1H), 2.33 (dd, 1H), 2.64 (q, 2H), 3.31 (m, 1H), 4.93 (s, 1H), 6.20 (d, 1H), 6.38 (d, 1H), 6.42 (d, 1H), 6.45 (d, 1H), 8.13 (d, 1H).

Example 141

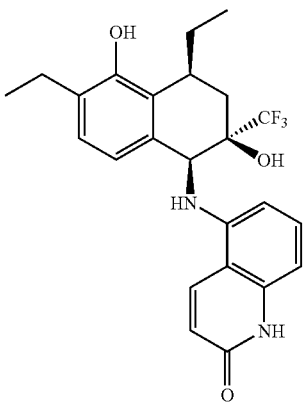

5-{[(1α,2α,4α)-4,6-Diethyl-2,5-dihydroxy-2-(trifluoromethyl)-1,2,3,4-tetrahydronaphthalen-1-yl]amino}-1H-quinolin-2-one 4-(3-Ethyl-2-methoxyphenyl)-2-hydroxy-2-(trifluoromethyl)hexanal 2.28 (7.12 mmol) of a mixture of 4-(3-ethyl-2-methoxyphenyl)-2-(trifluoromethyl)-hexane-1,2-diol and 4-(3-ethyl-2-methoxyphenyl)-3-methyl-2-(trifluoromethyl)-pentane-1,2-diol (prepared in analogy to the sequence described in Example 110: acetylation of the corresponding phenol, Fries displacement of the acetyl group, etherification of the phenol, Wittig reaction, ene reaction, reduction of the ester to the alcohol) are reacted conventionally with SO$_3$/pyridine complex (3.4 g, 21.35 mmol). After three-hour stirring at room temperature the reaction mixture is poured onto a mixture of saturated NH$_4$Cl solution and ice. It is extracted three times with diethyl ether. The combined organic extracts are washed twice with brine and dried (Na$_2$SO$_4$). Following removal of the solvent on a rotary evaporator, the residue is purified by means of chromatography. (silica gel, eluent: hexane/ethyl acetate). This gives 2.07 g (91.4%) of a mixture of the two aldehydes.

5-{[4-(3-Ethyl-2-methoxyphenyl)-2-hydroxy-2-(trifluoromethyl)hexylidene]amino}-1H-quinolin-2-one The mixture of 4-(3-ethyl-2-methoxyphenyl)-2-hydroxy-2-(trifluoromethyl)-hexanal and 4-(3-ethyl-2-methoxyphenyl)-2-hydroxy-3-methyl-2-(trifluoromethyl)-pentanal (690 mg, 2.16 mmol), 5-amino-1H-quinolin-2-one (347.2 mg, 2.17 mmol) and 3 ml of acetic acid are stirred at room temperature for two days.

The reaction mixture is stripped twice with toluene and dichloromethane and the residue is chromatographed (Flashmaster, eluent: dichloromethane/methanol). This isolates 709.7 mg (71.1%) of a mixture of the two imines.

The mixture described in the preceding section of 5-{[4-(3-ethyl-2-methoxyphenyl)-2-hydroxy-2-(trifluoromethyl) hexylidene]amino}-1H-quinolin-2-one and 5-{[4-(3-ethyl-2-methoxyphenyl)-2-hydroxy-3-methyl-2-(trifluoromethyl) pentylidene]amino}-1H-quinolin-2-one (709.7 mg, 1.54 mmol) is introduced in 7.1 ml of dichloromethane and admixed dropwise at −40° C. with 15.41 ml of a 1M solution of BBr$_3$ in dichloromethane. After three hours of stirring in the temperature range between −40 and +10° C. there is no longer any starting material present. The reaction mixture is poured cautiously onto a mixture of saturated NaHCO$_3$ solution and ice and is extracted three times with ethyl acetate. The combined organic extracts are washed with brine and dried over Na$_2$SO$_4$ and the residue, following removal of the solvent on a rotary evaporator, is chromatographed (NH$_2$ Flash, eluent: dichloromethane/methanol). This gives a mixture of the desired compound and the corresponding 3,4-dimethyltetrahydronaphthalene derivative, and this mixture is separated by HPLC (Kromasil 18 5μ, eluent water/methanol) into the constitutional isomers. 83.6 mg (33.6%) of the title compound are isolated. A further mixture is obtained which consists of the ethyl derivative epimeric in position 4, and a further 3,4 dimethyl derivative. The epimeric ethyl derivative is described in Example 142.

Examples 141A and 141B

5-{[(1R,2S,4R)-4,6-Diethyl-2,5-dihydroxy-2-(trifluoromethyl)-1,2,3,4-tetrahydronaphthalen-1-yl] amino}-1H-quinolin-2-one and 5-{[(1S,2R,4S)-4,6-diethyl-2,5-dihydroxy-2-(trifluoromethyl)-1,2,3,4-tetrahydronaphthalen-1-yl]amino}-1H-quinolin-2-one 66.4 mg of the racemate described in Example 141 are separated by means of chiral HPLC (Chiralpak AD-H 5μ, eluent: hexane/ethanol) into its enantiomers. 32.4 mg (48.5%) of one enantiomer (retention time 8.6-9.8 minutes) and 32.4 mg (48.5%) of the other enantiomer (retention time 11.3-12.8 minutes) are isolated. No conclusion can of course be drawn concerning the absolute configuration of the compounds.

Example 142

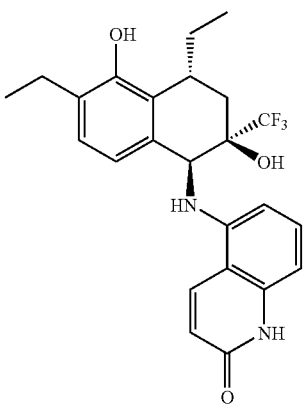

5-{[(1α,2α,4β)-4,6-Diethyl-2,5-dihydroxy-2-(trifluoromethyl)-1,2,3,4-tetrahydronaphthalen-1-yl]amino}-1H-quinolin-2-one The mixture (160 mg) described in Example 141 of the epimeric ethyl derivative and the 3,4-dimethyl derivative is separated by HPLC (Kromasil 18 5μ, eluent: water/acetonitrile). This gives 75.8 mg (47.4%) of the title compound and 65.9 mg (41.2%) of the corresponding 3,4-dimethyltetrahydronaphthalene derivative.

Examples 142A and 142B

5-{[(1R,2S,4S)-4,6-Diethyl-2,5-dihydroxy-2-(trifluoromethyl)-1,2,3,4-tetrahydronaphthalen-1-yl]amino}-1H-quinolin-2-one and 5-{[(1S,2R,4R)-4,6-diethyl-2,5-dihydroxy-2-(trifluoromethyl)-1,2,3,4-tetrahydronaphthalen-1-yl]amino}-1H-quinolin-2-one 53.9 mg of the racemate described in Example 142 are separated by means of chiral HPLC (Chiralpak AD-H 5μ, eluent: hexane/ethanol) into its enantiomers. 29 mg (>50%) of one enantiomer (retention time 10.6-12.2 minutes) and 28 mg (>50%) of the other enantiomer (retention time 13.5-15.7 minutes) are isolated. No conclusion can of course be drawn concerning the absolute configuration of the compounds.

Example 143

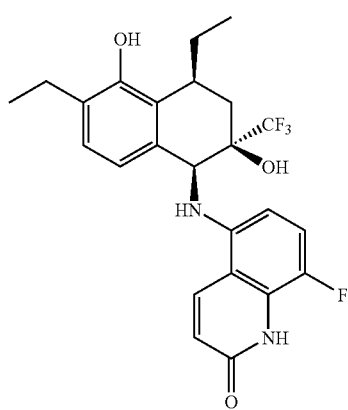

5-{[(1α,2α,4α)-4,6-Diethyl-2,5-dihydroxy-2-(trifluoromethyl)-1,2,3,4-tetrahydronaphthalen-1-yl]amino}-8-fluoro-1H-quinolin-2-one The mixture of 5-{[4-(3-ethyl-2-methoxyphenyl)-2-hydroxy-2-(trifluoromethyl)hexylidene]amino}-8-fluoro-1H-quinolin-2-one and 5-{[4-(3-ethyl-2-methoxyphenyl)-2-hydroxy-3-methyl-2-(trifluoromethyl)pentylidene]amino}-8-fluoro-1H-quinolin-2-one (721.6 mg, 1.5 mmol), prepared from the mixture of the two aldehydes described in Example 142 and 5-amino-8-fluoro-1H-quinolin-2-one, is introduced in 7.2 ml of dichloromethane and admixed dropwise at −40° C. with 15.1 ml of a 1M solution of BBr₃ in dichloromethane. After three hours of stirring in the temperature range between −40 and +10° C. there is no longer any starting material present. The reaction mixture is poured cautiously onto a mixture of saturated NaHCO₃ solution and ice and is extracted three times with ethyl acetate. The combined organic extracts are washed with brine and dried over Na₂SO₄ and the residue, following removal of the solvent on a rotary evaporator, is chromatographed (NH₂ Flash, eluent: dichloromethane/methanol). This gives a mixture of the desired compound and the corresponding 3,4-dimethyltetrahydronaphthalene derivative, and this mixture is separated by HPLC (Kromasil 18 5μ, eluent: water/acetonitrile) into the constitutional isomers. 98.9 mg (36.2%) of the title compound are isolated. A further mixture is obtained which consists of the ethyl derivative epimeric in position 4, and a further 3,4-dimethyl derivative. The epimeric ethyl derivative is described in Example 145.

Examples 143A and 143B

5-{[(1R,2S,4R)-4,6-Diethyl-2,5-dihydroxy-2-(trifluoromethyl)-1,2,3,4-tetrahydronaphthalen-1-yl]amino}-8-fluoro-1H-quinolin-2-one and 5-{[(1S,2R,4S)-4,6-diethyl-2,5-dihydroxy-2-(trifluoromethyl)-1,2,3,4-tetrahydronaphthalen-1-yl]amino}-8-fluoro-1H-quinolin-2-one 81.4 mg of the racemate described in Example 143 are separated by means of chiral HPLC (Chiralpak AD-H 5μ, eluent: hexane/ethanol) into its enantiomers. 40 mg (49.4%) of one enantiomer (retention time 9.4-10.8 minutes) and 40 mg (49.4%) of the other enantiomer (retention time 13.3-15.8 minutes) are isolated. No conclusion can of course be drawn concerning the absolute configuration of the compounds.

Example 144

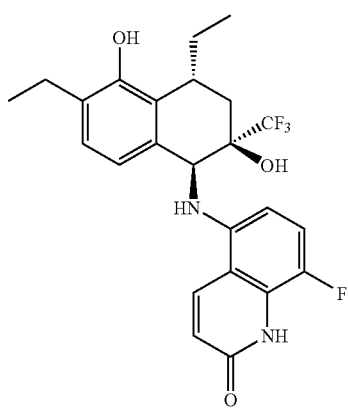

5-{[(1α,2α,4β)-4,6-Diethyl-2,5-dihydroxy-2-(trifluoromethyl)-1,2,3,4-tetrahydronaphthalen-1-yl]amino}-8-fluoro-1H-quinolin-2-one The mixture (200 mg) described in Example 143 of the epimeric ethyl derivative and the 3,4-dimethyl derivative is separated by HPLC (Kromasil 18 5μ, eluent: water/acetonitrile). This gives 72.7 mg (36%) of the title compound.

Examples 144A and 144B

5-{[(1R,2S,4S)-4,6-Diethyl-2,5-dihydroxy-2-(trifluoromethyl)-1,2,3,4-tetrahydronaphthalen-1-yl]amino}-8-fluoro-1H-quinolin-2-one and 5-{[(1S,2R,4R)-4,6-diethyl-2,5-dihydroxy-2-(trifluoromethyl)-1,2,3,4-tetrahydronaphthalen-1-yl]amino}-8-fluoro-1H-quinolin-2-one 59 mg of the racemate described in Example 145 are separated by means of chiral HPLC (Chiralpak AD-H 5μ, eluent: hexane/ethanol) into its enantiomers. 26 mg (44.1%) of one enantiomer (retention time 7.8-8.8 minutes) and 26 mg (44.1%) of the other enantiomer (retention time 16.5-18 minutes) are isolated. No conclusion can of course be drawn concerning the absolute configuration of the compounds.

Example 145

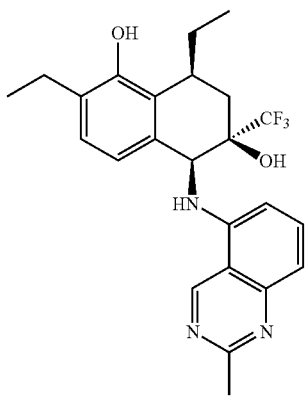

(5α,6α,8α)-2,8-Diethyl-5-[(2-methylquinazolin-5-yl)amino]-6-(trifluoromethyl)-5,6,7,8-tetrahydronaphthalene-1,6-diol 1,1,1-Trifluoro-2-[(2-methylquinazolin-5-ylimino)-methyl-]-4-(3-ethyl-2-methoxyphenyl)hexan-2-ol and 1,1,1-trifluoro-2-[(2-methylquinazolin-5-ylimino)-methyl-]-4-(3-ethyl-2-methoxyphenyl)-3-methylpentan-2-ol (525.5 mg, 1.14 mmol), prepared from the mixture of the two aldehydes described in Example 142 and 5-amino-2-methylquinazoline, are dissolved in 5.3 ml of dichloromethane and the solution is admixed dropwise at −20° C. with 11.43 ml of a 1M solution of boron tribromide in dichloromethane. After three and a half hours of stirring in the temperature range between −20 and +5° C., the batch is poured onto a mixture of saturated sodium hydrogen carbonate solution and ice and is extracted three times with ethyl acetate. Washing of the combined organic extracts with brine is followed by drying ($Na_2SO_4$) and the removal of the solvent on a rotary evaporator. Repeated chromatography (Flashmaster, different phases, eluent: dichloromethane/methanol) gives 14.7 mg (2.9%) of the desired compound.

Examples 145A and 145B (5R,6S,8R)-2,8-Diethyl-5-[2-methylquinazolin-5-ylamino]-6-(trifluoromethyl)-5,6,7,8-tetrahydronaphthalene-1,6-diol and (5S,6R,8S)-2,8-diethyl-5-[2-methylquinazolin-5-ylamino]-6-(trifluoromethyl)-5,6,7,8-tetrahydronaphthalene-1,6-diol 14 mg of the racemate described in Example 145 are separated by means of chiral HPLC (Chiralcel OD-H 5μ, eluent: hexane/ethanol) into its enantiomers. 3.3 mg (23.6%) of one enantiomer (retention time 13-14.5 minutes) and 2.9 mg (20.7%) of the other enantiomer (retention time 20.7-23.8 minutes) are isolated. No conclusion can of course be drawn concerning the absolute configuration of the compounds.

Example 146

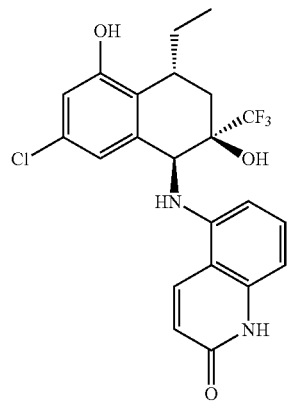

5-{[(1α,2α,4β)-7-Chloro-2,5-dihydroxy-4-ethyl-2-(trifluoromethyl)-1,2,3,4-tetrahydronaphthalen-1-yl]amino}-1H-quinolin-2-one The mixture of 5-{[4-(4-chloro-2-methoxyphenyl)-2-hydroxy-2-(trifluoromethyl)hexylidene]amino}-1H-quinolin-2-one and 5-{[4-(4-chloro-2-methoxyphenyl)-2-hydroxy-3-methyl-2-(trifluoromethyl)pentylidene]amino}-1H-quinolin-2-one (448.7 mg, 0.96 mmol), prepared from the reaction of the mixture of the corresponding aldehydes with 5-amino-1H-quinolin-2-one, is introduced in 4.5 ml of dichloromethane and admixed dropwise at −40° C. with 9.6 ml of a 1M solution of $BBr_3$ in dichloromethane. After four hours of stirring in the temperature range between −40° C. and room temperature, there is no longer any starting material present. The reaction mixture is poured cautiously onto a mixture of saturated $NaHCO_3$ solution and ice and is extracted three times with ethyl acetate. The combined organic extracts are washed with brine and dried over $Na_2SO_4$ and, after the removal of the solvent on a rotary evaporator, the residue is chromatographed ($NH_2$ Flash, eluent: dichloromethane/methanol). This gives a mixture of the desired compound and the corresponding 3,4-dimethyltetrahydronaphthalene derivative, and this mixture is separated by HPLC (Kromasil 18 5μ, eluent: water/methanol) into the constitutional isomers. 7 mg (3.2%) of the title compound are isolated.

1H-NMR (400 MHz, CD$_3$OD): δ=0.84 (3H), 1.60 (1H), 1.80-1.91 (2H), 2.29 (1H), 3.20 (1H, the signal lying partly beneath the solvent signal), 4.90 (1H), 6.38 (1H), 6.43 (1H), 6.58-6.67 (3H), 7.28 (1H), 8.12 (1H).

Example 147

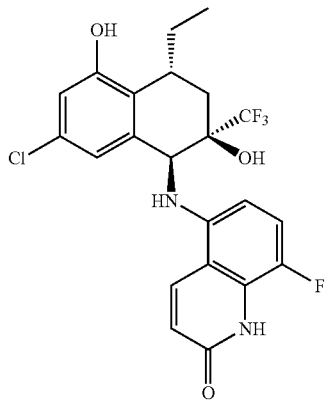

5-{[(1α,2α,4β)-7-Chloro-2,5-dihydroxy-4-ethyl-2-(trifluoromethyl)-1,2,3,4-tetrahydronaphthalen-1-yl]amino}-8-fluoro-1H-quinolin-2-one The mixture of 5-{[4-(4-chloro-2-methoxyphenyl)-2-hydroxy-2-(trifluoromethyl)hexylidene]amino}-8-fluoro-1H-quinolin-2-one and 5-{[4-(4-chloro-2-methoxyphenyl)-2-hydroxy-3-methyl-2-(trifluoromethyl)pentylidene]-amino}-8-fluoro-1H-quinolin-2-one (467.6 mg, 0.96 mmol), prepared from the reaction of the mixture of the corresponding aldehydes with 5-amino-8-fluoro-1H-quinolin-2-one, is introduced in 4.8 ml of dichloromethane and admixed dropwise at −40° C. with 9.6 ml of a 1M solution of BBr$_3$ in dichloromethane. After four hours of stirring in the temperature range between −40° C. and room temperature, there is no longer any starting material present. The reaction mixture is poured cautiously onto a mixture of saturated NaHCO$_3$ solution and ice and is extracted three times with ethyl acetate. The combined organic extracts are washed with brine and dried over Na$_2$SO$_4$ and, after the removal of the solvent on a rotary evaporator, the residue is chromatographed (NH$_2$ Flash, eluent: dichloromethane/methanol). This gives a mixture of the desired compound and the corresponding 3,4-dimethyltetrahydronaphthalene derivative, and this mixture is separated by HPLC (Kromasil 18 5μ, eluent: water/acetonitrile) into the constitutional isomers. 9.7 mg (4.3%) of the title compound are isolated.

1H-NMR (400 MHz, CD$_3$OD): δ=0.92 (3H), 1.69 (1H), 1.88-2.00 (2H), 2.34 (1H), 3.27 (1H, the signal lying partly beneath the solvent signal), 4.91 (1H), 6.37 (1H), 6.55 (1H), 6.68-6.73 (2H), 7.19 (1H), 8.18 (1H).

Example 148

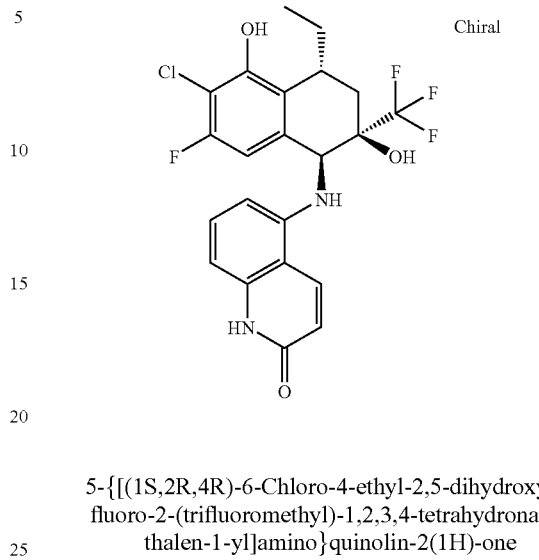

5-{[(1S,2R,4R)-6-Chloro-4-ethyl-2,5-dihydroxy-7-fluoro-2-(trifluoromethyl)-1,2,3,4-tetrahydronaphthalen-1-yl]amino}quinolin-2(1H)-one 4-(3-Chloro-4-fluoro-2-methoxyphenyl)-2-hydroxy-2-(trifluoromethyl)hexanal 21.5 g (146.7 mmol) of 2-chloro-3-fluorophenol (R. Sanz et al. J. Org. Chem. 2005, 70, 6548-51) in 97 ml of dichloromethane and 16.5 ml of pyridine are admixed dropwise at 0° C. with 14 ml (161 mmol) of propionyl chloride. The mixture is stirred for 16 hours and 100 ml of 2 M hydrochloric acid are added. The mixture is extracted with dichloromethane and the extracts are washed with water. Drying over sodium sulphate and the removal of the solvent in vacuo give 27.1 g of 2-chloro-3-fluorophenyl propionate. 30.1 g (133.7 mmol) of 2-chloro-3-fluorophenyl propionate in 42 ml of 1,2-dichlorobenzene are added dropwise to 19.6 g (133 mmol) of aluminum trichloride in 42 ml of 1,2-dichlorobenzene and the mixture is subsequently stirred at 100° C. for 18 hours. It is cooled, diluted with dichloromethane and poured cautiously onto a mixture of 2 M hydrochloric acid and ice. The phases are separated, extraction is carried out with dichloromethane and the extracts are washed with water and saturated sodium chloride solution and dried over sodium sulphate. The crude product is purified by column chromatography on silica gel (hexane/ethyl acetate 0-10%) to give 22.8 g of 1-(3-chloro-4-fluoro-2-hydroxyphenyl)propan-1-one. 22.8 g (112 mmol) of 1-(3-chloro-4-fluoro-2-hydroxyphenyl)propan-1-one are dissolved in 170 ml of acetone and the solution is admixed with 28.4 g (205 mmol) of potassium carbonate and 12.3 ml (198 mmol) of methyl iodide. The mixture is boiled under reflux for 4 hours and stirred at room temperature for 12 hours and then the solvent is largely removed. The residue is poured into water and extracted with diethyl ether. The extracts are washed with water and dried over sodium sulphate to give, following the removal of the solvent in vacuo, 24.4 g of 1-(3-chloro-4-fluoro-2-methoxyphenyl)propan-1-one. 63.3 g (969 mmol) of zinc dust and 1.33 g (4.77 mmol) of lead(II) chloride are suspended in 490 ml of THF and the suspension is admixed at 0° C. with 59 ml (846 mmol) of dibromomethane. The mixture is stirred at room temperature for a further 30 minutes and admixed dropwise at 0° C. with 113 ml (113 mmol) of a 1 M titanium(IV) chloride solution in dichloromethane. The cooling bath is removed and, after an hour, the reaction mixture is cooled again to 0° C. 124.4 g (113 mmol) of 1-(3-chloro-4-fluoro-2-methoxyphenyl)propan-1-one in 65 ml of THF are added dropwise. Stirring is carried out at room temperature for a further hour. The reaction mixture is diluted with diethyl ether and poured cautiously onto a mixture of 4 M hydrochloric acid and ice, the temperature not exceeding 5° C. The phases are separated, extraction is carried out with diethyl ether, the extracts are washed with water and saturated sodium chloride solution and dried over sodium sulphate, and the solvent is removed. The crude product is purified by column chromatography on silica gel (hexane/diisopropyl ether 0-20%) to give 12.7 g of 2-chloro-3-fluoro-6-(1-methylenepropyl)anisole 1H-NMR (300 MHz, CDCl3); δ=1.01 (t, 3H), 2.46 (q, 2H), 3.79 (s, 3H), 5.05 (s, 1H), 5.18 (s, 1H), 6.89 (dd, 1H), 7.02 (dd, 1H).

2 g (9.3 mmol) of 2-chloro-3-fluoro-6-(1-methylenepropyl)anisole, 2.46 ml (18.6 mmol) of ethyl trifluoropyruvate and 5 g of molecular sieve are admixed dropwise at 0° C. over 30 minutes with 440 mg (0.5 mmol) of [Cu(R,R)-2,2-bis(4,5-dihydro-4-tert-butyloxazolin-2-yl)propane)(H$_2$O)$_2$] ((SbF$_6$)$_2$ in 12 ml of dichloromethane. The reaction mixture is stirred at 0° C. for 16 hours and is purified by means of column chromatography on silica gel (hexane/diisopropyl ether 20%). This gives 1.04 g of ethyl (R)-4-(3-chloro-4-fluoro-2-methoxyphenyl)-2-hydroxy-2-(trifluoromethyl)-hex-4-enoate as an E/Z mixture with an enantiomeric excess of greater than 80%. 1.14 g (1.09 mmol) of (S)—(S)-(3,5-Me-4-MeOPh)$_2$PPhFc-CH(CH$_3$)—P(3,5-CF$_3$Ph)$_2$ and 389 mg (104 mmol) of [Rh(nbd)$_2$]BF$_4$ are dissolved under argon in 60 ml of degassed 2,2,2-trifluoroethanol and the solution is stirred for 10 minutes. The catalyst solution prepared in this way and a solution of 10 g (26 mmol) of ethyl (2R,4E/Z)-4-(3-chloro-4-fluoro-2-methoxyphenyl)-2-hydroxy-2-(trifluoromethyl)-hex-4-enoate in 340 ml of degassed 2,2,2-trifluoroethanol are transferred under argon to a steel autoclave and exposed to a hydrogen pressure of 80 bar at 80° C. for 20 hours. After cooling, the reaction mixture is concentrated and is purified by means of column chromatography on silica gel (hexane/ethyl acetate 0-15%). This gives 9.2 g of ethyl 4-(3-chloro-4-fluoro-2-methoxyphenyl)-2-hydroxy-2-(trifluoromethyl)-hexanoate. 9.2 g (24 mmol) of ethyl 4-(3-chloro-4-fluoro-2-methoxyphenyl)-2-hydroxy-2-(trifluoromethyl) hexanoate in 315 ml of diethyl ether are cooled to −10° C. and over 10 minutes 2.46 g (38 mmol) of lithium aluminum hydride in solid form are added in portions. The reaction mixture is stirred for 2 hours in the course of which it warms to 0° C., 5 ml of ethyl acetate are added and the mixture is poured into saturated ammonium chloride solution and ice. The suspension is filtered through Celite, the filter bed being rinsed thoroughly with ethyl acetate. The phases of the filtrate are separated and extraction is carried out again with ethyl acetate. The extracts are washed with saturated sodium chloride solution and dried over sodium sulphate and the solvent is removed in vacuo to give, after column chromatography on silica gel (hexane/diisopropyl ether 0-30%), 1.3 g of (2R,4R)-4-(3-chloro-4-fluoro-2-methoxyphenyl)-2-hydroxy-2-(trifluoromethyl)hexanal.

$^1$H-NMR (300 MHz, CDCl$_3$); δ=0.75 (t, 3H), 1.55-1.73 (m, 2H), 2.30 (dd, 1H), 2.54 (dd, 1H), 3.06 (m, 1H), 3.92 (s, 1H), 3.96 (s, 3H), 6.75-6.84 (m, 2H), 9.02 (s, 1H).

and 2.3 g of (2R,4R/S)-4-(,4-fluoro-2-methoxyphenyl)-2-hydroxy-2-(trifluoromethyl)hexanal 300 mg (0.88 mmol) of (2R,4R)-4-(3-chloro-4-fluoro-2-methoxyphenyl)-2-hydroxy-2-(trifluoromethyl)hexanal and 140 mg (0.88 mmol) of 5-aminoquinolin-2(1H)-one are dissolved in 19 ml of toluene and the solution is admixed with 0.55 ml (1.75 mmol) of titanium tert-butoxide and 0.1 ml of acetic acid. The reaction mixture is heated at 100° C. for 2 hours, cooled, poured into water and stirred vigorously. The suspension is filtered through Celite, the filter bed being rinsed thoroughly with ethyl acetate. The phases of the filtrate are separated and extraction is carried out again with ethyl acetate. The extracts are washed with saturated sodium chloride solution and dried over sodium sulphate and the solvent is removed in vacuo to give 539 mg of (5-{[(2R,4R)-4-(3-chloro-4-fluoro-2-methoxyphenyl)-2-hydroxy-2-(trifluoromethyl)hexylidene]amino}quinolin-2(1H)-one as a crude product. The imine is dissolved in 44 ml of CH$_2$Cl$_2$ and the solution is cooled to −30° C. 8.9 ml (8.9 mmol) of a 1M BBr$_3$ solution in dichloromethane are added slowly dropwise over 15 minutes and the mixture is allowed to warm to room temperature over 22 hours. The reaction solution is poured onto a mixture of saturated NaHCO$_3$ solution and ice. It is extracted repeatedly with ethyl acetate and the extracts are washed with saturated NaCl solution and dried over Na$_2$SO$_4$. Purification by column chromatography on silica gel (hexane/ethyl acetate 0-100%) yields 134 mg of the title compound.

$^1$H-NMR (300 MHz, CD$_3$OD); δ=0.92 (t, 3H), 1.70 (ddq, 1H), 1.19 (ddq, 1H), 1.99 (dd, 1H), 2.36 (dd, 1H), 3.32 (m, 1H), 4.97 (s, 1H), 6.44 (d, 1H), 6.50 (d, 1H), 6.63 (d, 1H), 6.68 (d, 1H), 7.33 (t, 1H), 8.18 (d, 1H).

Example 149

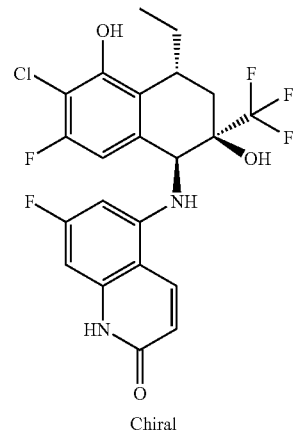

Chiral

5-{[(1S,2R,4R)-6-Chloro-4-ethyl-2,5-dihydroxy-7-fluoro-2-(trifluoromethyl)-1,2,3,4-tetrahydronaphthalen-1-yl]amino}-7-fluoroquinolin-2(1H)-one In the same way as in Example 148, 173 mg (0.51 mmol) of (2R,4R)-4-(3-chloro-4-fluoro-2-methoxyphenyl)-2-hydroxy-2-(trifluoromethyl)hexanal, 90 mg (0.51 mmol) of 5-amino-7-fluoroquinolin-2(1H)-one and 0.32 ml of titanium tert-butoxide are reacted to give 5-{[(2R,4R)-4-(3-chloro-4-fluoro-2-methoxyphenyl)-2-hydroxy-2-(trifluoromethyl) hexylidene]amino}-7-fluoroquinolin-2(1H)-one. 270 mg of crude imine are cyclized in the same way as in Example 148 at −30° C. with 7.6 ml (7.6 mmol) of 1 M boron tribromide solution to give the desired product. Column chromatography on silica gel (hexane/ethyl acetate 0-70%) yields 26 mg of desired product.

$^1$H-NMR (300 MHz, CD$_3$OD); δ=0.92 (t, 3H), 1.69 (ddq, 1H), 1.96 (m, 1H), 1.99 (dd, 1H), 2.37 (dd, 1H), 3.31 (m, 1H), 4.97 (s, 1H), 6.26 (d, 1H), 6.40 (d, 1H), 6.43 (d, 1H), 6.60 (d, 1H), 8.13 (d, 1H).

Example 150

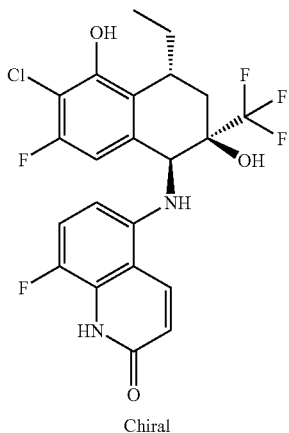

Chiral

5-{[(1S,2R,4R)-6-Chloro-4-ethyl-2,5-dihydroxy-7-fluoro-2-(trifluoromethyl)-1,2,3,4-tetrahydronaphthalen-1-yl]amino}-8-fluoroquinolin-2(1H)-one In the same way as in Example 148, 300 mg (0.88 mmol) of (2R,4R)-4-(3-chloro-4-fluoro-2-methoxyphenyl)-2-hydroxy-2-(trifluoromethyl)hexanal, 156 mg (0.88 mmol) of 5-amino-8-fluoroquinolin-2(1H)-one and 0.55 ml of titanium tert-butoxide is reacted to give 5-{[(2R,4R)-4-(3-chloro-4-fluoro-2-methoxyphenyl)-2-hydroxy-2-(trifluoromethyl)hexylidene]amino}-8-fluoroquinolin-2(1H)-one. 480 mg of crude imine are cyclized in the same way as in Example 148 at −30° C. with 7.6 ml (7.6 mmol) of 1 M boron tribromide solution to give the desired product. Column chromatography on silica gel (hexane/ethyl acetate 0-70%) yields 119 mg of desired product.

$^1$H-NMR (300 MHz, CD$_3$OD); δ=0.91 (t, 3H), 1.69 (ddq, 1H), 1.93 (m, 1H), 1.98 (dd, 1H), 2.35 (dd, 1H), 3.32 (m, 1H), 4.91 (s, 1H), 6.36 (dd, 1H), 6.54 (d, 1H), 6.65 (dd, 1H), 7.18 (dd, 1H), 8.17 (d, 1H).

Example 151

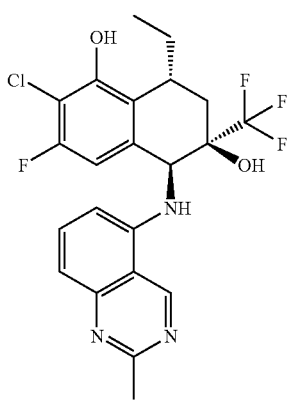

Chiral (5S,6R,8R)-2-Chloro-8-ethyl-3-fluoro-5-[(2-methylquinazolin-5-yl)amino]-6-(trifluoromethyl)-5,6,7,8-tetrahydronaphthalene-1,6-diol In the same way as in Example 48, 100 mg (0.29 mmol) of (2R,4R)-4-(3-chloro-4-fluoro-2-methoxyphenyl)-2-hydroxy-2-(trifluoromethyl)hexanal, 52 mg (0.33 mmol) of 5-aminoquinazoline and 0.27 ml of titanium tert-butoxide is reacted to give 5-{[(2R,4R)-4-(3-chloro-4-fluoro-2-methoxyphenyl)-1-[(2-methylquinazolin-5-yl)imino]-2-(trifluoromethyl)hexan-2-ol. 130 mg of crude imine are cyclized in the same way as in Example 148 at −30° C. with 5 ml (5 mmol) of 1 M boron tribromide solution to give the desired product. Preparative thin-layer chromatography on silica gel (hexane/ethyl acetate 50%) yields 19 mg of desired product.

$^1$H-NMR (300 MHz, CDCl$_3$); δ=0.92 (t, 3H), 1.69 (ddq, 1H), 1.93 (m, 1H), 2.04 (dd, 1H), 2.39 (dd, 1H), 2.91 (s, 3H), 3.34 (m, 1H), 4.88 (d, 1H), 6.18 (d, 1H), 6.64 (d, 1H), 6.79 (d, 1H), 7.31 (d, 1H), 7.75 (t, 1H), 9.57 (s, 1H).

Example 152

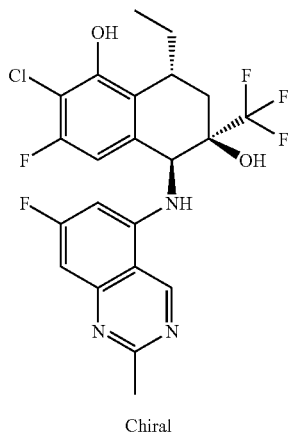

Chiral (5S,6R,8R)-2-Chloro-8-ethyl-3-fluoro-5-[(7-fluoro-2-methylquinazolin-5-yl)amino]-6-(trifluoromethyl)-5,6,7,8-tetrahydronaphthalene-1,6-diol In the same way as in Example 148, 300 mg (0.88 mmol) of (2R,4R)-4-(3-chloro-4-fluoro-2-methoxyphenyl)-2-hydroxy-2-(trifluoromethyl)hexanal, 172 mg (0.97 mmol) of 5-amino-7-fluoro-2-methylquinazoline and 0.55 ml of titanium tert-butoxide are reacted to give 5-{[(2R,4R)-4-(3-chloro-4-fluoro-2-methoxyphenyl)-1-[(7-fluoro-2-methylquinazolin-5-yl)imino]-2-(trifluoromethyl)hexan-2-ol. 450 mg of crude imine are cyclized in the same way as in Example 148 at −30° C. with 2.5 ml (2.5 mmol) of 1 M boron tribromide solution to give the desired product. Column chromatography on silica gel (hexane/ethyl acetate 0-50%) yields 56 mg of desired product.

$^1$H-NMR (300 MHz, CD$_3$OD); δ=0.93 (t, 3H), 1.71 (ddq, 1H), 1.98 (m, 1H), 2.01 (dd, 1H), 2.41 (dd, 1H), 2.75 (s, 3H), 3.31 (m, 1H), 5.14 (s, 1H), 6.62 (d, 1H), 6.63 (d, 1H), 6.78 (d, 1H), 9.50 (s, 1H).

Example 153

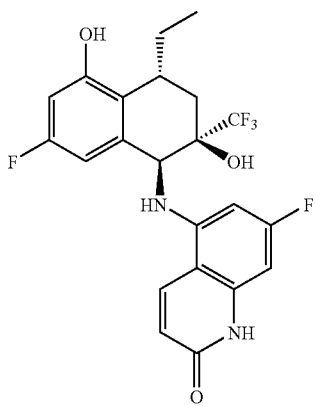

5-{[(1α,2α,4β)-7-Fluoro-2,5-dihydroxy-4-ethyl-2-(trifluoromethyl)-1,2,3,4-tetrahydronaphthalen-1-yl]amino}-7-fluoro-1H-quinolin-2-one 5-{[4-(4-Fluoro-2-methoxyphenyl)-2-hydroxy-2-(trifluoromethyl)hexylidene]amino}-7-fluoro-1H-quinolin-2-one (163.1 mg, 0.35 mmol), prepared from the aldehyde described in Example 148 and 5-amino-7-fluoro-1H-quinolin-2-one, is introduced in 3.5 ml of dichloromethane and admixed dropwise at –20° C. with 3.5 ml of a 1M solution of BBr$_3$ in dichloromethane. After three hours of stirring in the temperature range between –20 and +10° C. there is no longer any starting material present. The reaction mixture is poured cautiously onto a mixture of saturated NaHCO$_3$ solution and ice and is extracted three times with ethyl acetate. The combined organic extracts are washed with brine and dried over Na$_2$SO$_4$ and, following removal of the solvent on a rotary evaporator, the residue is subjected to repeated chromatography (NH$_2$ Flash, eluent: dichloromethane/methanol). This gives 12.6 mg (8%) of title compound.

1H-NMR (300 MHz, CD$_3$OD): δ=0.93 (3H), 1.68 (1H), 1.89-2.06 (2H), 2.35 (1H), 3.25 (1H, the signal lying partly beneath the solvent signal), 4.96 (1H), 6.22 (1H), 6.32-6.50 (4H), 8.13 (1H).

Example 154

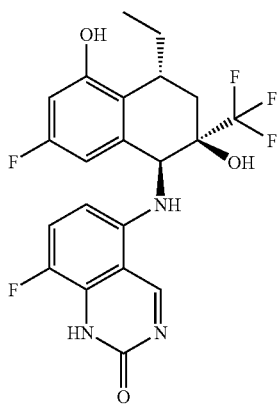

5-{[(5S,6R,8R)-8-Ethyl-3-fluoro-1,6-dihydroxy-6-(trifluoromethyl)-5,6,7,8-tetrahydronaphthalen-5-yl]amino}-8-fluoroquinolin-2(1H)-one is isolated as an additional product alongside Example 150.

1H-NMR (300 MHz, CD$_3$OD); δ=0.90 (t, 3H), 1.67 (ddq, 1H), 1.92 (m, 1H), 1.95 (dd, 1H), 2.33 (dd, 1H), 3.25 (m, 1H), 4.91 (s, 1H), 6.34 (dd, 1H), 6.44 (m, 2H), 6.54 (d, 1H), 7.18 (dd, 1H), 8.18 (d, 1H).

Example 155

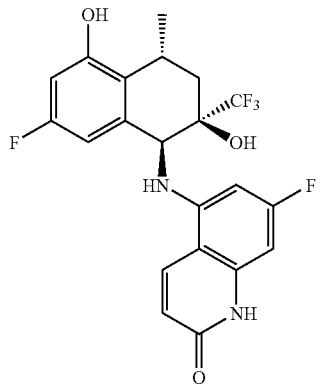

5-{[(1α,2α,4β)-7-Fluoro-2,5-Dihydroxy-4-methyl-2-(trifluoromethyl)-1,2,3,4-tetrahydronaphthalen-1-yl]amino}-7-fluoro-1H-quinolin-2-one 5-{[4-(4-Fluoro-2-methoxyphenyl)-2-hydroxy-2-(trifluoromethyl)pentylidene]-amino}-7-fluoro-1H-quinolin-2-one (241 mg, 0.53 mmol), prepared from the conventionally synthesized aldehyde and 5-amino-7-fluoro-1H-quinolin-2-one, is introduced in 3 ml of dichloromethane and admixed dropwise at –40° C. with 5.31 ml of a 1M solution of BBr$_3$ in dichloromethane. After three hours of stirring at –40° C. the batch is allowed to come to room temperature. After overnight stirring at room temperature the reaction mixture is poured cautiously onto a mixture of saturated NaHCO$_3$ solution and ice and is extracted three times with ethyl acetate. The combined organic extracts are washed with brine and dried over Na$_2$SO$_4$ and, after the solvent has been removed on a rotary evaporator, the residue is chromatographed (NH$_2$ Flash, eluent: dichloromethane/methanol). This gives 82.4 g (35.2%) of the title compound.

1H-NMR (300 MHz, CD$_3$OD): δ=1.45 (3H), 1.91 (1H), 2.47 (1H), 3.30 (1H, the signal lying practically beneath the solvent signal), 5.11 (1H), 6.33-6.52 (5H), 8.18 (1H).

Example 156

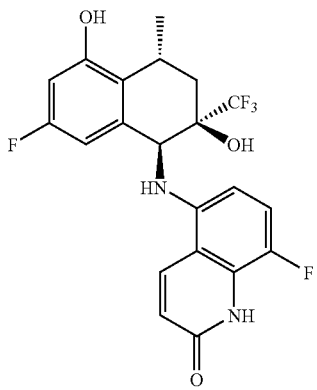

5-{[(1α,2α,4β)-7-Fluoro-2,5-dihydroxy-4-methyl-2-(trifluoromethyl)-1,2,3,4-tetrahydronaphthalen-1-yl]amino}-8-fluoro-1H-quinolin-2-one 5-{[4-(4-Fluoro-2-methoxyphenyl)-2-hydroxy-2-(trifluoromethyl)pentylidene]-amino}-8-fluoro-1H-quinolin-2-one (481.6 mg, 1.06 mmol), prepared from the conventionally synthesized aldehyde and 5-amino-8-fluoro-1H-quinolin-2-one, is introduced in 5 ml of dichloromethane and admixed dropwise at −40° C. with 10.6 ml of a 1M solution of BBr₃ in dichloromethane. After three hours of stirring at −40° C. the batch is allowed to come to room temperature. After overnight stirring at room temperature the reaction mixture is poured cautiously onto a mixture of saturated NaHCO₃ solution and ice and is extracted three times with ethyl acetate. The combined organic extracts are washed with brine and dried over Na₂SO₄ and, after the solvent has been removed on a rotary evaporator, the residue is chromatographed (Flash, eluent: dichloromethane/methanol). This gives 196.7 g (42.1%) of the title compound.

1H-NMR (300 MHz, CD₃OD): δ=1.39 (3H), 1.82 (1H), 2.39 (1H), 3.30 (1H, the signal lying practically beneath the solvent signal), 5.01 (1H), 6.38-6.50 (3H), 6.53 (1H), 7.19 (1H), 8.17 (1H).

Example 157

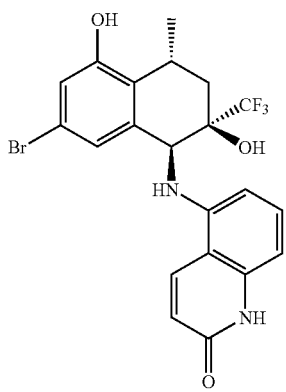

5-{[(1α,2α,4β)-7-Bromo-2,5-Dihydroxy-4-ethyl-2-(trifluoromethyl)-1,2,3,4-tetrahydronaphthalen-1-yl]amino}-1H-quinolin-2-one 5-{[4-(4-Bromo-2-methoxyphenyl)-2-hydroxy-2-(trifluoromethyl)hexylidene]-amino}-1H-quinolin-2-one (530 mg, 1.04 mmol), prepared from the aldehyde synthesized in analogy to Example 91 and 5-amino-1H-quinolin-2-one, is dissolved in 10 ml of dichloromethane and the solution is admixed dropwise at −50° C. with 10.4 ml of a 1M solution of BBr₃ in dichloromethane. After three hours of stirring at −40° C., two hours of stirring at between −40° C. and 0° C., one hour between 0° C. and room temperature, and 18 hours at room temperature, the reaction mixture is poured cautiously onto a mixture of saturated NaHCO₃ solution and ice. Following the addition of 150 ml of ethyl acetate, the mixture is stirred vigorously for 20 minutes. The ethyl acetate phase is separated off and the aqueous phase is extracted a further time with ethyl acetate. The combined organic extracts are washed with water (twice 40 ml) and brine (once 40 ml) and dried over Na₂SO₄ and, after the solvent has been removed on a rotary evaporator, the residue is subjected to chromatography (Flash, eluent: dichloromethane/methanol). This gives 216.6 g (42%) of the title compound.

1H-NMR (400 MHz, CD₃OD): δ =0.90 (3H), 1.70 (1H), 1.89-2.02 (2H), 2.35 (1H), 3.26 (1H, the signal lying partly beneath the solvent signal), 4.98 (1H), 6.45 (1H), 6.49 (1H), 6.69 (1H), 6.87 (2H), 7.33 (1H), 8.19 (1H).

Example 158

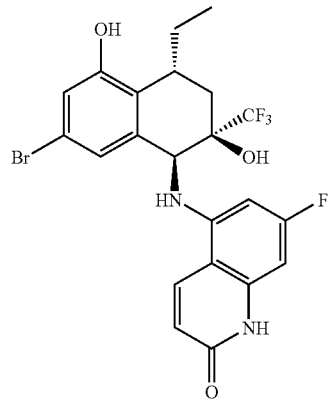

5-{[(1α,2α,4β)-7-Bromo-2,5-dihydroxy-4-ethyl-2-(trifluoromethyl)-1,2,3,4-tetrahydronaphthalen-1-yl]amino}-7-fluoro-1H-quinolin-2-one 5-{[4-(4-Bromo-2-methoxyphenyl)-2-hydroxy-2-(trifluoromethyl)hexylidene]-amino}-7-fluoro-1H-quinolin-2-one (500 mg, 0.94 mmol), prepared from the aldehyde synthesized in analogy to Example 91 and 5-amino-7-fluoro-1H-quinolin-2-one, is dissolved in 9.1 ml of dichloromethane and the solution is admixed dropwise at −50° C. with 9.45 ml of a 1M solution of BBr₃ in dichloromethane. After three hours of stirring at −40° C., two hours of stirring at between −40° C. and 0° C., one hour between 0° C. and room temperature, and 18 hours at room temperature, the reaction mixture is poured cautiously onto a mixture of saturated NaHCO₃ solution and ice. Following the addition of 150 ml of ethyl acetate, the mixture is stirred vigorously for 20 minutes. The ethyl acetate phase is separated off and the aqueous phase is extracted a further time with ethyl acetate (100 ml). The combined organic extracts are washed with water (twice 40 ml) and brine (once 40 ml) and dried over Na$_2$SO$_4$ and, after the solvent has been removed on a rotary evaporator, the residue is subjected to chromatography (Flash, eluent: dichloromethane/methanol). This gives 171.7 g (35.3%) of the title compound.

Examples 158A and 158B

5-{[(1R,2S,4S)-7-Bromo-2,5-Dihydroxy-4-ethyl-2-(trifluoromethyl)-1,2,3,4-tetrahydronaphthalen-1-yl]amino}-7-fluoro-1H-quinolin-2-one and 5-{[(1S,2R,4R)-7-bromo-2,5-Dihydroxy-4-ethyl-2-(trifluoromethyl)-1,2,3,4-tetrahydronaphthalen-1-yl]amino}-7-fluoro-1H-quinolin-2-one The racemate described in Example 158 is separated by means of chiral HPLC (Chiralpak AD-H 5μ, eluent: hexane/ethanol) into its enantiomers. This gives 85.2 mg of the (+)-enantiomer ([α]$_D$=+93.7°, MeOH) and 79 mg of the (−)-enantiomer ([α]$_D$=−95.9°, MeOH). No conclusion can of course be drawn concerning the absolute stereochemistry.

Example 159

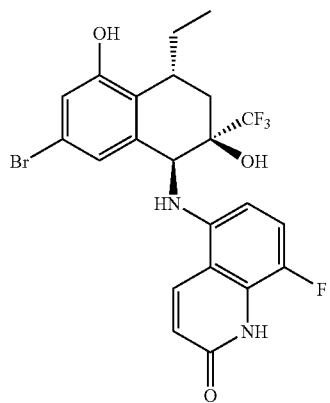

5-{[(1α,2α,4β)-7-Bromo-2,5-Dihydroxy-4-ethyl-2-(trifluoromethyl)-1,2,3,4-tetrahydronaphthalen-1-yl]amino}-8-fluoro-1H-quinolin-2-one 5-{[4-(4-Bromo-2-methoxyphenyl)-2-hydroxy-2-(trifluoromethyl)hexylidene]-amino}-8-fluoro-1H-quinolin-2-one (550 mg, 1.04 mmol), prepared from the aldehyde synthesized in analogy to Example 91 and 5-amino-8-fluoro-1H-quinolin-2-one, is dissolved in 10 ml of dichloromethane and the solution is admixed dropwise at −50° C. with 10.4 ml of a 1M solution of BBr$_3$ in dichloromethane. After three hours of stirring at −40° C., two hours of stirring at between −40° C. and 0° C., one hour between 0° C. and room temperature, and 18 hours at room temperature, the reaction mixture is poured cautiously onto a mixture of saturated NaHCO$_3$ solution and ice. Following the addition of 150 ml of ethyl acetate, the mixture is stirred vigorously for 20 minutes. The ethyl acetate phase is separated off and the aqueous phase is extracted a further time with ethyl acetate (100 ml). The combined organic extracts are washed with water (twice 40 ml) and brine (once 40 ml) and dried over Na$_2$SO$_4$ and, after the solvent has been removed on a rotary evaporator, the residue is subjected to chromatography (NH$_2$ Flash, eluent: dichloromethane/methanol). This gives 209.4 g (39.1%) of the title compound.

1H-NMR (300 MHz, CD$_3$OD): δ =0.92 (3H), 1.69 (1H), 1.86-2.01 (2H), 2.33 (1H), 3.25 (1H, the signal lying partly beneath the solvent signal), 4.92 (1H), 6.36 (1H), 6.53 (1H), 6.86 (2H), 7.19 (1H), 8.19 (1H).

Example 160

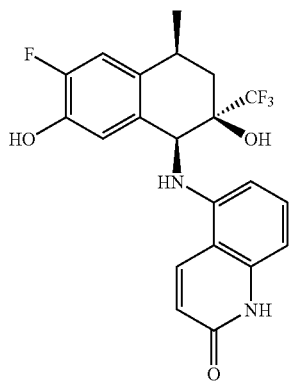

5-{[(1α,2α,4α)-6-Fluoro-2,7-dihydroxy-4-methyl-2-(trifluoromethyl)-1,2,3,4-tetrahydronaphthalen-1-yl]amino}-1H-quinolin-2-one 5-{[4-(3-Fluoro-4-methoxyphenyl)-2-hydroxy-2-(trifluoromethyl)pentylidene]-amino}-1H-quinolin-2-one (160 mg, 0.37 mmol), prepared from the corresponding aldehyde and 5-amino-1H-quinolin-2-one, is dissolved in 3.5 ml of dichloromethane and the solution is admixed dropwise at −20° C. with 3.7 ml of a 1M solution of BBr$_3$ in dichloromethane. After three hours of stirring at between −20 and +5° C. the reaction mixture is poured cautiously onto a mixture of saturated NaHCO$_3$ solution and ice. Following the addition of 100 ml of ethyl acetate the mixture is stirred vigorously for 20 minutes. The ethyl acetate phase is separated off and the aqueous phase is extracted a further time with ethyl acetate (50 ml). The combined organic extracts are washed with water (20 ml) and brine (20 ml) and dried over Na$_2$SO$_4$ and, following the removal of the solvent on a rotary evaporator, the residue is subjected to chromatography (Isolute NH$_2$, eluent: dichloromethane/methanol). This gives a diastereomer mixture (145 mg), which is separated via HPLC (Kromasil C18, 5μ, eluent: water/methanol) into the pure diastereomers. This gives 55.3 mg (35.7%) of the title compound and 89.4 mg (57.7%) of the compound which is epimeric in position 4, and which is described in Example 162.

1H-NMR (300 MHz, DMSO-d6): δ =1.32 (3H), 1.80 (1H), 2.18 (1H), 3.09 (1H), 5.28 (1H), 6.10 (1H), 6.25 (1H), 6.39 (1H), 6.55-6.63 (2H), 6.82 (1H), 7.10 (1H), 7.28 (1H), 8.18 (1H), 9.57 (1H), 11.53 (1H).

Example 161

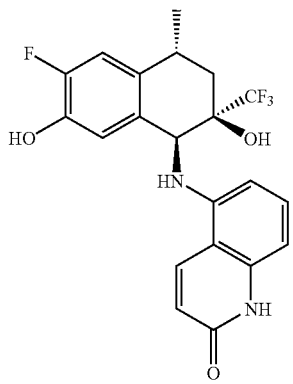

5-{[(1α,2α,4β)-6-Fluoro-2,7-dihydroxy-4-methyl-2-(trifluoromethyl)-1,2,3,4-tetrahydronaphthalen-1-yl]amino}-1H-quinolin-2-one Diastereomer separation, described in Example 160, gives 89.4 mg (57.7%) of the title compound.

1H-NMR (300 MHz, DMSO-d6): δ =1.39 (3H), 1.59 (1H), 2.39 (1H), 2.93 (1H), 4.90 (1H), 6.10 (1H), 6.12 (1H), 6.35-6.48 (2H), 6.59 (1H), 6.80 (1H), 7.06 (1H), 7.22 (1H), 8.23 (1H), 9.52 (1H), 11.58 (1H).

Example 162

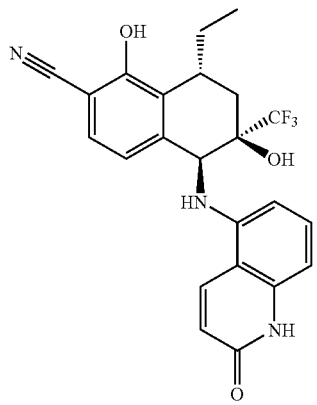

(5α,6α,8β)-8-Ethyl-1,6-dihydroxy-5-(2-oxo-1,2-dihydroquinolin-5-ylamino)-6-(trifluoromethyl)-5,6,7,8-tetrahydronaphthalene-2-carbonitrile 5-{[(1α,2α,4β)-6-Chloro-2,5-Dihydroxy-4-ethyl-2-(trifluoromethyl)-1,2,3,4-tetrahydronaphthalen-1-yl]amino}-1H-quinolin-2-one, described in Examples 92A and 92B (16.7 mg, 0.037 mmol), sodium cyanide (3.6 mg, 0.074 mmol) and nickel(I) bromide (8.17 mg, 0.037 mmol) are introduced into 0.33 ml of N-methylpyrrolidinone and reacted in a microwave apparatus under a pressure of 20 bar and at a temperature of 200° C. The reaction mixture is subsequently diluted with five ml of ethyl acetate. Following the addition of two ml of water it is stirred vigorously for 15 minutes. A further 50 ml of ethyl acetate are added and the organic phase is shaken twice with water (10 ml each time) and once with brine (10 ml). After drying over $Na_2SO_4$ has taken place, the solvent is removed on a rotary evaporator and the residue is chromatographed on silica gel (eluent: dichloromethane/methanol). This isolates 7.7 mg (47.7%) of the desired compound.

IR (diamond): 2225 $cm^{-1}$.

Example 163

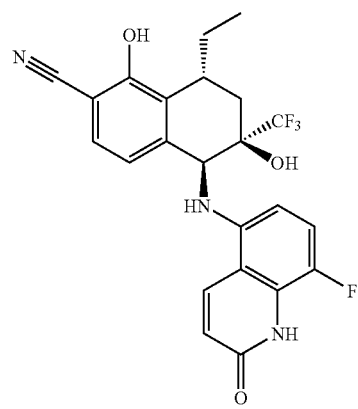

((5α,6α,8β)-8-Ethyl-1,6-dihydroxy-5-(8-fluoro-2-oxo-1,2-dihydroquinolin-5-ylamino)-6-(trifluoromethyl)-5,6,7,8-tetrahydronaphthalene-2-carbonitrile 5-{[(1α,2α,4β)-6-Chloro-4-ethyl-2,5-dihydroxy-2-(trifluoromethyl)-1,2,3,4-tetrahydronaphthalen-1-yl]amino}-8-fluoro-1H-quinolin-2-one, described in Examples 94A and 94B (13.8 mg, 0.029 mmol), sodium cyanide (2.87 mg, 0.059 mmol) and nickel(I) bromide (6.4 mg, 0.029 mmol) are introduced into 0.26 ml of N-methylpyrrolidinone and reacted in a microwave apparatus under a pressure of 20 bar and at a temperature of 200° C. The reaction mixture is subsequently diluted with five ml of ethyl acetate. Following the addition of two ml of water it is stirred vigorously for 15 minutes. A further 50 ml of ethyl acetate are added and the organic phase is shaken twice with water (10 ml each time) and once with brine (10 ml). After drying over $Na_2SO_4$ has taken place, the solvent is removed on a rotary evaporator and the residue is chromatographed on silica gel (eluent: dichloromethane/methanol). This isolates 10.8 mg (79.9%) of the desired compound.

IR (diamond): 2230 $cm^{-1}$.

Example 164

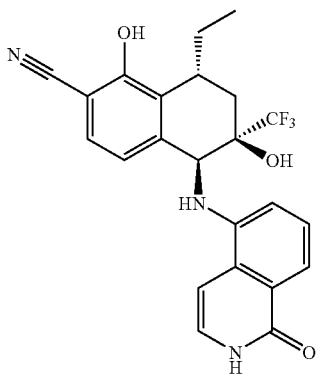

(5α,6α,8β)-8-Ethyl-1,6-dihydroxy-5-[(1-oxo-1,2-dihydroisoquinolin-5-yl)amino]-6-(trifluoromethyl)-5,6,7,8-tetrahydronaphthalene-2-carbonitrile 5-{[(1α,2α,4β)-6-Chloro-2,5-Dihydroxy-4-ethyl-2-(trifluoromethyl)-1,2,3,4-tetrahydronaphthalen-1-yl]amino}-2H-quinolin-1-one, described in Examples 96A and 96B, (34.8 mg, 0.077 mmol), sodium cyanide (7.53 mg, 0.15 mmol) and nickel(I) bromide (16.8 mg, 0.077 mmol are introduced into 0.68 ml of N-methylpyrrolidinone and reacted in a microwave apparatus under a pressure of 20 bar and at a temperature of 200° C. The reaction mixture is subsequently diluted with five ml of ethyl acetate. Following the addition of two ml of water it is stirred vigorously for 15 minutes. A further 50 ml of ethyl acetate are added and the organic phase is shaken twice with water (10 ml each time) and once with brine (10 ml). After drying over Na$_2$SO$_4$ has taken place, the solvent is removed on a rotary evaporator and the residue is chromatographed on silica gel (eluent: dichloromethane/methanol). This isolates 18.8 mg (55.2%) of the desired compound.

IR (diamond): 2230 cm$^{-1}$.

Example 165

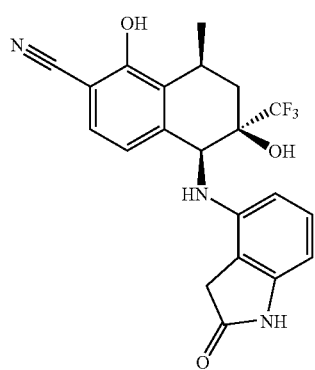

(5α,6α,8α)-8-Methyl-1,6-dihydroxy-5-(2-oxo-2,3-dihydro-1H-indol-4-ylamino)-6-(trifluoromethyl)-5,6,7,8-tetrahydronaphthalene-2-carbonitrile 4-{[(6-Chloro-2,5-dihydroxy-4-methyl-2-(trifluoromethyl)-1,2,3,4-tetrahydronaphthalen-1-yl]amino}-1,3-dihydroindol-2-one (70 mg, 0.16 mmol), described in Examples 89A and 89B—specifically a fraction containing both diastereomers, as a racemate—sodium cyanide (16.1 mg, 0.33 mmol) and nickel(I) bromide (35.8 mg, 0.16 mmol) are introduced into 1.45 ml of N-methylpyrrolidinone and reacted in a microwave apparatus under a pressure of 20 bar and at a temperature of 200° C. The reaction mixture is subsequently diluted with five ml of ethyl acetate. Following the addition of two ml of water it is stirred vigorously for 15 minutes. A further 50 ml of ethyl acetate are added and the organic phase is shaken twice with water (10 ml each time) and once with brine (10 ml). After drying over Na$_2$SO$_4$ has taken place, the solvent is removed on a rotary evaporator and the residue is chromatographed on silica gel (eluent: dichloromethane/methanol). This isolates 15.9 mg (23.2%) of the title compound and 9.1 mg (13.3%) of the compound which is epimeric in position 8, and which is characterized in Example 167.

IR (diamond): 2225 cm$^{-1}$.

Example 166

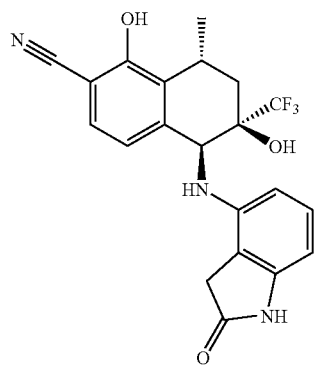

(5α,6α,8β)-1,6-Dihydroxy-8-methyl-5-[(2-oxo-2,3-dihydro-1H-indol-4-yl)amino]-6-(trifluoromethyl)-5,6,7,8-tetrahydronaphthalene-2-carbonitrile 9.1 mg of the title compound are obtained after reaction and chromatography, described in Example 166.

IR (KBr): 2225 cm$^{-1}$.

Example 167

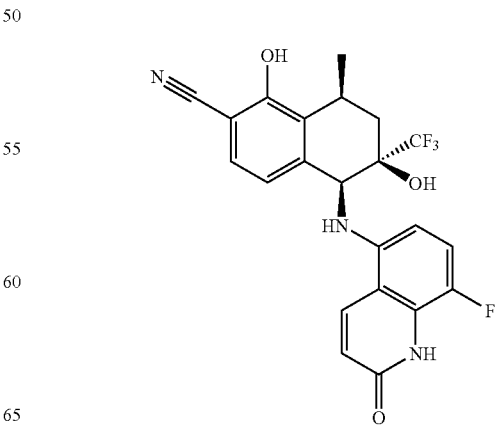

(5α,6α,8α)-5-(8-fluoro-2-oxo-1,2-dihydroquinolin-5-ylamino)-1,6-dihydroxy-8-methyl-6-(trifluoromethyl)-5,6,7,8-tetrahydronaphthalene-2-carbonitrile 5-{[(1α,2α,4β)-6-Chloro-2,5-Dihydroxy-4-methyl-2-(trifluoromethyl)-1,2,3,4-tetrahydronaphthalen-1-yl]amino}-8-fluoro-1H-quinolin-2-one (30.5 mg, 0.067 mmol), described in Examples 83A and 83B, sodium cyanide (6.54 mg, 0.13 mmol) and nickel(I) bromide (14.6 mg, 0.067 mmol) are introduced into 0.59 ml of N-methylpyrrolidinone and reacted in a microwave apparatus in the conventional way, already described a number of times. Work-up and chromatography give 16.5 mg (55.2%) of the desired compound.

IR (diamond): 2225 cm$^{-1}$.

Example 168

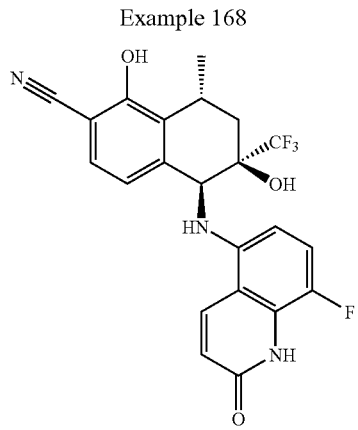

(5α,6α,8β)-5-[(8-Fluoro-2-oxo-1,2-dihydroquinolin-5-yl)amino]-1,6-dihydroxy-8-methyl-6-(trifluoromethyl)-5,6,7,8-tetrahydronaphthalene-2-carbonitrile 5-{[(1α,2α,4β)-6-Chloro-2,5-Dihydroxy-4-methyl-2-(trifluoromethyl)-1,2,3,4-tetrahydronaphthalen-1-yl]amino}-8-fluoro-1H-quinolin-2-one, described in Examples 84A and 84B, (21.4 mg, 0.047 mmol), sodium cyanide (4.6 mg, 0.094 mmol) and nickel(I) bromide (10.2 mg, 0.047 mmol) are introduced into 0.41 ml of N-methylpyrrolidinone and reacted in a microwave apparatus at a pressure of 20 bar and at a temperature of 200° C. Work-up and chromatography as already described a number of times, under identical conditions, isolate 15.4 mg (73.5%) of the desired compound.

IR (diamond): 2230 cm$^{-1}$.

Example 169

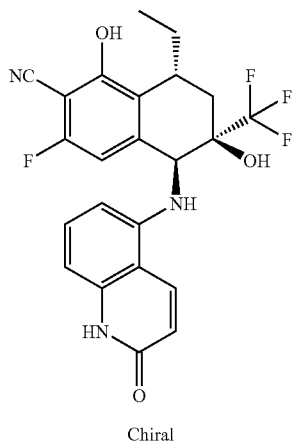

Chiral

5-{[(5S,6R,8R)-8-Ethyl-1,6-dihydroxy-3-fluoro-5-[(2-oxo-1,2-dihydroquinolin-5-yl)amino]-6-(trifluoromethyl)-5,6,7,8-tetrahydronaphthalene-2-carbonitrile 20 mg (0.04 mmol) of 5-{[(5S,6R,8R)-2-chloro-8-ethyl-3-fluoro-1,6-dihydroxy-2-6-(trifluoromethyl)-5,6,7,8-tetrahydronaphthalen-5-yl]amino}quinolin-2(1H)-one, 4.2 mg (0.08 mmol) of sodium cyanide and 9.3 mg (0.04 mmol) of nickel(II) bromide in 1.4 ml of N-methyl-2-pyrrolidinone are irradiated with microwaves for 20 minutes (CEM Discover®, max. temperature 200° C., energy 120 W, max. pressure 20 bar). The reaction mixture is diluted with ethyl acetate and water and stirred vigorously. The phases are separated and washing is carried out with water and saturated sodium chloride solution. Drying over sodium sulphate and removal of the solvent, followed by preparative thin-layer chromatography on an amine phase (Merck NH$_2$F$_{254}$, ethyl acetate/methanol/triethylamine 15:3:1), yield 7 mg of desired product.

$^1$H-NMR (300 MHz, CD$_3$OD); δ=0.90 (t, 3H), 1.66 (ddq, 1H), 1.86 (m, 1H), 1.98 (dd, 1H), 2.33 (dd, 1H), 3.28 (m, 1H), 4.99 (s, 1H), 5.97 (d, 1H), 6.41 (d, 1H), 6.50 (d, 1H), 6.66 (d, 1H), 7.32 (t, 1H), 8.18 (d, 1H).

Example 170

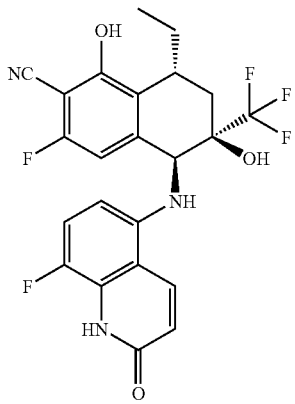

(5α,6α,8β)-8-Ethyl-1,6-dihydroxy-3-fluoro-5-[(8-fluoro-2-oxo-1,2-dihydroquinolin-5-yl)amino]-6-(trifluoromethyl)-5,6,7,8-tetrahydronaphthalene-2-carbonitrile 15 mg (0.03 mmol) of 5-{[(5S,6R,8R)-2-chloro-8-ethyl-3-fluoro-1,6-dihydroxy-2-6-(trifluoromethyl)-5,6,7,8-tetrahydronaphthalen-5-yl]amino}-8-fluoroquinolin-2(1H)-one, 3.0 mg (0.06 mmol) of sodium cyanide and 6.7 mg (0.03 mmol) of nickel(II) bromide in 1 ml of N-methyl-2-pyrrolidinone are irradiated with microwaves for 20 minutes (CEM Discover®, max. temperature 200° C., energy 120 W, max. pressure 20 bar). The reaction mixture is diluted with ethyl acetate and water and stirred vigorously. The phases are separated and washing is carried out with water and saturated sodium chloride solution. Drying over sodium sulphate and removal of the solvent, followed by preparative thin-layer chromatography on silica gel (ethyl acetate), yield 8 mg of desired product ¹H-NMR (300 MHz, CD₃OD); δ=0.90 (t, 3H), 1.66 (ddq, 1H), 1.86 (m, 1H), 1.98 (dd, 1H), 2.33 (dd, 1H), 3.28 (m, 1H), 4.99 (s, 1H), 5.97 (d, 1H), 6.41 (d, 1H), 6.50 (d, 1H), 6.66 (d, 1H), 7.32 (t, 1H), 8.18 (d, 1H).

Example 171

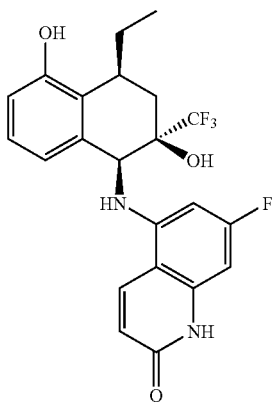

5-{[(1α,2α,4α)-2,5-Dihydroxy-4-ethyl-2-(trifluoromethyl)-1,2,3,4-tetrahydronaphthalen-1-yl]amino}-7-fluoro-1H-quinolin-2-one 5-{[4-(2-Methoxyphenyl)-2-hydroxy-2-(trifluoromethyl)hexylidene]amino}-7-fluoro-1H-quinolin-2-one (670 mg, 1.49 mmol), prepared from 4-(2-methoxyphenyl)-2-hydroxy-2-(trifluoromethyl)hexanal (synthesized in analogy to the process described in Example 91) and 5-amino-7-fluoro-1H-quinolin-2-one, is dissolved in 14.9 ml of dichloromethane and the solution is admixed dropwise at −50° C. with 14.87 ml of a 1M solution of boron tribromide in dichloromethane. After two hours of stirring at −40° C., one hour of stirring at between −40 and −20° C., one hour of stirring at between −20 and −10° C., one hour of stirring at between −10° C. and room temperature, stirring is continued at room temperature for 18 hours. The batch is poured onto a mixture of sodium hydrogen carbonate solution and ice, diluted with 150 ml of ethyl acetate and then stirred vigorously for 20 minutes. The ethyl acetate phase is separated off and the aqueous phase is extracted a further time with ethyl acetate (100 ml). The combined organic extracts are washed twice with water (40 ml each time) and once with brine (40 ml) and dried and the solvent is removed on a rotary evaporator. Repeated chromatography (Flashmaster, eluent: dichloromethane/methanol) gives 97.4 mg of the title compound and 178.4 mg of the diastereomer epimeric in position 4 (characterized in Example 172) (in each case as a racemate). Additionally a slightly contaminated fraction of the title compound is obtained (118.6 mg).

1H-NMR (400 MHz, CD₃OD): δ=1.09 (3H), 1.89 (1H), 2.02-2.13 (2H), 2.39 (1H), 3.00 (1H), 5.07 (1H), 6.32-6.42 (3H), 6.55-6.73 (2H), 6.96 (1H), 8.13 (1H).

Example 172

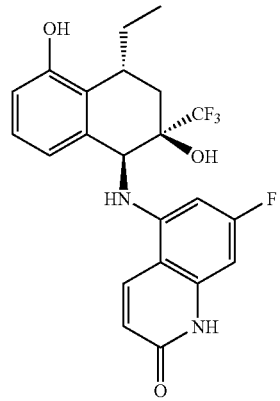

5-{[(1α,2α,4β)-2,5-Dihydroxy-4-ethyl-2-(trifluoromethyl)-1,2,3,4-tetrahydronaphthalen-1-yl]amino}-7-fluoro-1H-quinolin-2-one 178.4 mg of the title compound are isolated, its preparation having been described in Example 171.

1H-NMR (400 MHz, CD₃OD): δ=0.93 (3H), 1.70 (1H), 1.92-2.05 (2H), 2.37 (1H), 3.30 (1H, the signal lying practically beneath the solvent signal), 4.99 (1H), 6.22 (1H), 6.37 (1H), 6.42 (1H), 6.69 (2H), 6.95 (1H), 8.12 (1H).

Example 173

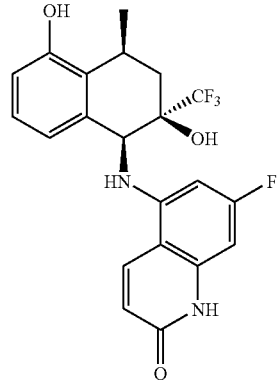

5-{[(1α,2α,4β)-2,5-Dihydroxy-4-methyl-2-(trifluoromethyl)-1,2,3,4-tetrahydronaphthalen-1-yl]amino}-7-fluoro-1H-quinolin-2-one 5-{[4-(2-Methoxyphenyl)-2-hydroxy-2-(trifluoromethyl)pentylidene]amino}-7-fluoro-1H-quinolin-2-one (290 mg, 0.66 mmol), prepared from 4-(2-methoxyphenyl)-2-hydroxy-2-(trifluoromethyl)pentanal and 5-amino-7-fluoro-1H-quinolin-2-one by the titanate process, is dissolved in 6.6 ml of dichloromethane and the solution is admixed dropwise at −50° C. with 6.65 ml of a 1M solution of boron tribromide in dichloromethane. After the reaction regime described in Example 172 (temperature programme) and work-up, the residue is subjected to repeated chromatography (Flashmaster NH₂ phase, eluent: dichloromethane/methanol). This gives 37.8 mg (13.5%) of the title compound and 79.3 mg (28.3%) of the diastereomer epimeric in position 4 (characterized in Example 175) (in each case as a racemate).

Examples 173A and 173B

5-{[(1R,2S,4R)-2,5-Dihydroxy-4-methyl-2-(trifluoromethyl)-1,2,3,4-tetrahydronaphthalen-1-yl]amino}-7-fluoro-1H-quinolin-2-one and 5-{[(1S,2R,4S)-2,5-Dihydroxy-4-methyl-2-(trifluoromethyl)-1,2,3,4-tetrahydronaphthalen-1-yl]amino}-7-fluoro-1H-quinolin-2-one The diastereomer (69.5 mg) described in Example 173 is separated by means of chiral HPLC (Chiralcel OD 5μ, eluent: hexane/ethanol) into its enantiomers. This gives 13.9 mg (20%) of the (−)-enantiomer ([α]$_D$=−46.6°, MeOH) and 14.1 mg (20.3%) of the (+)-enantiomer ([α]$_D$=+46.9°, MeOH). No conclusion can of course be drawn concerning the absolute stereochemistry.

Example 174

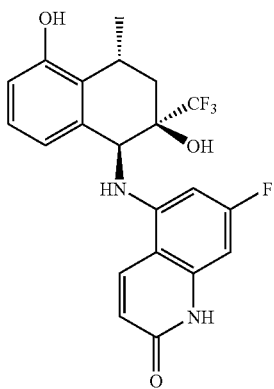

5-{[(1α,2α,4β)-2,5-Dihydroxy-4-methyl-2-(trifluoromethyl)-1,2,3,4-tetrahydronaphthalen-1-yl]amino}7-fluoro-1H-quinolin-2-one 79.3 mg (28.3%) of the title compound are obtained by the reaction described in Example 174.

Examples 174A and 174B

5-{[(1R,2S,4S)-2,5-Dihydroxy-4-methyl-2-(trifluoromethyl)-1,2,3,4-tetrahydronaphthalen-1-yl]amino}-7-fluoro-1H-quinolin-2-one and 5-{[(1S,2R,4R)-2,5-Dihydroxy-4-methyl-2-(trifluoromethyl)-1,2,3,4-tetrahydronaphthalen-1-yl]amino}-7-fluoro-1H-quinolin-2-one The diastereomer (67.4 mg) described in Example 174 is separated by means of chiral HPLC (Chiralcel OD 5μ, eluent: hexane/ethanol) into its enantiomers. This gives 33.1 mg (49.1%) of the (+)-enantiomer ([α]$_D$=+39.9°, MeOH) and 27.2 mg (40.4%) of the (−)-enantiomer ([α]$_D$=−48.7°, MeOH). No conclusion can of course be drawn concerning the absolute stereochemistry.

Example 175

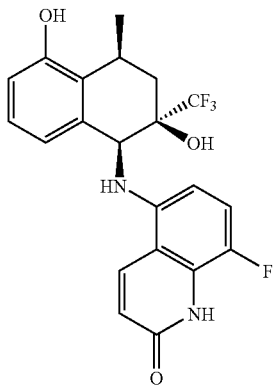

5-{[(1α,2α,4α)-2,5-Dihydroxy-4-methyl-2-(trifluoromethyl)-1,2,3,4-tetrahydronaphthalen-1-yl]amino}-8-fluoro-1H-quinolin-2-one 5-{[4-(2-Methoxyphenyl)-2-hydroxy-2-(trifluoromethyl)pentylidene]amino}-8-fluoro-1H-quinolin-2-one (455 mg, 1.04 mmol), prepared from 4-(2-methoxyphenyl)-2-hydroxy-2-(trifluoromethyl)pentanal and 5-amino-8-fluoro-1H-quinolin-2-one by the glacial acetic acid process, is dissolved in 10.4 ml of dichloromethane and the solution is admixed dropwise at −50° C. with 10.4 ml of a 1M solution of boron tribromide in dichloromethane. After the reaction regime described in Example 172 (temperature programme) and work-up, the residue is subjected to repeated chromatography (Flashmaster NH₂ phase, eluent: dichloromethane/methanol). This gives 88.3 mg (20.1%) of the title compound and 223.1 mg (50.7%) of the diastereomer epimeric in position 4 (characterized in Example 177) (in each case as a racemate).

Examples 175A and 175B

5-{[(1R,2S,4R)-2,5-Dihydroxy-4-methyl-2-(trifluoromethyl)-1,2,3,4-tetrahydronaphthalen-1-yl]amino}-8-fluoro-1H-quinolin-2-one and 5-{[(1S,2R,4S)-2,5-Dihydroxy-4-methyl-2-(trifluoromethyl)-1,2,3,4-tetrahydronaphthalen-1-yl]amino}-8-fluoro-1H-quinolin-2-one The diastereomer (71.8 mg) described in Example 176 is separated by means of chiral HPLC (Chiralcel OD-H 5μ, eluent: hexane/ethanol) into its enantiomers. This gives 35.5 mg (49.4%) of the (−)-enantiomer ([α]$_D$=−27.2°, MeOH) and 35.6 mg (49.6%) of the (+)-enantiomer ([α]$_D$=+26.5°, MeOH). No conclusion can of course be drawn concerning the absolute stereochemistry.

Example 176

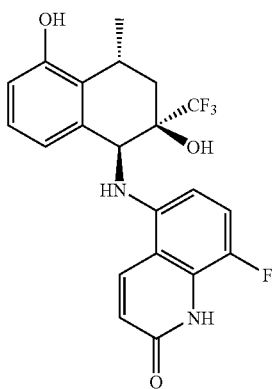

5-{[(1α,2α,4β)-2,5-dihydroxy-4-methyl-2-(trifluoromethyl)-1,2,3,4-tetrahydronaphthalen-1-yl]amino}-8-fluoro-1H-quinolin-2-one 223.1 mg (50.7%) of the title compound are obtained by the reaction described in Example 176.

Examples 176A and 176B

5-{[(1R,2S,4S)-2,5-Dihydroxy-4-methyl-2-(trifluoromethyl)-1,2,3,4-tetrahydronaphthalen-1-yl]amino}-8-fluoro-1H-quinolin-2-one and 5-{[(1S,2R,4R)-2,5-Dihydroxy-4-methyl-2-(trifluoromethyl)-1,2,3,4-tetrahydronaphthalen-1-yl]amino}-8-fluoro-1H-quinolin-2-one The diastereomer (192.7 mg) described in Example 177 is separated by means of chiral HPLC (Chiralcel OD 5μ, eluent: hexane/ethanol) into its enantiomers. This gives 97.9 mg (50.8%) of the (+)-enantiomer ([α]$_D$=+74.6°, MeOH) and 104.1 mg (54.1%) of the (−)-enantiomer ([α]$_D$=−78.6°, MeOH). No conclusion can of course be drawn concerning the absolute stereochemistry.

Example 177

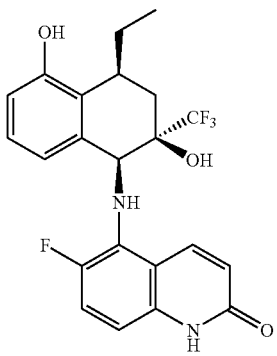

5-{[(1α,2α,4α)-4-Ethyl-2,5-dihydroxy-2-(trifluoromethyl)-1,2,3,4-tetrahydronaphthalen-1-yl]amino}-6-fluoro-1H-quinolin-2-one 5-{[4-(2-Methoxyphenyl)-2-hydroxy-2-trifluoromethyl)hexylidene]amino}-6-fluoro-1H-quinolin-2-one (271 mg, 0.6 mmol), prepared from 4-(2-methoxyphenyl)-2-hydroxy-2-(trifluoromethyl)-hexanal (synthesized in analogy to the process described in Example 91) and 5-amino-6-fluoro-1H-quinolin-2-one by the modified titanate method (addition of glacial acetic acid and dioxane) is dissolved in 6 ml of dichloromethane and the solution is admixed dropwise at −50° C. with 6 ml of a 1M solution of boron tribromide in dichloromethane. After two hours of stirring at −40° C., one hour of stirring at between −40 and −20° C., one hour of stirring at between −20 and −10° C., one hour of stirring at between −10° C. and room temperature, stirring is continued at room temperature for 18 hours. The batch is poured onto a mixture of saturated sodium hydrogen carbonate solution and ice, diluted with 100 ml of ethyl acetate and then stirred vigorously for 20 minutes. The ethyl acetate phase is separated off and the aqueous phase is extracted a further time with ethyl acetate (50 ml). The combined organic extracts are washed twice with water (20 ml each time) and once with brine (20 ml) and dried and the solvent is removed on a rotary evaporator. Repeated chromatography (Flashmaster, eluent: dichloromethane/methanol) gives 28.6 mg (10.9%) of the title compound and 59.8 mg (22.8%) of the diastereomer epimeric in position 4 (characterized in Example 178) (in each case as a racemate).

1H-NMR (300 MHz, DMSO-d6): δ =1.04 (3H), 1.88 (1H), 2.05 (1H), 2.23 (1H), 2.43 (1H), 5.18 (1H), 5.55 (1H), 6.19 (1H), 6.42 (1H), 6.62-6.80 (2H), 6.85 (1H), 6.99 (1H), 7.28 (1H), 8.19 (1H), 9.44 (1H), 11.65 (1H).

Example 178

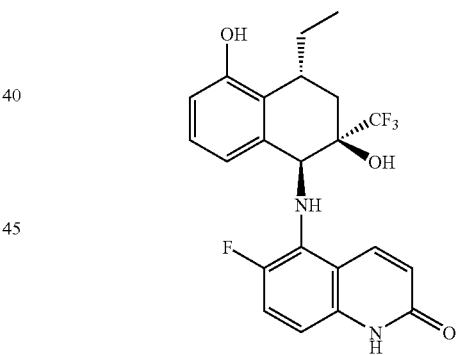

5-{[(1α,2α,4β)-4-Ethyl-2,5-dihydroxy-2-(trifluoromethyl)-1,2,3,4-tetrahydronaphthalen-1-yl]amino}-6-fluoro-1H-quinolin-2-one 59.8 mg (22.8%) of the title compound (described in Example 177) are obtained.

1H-NMR (400 MHz, CD$_3$OD): δ =0.89 (3H), 1.69 (1H), 1.82-1.99 (2H), 2.30 (1H), 3.32 (1H, the signal lying practically beneath the solvent signal), 5.30 (1H), 6.49 (1H), 6.66-6.74 (2H), 7.02 (1H), 7.10 (1H), 7.25 (1H), 8.15 (1H).

Example 179

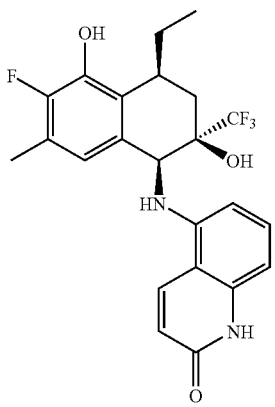

5-{[(1α,2α,4α)-4-Ethyl-6-fluoro-2,5-dihydroxy-7-methyl-2-(trifluoromethyl)-1,2,3,4-tetrahydronaphthalen-1-yl]amino}-1H-quinolin-2-one A mixture of 5-{[4-(3-fluoro-4-methyl-2-methoxyphenyl)-2-hydroxy-2-(trifluoromethyl)hexylidene]amino}-1H-quinolin-2-one and 5-{[4-(3-fluoro-4-methyl-2-methoxyphenyl)-2-hydroxy-3-methyl-2-(trifluoromethyl)pentylidene]-amino}-1H-quinolin-2-one (676.4 mg, 1.46 mmol), prepared from the mixture of the corresponding aldehydes and 5-amino-1H-quinolin-2-one, is dissolved in 7 ml of dichloromethane and the solution is admixed dropwise at −40° C. with 7.3 ml of a 1M solution of boron tribromide in dichloromethane. After three-hour stirring at −40° C. the reaction is allowed to come slowly to room temperature. After overnight stirring at room temperature, the batch is poured onto a mixture of saturated sodium hydrogen carbonate solution and ice and is extracted three times with ethyl acetate. The combined organic extracts are washed with brine and dried and the solvent is removed on a rotary evaporator. Twofold chromatography (Flashmaster, eluent: dichloromethane/methanol) and subsequent HPLC (XBridge C18, 5µ, eluent: water/acetonitrile) give 23.1 mg (7.1%) of the title compound (still contains 11% of a dimethyl derivative) and 30.1 mg (9.2%) of the diastereomer epimeric in position 4 (characterized in Example 180) (in each case as a racemate).

1H-NMR (400 MHz, CD$_3$OD): δ=1.08 (3H), 1.90 (1H), 1.98-2.13 (5H), 2.35 (1H), 2.98 (1H), 5.02 (1H), 6.45 (1H), 6.50-6.70 (3H), 7.34 (1H), 8.19 (1H).

Example 180

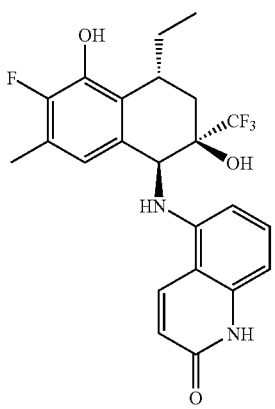

5-{[(1α,2α,4β)-4-Ethyl-6-fluoro-2,5-Dihydroxy-7-methyl-2-(trifluoromethyl)-1,2,3,4-tetrahydronaphthalen-1-yl]amino}-1H-quinolin-2-one 30.1 mg (9.2%) of the title compound are obtained from the reaction described in Example 180.

1H-NMR (400 MHz, CD$_3$OD): δ=0.90 (3H), 1.71 (1H), 1.89-2.00 (2H), 2.08 (1H), 2.32 (1H), 3.30 (1H, the signal lying practically beneath the solvent signal), 4.93 (1H), 6.40-6.50 (2H), 6.56 (1H), 6.65 (1H), 7.32 (1H), 8.18 (1H).

Example 181

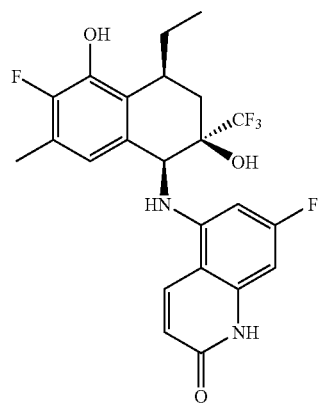

5-{[(1α,2α,4α)-4-Ethyl-6-fluoro-2,5-dihydroxy-7-methyl-2-(trifluoromethyl)-1,2,3,4-tetrahydronaphthalen-1-yl]amino}-7-fluoro-1H-quinolin-2-one A mixture of 5-{[4-(3-fluoro-4-methyl-2-methoxyphenyl)-2-hydroxy-2-(trifluoromethyl)hexylidene]amino}-7-fluoro-1H-quinolin-2-one and 5-{[4-(3-fluoro-4-methyl-2-methoxyphenyl)-2-hydroxy-3-methyl-2-(trifluoromethyl)pentylidene]amino}-7-fluoro-1H-quinolin-2-one (307.5 mg, 0.64 mmol), prepared from the mixture of the corresponding aldehydes and 5-amino-7-fluoro-1H-quinolin-2-one, is dissolved in 4 ml of dichloromethane and the solution is admixed dropwise at −40° C. with 6.4 ml of a 1M solution of boron tribromide in dichloromethane. After three-hour stirring at −40° C. the reaction is allowed to come slowly to room temperature. After overnight stirring at room temperature, the batch is poured onto a mixture of saturated sodium hydrogen carbonate solution and ice and is extracted three times with ethyl acetate. The combined organic extracts are washed with brine and dried and the solvent is removed on a rotary evaporator. Twofold chromatography (Flashmaster, eluent: dichloromethane/methanol) and subsequent HPLC (XBridge C18, 5µ, eluent: water/acetonitrile) give 20 mg (13.4%) of the title compound (still contains a diastereomer of the dimethyl compound) and 38.3 mg (25.7%) of the diastereomer epimeric in position 4 (still contains a diastereomer of the dimethyl compound; characterized in Example 182) (in each case as a racemate).

1H-NMR (300 MHz, CD$_3$OD): δ=1.12 (3H), 1.93 (1H), 2.05-2.20 (5H), 2.39 (1H), 3.04 (1H), 5.05 (1H), 6.38-6.51 (3H), 6.61 (1H), 8.18 (1H).

Example 182

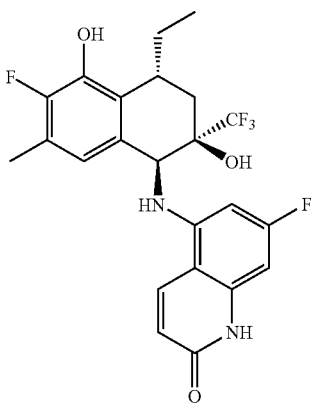

5-{[(1α,2α,4β)-4-Ethyl-6-fluoro-2,5-dihydroxy-7-methyl-2-(trifluoromethyl)-1,2,3,4-tetrahydronaphthalen-1-yl]amino}-7-fluoro-1H-quinolin-2-one 38.3 mg (25.7%) of the title compound are obtained from the reaction described in Example 181.

1H-NMR (300 MHz, CD$_3$OD): δ=0.98 (3H), 1.79 (1H), 1.95-2.05 (2H), 2.18 (3H), 2.40 (1H), 3.32 (1H, the signal lying practically beneath the solvent signal), 4.99 (1H), 6.29 (1H), 6.42 (1H), 6.48 (1H), 6.60 (1H), 8.19 (1H).

Example 183

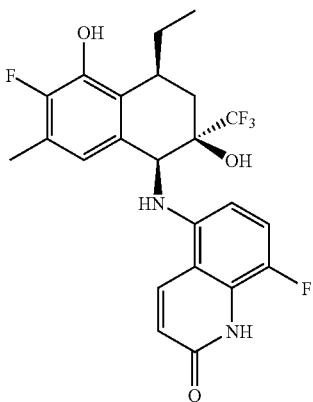

5-{[(1α,2α,4α)-4-Ethyl-6-fluoro-2,5-Dihydroxy-7-methyl-2-(trifluoromethyl)-1,2,3,4-tetrahydronaphthalen-1-yl]amino}-8-fluoro-1H-quinolin-2-one A mixture of 5-{[4-(3-fluoro-4-methyl-2-methoxyphenyl)-2-hydroxy-2-(trifluoromethyl)hexylidene]amino}-8-fluoro-1H-quinolin-2-one and 5-{[4-(3-fluoro-4-methyl-2-methoxyphenyl)-2-hydroxy-3-methyl-2-(trifluoromethyl)pentylidene]amino}-8-fluoro-1H-quinolin-2-one (867.4 mg, 1.8 mmol), prepared from the mixture of the corresponding aldehydes and 5-amino-8-fluoro-1H-quinolin-2-one, is dissolved in 9 ml of dichloromethane and the solution is admixed dropwise at −40° C. with 18 ml of a 1M solution of boron tribromide in dichloromethane. After three-hour stirring at −40° C. the reaction is allowed to come slowly to room temperature. After overnight stirring at room temperature, the batch is poured onto a mixture of saturated sodium hydrogen carbonate solution and ice and is extracted three times with ethyl acetate. The combined organic extracts are washed with brine and dried and the solvent is removed on a rotary evaporator. Chromatography (Flashmaster, eluent: dichloromethane/methanol) and subsequent HPLC (XBridge C18, 5μ, eluent: water/acetonitrile) give 10.7 mg (2.5%) of the title compound and 18.8 mg (4.5%) of the diastereomer epimeric in position 4 (characterized in Example 184) (in each case as a racemate).

1H-NMR (300 MHz, CD$_3$OD): δ=1.12 (3H), 1.93 (1H), 2.05-2.19 (5H), 2.39 (1H), 3.04 (1H), 5.00 (1H), 6.51-6.68 (3H), 7.25 (1H), 8.21 (1H).

Example 184

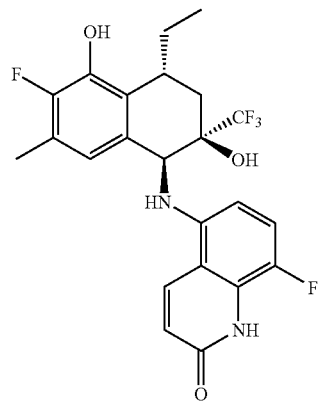

5-{[(1α,2α,4β)-4-Ethyl-6-fluoro-2,5-dihydroxy-7-methyl-2-(trifluoromethyl)-1,2,3,4-tetrahydronaphthalen-1-yl]amino}-8-fluoro-1H-quinolin-2-one 18.8 mg (4.2%) of the title compound are obtained from the reaction described in Example 183.

1H-NMR (300 MHz, CD$_3$OD): δ=0.98 (3H), 1.78 (1H), 1.93-2.05 (2H), 2.12 (3H), 2.39 (1H), 3.32 (1H, the signal lying practically beneath the solvent signal), 4.95 (1H), 6.40 (1H), 6.53-6.65 (2H), 7.22 (1H), 8.20 (1H).

Example 185

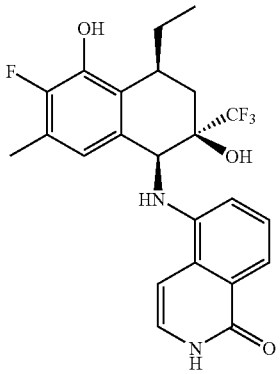

5-{[(1α,2α,4α)-4-Ethyl-6-fluoro-2,5-dihydroxy-7-methyl-2-(trifluoromethyl)-1,2,3,4-tetrahydronaphthalen-1-yl]amino}-2H-quinolin-1-one A mixture of 5-{[4-(3-fluoro-4-methyl-2-methoxyphenyl)-2-hydroxy-2-(trifluoromethyl)hexylidene]amino}-2H-quinolin-1-one and 5-{[4-(3-fluoro-4-methyl-2-methoxyphenyl)-2-hydroxy-3-methyl-2-(trifluoromethyl)pentylidene]-amino}-2H-quinolin-1-one (845.2 mg, 1.84 mmol), prepared from the mixture of the corresponding aldehydes and 5-amino-2H-quinolin-1-one, is dissolved in 9 ml of dichloromethane and the solution is admixed dropwise at −40° C. with 9.1 ml of a 1M solution of boron tribromide in dichloromethane. After three-hour stirring at −40° C. the reaction is allowed to come slowly to room temperature. After overnight stirring at room temperature, the batch is poured onto a mixture of saturated sodium hydrogen carbonate solution and ice and is extracted three times with ethyl acetate. The combined organic extracts are washed with brine and dried and the solvent is removed on a rotary evaporator. Chromatography (Flashmaster, eluent: dichloromethane/methanol) and subsequent HPLC (XBridge C18, 5μ, eluent: water/acetonitrile) give 66.5 mg (16.2%) of the title compound and 51.4 mg (12.5%) of the compound epimeric in position 4 (characterized in Example 186) (in each case as a racemate).

1H-NMR (400 MHz, CD₃OD): δ=1.06 (3H), 1.90 (1H), 1.99-2.11 (5H), 2.36 (1H), 3.01 (1H), 5.00 (1H), 6.54 (1H), 6.78 (1H), 7.06-7.13 (2H), 7.35 (1H), 7.68 (1H).

Example 186

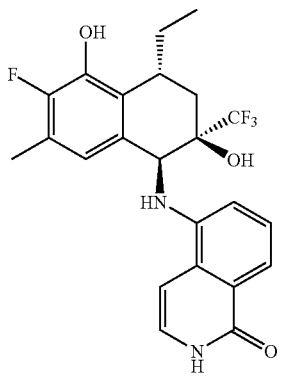

5-{[(1α,2α,4β)-4-Ethyl-6-fluoro-2,5-dihydroxy-7-methyl-2-(trifluoromethyl)-1,2,3,4-tetrahydronaphthalen-1-yl]amino}-2H-quinolin-1-one 51.4 mg (12.5%) of the title compound are obtained from the reaction described in Example 185.

1H-NMR (400 MHz, CD₃OD): δ=0.92 (3H), 1.72 (1H), 1.89-2.00 (2H), 2.07 (3H), 2.32 (1H), 3.31 (1H), 4.93 (1H), 6.56 (1H), 6.81 (1H), 6.88 (1H), 7.13 (1H), 7.32 (1H), 7.62 (1H).

Example 187

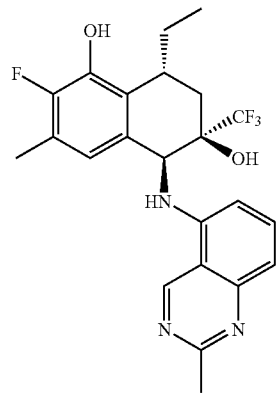

(5α,6α,8β)-8-Ethyl-2-fluoro-3-methyl-5-[(2-methylquinazolin-5-yl)amino]-6-(trifluoromethyl)-5,6,7,8-tetrahydronaphthalene-1,6-diol The mixture of 1,1,1-trifluoro-2-[(2-methylquinazolin-5-ylimino)methyl-]-4-(3-fluoro-4-methyl-2-methoxyphenyl)hexan-2-ol and 1,1,1-trifluoro-3-methyl-2-[(2-methylquinazolin-5-ylimino)-methyl-]-4-(3-fluoro-4-methyl-2-methoxyphenyl)-pentan-2-ol (536.4 mg, 1.16 mmol), prepared from the mixture of the corresponding aldehydes and 5-amino-2-methylquinazoline, is dissolved in 7 ml of dichloromethane and the solution is admixed dropwise at −40° C. with 11.6 ml of a 1M solution of boron tribromide in dichloromethane. After three-hour stirring at −40° C. the reaction is allowed to come slowly to room temperature. After overnight stirring at room temperature the batch is poured onto a mixture of saturated sodium hydrogen carbonate solution and ice and is extracted three times with ethyl acetate. The combined organic extracts are washed with brine and dried and the solvent is removed on a rotary evaporator. Repeated chromatography (Flashmaster, eluent: dichloromethane/methanol) gives 4.1 mg (1.6%) of the title compound as a racemate (contaminated with the corresponding dimethyl compound).

1H-NMR (300 MHz, CD₃OD): δ=0.98 (3H), 1.80 (1H), 1.95-2.10 (2H), 2.11 (3H), 2.42 (1H), 2.83 (3H), 3.39 (1H, the signal lying practically beneath the solvent signal), 5.15 (1H), 6.62 (1H), 6.81 (1H), 7.20 (1H), 7.80 (1H), 9.62 (1H).

Example 188

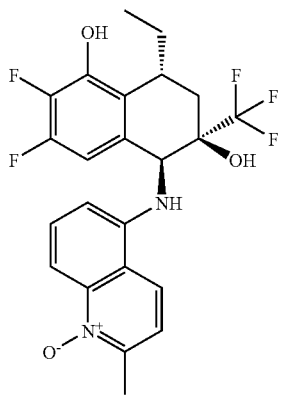

(5S,6R,8R)-8-Ethyl-2,3-difluoro-5-[(2-methyl-1-oxyquinolin-5-yl)amino]-6-(trifluoromethyl)-5,6,7,8-tetrahydronaphthalene-1,6-diol 91 mg (0.2 mmol) of (5S,6R,8R)-8-ethyl-2,3-difluoro-5-[(2-methylquinolin-5-yl)amino]-6-(trifluoromethyl)-5,6,7,8-tetrahydronaphthalene-1,6-diol in 20 ml of dichloromethane are admixed with 85 mg (0.49 mmol) of 3-chloroperoxybenzoic acid. The mixture is stirred at room temperature for two hours and saturated NaHCO$_3$ solution is added. After 15 minutes the mixture is diluted with water and extracted repeatedly with dichloromethane, the extracts are washed with saturated sodium chloride solution and dried over sodium sulphate and the solvent is removed in vacuo. Column chromatography on silica gel (hexane/ethyl acetate 0-100%, then ethyl acetate/acetone 25%) yields 51 mg of desired product.

$^1$H-NMR (300 MHz, CD$_3$OD); δ=0.93 (t, 3H), 1.73 (ddq, 1H), 1.96 (m, 1H), 1.99 (dd, 1H), 2.37 (dd, 1H), 2.71 (s, 3H), 3.32 (m, 1H), 5.06 (s, 1H), 6.57 (dd, 1H), 6.83 (d, 1H), 7.47 (d, 1H), 7.66 (t, 1H), 7.94 (d, 1H), 8.22 (d, 1H).

Example 189

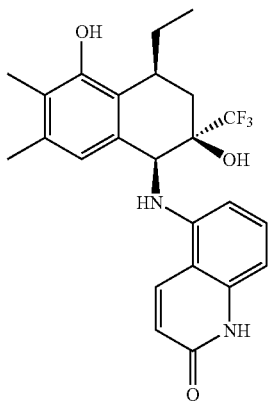

5-{[(1α,2α,4α)-4-Ethyl-2,5-dihydroxy-6,7-dimethyl-2-(trifluoromethyl)-1,2,3,4-tetrahydronaphthalen-1-yl]amino}-1H-quinolin-2-one A mixture of 5-{[4-(3,4-dimethyl-2-methoxyphenyl)-2-hydroxy-2-(trifluoromethyl)hexylidene]amino}-1H-quinolin-2-one and 5-{[4-(3,4-dimethyl-2-methoxyphenyl)-2-hydroxy-3-methyl-2-(trifluoromethyl)pentylidene]amino}-1H-quinolin-2-one (543.5 mg, 1.18 mmol), prepared from the mixture of the corresponding aldehydes and 5-amino-1H-quinolin-2-one, is dissolved in 7 ml of dichloromethane and the solution is admixed dropwise at –40° C. with 11.8 ml of a 1M solution of boron tribromide in dichloromethane. After three-hour stirring at –40° C. the reaction is allowed to come slowly to room temperature. After overnight stirring at room temperature, the batch is poured onto a mixture of saturated sodium hydrogen carbonate solution and ice (200 ml). 150 ml of ethyl acetate are added and the mixture is vigorously stirred. The organic phase is separated off and the aqueous phase is extracted twice with ethyl acetate (150 ml each time). The combined organic extracts are washed with 100 ml of brine and dried and the solvent is removed on a rotary evaporator. Repeated chromatography (Flashmaster, eluent: dichloromethane/methanol) and subsequent HPLC (XBridge C18, 5µ, eluent: water/acetonitrile) give 7.6 mg (1.5%) of the title compound. 20 mg (3.8%) of compound epimeric in position 4 (characterized in Example 190) (in each case as a racemate) are obtained.

1H-NMR (300 MHz, DMSO-d6): δ =1.02 (3H), 1.82-2.14 (9H), 2.25 (1H), 2.95 (1H), 5.12 (1H), 5.92 (1H), 6.05 (1H), 6.38 (1H), 6.45-6.61 (3H), 7.23 (1H), 8.12 (1H), 8.22 (1H), 11.54 (1H).

Example 190

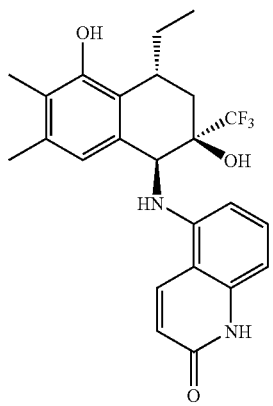

5-{[(1α,2α,4β)-2,5-Dihydroxy-6,7-dimethyl-4-ethyl-2-(trifluoromethyl)-1,2,3,4-tetrahydronaphthalen-1-yl]amino}-1H-quinolin-2-one 20 mg (3.8%) of the title compound are obtained from the reaction described in Example 189.

1H-NMR (400 MHz, DMSO-d6): δ =0.82 (3H), 1.52 (1H), 1.69-1.91 (2H), 1.95-2.10 (6H), 2.18 (1H), 3.19 (1H), 4.98 (1H), 5.85 (1H), 6.05 (1H), 6.30-6.41 (2H), 6.48 (1H), 6.52 (1H), 7.19 (1H), 8.04 (1H), 8.12 (1H), 11.53 (1H).

Example 191

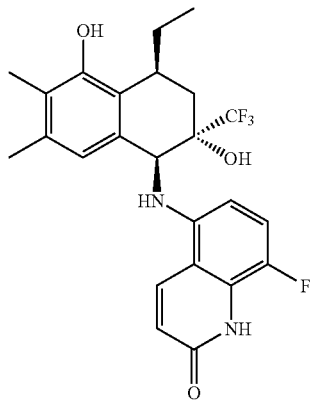

5-{[(1α,2α,4α)-2,5-Dihydroxy-6,7-dimethyl-4-ethyl-2-(trifluoromethyl)-1,2,3,4-tetrahydronaphthalen-1-yl]amino}-8-fluoro-1H-quinolin-2-one A mixture of 5-{[4-(3,4-dimethyl-2-methoxyphenyl)-2-hydroxy-2-(trifluoromethyl)hexylidene]amino}-8-fluoro-1H-quinolin-2-one and 5-{[4-(3,4-dimethyl-2-methoxyphenyl)-2-hydroxy-3-methyl-2-(trifluoromethyl)pentylidene]amino}-8-fluoro-1H-quinolin-2-one (703.5 mg, 1.47 mmol), prepared from the mixture of the corresponding aldehydes and 5-amino-8-fluoro-1H-quinolin-2-one, is dissolved in 8 ml of dichloromethane and the solution is admixed dropwise at −40° C. with 14.7 ml of a 1M solution of boron tribromide in dichloromethane. After three-hour stirring at −40° C. the reaction is allowed to come slowly to room temperature. After overnight stirring at room temperature, the batch is poured onto a mixture of saturated sodium hydrogen carbonate solution and ice (250 ml). 200 ml of ethyl acetate is added and the mixture is vigorously stirred. The organic phase is separated off and the aqueous phase is extracted twice with ethyl acetate (200 ml each time). The combined organic extracts are washed with 100 ml of brine and dried and the solvent is removed on a rotary evaporator. Repeated chromatography (Flashmaster, different phases, eluent: dichloromethane/methanol) and subsequent HPLC (XBridge C18, 5μ, eluent: water/acetonitrile) isolate 18.7 mg (2.7%) of the title compound. 39.6 mg (5.8%) of the compound epimeric in position 4 (characterized in Example 193) (in each case as a racemate) are obtained.

1H-NMR (300 MHz, DMSO-d6): δ =1.02 (3H), 1.80-2.18 (9H), 2.22 (1H), 2.94 (1H), 5.08 (1H), 5.89 (1H), 5.92 (1H), 6.40-6.50 (2H), 6.53 (1H), 7.20 (1H), 8.13 (1H), 8.25 (1H), 11.45 (1H).

Example 192

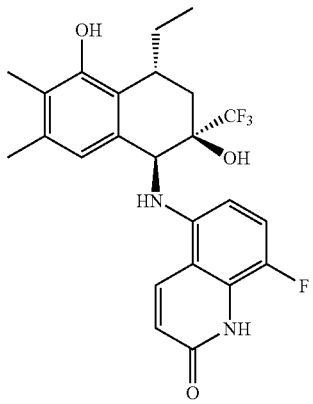

5-{[(1α,2α,4β)-2,5-Dihydroxy-6,7-dimethyl-4-ethyl-2-(trifluoromethyl)-1,2,3,4-tetrahydronaphthalen-1-yl]amino}-8-fluoro-1H-quinolin-2-one 39.6 mg (5.8%) of the title compound are obtained from the reaction described in Example 191.

1H-NMR (300 MHz, CD3OD): δ =0.90 (3H), 1.68 (1H), 1.80-2.00 (2H), 2.03-2.16 (6H), 2.30 (1H), 3.30 (1H, the signal lying practically beneath the solvent signal), 4.89 (1H), 6.32 (1H), 6.52 (1H), 6.61 (1H), 7.18 (1H), 8.19 (1H).

Example 193

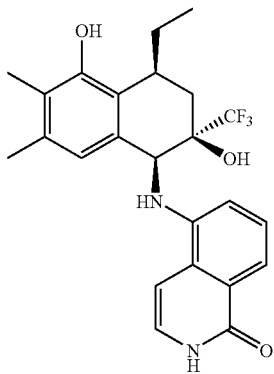

5-{[(1α,2α,4α)-2,5-Dihydroxy-6,7-dimethyl-4-ethyl-2-(trifluoromethyl)-1,2,3,4-tetrahydronaphthalen-1-yl]amino}-2H-quinolin-1-one A mixture of 5-{[4-(3,4-dimethyl-2-methoxyphenyl)-2-hydroxy-2-(trifluoromethyl)hexylidene]amino}-2H-quinolin-1-one and 5-{[4-(3,4-dimethyl-2-methoxyphenyl)-2-hydroxy-3-methyl-2-(trifluoromethyl)pentylidene]amino}-2H-quinolin-1-one (1.08 g, 2.35 mmol), prepared from the mixture of the corresponding aldehydes and 5-amino-2H-quinolin-1-one, is dissolved in 13 ml of dichloromethane and the solution is admixed dropwise at −40° C. with 23.5 ml of a 1M solution of boron tribromide in dichloromethane. After three-hour stirring at −40° C. the reaction is allowed to come slowly to room temperature. After overnight stirring at room temperature, the batch is poured onto a mixture of saturated sodium hydrogen carbonate solution and ice (350 ml). The mixture is extracted three times with ethyl acetate (250 ml each time). The combined organic extracts are washed with 200 ml of brine and dried and the solvent is removed on a rotary evaporator. Repeated chromatography (Flashmaster, different phases, eluent: dichloromethane/methanol) and subsequent HPLC (XBridge C18, 5μ, eluent: water/acetonitrile) isolate 22.4 mg (2.1%) of the title compound. 23.2 mg (2.2%) of the compound epimeric in position 4 (characterized in Example 195) (in each case as a racemate) are obtained.

1H-NMR (300 MHz, CD3OD): δ =1.08 (3H), 1.82-2.18 (9H), 2.38 (1H), 3.02 (1H), 5.00 (1H), 6.59 (1H), 6.78 (1H), 7.07-7.14 (2H), 7.36 (1H), 7.68 (1H).

Example 194

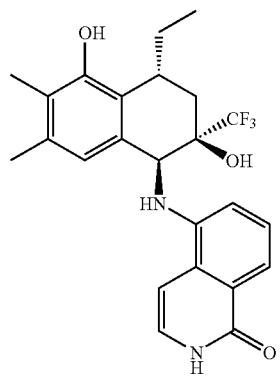

5-{[(1α,2α,4β)-2,5-Dihydroxy-6,7-dimethyl-4-ethyl-2-(trifluoromethyl)-1,2,3,4-tetrahydronaphthalen-1-yl]amino}-2H-quinolin-1-one 23.2 mg (2.2%) of the title compound are obtained from the reaction described in Example 193.

1H-NMR (300 MHz, CD3OD): δ =0.98 (3H), 1.75 (1H), 1.89-2.19 (8H), 2.37 (1H), 3.38 (1H, the signal lying practically beneath the solvent signal), 5.01 (1H), 6.68 (1H), 6.85-6.95 (2H), 7.19 (1H), 7.39 (1H), 7.69 (1H).

Example 195

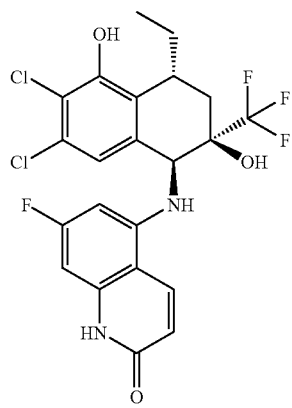

5-{[(5S,6R,8R)-2-Chloro-8-ethyl-1,6-dihydroxy-3-fluoro-2-6-(trifluoromethyl)-5,6,7,8-tetrahydronaphthalen-5-yl]amino}quinolin-2(1H)-one

4-(3-Chloro-4-fluoro-2-methoxyphenyl)-2-hydroxy-2-(trifluoromethyl)hexanal 20 g (122.7 mmol) of 2,3-dichlorophenol in 122 ml of dichloromethane and 13.8 ml of pyridine are admixed dropwise at 0° C. with 11.3 ml (128 mmol) of propionyl chloride. The mixture is stirred for 16 hours and 100 ml of 2 M hydrochloric acid are added. The mixture is extracted with dichloromethane and the extracts are washed with water. Drying over sodium sulphate and the removal of the solvent in vacuo give 25.2 g of 2,3-dichlorophenyl propionate. 25.2 g (115.2 mmol) of 2,3-dichlorophenyl propionate in 12 ml of 1,2-dichlorobenzene are added dropwise to 15.4 g (115.2 mmol) of aluminum trichloride in 12 ml of 1,2-dichlorobenzene and the mixture is subsequently stirred at 100° C. for 5 hours. It is cooled, diluted with dichloromethane and poured cautiously onto a mixture of 2 M hydrochloric acid and ice. The phases are separated, extraction is carried out with dichloromethane and the extracts are washed with water and saturated sodium chloride solution and dried over sodium sulphate. The crude product is purified by column chromatography on silica gel (hexane/ethyl acetate 10-25%) to give 22.1 g of 1-(3,4-dichloro-2-hydroxyphenyl)propan-1-one. 22.1 g (101 mmol) of 1-(3,4-dichloro-2-hydroxyphenyl)propan-1-one are dissolved in 150 ml of acetone and the solution is admixed with 25.9 g (187 mmol) of potassium carbonate and 11.4 ml (183 mmol) of methyl iodide. The mixture is boiled under reflux for 16 hours and then the solvent is largely removed. The residue is poured into saturated sodium chloride solution and extracted with diethyl ether. The extracts are dried over sodium sulphate to give, following the removal of the solvent in vacuo, 23.2 g of 1-(3,4-dichloro-2-methoxyphenyl)propan-1-one. 29 g (444 mmol) of zinc dust and 0.69 g (2.5 mmol) of lead(II) chloride are suspended in 296 ml of THF and the suspension is admixed at 0° C. with 27.8 ml (174 mmol) of dibromomethane. The mixture is stirred at room temperature for a further 30 minutes and admixed dropwise at 0° C. with 49 ml (49 mmol) of a 1 M titanium(IV) chloride solution in dichloromethane. The cooling bath is removed and, after an hour, the reaction mixture is cooled again to 0° C. 11.5 g (49 mmol) of 1-(3,4-dichloro-2-methoxyphenyl)propan-1-one in 65 ml of THF are added dropwise. Stirring is carried out at room temperature for a further hour. The reaction mixture is diluted with diethyl ether and poured cautiously onto a mixture of 4 M hydrochloric acid and ice, the temperature not exceeding 5° C. The phases are separated, extraction is carried out with diethyl ether, the extracts are washed with water and saturated sodium chloride solution and dried over sodium sulphate, and the solvent is removed. The crude product is purified by column chromatography on silica gel (hexane/ethyl acetate 0-30%) to give 5.8 g of 2,3-dichloro-6-(1-methylenepropyl)anisole.

1H-NMR (300 MHz, CDCl3); δ=1.01 (t, 3H), 2.47 (q, 2H), 3.77 (s, 3H), 7.00 (d, 1H), 7.18 (d, 1H).

5.8 g (25 mmol) of 2,3-dichloro-6-(1-methylenepropyl)anisole, 6.6 ml (50 mmol) of ethyl trifluoropyruvate and 12 g of molecular sieve are admixed dropwise at 0° C. over 30 minutes with 652 mg (0.75 mmol) of [Cu(R,R)-2,2-bis(4,5-dihydro-4-tert-butyloxazolin-2-yl)propane)(H$_2$O)$_2$]((SbF$_6$)$_2$ in 32 ml of dichloromethane. The reaction mixture is stirred at 0° C. for 16 hours and is purified by means of column chromatography on silica gel (hexane/ethyl acetate 10-20%). This gives 7.23 g of ethyl (R)-4-(3,4-dichloro-2-methoxyphenyl)-2-hydroxy-2-(trifluoromethyl)-hex-4-enoate as an E/Z mixture with an enantiomeric excess of greater than 80%.

383 mg (0.37 mmol) of (S)—(S)-(3,5-Me-4-MeOPh)$_2$PPhFc-CH(CH$_3$)—P(3,5-CF$_3$Ph)$_2$ and 130 mg (0.35 mmol) of [Rh(nbd)$_2$]BF$_4$ are dissolved under argon in 25 ml of degassed 2,2,2-trifluoroethanol and the solution is stirred for 10 minutes. The catalyst solution prepared in this way and a solution of 3.5 g (26 mmol) of ethyl (2R,4E/Z)-4-(3,4-dichloro-2-methoxyphenyl)-2-hydroxy-2-(trifluoromethyl)-hex-4-enoate in 115 ml of degassed 2,2,2-trifluoroethanol are transferred under argon to a steel autoclave and exposed to a hydrogen pressure of 80 bar at 80° C. for 20 hours. After cooling, the reaction mixture is concentrated and is purified by means of column chromatography on silica gel (hexane/ethyl acetate 10-30%). This gives 3.0 g of ethyl 4-(3,4-dichloro-2-methoxyphenyl)-2-hydroxy-2-(trifluoromethyl)-hexanoate. 1.0 g (2.5 mmol) of ethyl 4-(3,4-dichloro-2-methoxyphenyl)-2-hydroxy-2-(trifluoromethyl)hexanoate in 26 ml of diethyl ether are cooled to −20° C. and over 10 minutes 188 mg (5.0 mmol) of lithium aluminum hydride in solid form are added in portions. The reaction mixture is stirred for one hour in the course of which it warms to −5° C., 2 ml of ethyl acetate are added and the mixture is poured into saturated ammonium chloride solution and ice. The phases are separated and extraction is carried out repeatedly with diethyl ether. The extracts are washed with saturated sodium chloride solution and dried over sodium sulphate and the solvent is removed in vacuo to give, after column chromatography on silica gel (hexane/ethyl acetate 0-30%), 370 mg of (2R,4R)-4-(3,4-dichloro-2-methoxyphenyl)-2-hydroxy-2-(trifluoromethyl)hexanal.

$^1$H-NMR (300 MHz, CDCl$_3$); δ=0.80 (t, 3H), 1.55-1.73 (m, 2H), 2.32 (dd, 1H), 2.52 (dd, 1H), 3.07 (m, 1H), 3.91 (s, 3H), 7.00 (d, 1H), 7.14 (d, 1H), 9.04 (s, 1H). In a mixture with (2R,4R)-4-(3/4-chloro-2-methoxyphenyl)-2-hydroxy-2-(trifluoromethyl)hexanal.

300 mg (0.88 mmol) of (2R,4R)-4-(3-chloro-4-fluoro-2-methoxyphenyl)-2-hydroxy-2-(trifluoromethyl)hexanal and 140 mg (0.88 mmol) of 5-aminoquinolin-2(1H)-one are dissolved in 19 ml of toluene and the solution is admixed with 0.55 ml (1.75 mmol) of titanium tert-butoxide and 0.1 ml of acetic acid. The reaction mixture is heated at 100° C. for 2 hours, cooled, poured into water and stirred vigorously. The suspension is filtered through Celite, the filter bed being rinsed thoroughly with ethyl acetate. The phases of the filtrate are separated and extraction is carried out again with ethyl acetate. The extracts are washed with saturated sodium chloride solution and dried over sodium sulphate and the solvent is removed in vacuo to give 539 mg of (5-{[(2R,4R)-4-(3-chloro-4-fluoro-2-methoxyphenyl)-2-hydroxy-2-(trifluoromethyl)hexylidene]amino}quinolin-2(1H)-one as a crude product. The imine is dissolved in 44 ml of CH$_2$Cl$_2$ and the solution is cooled to −30° C. 8.9 ml (8.9 mmol) of a 1M BBr$_3$ solution in dichloromethane are added slowly dropwise over 15 minutes and the mixture is allowed to warm to room temperature over 22 hours. The reaction solution is poured onto a mixture of saturated NaHCO$_3$ solution and ice. It is extracted repeatedly with ethyl acetate and the extracts are washed with saturated NaCl solution and dried over Na$_2$SO$_4$. Purification by column chromatography on silica gel (hexane/ethyl acetate 0-100%) yields 134 mg of the title compound.

$^1$H-NMR (300 MHz, CD$_3$OD); δ=0.92 (t, 3H), 1.70 (ddq, 1H), 1.19 (ddq, 1H), 1.99 (dd, 1H), 2.36 (dd, 1H), 3.32 (m, 1H), 4.97 (s, 1H), 6.44 (d, 1H), 6.50 (d, 1H), 6.63 (d, 1H), 6.68 (d, 1H), 7.33 (t, 1H), 8.18 (d, 1H).

Example 196

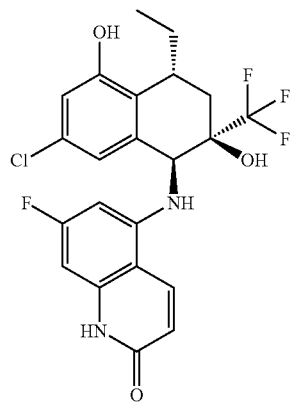

5-{[(5S,6R,8R)-3-Chloro-8-ethyl-1,6-dihydroxy-2-6-(trifluoromethyl)-5,6,7,8-tetrahydronaphthalen-5-yl]amino}-7-fluoroquinolin-2(1H)-one is isolated as an additional product alongside Example 195.

$^1$H-NMR (300 MHz, CD$_3$OD); δ=0.91 (t, 3H), 1.68 (ddq, 1H), 1.95 (d, 1H), 1.96 (m, 1H), 2.35 (dd, 1H), 3.24 (m, 1H), 4.97 (d, 1H), 6.10 (d, 1H), 6.25 (d, 1H), 6.39 (d, 1H), 6.43 (d, 1H), 6.67 (s, 1H), 6.70 (s, 1H), 8.14 (d, 1H).

Example 197

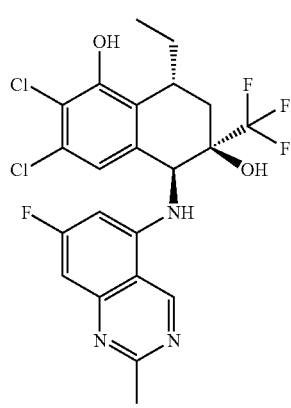

(5S,6R,8R)-2,3-Dichloro-8-ethyl-5-[(7-fluoro-2-methylquinazolin-5-yl)amino]-6-(trifluoromethyl)-5,6,7,8-tetrahydronaphthalene-1,6-diol In the same way as in Example 195, 300 mg (0.93 mmol) of (2R,4R)-4-(3,4-dichloro-2-methoxyphenyl)-2-hydroxy-2-(trifluoromethyl)hexanal, 183 mg (1.03 mmol) of 5-amino-7-fluoro-2-methylquinazoline and 0.58 ml (1.86 mmol) of titanium tert-butoxide are reacted to give 5-{[(2R,4R)-4-(4-fluoro-2-methoxy-3-methylphenyl)-1-[(7-fluoro-2-methylquinazolin-5-yl)imino]-2-(trifluoromethyl)hexan-2-ol.
460 mg of crude imine are cyclized in the same way as in Example 130 at −30° C. with 7.6 ml (7.6 mmol) of 1 M boron tribromide solution to give the desired product. Column chromatography on silica gel (hexane/ethyl acetate 0-65%) yields 135 mg of desired product.

$^1$H-NMR (300 MHz, CD$_3$OD); δ=0.94 (t, 3H), 1.71 (ddq, 1H), 1.99 (dd, 1H), 2.00 (m, 1H), 2.41 (dd, 1H), 3.32 (m, 1H), 5.15 (s, 1H), 6.64 (d, 1H), 6.79 (d, 1H), 6.89 (s, 1H), 9.50 (s, 1H).

Example 198

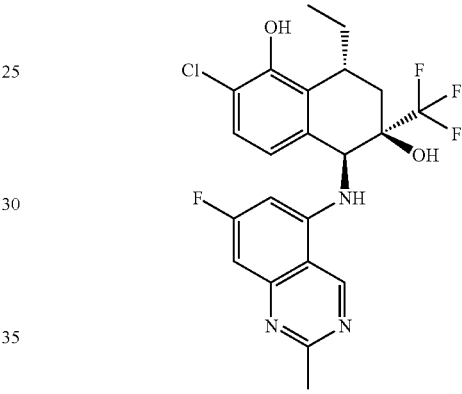

(5S,6R,8R)-2-chloro-8-ethyl-5-[(7-fluoro-2-methylquinazolin-5-yl)amino]-6-(trifluoromethyl)-5,6,7,8-tetrahydronaphthalene-1,6-diol is isolated as an additional product alongside Example 197.

$^1$H-NMR (300 MHz, CD$_3$OD); δ=0.93 (t, 3H), 1.72 (ddq, 1H), 2.00 (dd, 1H), 2.01 (m, 1H), 2.40 (dd, 1H), 3.36 (m, 1H), 5.14 (s, 1H), 6.60 (d, 1H), 6.74 (d, 1H), 6.75 (d, 1H), 7.11 (d, 1H), 9.49 (s, 1H).

Example 199

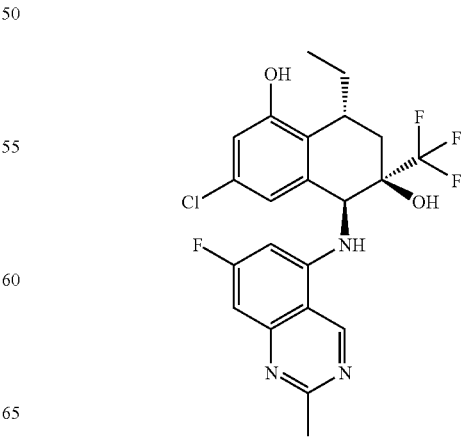

(5S,6R,8R)-3-Chloro-8-ethyl-5-[(7-fluoro-2-methylquinazolin-5-yl)amino]-6-(trifluoromethyl)-5,6,7,8-tetrahydronaphthalene-1,6-diol is isolated as an additional product alongside Example 197.
¹H-NMR (300 MHz, CD₃OD); δ=0.92 (t, 3H), 1.69 (ddq, 1H), 1.97 (dd, 1H), 1.99 (m, 1H), 2.38 (dd, 1H), 3.25 (m, 1H), 5.13 (s, 1H), 6.61 (d, 1H), 6.69 (s, 1H), 6.71 (s, 1H), 6.78 (d, 1H), 9.50 (s, 1H).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding European application No. 06090031.3, filed Mar. 15, 2006, and U.S. Provisional Application Ser. No. 60/748,441 filed Mar. 22, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of the formula (Ia):

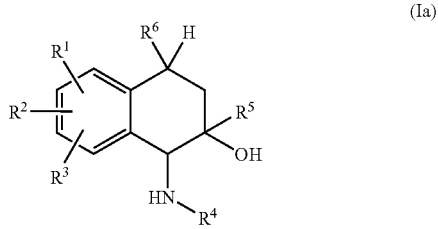

(Ia)

wherein
the compounds of the 1-amino-1,2,3,4-tetrahydronaphthalen-2-ol parent structure are present in the 1α,2α,4β stereoisomer configuration and the compounds of the 5,6,7,8-tetrahydronaphthalen-1,6-diol parent structure are present in the 5α,6α,8β stereoisomer configuration;
the radicals R¹, R² and R³ independently of one another are selected from —OH, —O—CH₃, Cl, F, or H;
the radical R⁴ is selected from:
2-methylquinolin-5-yl,
2-methylquinazolin-5-yl,
2-ethylquinazolin-5-yl,
7-fluoro-2-methylquinazolin-5-yl,
8-fluoro-2-methylquinazolin-5-yl,
7,8-difluoro-2-methylquinazolin-5-yl,
quinolin-2(1H)-on-5-yl,
8-fluoroquinolin-2(1H)-on-5-yl,
isochromen-1-on-5-yl,
2-methylphthalazin-1-on-5-yl, or
isoquinolin-2(1H)-on-5-yl;
the radical R⁵ is —CF₃; and
the radical R⁶ is selected from —CH₃, —CH₂—CH₃, —(CH₂)₂—CH₃, or —CH═CH₂;
or a stereoisomer thereof or a salt thereof with a physiologically tolerated anion.

2. A compound of the formula (Ia.):

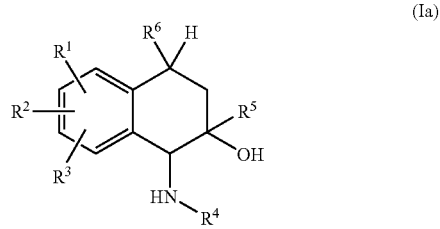

(Ia)

wherein
the compounds with the 1-amino-1,2,3,4-tetrahydronaphthalen-2-ol parent structure have an absolute configuration of (1S,2R,4R) or (1S,2R,4S), and
the compounds with the 5,6,7,8-tetrahydronaphthalen-1,6-diol parent structure have an absolute configuration of (5S,6R,8R) or (5S,6R,8S),
the radicals R¹, R² and R³ independently of one another are selected from —OH, —O—CH₃, Cl, F, or H;
the radical R⁴ is selected from:
2-methylquinolin-5-yl,
2-methylquinazolin-5-yl,
2-ethylquinazolin-5-yl,
7-fluoro-2-methylquinazolin-5-yl,
8-fluoro-2-methylquinazolin-5-yl,
7,8-difluoro-2-methylquinazolin-5-yl,
quinolin-2(1H)-on-5-yl,
8-fluoroquinolin-2(1H)-on-5-yl,
isochromen-1-on-5-yl,
2-methylphthalazin-1-on-5-yl, or
isoquinolin-2(1H)-on-5-yl;
the radical R⁵ is —CF₃; and
the radical R⁶ is selected from —CH₃, —CH₂—CH₃, —(CH₂)₂—CH₃, or —CH═CH₂;
or a stereoisomer thereof or a salt thereof with a physiologically tolerated anion.

3. A compound according to claim 1, excluding the compound wherein, simultaneously, R¹, R² and R³ provide 6-fluoro and 5-OH substitution on the ring, R⁴ is 2-methylquinolin-5-yl, and R⁶ is —CH₂—CH₃.

4. A compound according to claim 1, wherein at least one of R¹, R² and R³ is fluoro.

5. A compound according to claim 1, wherein R⁴ is 7-fluoro-2-methylquinazolin-5-yl.

6. A compound according to claim 1, wherein R¹, R² and R³ provide 6-fluoro and 5-OH substitution on the ring.

7. A pharmaceutical composition containing at least one compound of claim 1 together with at least one physiologically acceptable excipient.

8. A compound selected from one of the following compounds:
(5α,6α,8β)-2-fluoro-8-methyl-5-[(2-methylquinoline-5-yl)amino]-6-(trifluoromethyl)-5,6,7,8-tetrahydronaphthalene-1,6-diol;
(+)-(5α,6α,8β)-2-fluoro-5-[(7-fluoro-2-methylquinazoline-5-yl)amino]-8-methyl-6-(trifluoromethyl)-5,6,7,8-tetrahydronaphthalene-1,6-diol;
(−)-(5α,6α,8β)-2-fluoro-5-[(7-fluoro-2-methylquinazoline-5-yl)amino]-8-methyl-6-(trifluoromethyl)-5,6,7,8-tetrahydronaphthalene-1,6-diol;

(5α,6α,8β)-2-fluoro-5-[(8-fluoro-2-methylquinazoline-5-yl)amino]-8-methyl-6-(trifluoromethyl)-5,6,7,8-tetrahydronaphthalene-1,6-diol;

(5α,6α,8β)-5-[(7,8-difluoro-2-methylquinazoline-5-yl)amino]-2-fluoro-8-methyl-6-(trifluoromethyl)-5,6,7,8-tetrahydronaphthalene-1,6-diol;

(5α,6α,8β)-2-fluoro-8-methyl-5-[-2-methylquinazoline-5-yl)amino]-6-(trifluoromethyl)-5,6,7,8-tetrahydronaphthalene-1,6-diol;

5-{[(5α,6α,8β)-1,6-dihydroxy-2-fluoro-8-methyl-6-(trifluoromethyl)-5,6,7,8-tetrahydronaphthalene-5-yl]amino}quinolin-2(1H)-one;

8-fluoro-5-{[(1α,2α,4β)-6-fluoro-2-hydroxy-5-methoxy-4-methyl-2-(trifluoromethyl)-1,2,3,4-tetrahydronaphthalene-1-yl]amino}-quinolin-2(1H)-one;

(+) -5-{[(1α,2α,4β)-6-fluoro-2,5-dihydroxy-4-methyl-2-(trifluoromethyl)-1,2,3,4-tetrahydronaphthalene-1-yl]amino}-8-fluoroquinolin-2(1H)-one;

(−)-5-{[(1α,2α,4β)-6-fluoro-2,5-dihydroxy-4-methyl-2-(trifluoromethyl)-1,2,3,4-tetrahydronaphthalene-1-yl]amino}-8-fluoroquinolin-2(1H)-one;

5-{[(1α,2α,4β)-6-fluoro-2,5-dihydroxy-4-methyl-2-(trifluoromethyl)-1,2,3,4-tetrahydronaphthalene-1-yl]amino}-2-methylphthalazin-1-one;

(5α,6α,8β)-3-chloro-2-fluoro-8-methyl-5-[(2-methylquinazoline-5-yl)amino]-6-(trifluoromethyl)-5,6,7,8-tetrahydronaphthalene-1,6-diol;

(5α,6α,8β)-3-chloro-2-fluoro-5-[(7-fluoro-2-methylquinazoline-5-yl)amino]-1-methoxy-8-methyl-6-(trifluoromethyl)-5,6,7,8-tetrahydronaphthalene-6-ol;

(5α,6α,8β)-3-chloro-2-fluoro-5-[(7-fluoro-2-methylquinazoline-5-yl)amino]-8-methyl-6-(trifluoromethyl)-5,6,7,8-tetrahydronaphthalene-1,6-diol;

(5α,6α,8β)-3-chloro-2-fluoro-5-[(8-fluoro-2-methylquinazoline-5-yl)amino]-1-methoxy-8-methyl-6-(trifluoromethyl)-5,6,7,8-tetrahydronaphthalene-6-ol;

(5α,6α,8β)-3-chloro-2-fluoro-5-[(8-fluoro-2-methylquinazoline-5-yl)amino]-8-methyl-6-(trifluoromethyl)-5,6,7,8-tetrahydronaphthalene-1,6-diol;

(5α,6α,8β)-3-chloro-5-[(7,8-difluoro-2-methylquinazoline-5-yl)amino]-2-fluoro-8-methyl-6-(trifluoromethyl)-5,6,7,8-tetrahydronaphthalene-1,6-diol;

(5α,6α,8β)-3-chloro-2-fluoro-8-methyl-5-[-2-methylquinoline-5-yl)amino]-6-(trifluoromethyl)-5,6,7,8-tetrahydronaphthalene-1,6-diol;

(+)-5-{[(1α,2α,4β)-7-chloro-2,5-dihydroxy-6-fluoro-4-methyl-2-(trifluoromethyl)-1,2,3,4-tetrahydronaphthalene-1-yl]-amino}-quinolin-2(1H)-one;

(−)-5-{[(1α,2α,4β)-7-chloro-2,5-dihydroxy-6-fluoro-4-methyl-2-(trifluoromethyl)-1,2,3,4-tetrahydronaphthalene-1-yl]-amino}-quinolin-2(1H)-one;

5-{[(1α,2α,4β)-7-chloro-2,5-dihydroxy-6-fluoro-4-methyl-2-(trifluoromethyl)-1,2,3,4-tetrahydronaphthalene-1-yl]-amino}-8-fluoroquinolin-2(1H)-one;

(5α,6α,8β)-8-methyl-5-[-2-methylquinoline-5-yl)amino]-6-(trifluoromethyl)-5,6,7,8-tetrahydronaphthalene-1,6-diol;

(5α,6α,8β)-8-ethyl-5-[2-methylquinazoline-5-yl)amino]-6-(trifluoromethyl)-5,6,7,8-tetrahydronaphthalene-1,6-diol;

(+)-(5α,6α,8β)-8-ethyl-2-fluoro-5-[(2-methylquinazoline-5-yl)amino]-6-(trifluoromethyl)-5,6,7,8-tetrahydronaphthalene-1,6-diol;

(−)-(5α,6α,8β)-8-ethyl-2-fluoro-5-[(2-methylquinazoline-5-yl)amino]-6-(trifluoromethyl)-5,6,7,8-tetrahydronaphthalene-1,6-diol;

(5S,6R,8R)-8-ethyl-2-fluoro-5-[(7-fluoro-2-methylquinazoline-5-yl)amino]-6-(trifluoromethyl)-5,6,7,8-tetrahydronaphthalen-1,6-diol;

(+)-(5α,6α,8β)-8-ethyl-2-fluoro-5-[(8-fluoro-2-methylquinazoline-5-yl)amino]-6-(trifluoromethyl)-5,6,7,8-tetrahydronaphthalene-1,6-diol;

(−)-(5α,6α,8β)-8-ethyl-2-fluoro-5-[(8-fluoro-2-methylquinazoline-5-yl)amino]-6-(trifluoromethyl)-5,6,7,8-tetrahydronaphthalene-1,6-diol;

(5α,6α,8β)-5-[(7,8-difluoro-2-methylquinazoline-5-yl)amino]-8-ethyl-2-fluoro-6-(trifluoromethyl)-5,6,7,8-tetrahydronaphthalene-1,6-diol;

5-{[(1a,2a,4b)-4-ethyl-6-fluoro-2,5-dihydroxy-2-(trifluoromethyl)-1,2,3,4-tetrahydronaphthalene-1-yl]amino}-quinoline-2(1H)-one;

5-{[(1α,2α,4β)-4-ethyl-6-fluoro-2-hydroxy-5-methoxy-2-(trifluoromethyl)-1,2,3,4-tetrahydronaphthalene-1-yl]amino}-8-fluoroquinolin-2(1H)-one;

(+)-5-{[(1α,2α,4β)-4-ethyl-6-fluoro-2,5-dihydroxy-2-(trifluoromethyl)-1,2,3,4-tetrahydronaphthalene-1-yl]amino}-8-fluoroquinolin-2(1H)-one;

(−)-5-{[(1α,2α,4β)-4-ethyl-6-fluoro-2,5-dihydroxy-2-(trifluoromethyl)-1,2,3,4-tetrahydronaphthalene-1-yl]amino}-8-fluoroquinolin-2(1H)-one;

5-{[(1α,2α,4β)-4-ethyl-6-fluoro-2,5-dihydroxy-2-(trifluoromethyl)-1,2,3,4-tetrahydronaphthalene-1-yl]amino}-2-methylphthalazin-1-one;

5-{[(1α,2α,4β)-4-ethyl-6-fluoro-2,5-dihydroxy-2-(trifluoromethyl)-1,2,3,4-tetrahydronaphthalene-1-yl]amino}-isoquinoline-(2H)-one;

5-{[(1α,2α,4β)-4-ethyl-6-fluoro-2,5-dihydroxy-2-(trifluoromethyl)-1,2,3,4-tetrahydronaphthalene-1-yl]amino}isochromen-1-one;

(5α,6α,8β)-5-[(2-ethylquinazoline-5-yl)amino]-2-fluoro-8-propyl-6-(trifluoromethyl)-5,6,7,8-tetrahydronaphthalene-1,6-diol;

(5S,6R,8R)-8-ethyl-2,3-difluoro-5-[(2-methylquinazoline-5-yl)amino]-6-(trifluoromethyl)-5,6,7,8-tetrahydronaphthalene-1,6-diol;

(+)-(5α,6α,8β)-8-ethyl-2,3-difluoro-5-[(7-fluoro-2-methylquinazoline-5-yl)amino]-6-(trifluoromethyl)-5,6,7,8-tetrahydronaphthalene-1,6-diol;

(−)-(5α,6α,8β)-8-ethyl-2,3-difluoro-5-[(7-fluoro-2-methylquinazoline-5-yl)amino]-6-(trifluoromethyl)-5,6,7,8-tetrahydronaphthalene-1,6-diol;

(5S,6R,8R)-8-ethyl-2,3-difluoro-5-[(8-fluoro-2-methylquinazoline-5-yl)amino]-6-(trifluoromethyl)-5,6,7,8-tetrahydronaphthalene-1,6-diol;

(5S,6R,8R)-8-ethyl-2,3-difluoro-5-[(7,8-difluoro-2-methylquinazoline-5-yl)amino]-6-(trifluoromethyl)-5,6,7,8-tetrahydronaphthalene-1,6-diol;

(+)-5-{[(1a,2a,4b)-4-ethyl-6,7-difluoro-2,5-dihydroxy-2-(trifluoromethyl)-1,2,3,4-tetrahydronaphthalene-1-yl]amino}quinolin-2(1H)-one;

(−)-5-{[(1α,2α,4β)-4-ethyl-6,7-difluoro-2,5-dihydroxy-2-(trifluoromethyl)-1,2,3,4-tetrahydronaphthalene-1-yl]amino}quinoline-2(1H)-one;

(5α,6α,8β)-8-ethyl-2,3-difluoro-5-[(2-methylquinoline-5-yl)amino]-6-(trifluoromethyl)-5,6,7,8-tetrahydronaphthalene-1,6-diol;

5-{[(1α,2α,4β)-4-ethyl-6,7-difluoro-2,5-dihydroxy-2-(trifluoromethyl)-1,2,3,4-tetrahydronaphthalene-1-yl]amino}phthalazin-1-one;

(5α,6α,8β)-2-fluoro-5-[(2-methylquinazoline-5-yl)amino]-8-prop-1-yl-6-(trifluoromethyl)-5,6,7,8-tetrahydronaphthalene-1,6-diol;

(5α,6α,8β)-2-fluoro-5-[(7-fluoro-2-methylquinazolin-5-yl)amino]-8-prop-1-yl-6-(trifluoromethyl)-5,6,7,8-tetrahydronaphthalene-1,6-diol;

5-{[(1α,2α,4β)4-ethyl-6,7-difluoro-2,5-dihydroxy-2-(trifluoromethyl)-1,2,3,4-tetrahydronaphthalene-1-yl]amino}quinoline-2(1H)-one;

5-{[(1α,2α,4β)4-ethyl-6,7-difluoro-2,5-dihydroxy-2-(trifluoromethyl)-1,2,3,4-tetrahydronaphthalene-1-yl]amino}isoquinoline-1(2H)-one;

5-{[(1S,2R,4S)-6-chloro-2,5-dihydroxy-4-methyl-2-(trifluoromethyl)-1,2,3,4-tetrahydronaphthalene-1-yl]amino}-1H-quinolin-2-one;

5-{[(1S,2R,4R)-6-chloro-2,5-dihydroxy-4-methyl-2-(trifluoromethyl)-1,2,3,4-tetrahydronaphthalene-1-yl]amino}-1H-quinolin-2-one;

5-{[(1S,2R,4S)-6-chloro-2,5-dihydroxy-4-methyl-2-(trifluoromethyl)-1,2,3,4-tetrahydronaphthalene-1-yl]amino}-8-fluoro-1H-quinolin-2-one;

5-{[(1S,2R,4R)-6-chloro-2,5-dihydroxy-4-methyl-2-(trifluoromethyl)-1,2,3,4-tetrahydronaphthalene-1-yl]amino}-8-fluoro-1H-quinolin-2-one;

5-{[(1S,2R,4S)-6-chloro-2,5-dihydroxy-4-methyl-2-(trifluoromethyl)-1,2,3,4-tetrahydronaphthalene-1-yl]amino}-2H-quinolin-1-one;

5-{[(1S,2R,4R)-6-chloro-2,5-dihydroxy-4-methyl-2-(trifluoromethyl)-1,2,3,4-tetrahydronaphthalene-1-yl]amino}-2H-quinolin-1-one;

5-{[(1S,2R,4S)-6-chloro-2,5-dihydroxy-4-methyl-2-(trifluoromethyl)-1,2,3,4-tetrahydronaphthalene-1-yl]amino}-isochromen-1-one;

5-{[(1S,2R,4R)-6-chloro-2,5-dihydroxy-4-methyl-2-(trifluoromethyl)-1,2,3,4-tetrahydronaphthalene-1-yl]amino}-isochromen-1-one;

4-{[(1S,2R,4S)-6-chloro-2,5-dihydroxy-4-methyl-2-(trifluoromethyl)-1,2,3,4-tetrahydronaphthalene-1-yl]amino}-1,3-dihydroindol-2-one;

4-{[(1S,2R,4R)-6-chloro-2,5-dihydroxy-4-methyl-2-(trifluoromethyl)-1,2,3,4-tetrahydronaphthalene-1-yl]amino}-1,3-dihydroindol-2-one;

5-{[(1S,2R,4S)-chloro-2,5-dihydroxy-4-ethyl-2-(trifluoromethyl)-1,2,3,4-tetrahydronaphthalene-1-yl]amino}-1H-quinolin-2-one;

5-{[(1a,2a,4b)-6-chloro-2,5-dihydroxy-4-ethyl-2-(trifluoromethyl)-1,2,3,4-tetrahydronaphthalene-1-yl]amino}-1H-quinolin-2-one;

5-{[(1S,2R,4S)-6-chloro-2,5-dihydroxy-4-ethyl-2-(trifluoromethyl)-1,2,3,4-tetrahydronaphthalene-1-yl]amino}-8-fluoro-1H-quinolin-2one;

5-{[(1S,2R,4R)-6-chloro-4-ethyl-2,5-dihydroxy-2-(trifluoromethyl)-1,2,3,4-tetrahydronaphthalene-1-yl]amino}-8-fluoro-1H-quinolin-2-one;

5-{[(1S,2R,4S)-6-chloro-2,5-dihydroxy-4-ethyl-2-(trifluoromethyl)-1,2,3,4-tetrahydronaphthalene-1-yl]amino}-2H-quinolin-1-one;

5-{[(1S,2R,4R)-6-chloro-4-ethyl-2,5-dihydroxy-2-(trifluoromethyl)-1,2,3,4-tetrahydronaphthalene-1-yl]amino}-2H-quinolin-1-one;

5-{[(1S,2R,4S)-6-chloro-2,5-dihydroxy-4-ethyl-2-(trifluoromethyl)-1,2,3,4-tetrahydronaphthalene-1-yl]amino}-isochromen-1-one;

5-{[(1S,2R,4R)-6-chloro-4-ethyl-2,5-dihydroxy-4-2-(trifluoromethyl)-1,2,3,4-tetrahydronaphthalene-1-yl]amino}-isochromen-1-one;

4-{[(1S,2R,4S)-6-chloro-2,5-dihydroxy-4-ethyl-2-(trifluoromethyl)-1,2,3,4-tetrahydronaphthalene-1-yl]amino}-1,3-dihydroindol-2-one;

4-{[(1S,2R,4R)-6-chloro-2,5-dihydroxy-4-ethyl-2-(trifluoromethyl)-1,2,3,4-tetrahydronaphthalene-1-yl]amino}-1,3-dihydroindol-2-one;

5-{[(1S,2R,4S)-6-chloro-2,5-dihydroxy-4-ethyl-2-(trifluoromethyl)-1,2,3,4-tetrahydronaphthalene-1-yl]amino}-7-fluoro-1H-quinolin-2-one;

5-{[(1S,2R,4R)-6-chloro-4-ethyl-2,5-dihydroxy-2-(trifluoromethyl)-1,2,3,4-tetrahydronaphthalene-1-yl]amino}-7-fluoro-1H-quinolin-2-one;

5-{[(1S,2R,4S)-6-chloro-2,5-dihydroxy-4-methyl-2-(trifluoromethyl)-1,2,3,4-tetrahydronaphthalene-1-yl]amino}-7-fluoro-1H-quinolin-2-one;

5-{[(1S,2R,4R)-6-chloro-2,5-dihydroxy-4-methyl-2-(trifluoromethyl)-1,2,3,4-tetrahydronaphthalene-1-yl]amino}-7-fluoro-1H-quinolin-2-one;

(5α,6α,8β)-2-chloro-8-ethyl-5-[(indazol-5-yl)amino]-6-(trifluoromethyl)-5,6,7,8-tetrahydronaphthalene-1,6-diol;

6-{[(1α,2α,4β)-6-chloro-2,5-dihydroxy-4-ethyl-2-(trifluoromethyl)-1,2,3,4-tetrahydronaphthalene-1-yl]amino}-4-methylbenzo[d][1,2]oxazin-1-one;

5-{[(1α,2α,4β)-7-isopropyl-2,5-dihydroxy-4-ethyl-2-(trifluoromethyl)-1,2,3,4-tetrahydronaphthalene-1-yl]amino}-1H-quinolin-2-one;

(5α,6α,8β)-8-ethyl-3-isopropyl-5-[2-methylquinazoline-5-ylamino]-6-(trifluoromethyl)-5,6,7,8-tetrahydronaphthalene-1,6-diol;

5-{[(1α,2α,4β)-7-isopropyl-2,5-dihydroxy-4-ethyl-2-(trifluoromethyl)-1,2,3,4-tetrahydronaphthalene-1-yl]amino}-2H-quinolin-1-one;

4-{[(1α,2α,4β)-7-isopropyl-2,5-dihydroxy-4-ethyl-2-(trifluoromethyl)-1,2,3,4-tetrahydronaphthalene-1-yl]amino}-1,3-dihydroindol-2-one;

5-{[(1α,2α,4β)-7-isopropyl-2,5-dihydroxy-4-ethyl-2-(trifluoromethyl)-1,2,3,4-tetrahydronaphthalene-1-yl]amino}-isochromen-1-one;

5-{[(1α,2α,4β)-7-isopropyl-2,5-dihydroxy-4-ethyl-2-(trifluoromethyl)-1,2,3,4-tetrahydronaphthalene-1-yl]amino}-8-fluoro-1H-quinolin-2-one;

5-{[(1α,2α,4β)-7-isopropyl-2,5-dihydroxy-4-ethyl-2-(trifluoromethyl)-1,2,3,4-tetrahydronaphthalene-1-yl]amino}-8-fluoro-1H-quinolin-2-one;

5-{[(1α,2α,4β)7-chloro-2,5-dihydroxy-4-ethyl-6-methyl-2-(trifluoromethyl)-1,2,3,4-tetrahydronaphthalene-1-yl]amino}-1H-quinolin-2-one;

5-{[(1α,2α,4β)-7-chloro-2,5-dihydroxy-6-methyl-4-ethyl-2-(trifluoromethyl)-1,2,3,4-tetrahydronaphthalene-1-yl]amino}-2H-quinolin-1-one;

4-{[(1α,2α,4β)7-chloro-2,5-dihydroxy-6-methyl-4-ethyl-2-(trifluoromethyl)-1,2,3,4-tetrahydronaphthalene-1-yl]amino}-1,3-dihydroindol-2-one;

5-{[(1α,2α,4β)-7-chloro-2,5-dihydroxy-4-ethyl-6-methyl-2-(trifluoromethyl)-1,2,3,4-tetrahydronaphthalene-1-yl]amino}-8-fluoro-1H-quinolin-2-one;

5-{[(1S,2R,4R)-7-chloro-2,5-dihydroxy-4-ethyl-6-methyl-2-(trifluoromethyl)-1,2,3,4-tetrahydronaphthalene-1-yl]amino}-8-fluoro-1H-quinolin-2-one;

(5α,6α,8β)-3-chloro-8-ethyl-2-methyl-5-[2-methylquinazoline-5-ylamino]-6-(trifluoromethyl)-5,6,7,8-tetrahydronaphthalene-1,6-diol;

5-{[(1S,2R,4S)-7-chloro-2,5-dihydroxy-4-ethyl-6-methyl-2-(trifluoromethyl)-1,2,3,4-tetrahydronaphthalene-1-yl]amino}-7-fluoro-1H-quinolin-2-one;

5-{[(1a,2a, 4b)-7-chloro-2,5-dihydroxy-4-ethyl-6-methyl-2-(trifluoromethyl)-1,2,3,4-tetrahydronaphthalene-1-yl]amino}-7-fluoro-1H-quinolin-2-one;

5-{[(1S,2R,4R)-7-chloro-2,5-dihydroxy-4-ethyl-6-methyl-2-(trifluoromethyl)-1,2,3,4-tetrahydronaphthalene-1-yl]amino}-7-fluoro-1H-quinolin-2-one;

(5S,6R,8R)-8-ethyl-2,3-difluoro-5-[(2-methylquinazoline-5-yl)amino]-6-(trifluoromethyl)-5,6,7,8-tetrahydronaphthalene-1,6-diol;

5-{[(1S,2R,4R)-4-ethyl-7-fluoro-2,5-dihydroxy-6-methyl-2-(trifluoromethyl)-1,2,3,4-tetrahydronaphthalene-1-yl]amino}quinolin-2(1H)-one;

5-{[(1S,2R,4R)-4-ethyl-7-fluoro-2,5-dihydroxy-6-methyl-2-(trifluoromethyl)-1,2,3,4-tetrahydronaphthalene-1-yl]amino}-7-fluoroquinolin-2(1H)-one;

5-{[(1S,2R,4R)-4-ethyl-7-fluoro-2,5-dihydroxy-6-methyl-2-(trifluoromethyl)-1,2,3,4-tetrahydronaphthalene-1-yl]amino}-8-fluoroquinolin-2(1H)-one;

5-{[(1S,2R,4R)-4-ethyl-7-fluoro-2,5-dihydroxy-6-methyl-2-(trifluoromethyl)-1,2,3,4-tetrahydronaphthalene-1-yl]amino}isoquinolin-1(2H)-one;

(5S,6R,8R)-8-ethyl-3-fluoro-5-[(7-fluoro-2-methylquinazoline-5-yl)amino]-2-methyl-6-(trifluoromethyl)-5,6,7,8-tetrahydronaphthalene-1,6-diol;

(5S,6R,8R)-8-ethyl-3-fluoro-5-[(8-fluoro-2-methylquinazoline-5-yl)amino]-2-methyl-6-(trifluoromethyl)-5,6,7,8-tetrahydronaphthalene-1,6-diol;

5-{[(1S,2R,4S)-4,6-diethyl-7-fluoro-2,5-dihydroxy-2-(trifluoromethyl)-1,2,3,4-tetrahydronaphthalene-1-yl]amino}quinolin-2(1H)-one;

5-{[(1S,2R,4R)-4,6-diethyl-7-fluoro-2,5-dihydroxy-2-(trifluoromethyl)-1,2,3,4-tetrahydronaphthalene-1-yl]amino}quinolin-2(1H)-one;

5-{[(1S,2R,4S)-4,6-diethyl-7-fluoro-2,5-dihydroxy-2-(trifluoromethyl)-1,2,3,4-tetrahydronaphthalene-1-yl]amino}-7-fluoroquinolin-2(1H)-one;

5-{[(1S,2R,4R)-4,6-diethyl-7-fluoro-2,5-dihydroxy-2-(trifluoromethyl)-1,2,3,4-tetrahydronaphthalene-1-yl]amino}-7-fluoroquinolin-2(1H)-one;

5-{[(1S,2R,4S)-4,6-diethyl-2,5-dihydroxy-2-(trifluoromethyl)-1,2,3,4-tetrahydronaphthalene-1-yl]amino}-1H-quinolin-2-one;

5-{[(1S,2R,4R)-4,6-diethyl-2,5-dihydroxy-2-(trifluoromethyl)-1,2,3,4-tetrahydronaphthalene-1-yl]amino}-1H-quinolin-2-one;

5-{[(1S,2R,4S)-4,6-diethyl-2,5-dihydroxy-2-(trifluoromethyl)-1,2,3,4-tetrahydronaphthalene-1-yl]amino}-8-fluoro-1H-quinolin-2-one;

5-{[(1S,2R,4R)-4,6-diethyl-2,5-dihydroxy-2-(trifluoromethyl)-1,2,3,4-tetrahydronaphthalene-1-yl]amino}-8-fluoro-1H-quinolin-2-one;

(5S,6R,8S)-2,8-diethyl-5-[2-methylquinazoline-5-ylamino]-6-(trifluoromethyl)-5,6,7,8-tetrahydronaphthalene-1,6-diol;

5-{[(1α,2α,4β)-7-chloro-2,5-dihydroxy-4-ethyl-2-(trifluoromethyl)-1,2,3,4-tetrahydronaphthalene-1-yl]amino}-1H-quinolin-2-one;

5-{[(1α,2α,4β)7-chloro-2,5-dihydroxy-4-ethyl-2-(trifluoromethyl)-1,2,3,4-tetrahydronaphthalene-1-yl]amino}-8-fluoro-1H-quinolin-2-one;

5-{[(1S,2R,4R)-6-chloro-4-ethyl-2,5-dihydroxy-7-fluoro-2-(trifluoromethyl)-1,2,3,4-tetrahydronaphthalene-1-yl]amino}quinolin-2(1H)-one;

5-{[(1S,2R,4R)-6-chloro-4-ethyl-2,5-dihydroxy-7-fluoro-2-(trifluoromethyl)-1,2,3,4-tetrahydronaphthalene-1-yl]amino}-7-fluoroquinolin-2(1H)-one;

5-{[(1S,2R,4R)-6-chloro-4-ethyl-2,5-dihydroxy-7-fluoro-2-(trifluoromethyl)-1,2,3,4-tetrahydronaphthalene-1-yl]amino}-8-fluoroquinolin-2(1H)-one;

(5S,6R,8R)-2-chloro-8-ethyl-3-fluoro-5-[(2-methylquinazoline-5-yl)amino]-6-(trifluoromethyl)-5,6,7,8-tetrahydronaphthalene-1,6-diol;

(5S,6R,8R)-2-chloro-8-ethyl-3-fluoro-5-[(7-fluoro-2-methylquinazoline-5-yl)amino]-6-(trifluoromethyl)-5,6,7,8-tetrahydronaphthalene-1,6-diol;

5-{[(1α,2α,4β)-7-fluoro-2,5-dihydroxy-4-ethyl-2-(trifluoromethyl)-1,2,3,4-tetrahydronaphthalene-1-yl]amino}-7-fluoro-1H-quinolin-2-one;

5-{[(5S,6R,8R)-8-ethyl-3-fluoro-1,6-dihydroxy-6-(trifluoromethyl)-5,6,7,8-tetrahydronaphthalene-5-yl]amino}-8-fluoroquinolin-2(1H)-one;

5-{[(1α,2α,4β)7-fluoro-2,5-dihydroxy-4-methyl-2-(trifluoromethyl)-1,2,3,4-tetrahydronaphthalene-1-yl]amino}-7-fluoro-1H-quinolin-2-one;

5-{[(1α,2α,4β)-7-fluoro-2,5-dihydroxy-4-methyl-2-(trifluoromethyl)-1,2,3,4-tetrahydronaphthalene-1-yl]amino}-8-fluoro-1H-quinolin-2-one;

5-{[(1α,2α,4β)7-Brom-2,5-dihydroxy-4-ethyl-2-(trifluoromethyl)-1,2,3,4-tetrahydronaphthalene-1-yl]amino}-1H-quinolin-2-one;

5-{[(1S,2R,4R)-7-Brom-2,5-dihydroxy-4-ethyl-2-(trifluoromethyl)-1,2,3,4-tetrahydronaphthalene-1-yl]amino}-7-fluoro-1H-quinolin-2-one;

5-{[(1α,2α,4β)7-Brom-2,5-dihydroxy-4-ethyl-2-(trifluoromethyl)-1,2,3,4-tetrahydronaphthalene-1-yl]amino}-8-fluoro-1H-quinolin-2-one;

5-{[(1α,2α,4β)6-fluoro-2,7-dihydroxy-4-methyl-2-(trifluoromethyl)-1,2,3,4-tetrahydronaphthalene-1-yl]amino}-1H-quinolin-2-one;

(5α,6α,8β)-8-ethyl-1,6-dihydroxy-5-(2-oxo-1,2-dihydroquinoline-5-ylamino)-6-(trifluoromethyl)-5,6,7,8-tetrahydronaphthalene-2-carbonitrile;

(5α,6α,8β)-8-ethyl-1,6-dihydroxy-5-(8-fluoro-2-oxo-1,2-dihydroquinoline-5-ylamino)-6-(trifluoromethyl)-5,6,7,8-tetrahydronaphthalene-2-carbonitrile;

(5α,6α,8β)-8-ethyl-1,6-dihydroxy-5-[(1-oxo-1,2-dihydroisoquinoline-5-yl)amino]-6-(trifluoromethyl)-5,6,7,8-tetrahydronaphthalene-2-carbonitrile;

(5α,6α,8β)-1,6-dihydroxy-8-methyl-5-[(2-oxo-2,3-dihydro-1H-indol-4-yl)amino]-6-(trifluoromethyl)-5,6,7,8-tetrahydronaphthalene-2-carbonitrile;

(5α,6α,8β)-5-[(8-fluoro-2-oxo-1,2-dihydroquinoline-5-yl)amino]-1,6-dihydroxy-8-methyl-6-(trifluoromethyl)-5,6,7,8-tetrahydronaphthalene-2-carbonitrile;

5-{[(5S,6R,8R)-8-ethyl-1,6-dihydroxy-3-fluoro-5-[(2-oxo-1,2-dihydroquinoline-5-yl)amino]-6-(trifluoromethyl)-5,6,7,8-tetrahydronaphthalene-2-carbonitrile;

(5α,6α,8β)-8-ethyl-1,6-dihydroxy-3-fluoro-5-[(8-fluoro-2-oxo-1,2-dihydroquinoline-5-yl)amino]-6-(trifluoromethyl)-5,6,7,8-tetrahydronaphthalene-2-carbonitrile;

5-{[(1S,2R,4S)-2,5-dihydroxy-4-methyl-2-(trifluoromethyl)-1,2,3,4-tetrahydronaphthalene-1-yl]amino}-7-fluoro-1H-quinolin-2-one;

5-{[(1S,2R,4R)-2,5-dihydroxy-4-methyl-2-(trifluoromethyl)-1,2,3,4-tetrahydronaphthalene-1-yl]amino}-7-fluoro-1H-quinolin-2-one;

5-{[(1S,2R,4S)-2,5-dihydroxy-4-methyl-2-(trifluoromethyl)-1,2,3,4-tetrahydronaphthalene-1-yl]amino}-8-fluoro-1H-quinolin-2-one;

5-{[(1S,2R,4R)-2,5-dihydroxy-4-methyl-2-(trifluoromethyl)-1,2,3,4-tetrahydronaphthalene-1-yl]amino}-8-fluoro-1H-quinolin-2-one;

5-{[(1α,2α,4β)-4-ethyl-2,5-dihydroxy-2-(trifluoromethyl)-1,2,3,4-tetrahydronaphthalene-1-yl]amino}-6-fluoro-1H-quinolin-2-one;

5-{[(1α,2α,4β)4-ethyl-6-fluoro-2,5-dihydroxy-7-methyl-2-(trifluoromethyl)-1,2,3,4-tetrahydronaphthalene-1-yl]amino}-1H-quinoline-2-one;

5-{[(1α,2α,4β)4-ethyl-6-fluoro-2,5-dihydroxy-7-methyl-2-(trifluoromethyl)-1,2,3,4-tetrahydronaphthalene-1-yl]amino}-7-fluoro-1H-quinoline-2-one;

5-{[(1α,2α,4β)4-ethyl-6-fluoro-2,5-dihydroxy-7-methyl-2-(trifluoromethyl)-1,2,3,4-tetrahydronaphthalene-1-yl]amino}-8-fluoro-1H-quinolin-2-one;

5-{[(1α,2α,4β)4-ethyl-6-fluoro-2,5-dihydroxy-7-methyl-2-(trifluoromethyl)-1,2,3,4-tetrahydronaphthalene-1-yl]amino}-2H-quinolin-1-one;

(5α,6α,8β)-8-ethyl-2-fluoro-3-methyl-5-[2-methylquinazoline-5-ylamino]-6-(trifluoromethyl)-5,6,7,8-tetrahydronaphthalene-1,6-diol;

(5S,6R,8R)-8-ethyl-2,3-difluoro-5-[(2-methyl-1-oxyquinoline-5-yl)amino]-6-(trifluoromethyl)-5,6,7,8-tetrahydronaphthalene-1,6-diol;

5-{[(1α,2α,4β)2,5-dihydroxy-6,7-dimethyl-4-ethyl-2-(trifluoromethyl)-1,2,3,4-tetrahydronaphthalene-1-yl]amino}-1H-quinolin-2-one;

5-{[(1α,2α,4β)2,5-dihydroxy-6,7-dimethyl-4-ethyl-2-(trifluoromethyl)-1,2,3,4-tetrahydronaphthalene-1-yl]amino}-8-fluoro-1H-quinolin-2-one;

5-{[(1α,2α,4β)2,5-dihydroxy-6,7-dimethyl-4-ethyl-2-(trifluoromethyl)-1,2,3,4-tetrahydronaphthalene-1-yl]amino}-2H-quinolin-1-one;

5-{[(5S,6R,8R)-2-chloro-8-ethyl-1,6-dihydroxy-3-fluoro-2-6-(trifluoromethyl)-5,6,7,8-tetrahydronaphthalene-5-yl]amino}quinolin-2(1H)-one;

5-{[(5S,6R,8R)-3-chloro-8-ethyl-1,6-dihydroxy-2-6-(trifluoromethyl)-5,6,7,8-tetrahydronaphthalene-5-yl]amino}-7-fluoroquinolin-2(1H)-one (5S,6R,8R)-2,3-dichloro-8-ethyl-5-[(7-fluoro-2-methylquinazoline-5-yl)amino]-6-(trifluoromethyl)-5,6,7,8-tetrahydronaphthalene-1,6-diol;

(5S,6R,8R)-2-chloro-8-ethyl-5-[(7-fluoro-2-methylquinazoline-5-yl)amino]-6-(trifluoromethyl)-5,6,7,8-tetrahydronaphthalene-1,6-diol;

or (5S,6R,8R)-3-chloro-8-ethyl-5-[(7-fluoro-2-methylquinazoline-5-yl)amino]-6-(trifluoromethyl)-5,6,7,8-tetrahydronaphthalene-1,6-diol.

* * * * *